United States Patent
Yao

(10) Patent No.: US 11,390,650 B2
(45) Date of Patent: Jul. 19, 2022

(54) RECOMBINANT HERPES SIMPLEX VIRUS-2 EXPRESSING GLYCOPROTEIN B AND D ANTIGENS

(71) Applicant: THE BRIGHAM AND WOMEN'S HOSPITAL, INC., Boston, MA (US)

(72) Inventor: Feng Yao, Southborough, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 16/967,275

(22) PCT Filed: Feb. 1, 2019

(86) PCT No.: PCT/US2019/016316
§ 371 (c)(1),
(2) Date: Aug. 4, 2020

(87) PCT Pub. No.: WO2019/152821
PCT Pub. Date: Aug. 8, 2019

(65) Prior Publication Data
US 2021/0107946 A1    Apr. 15, 2021

Related U.S. Application Data

(60) Provisional application No. 62/626,438, filed on Feb. 5, 2018.

(51) Int. Cl.
| | | |
|---|---|---|
| *C07K 14/005* | (2006.01) | |
| *A61P 31/22* | (2006.01) | |
| *A61K 39/245* | (2006.01) | |
| *C12N 7/00* | (2006.01) | |
| *A61K 39/00* | (2006.01) | |

(52) U.S. Cl.
CPC .......... *C07K 14/005* (2013.01); *A61K 39/245* (2013.01); *A61P 31/22* (2018.01); *C12N 7/00* (2013.01); *A61K 2039/5254* (2013.01); *C12N 2710/16621* (2013.01); *C12N 2710/16622* (2013.01); *C12N 2710/16634* (2013.01); *C12N 2710/16662* (2013.01); *C12N 2710/16671* (2013.01)

(58) Field of Classification Search
CPC ................ C07K 14/005; A61K 39/245; A61K 2039/5254; A61K 39/12; A61P 31/22; A61P 15/00; C12N 7/00; C12N 2710/16621; C12N 2710/16622; C12N 2710/16634; C12N 2710/16662; C12N 2710/16671; C12N 2710/16643
See application file for complete search history.

(56) References Cited

U.S. PATENT DOCUMENTS

| | | | |
|---|---|---|---|
| 5,464,758 A | 11/1995 | Gossen et al. | |
| 5,589,362 A | 12/1996 | Bujard et al. | |
| 5,763,217 A | 6/1998 | Cynader et al. | |
| 5,770,414 A | 6/1998 | Gage et al. | |
| 5,917,122 A | 6/1999 | Byrne | |
| 5,965,440 A | 10/1999 | Reeves | |
| 5,972,650 A | 10/1999 | Yao | |
| 6,027,730 A | 2/2000 | Francotte et al. | |
| 6,183,753 B1 | 2/2001 | Cochran et al. | |
| 6,251,640 B1 | 6/2001 | Yao | |
| 6,261,552 B1 | 7/2001 | DeLuca | |
| 6,410,311 B1 | 6/2002 | Cochran et al. | |
| 6,444,871 B1 | 9/2002 | Yao | |
| 6,635,478 B1 | 10/2003 | Hippenmeyer et al. | |
| 6,846,670 B2 | 1/2005 | Schwartz et al. | |
| 7,223,411 B1 | 5/2007 | Knipe et al. | |
| 8,236,941 B2 | 8/2012 | Yao | |
| 9,273,326 B2 | 3/2016 | Yao | |
| 9,745,599 B2 | 8/2017 | Yao | |
| 2002/0028484 A1 | 3/2002 | Yao | |
| 2003/0113348 A1 | 6/2003 | Coffin | |
| 2003/0165537 A1 | 9/2003 | Fehler et al. | |
| 2004/0029229 A1 | 2/2004 | Reeves et al. | |
| 2004/0063094 A1 | 4/2004 | Coffin et al. | |
| 2004/0229362 A1 | 11/2004 | Epstein et al. | |
| 2005/0266564 A1 | 12/2005 | Yao | |
| 2006/0116340 A1 | 6/2006 | Lewin | |
| 2008/0008686 A1 | 1/2008 | Yao | |
| 2008/0299140 A1 | 12/2008 | Georges et al. | |
| 2010/0015687 A1 | 1/2010 | Yao | |
| 2012/0171191 A1 | 7/2012 | Choulika et al. | |
| 2012/0190106 A1 | 7/2012 | Yao | |
| 2012/0237481 A1 | 9/2012 | Zhang et al. | |

(Continued)

FOREIGN PATENT DOCUMENTS

| | | |
|---|---|---|
| CN | 1065997 A | 11/1992 |
| CN | 1503843 A | 6/2004 |

(Continued)

OTHER PUBLICATIONS

Akhrameyeva NV, Zhang P, Sugiyama N, Behar SM, Yao F. Development of a glycoprotein D-expressing dominant-negative and replication-defective herpes simplex virus 2 (HSV-2) recombinant viral vaccine against HSV-2 infection in mice. J Virol. May 2011; 85(10):5036-47. Epub Mar. 9, 2011. (Year: 2011).*
Adamiak B, Ekblad M, Bergström T, Ferro V, Trybala E. Herpes simplex virus type 2 glycoprotein G is targeted by the sulfated oligo- and polysaccharide inhibitors of virus attachment to cells. J Virol. Dec. 2007;81(24):13424-34. Epub Oct. 10, 2007. (Year: 2007).*
Tran LC, Kissner JM, Westerman LE, Sears AE. A herpes simplex virus 1 recombinant lacking the glycoprotein G coding sequences is defective in entry through apical surfaces of polarized epithelial cells in culture and in vivo. Proc Natl Acad Sci U S A. Feb. 15, 2000;97(4):1818-22. (Year: 2000).*
Rasty S, Poliani PL, Fink DJ, Glorioso JC. Deletion of the S component inverted repeat sequence c' and the nonessential genes U(S)1 through U(S)5 from the herpes simplex virus type 1 genome . . . J Neurovirol. Aug. 1997;3(4):247-64. (Year: 1997).*

(Continued)

*Primary Examiner* — Rachel B Gill
(74) *Attorney, Agent, or Firm* — Nixon Peabody LLP; David S. Resnick; Jeanne Jodoin

(57) ABSTRACT

The present invention is directed to Herpes simplex-2 viruses that may be used in vaccines to immunize patients against genital herpes.

8 Claims, 39 Drawing Sheets

Specification includes a Sequence Listing.

(56) References Cited

U.S. PATENT DOCUMENTS

| | | | | |
|---|---|---|---|---|
| 2014/0314811 | A1* | 10/2014 | Yao | C12N 7/00 424/231.1 |
| 2015/0110822 | A1 | 4/2015 | Mohr et al. | |
| 2017/0258894 | A1 | 9/2017 | Yang et al. | |

FOREIGN PATENT DOCUMENTS

| | | |
|---|---|---|
| JP | 2006-500062 A | 1/2006 |
| WO | 1992016231 A1 | 10/1992 |
| WO | 1994004672 A1 | 3/1994 |
| WO | 2002012288 A1 | 2/2002 |
| WO | 2004029258 A1 | 4/2004 |
| WO | 2011025717 A2 | 3/2011 |
| WO | 2011079073 A2 | 6/2011 |
| WO | 2018226638 A1 | 12/2018 |

OTHER PUBLICATIONS

Genway Biotech .Mammalian Expression Technologies: Mammalian Expression System, "https://www.genwaybio.com/technologies/protein-expression/mammalian-expression". Mar. 4, 2015. (Year: 2015).*

Morimoto et al. "Identification of multiple sites suitable for insertion of foreign genes in herpes simplex virus genomes." Microbiology and Immunology 53(3): 155-161 (2009).

Mertz et al., "Risk Factors for the Sexual Transmission of Genital Herpes", Ann. Intern. Med. 116(3):197-202 (1992).

Mikloska et al., "Herpes Simplex Virus Type 1 Glycoproteins gB, gC and gD are Major Targets for CD4 T-Lymphocyte Cytotoxicity in HLA-DR Expressing Human Epidermal Keratinocytes", J. Gen. Virol. 79:353-361 (1998).

Mikloska et al., "Monophosphoryl Lipid A and QS21 Increase CD8 T Lymphocyte Cytotoxicity to Herpes Simplex Virus-2 Infected Cell Proteins 4 and 27 Through IFN-Gamma and IL-12 Production", J. Immunol. 164:5167-5176 (2000).

Minson et al., "An Analysis of the Biological Properties of Monoclonal Antibodies against Glycoprotein D of Herpes Simplex Virus and Identification of Amino Acid Substitutions that Confer Resistance to Neutralization", J. Gen. Virol. 67:1001-1013 (1986).

Morrison et al., "Influence of Mucosal and Parenteral Immunization with a Replication-Defective Mutant of HSV-2 on Immune Responses and Protection from Genital Challenge", Virology 243:178-187 (1998).

Muller, "Binding of the Herpes Simplex Virus Immediate-Early Gene Product ICP4 to Its Own Transcription Start Site", J. Virol. 61(3):858-865 (1987).

Nagot et al., "Reduction of HIV-1 RNA Levels with Therapy to Suppress Herpes Simplex Virus", N. Engl. J. Med. 356(8):790-799 (2007).

No et al., "Ecdysone-inducible gene expression in mammalian cells and transgenic mice", Proc. Natl. Acad. Sci. U.S.A. 93:3346-3351 (1996).

Notice of Noncompliant Amendment dated Apr. 21, 2009 in the prosecution of U.S. Appl. No. 11/117,375.

Nover, "Gene Technology and Functional Analyses of Heat Shock Genes", In Heat Shock Response, pp. 167-220, crc, Fla. 1991.

Office Action dated Aug. 16, 2011 in the prosecution of U.S. Appl. No. 11/117,375.

Office Action dated Aug. 5, 2010 in the prosecution of U.S. Appl. No. 11/117,375.

Office Action dated Jan. 20, 2011 in the prosecution of U.S. Appl. No. 11/117,375.

Office Action dated Jan. 26, 2009 in the prosecution of U.S. Appl. No. 11/822,373 along with claims under consideration in the Office Action.

Office Action dated Jun. 12, 2007 in the prosecution of U.S. Appl. No. 11/117,375.

Office Action dated Nov. 27, 2007 in the prosecution of U.S. Appl. No. 11/117,375.

Office Action dated Nov. 9, 2009 in the prosecution of U.S. Appl. No. 11/117,375

Office Action dated Oct. 15, 2008 in the prosecution of U.S. Appl. No. 11/117,375.

Palmer et al., "Development and Optimization of Herpes Simplex Virus Vectors for Multiple Long-Term Gene Delivery to the Peripheral Nervous System", J. Virol. 74(12):5604-5618 (2000).

Para et al., "Potent Neutralizing Activity Associated with Anti-Glycoprotein D Specificity Among Monoclonal Antibodies Selected for Binding to Herpes Simplex Virions", J. Virol. 55(2):483-488 (1985).

Pereira et al., "Type-Common and Type-Specific Monoclonal Antibody to Herpes Simplex Virus Type 1", Infect. Immun. 29(2):724-732 (1980).

Pereira et al., "Use of Monoclonal Antibodies to HSV-1 and HSV-2 for Serological Analysis of the Viral Glycoproteins", Dev. Biol. Stand. 52:115-131 (1982).

Perry et al., "Characterization of the IE110 Gene of Herpes Simplex Virus Type 1", J. Gen. Virol. 67:2365-2380 (1986).

Postle et al., "Nucleotide Sequence of the Repressor Gene of the TN10 Tetracycline Resistance Determinant", Nucleic Acids Res. 12(12):4849-4863 (1985).

Preston et al., "Construction and Characterization of Herpes Simplex Virus Type 1 Mutants with Conditional Defects in Immediate Early Gene Expression", Virology 229(1):228-239 (1997).

Preston et al., "Repression of Gene Expression upon Infection of Cells with Herpes Simplex Virus Type 1 Mutants Impaired for Immediate-Early Protein Synthesis", J. Virol. 71(10):7807-7813 (1997).

Radomska et al., "Transgenic targeting with regulatory elements of the human CD34 gene", Blood 100(13):4410-4419 (2002).

Ramos et al., "The TetR Family of Transcriptional Repressors", Microbiol. Mol. Biol. Rev. 69(2):326-356 (2005).

Resnick et al., "DNA Binding by the Herpes Simplex Virus Type 1 ICP4 Protein is Necessary for Efficient Down Regulation of the ICP0 Promoter", J. Virol. 63(3):2497-2503 (1989).

Response to Notice of Noncompliant Amendment dated Apr. 21, 2009 in the prosecution of U.S. Appl. No. 11/117,375, filed May 4, 2009.

Response to Office Action dated Aug. 5, 2010 in the prosecution of U.S. Appl. No. 11/117,375, filed Nov. 10, 2010.

Response to Office Action dated Jan. 20, 2011 filed in the prosecution of U.S. Appl. No. 11/117,375, filed May 20, 2011 along with RCE Response to Office Action dated Jan. 26, 2009 in the prosecution of U.S. Appl. No. 11/822,373, filed Mar. 31, 2009.

Response to Office Action dated Jun. 12, 2007 in the prosecution of U.S. Appl. No. 11/117,375, filed Sep. 12, 2007.

Response to Office Action dated Nov. 27, 2007 in the prosecution of U.S. Appl. No. 11/117,375.

Response to Office Action dated Nov. 9, 2009 in the prosecution of U.S. Appl. No. 11/117,375, filed Feb. 10, 2010.

Response to Office Action dated Oct. 15, 2008 in the prosecution of U.S. Appl. No. 11/117,375, filed Jan. 15, 2009.

Rivera et al., "A Humanized System for Pharmacologic Control of Gene Expression", Nat. Med. 2(9):1028-1032 (1996).

Roberts et al., "Direct Correlation Between a Negative Autoregulatory Response Element at the Cap Site of the Herpes Simplex Virus Type 1 IE175 (alpha 4) Promoter and a Specific Binding Site for the IE175 (ICP4) Protein", J. Virol. 62(11):4307-4320 (1988).

Roizman et al., "Herpes Simplex Viruses and Their Replication," Chapter 72, pp. 2399-2459; D.M. Knipe (ed.), Fields Virology, 4th ed. Lippencott Williams & Wilkins, Philadelphia, PA (2001).

Ross et al., Gene Therapy in the United States: a Five-Year Status Report, Hum. Gene Ther. 7:1781-1790 (1996).

Scarpini et al., "Latency Associated Promoter Transgene Expression in the Central Nervous System After Stereotaxic Delivery of Replication-Defective HSV-1-Based Vectors", Gene Ther. 8(14):1057-1071 (2001).

Schmeisser et al., "Tetracycline-Regulated Gene Expression in Replication-Incompetent Herpes Simplex Virus Vectors", Hum. Gene Ther. 13(18):2113-2124 (2002).

(56) References Cited

OTHER PUBLICATIONS

Schmidt et al., "Reinfection is an Uncommon Occurrence in Patients with Symptomatic Recurrent Genital Herpes", J. Infect. Dis. 149(4):645-646 (1984).
Schmidt et al., "The Cytomegalovirus Enhancer: a Pan-Active Control Element in Transgenic Mice", Mol. Cell. Biol. 10(8):4406-4411 (1990).
Stanberry et al., "Glycoprotein-D-Adjuvant Vaccine to Prevent Genital Herpes", N. Engl. J. Med. 347(21):1652-1661 (2002).
Stanberry et al., "Prospects for Control of Herpes Simplex Virus Disease Through Immunization", Clin. Infect. Dis. 30:549-566 (2000).
Stanberry, "Clinical Trials of Prophylactic and Therapeutic Herpes Simplex Virus Vaccines", Herpes 11(Suppl 3):161A-169A (2004).
Starr et al., "Long-Term Persistence of Defective HSV-1 Vectors In the Rat Brain is Demonstrated by Reactivation of Vector Gene Expression", Gene Ther. 3:615-623 (1996).
Mcgeoch et al., "The Complete DNA Sequence of the Long Unique Region in the Genome of Herpes Simplex Virus Type 1", J. Gen. Virol. 69:1531-1574 (1988).
Abu-Raddad et al., "Genital Herpes Has Played a More Important Role than Any Other Sexually Transmitted Infection in Driving HIV Prevalence in Africa", PLoS One 3(5):e2230 (2008).
Ackermann et al., "Characterization of Herpes Simplex Virus 1 Alpha Proteins 0, 4, and 27 with Monoclonal Antibodies", J. Virol. 52(1):103-118 (1984).
Adelson et al., "Simultaneous Detection of Herpes Simplex Virus Types 1 and 2 by Real-Time PCR and Pyrosequencing", J. Clin. Virol. 33(1):25-34 (2005).
Advani et al., "Friendly Fire: Redirecting Herpes Simplex Virus-1 for Therapeutic Applications", Clin. Microbiol. Infect. 8(9):551-563 (2002).
Anderson, "Human Gene Therapy", Nature 392(6679 Suppl):25-30 (1998).
Appeal Brief filed by Applicant on May 27, 2008 in the prosecution of U.S. Appl. No. 11/117,375.
Appeal Brief filed by Applicant on Nov. 26, 2011 for U.S. Appl. No. 11/117,375
Armentano et al., "E4ORF3 Requirement for Achieving Long-Term Transgene Expression from the Cytomegalovirus Promoter in Adenovirus Vectors", J. Virol. 73(8):7031-7034 (1999).
Arvin et al., "Detection of Type-Specific Antibody to Herpes Simplex Virus Type 1 by Radioimmunoassay with Herpes Simplex Virus Type 1 Glycoprotein C Purified with Monoclonal Antibody", Infect. Immun. 40(1):184-189 (1983).
Augustinova et al.,"The Dominant-Negative Herpes Simplex Virus Type 1 (HSV-1) Recombinant CJ83193 Can Serve as an Effective Vaccine against Wild-Type HSV-1 Infection in Mice", J. Virol. 78(11):5756-5765 (2004).
Baron et al., "Co-regulation of two gene activities by tetracycline via a bidrectional promoter", Nucleic Acids Res. 23(17):3605-3606 (1995).
Baskar et al., "Developmental Analysis of the Cytomegalovirus Enhancer in Transgenic Animals", J. Virol. 70(5):3215-3226 (1996).
Berens et al., "Gene Regulation by Tetracyclines. Constraints of Resistance Regulation in Bacteria Shape TetR for Application in Eukaryotes", Eur. J. Biochem. 270(15):3109-3121 (2003).
Boshart et al., "A Very Strong Enhancer Is Located Upstream of an Immediate Early Gene of Human Cytomegaloviurs", Cell 41(2):521-530 (1985).
Bourne et al., "DNA Immunization Confers Protective Immunity on Mice Challenged Intravaginally with Herpes Simplex Virus Type 2", Vaccine 14(13):1230-1234 (1996).
Brans et al., "Immunization with a Dominant-Negative Recombinant HSV Type 1 Protects against HSV-1 Skin Disease in Guinea Pigs", J. invest. Dermatol. 128:2825-2832 (2008).
Brans et al., "Prevention of Genital Herpes Simplex Virus Type 1 and 2 Disease in Mice Immunized with a gD-Expressing Dominant-Negative Recombinant HSV-1", J. Invest. Dermatol. 129:2470-2479 (2009).

Brinster et al., "Regulation of metallothionein-thymidine kinase fusion plasmids injected into mouse eggs" Nature 296(5852):39-42 (1982).
Brown, et al., "Iac Repressor Can Regulate Expression from a Hybrid SV40 Early Promoter Containing a Iac Operator in Animal Cells", Cell 49:603-612 (1987).
Bryson et al., "Risk of Acquisition of Genital Herpes Simplex Virus Type 2 in Sex Partners of Persons with Genital Herpes: a Prospective Couple Study", J. Infect. Dis. 167(4):942-946 (1993).
Cai et al., "Herpes Simplex Virus Type 1 ICP0 Plays a Critical Role In the De Novo Synthesis of Infectious Virus Following Transfection of Viral DNA", J. Virol. 63(11):4579-4589 (1989).
Cai et al., "The Herpes Simplex Virus Type 1 Regulatory Protein ICP0 Enhances Virus Replication During Acute Infection and Reactivation from Latency", J. Virol. 67(12):7501-7512 (1993).
Clackson, "Regulated Gene Expression Systems", Gene Therapy 7:120-125 (2000).
Claims pending in U.S. Appl. No. 11/822,373 division of U.S. Appl. No. 11/822,373, filed Sep. 2, 2009.
Cohen et al., "Localization and Synthesis of an Antigenic Determinant of Herpes Simplex Virus Glycoprotein D That Stimulates the Production of Neutralizing Antibody", J. Virol. 49(1):102-108 (1984).
Cohen, "Bumps on the Vaccine Road", Science 265:1371-1373 (1994).
Coleman et al., "Determination of Herpes Simplex Virus Type-Specific Antibodies by Enzyme-Linked Immunosorbent Assay", J. Clin. Microbiol. 18(2):287-291 (1983).
Communication re Nonresponsive Amendment mailed in connection with prosecution of U.S. Appl. No. 11/822,373 dated Aug. 3, 2009.
Cooper et al., "Epitope Mapping of Full-Length Glycoprotein D from HSV-2 Reveals a Novel CD4+ CTL Epitope Located at the Transmembrane-Cytoplasmic Junction", Cell Immunol. 239(2):113-120 (2006),
Corbel et al., "Latest Developments and In Vivo Use of the Tet System: Ex Vivo and In Vivo Delivery of Tetracycline-Regulated Genes", Curr. Opin. Biotechnol. 13:448-452 (2002).
Corey et al., "Infections with Herpes Simplex Viruses (Second of Two Parts)", N. Engl. J. Med. 314(12):749-757 (1986).
Davido et al., "Role of Cis-Acting Sequences of the ICP0 Promoter of Herpes Simplex Virus Type 1 in Viral Pathogenesis, Latency and Reactivation", J. Gen. Virol. 77:1853-1863 (1996).
Declaration Under CFR Sec. 1.132 filed in the prosecution of U.S. Appl. No. 11/117,375 dated May 20, 2011.
Deluca et al., "Physical and functional Domains of the Herpes Simplex Virus Transcriptional Regulatory Protein ICP4", J. Virol. 62(3):732-743 (1988).
Deuschle et al., "Tetracycline-Reversible Silencing of Eukaryotic Promoters", Mol. Cell. Biol. 15(4):1907-1914 (1995).
Dolan et al., "The Genome Sequence of Herpes Simplex Virus Type 2", J. Virol. 72(3):2010-2021 (1998).
Dudek et al., "Replication-Defective Viruses as Vaccines and Vaccine Vectors", Virology 344(1):230-239 (2006).
English translation of Office action dated Apr. 24, 2013 for corresponding Chinese application 201080058385.7, with Search Report and claims currently pending in China attached.
Examiner's Answer mailed by the USPTO dated Feb. 2, 2012 for U.S. Appl. No. 11/117,375.
Fleming et al., "Herpes Simplex Virus Type 2 In the United States, 1976 TO 1994", N. Engl. J. Med. 337(16):1105-1111 (1997).
Foecking, et al., "Powerful and versatile enhancer-promoter unit for mammalian expression vectors", Gene 45:101-105 (1986).
Fox, "Investigation of Gene Therapy Begins", Nat. Biotechnol. 18(2):143-144 (2000).
Freeman et al., "Herpes Simplex Virus 2 Infection Increases HIV Acquisition In Men and Women: Systematic Review and Meta-Analysis of Longitudinal Studies", Aids 20:73-83 (2006).
Ghosh et al., "Expanding Adeno-associated Viral Vector Capacity: A Tale of Two Vectors", Biotechnol, Genet. Eng. Rev. 24:165-177 (2007).
Glorioso et al., "Immunogenicity of Herpes Simplex Virus Glycoproteins gC and gB and their Role in Protective Immunity", J. Virol. 50(3):805-812 (1984).

(56) References Cited

OTHER PUBLICATIONS

Glorioso et al., "Therapeutic Gene Transfer to the Nervous System Using Viral Vectors", J. Neurovirol. 9:165-172 (2003).
Gossen et al., "Tight Control of Gene Expression in Mammalian Cells by Tetracycline-Responsive Promoters", Proc. Natl. Acad. Sci. U.S.A. 89(12):5547-5551 (1992).
Gossen et al., "Transcriptional Activation by Tetracyclines in Mammalian Cells", Science 268(5218):1766-1769 (1995).
Stow et al., "Isolation and Characterization of a Herpes Simplex Virus Type 1 Mutant Containing a Deletion within the Gene Encoding the Immediate Early Polypeptide Vmw110", J. Gen. Virol. 67:2571-2585 (1986).
Tigges et al., "Human CD8+ Herpes Simplex Virus-Specific Cytotoxic T-Lymphocyte Clones Recognize Diverse Virion Protein Antigens", J. Virol. 66(3):1622-1634 (1992).
Toka et al., "Rescue of memory CD8+ T cell reactivity in peptide/TLR9 ligand immunization by codelivery of cytokines or CD40 ligation", Virology 331(1):151-158 (2005).
Verma, et al., "Gene Therapy—Promises, Problems and Prospects", Nature 389:239-242 (1997).
Wang et al., "A Regulatory System For Use in Gene Transfer", Proc. Natl. Acad. Sci. U.S.A. 91:8180-8184 (1994).
Wang et al., "Mammary Hyperplasia and Carcinoma in MMTV-Cyclin D1 Transgenic Mice", Nature 369(6482):669-671 (1994).
Whitley et al., "Herpes Simplex Viruses", Clin. Infect. Dis. 26:541-553; quiz 554-5 (1998).
Wissmann et al., "Saturation Mutagenesis of the Tn10-Encoded Tet Operator O1. Identification of Base-Pairs Involved in Tet Repressor Recognition", J. Mol. Biol. 202(3):397-406 (1988).
Written Opinion of the International Searching Authority for PCT/US07/15540 filed Jul. 6, 2007.
Written Opinion of the International Searching Authority for PCT/US2010/046252 filed Aug. 20, 2010.
Written Opinion of the International Searching Authority for PCT/US2010/061320 filed Dec. 20, 2010.
Xu et al., "Seroprevalence and Coinfection with Herpes Simplex Virus Type 1 and Type 2 in the United States, 1988-1994", J. Infect. Dis. 185:1019-1024 (2002).
Yao et al., "A Novel Anti-Herpes Simplex Virus Type 1-Specific Herpes Simplex Virus Type 1 Recombinant", Hum. Gene Ther. 10:1811-1818 (1999).
Yao et al., "A Novel Tetracycline-Inducible Viral Replication Switch", Hum. Gene Ther. 10:419-427 (1999).
Yao et al., "An Activity Specified by the Osteosarcoma Line U2OS Can Substitute Functionally for ICP0, a Major Regulatory Protein of Herpes Simplex Virus Type 1", J. Virol. 69(10):6249-6258 (1995).
Yao et al., "Highly Efficient Regulation of Gene Expression by Tetracycline in a Replication-Defective Herpes Simplex Viral Vector", Mol. Ther. 13(6):1133-1141 (2006).
Yao et al., "Inhibition of Herpes Simplex Virus Type 2 (HSV-2) Viral Replication by the Dominant Negative Mutant Polypeptide of HSV-1 Origin Binding Protein", Antiviral Res. 53:127-133 (2002).
Yao et al., "Physical Interaction Between the Herpes Simplex Virus Type 1 Immediate-Early Regulatory Proteins ICP0 and ICP4" J. Virol. 68(12):8158-8168 (1994).
Yao et al., "Tetracycline Repressor, tetR, Rather Than the tetR-Mammalian Cell Transcription Factor Fusion Derivatives, Regulates Inducible Gene Expression in Mammalian Cells", Hum. Gene Ther. 9(13):1939-1950 (1998).
Zarling et al., "Human Cytotoxic T Cell Clones Directed Against Herpes Simplex Virus-Infected Cells. IV. Recognition and Activation by Cloned Glycoproteins gB and gD", J. Immunol. 136(12):4669-4673 (1986).
Stinski et al., "Activation of the Major Immediate Early Gene of Human Cytomegalovirus by cis-Action Elements in the Promoter-Regulatory Sequence and by Virus-Specific trans-Acting Components", J. Virol. 55(2):431-441 (1985).
Gupta et al., "Genital Herpes", Lancet 370(9605):2127-2137 (2007).

Handler et al., "Oligomeric Structure of Glycoproteins in Herpes Simplex Virus Type 1", J. Virol. 70(9):6067-6075 (1996).
Hennighausen et al., "Conditional Gene Expression in Secretory Tissues and Skin of Transgenic Mice Using the MMTV-LTR and the Tetracycline Responsive System", J. Cell. Biochem, 59:463-472 (1995).
Herrlinger et al., "HSV-1 infected cell proteins influence tetracycline-regulated transgene expression", J. Gene. Med. 2:379-389 (2000).
Heuer et al., "Tet Repressor-Tet Operator Contacts Probed by Operator DNA-Modification Interference Studies", J. Mol. Biol. 202(3):407-415 (1988).
Hillen et al., "Mechanisms Underlying Expression of Tn10 Encoded Tetracycline Resistance", Annu. Rev. Microbiol. 48:345-369 (1994).
Hirsch, "Herpes Simplex Virus", p. 1144-1153. In G.L. Mandell, R.G.J. Douglas and J.E. Bennett (ed.), Principles and practice of infectious diseases. Churchill Livingstone Inc., New York (1990).
Honess et al., "Type Specific and Type Common Antigens in Cells Infected with Herpes Simplex Virus Type 1 and on the Surfaces of Naked and Enveloped Particles of the Virus", J. Gen. Virol. 22:159-169 (1974).
Hosken et al., "Diversity of the CD8+ T-Cell Response to Herpes Simplex Virus Type 2 Proteins Among Persons with Genital Herpes", J. Virol. 80(11):5509-5515 (2006).
International Preliminary Examination Report for PCT/US2010/046252 filed Aug. 20, 2010.
International Preliminary Report on Patentability for PCT/US2007/15540 filed Jul. 6, 2007.
International Preliminary Report on Patentability for PCT/US2010/061320 filed on Dec. 20, 2010.
International Search Report for PCT/US07/15540 filed Jul. 6, 2007.
ISR for PCT/US2010/046252 filed Aug. 20, 2010.
ISR for PCT/US2010/061320 filed Dec. 20, 2010.
Jacobs et al., "HSV-1-Based Vectors for Gene Therapy of Neurological Diseases and Brain Tumors: Part I. HSV-1 Structure, Replication and Pathogenesis", Neoplasia 1(5):387-401 (1999).
Jacobs et al., "HSV-1-Based Vectors for Gene Therapy of Neurological Diseases and Brain Tumors: Part II. Vector Systems and Applications", Neoplasia 1(5):402-416 (1999).
Johnson et al., "Herpes Simplex Virus Glycoprotein D is Recognized as Antigen by CD4+ and CD8+ T Lymphocytes from Infected Mice. Characterization of T Cell Clones", J. Immunol. 145(2):702-710 (1990).
Jones et al., "Vaccination Strategies to Prevent Genital Herpes and Neonatal Herpes Simplex Virus (HSV) Disease", Herpes 11(1):12-17 (2004).
Kemble, G., et al., "Herpes simplex vaccines" In: Arvin A. Campadelli-Fiume G., Mocarski E., et al., editors, Human Herpesviruses: Biology, Therapy and Immunoprophylaxis, Cambridge University Press; 2007, Chapter 69. Available from http://www.ncbi.nim.nih.gov/books/NBK47451/?report=printable.
Kim et al., Immunodominant Epitopes in Herpes Simplex Virus Type 2 Glycoprotein D are Recognized by CD4 Lymphocytes from Both HSV-1 and HSV-2 Seropositive Subjects', J. Immunol. 181:6604-6615 (2008).
Kim et al., "Tetracycline Repressor-Regulated Gene Repression in Recombinant Human Cytomegalovirus", J. Virol. 69(4):2565-2573(1995).
Klock et al., "Oestrogen and glucocorticoid responsive elements are closely related but distinct", Nature 329:734-736 (1987).
Klucher et al., "Sequences in the Human Cytomegalovirus 2.7-Kilobase RNA Promoter Which Mediate Its Regulation as an Early Gene", J. Virol. 63(12):5334-5343 (1989).
Kmiec et al. "Investigators Have Been Searching for Ways to Add Corrective Genes to Cells Harboring Defective Genes. A Better Strategy Might Be to Correct the Defects", American Scientist 87:240-247 (1999).
Knopf et al., Evaluation of the T-REx Transcription Switch for Conditional Expression and Regulation of HSV-1 Vectors', Virus Genes 36(1):55-66 (2008).
Koedood et al., "Human Cytomegalovirus (HCMV) Immediate-Early Enhancer/Promoter Specificity during Embryogenesis Defines Target Tissues of Congenital HCMV Infection", J. Virol. 69(4):2194-2207 (1995).

(56) References Cited

OTHER PUBLICATIONS

Koelle et al., "Herpes Simplex Virus Infection of Human Fibroblasts and Keratinocytes Inhibits Recognition by Cloned CD8+ Cytotoxic T Lymphocytes", J. Clin. Invest. 91:961-968 (1993).
Koelle et al., "Herpes Simplex: Insights on Pathogenesis and Possible Vaccines", Annu. Rev. Med. 59:381-395 (2008).
Koelle et al., "Prospects for Developing an Effective Vaccine Against Ocular Herpes Simplex Virus Infection", Curr. Eye Res. 30:929-942 (2005).
Koelle et al., "Recent Progress in Herpes Simplex Virus Immunobiology and Vaccine Research", Ciin. Microbiol. Rev. 16(1):96-113 (2003).
Kousoulas et al., "Antibody-Resistant Mutations in Cross-Reactive and Type-Specific Epitopes of Herpes Simplex Virus 1 Glycoprotein B Map in Separate Domains", Virology 166(2):423-431 (1988).
Kwissa et al., "Polyvalent DNA vaccines with bidirectional promoters", J. Mol. Med. 78:495-506 (2000).
Labow et al., "Conversion of the lac Repressor into an Allosterically Regulated Transcriptional Activator for Mammalian Cells", Mol. Cell. Biol. 10(7):3343-3356 (1990).
Lakeman et al., "Analysis of DNA From Recurrent Genital Herpes Simplex Virus Isolates by Restriction Endonuclease Digestion", Sex. Transm. Dis. 13:61-66 (1986).
Latchman, "Herpes Simplex Virus Vectors for Gene Delivery to a Variety of Different Cell Types", Curr. Gene Ther. 2:415-426 (2002).
Le et al., "Inducible expression of Cre Rcombinase in the Retinal Pigmented Epithelium", Invest. Ophthalmol. Vis. Sci. 49(3):1248-1253 (2008).
Leib et al., "Immediate-Early Regulatory Gene Mutants Define Different Stages in the Establishment and Reactivation of Herpes Simplex Virus Latency", J. Virol. 63(2):759-768 (1989).
Lewandowski et al., "Evidence that Deficient IFN-Gamma Production is a Biological Basis of Herpes Simplex Virus Type-2 Neurovirulence", J. Neuroimmunol. 81:66-75 (1998).
Liesegang et al., "Herpes Simplex Virus Epidemiology and Ocular Importance", Cornea 20(1):1-13 (2001).
Looker et al., "A Systematic Review of the Epidemiology and Interaction of Herpes Simplex Virus Types 1 and 2", Sex. Transm. Infect. 81:103-107 (2005).
Loser et al., "Enhanced contact hypersensitivity and antiviral immune responses in vivo by keratinocyte-targeted overexpression of IL-15", Eur. J. Immunol. 34:2022-2031 (2004).
Lu et al., "High-Level Expression of Glycoprotein D by a Dominant-Negative HSV-1 Virus Augments its Efficacy as a Vaccine Against HSV-1 Infection", J. Invest. Dermatol. 129:1174-1184 (2009). (Epub 2008).
Martinez et al., "The Conserved Helicase Motifs of the Herpes Simplex Virus Type 1 Origin-Binding Protein UL9 Are Important for Function", J. Virol. 66(11):6735-6746 (1992).
Martuza et al., "Experimental Therapy of Human Glioma by Means of a Genetically Engineered Virus Mutant", Science 252:854-856 (1991).
McGeoch DJ. UL9 [Human herpesvirus 1]. GenBank Acc. No. CAA32345.1. Dep. Oct. 23, 2008
Mcgeoch et al., "Comparative Sequence Analysis of the Long Repeat Regions and Adjoining Parts of the Long Unique Regions in the Genomes of Herpes Simplex Viruses Types 1 and 2", J. Gen Virol. 72:3057-3075 (1991).
Mcgeoch et al., "Complete DNA Sequence of the Short Repeat Region in the Genome of Herpes Simplex Virus Type 1", Nucleic Acids Res. 14(4):1727-1745 (1986).
Mcgeoch et al., "DNA Sequence of the Region in the Genome of Herpes Simplex Virus Type 1 Containing the Exonuclease Gene and Neighbouring Genes", Nucleic Acids Res. 14(8):3435-3448 (1986).
Grammer et al., "Identification of an HSV-1/HSV-2 Cross-Reactive T Cell Determinant", J. Immunol. 145(7):2249-2253 (1990).

\* cited by examiner

Figs. 23A-23B
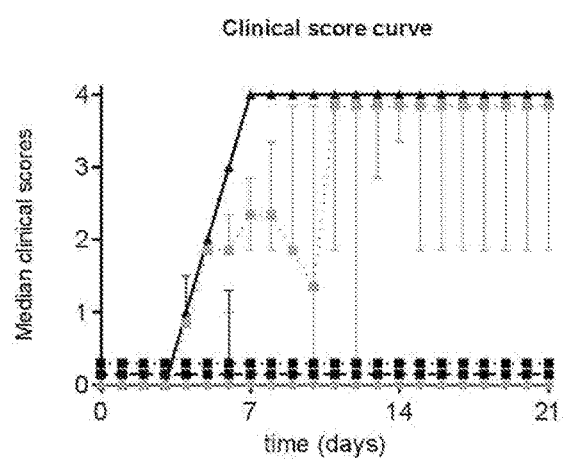
Fig. 23A
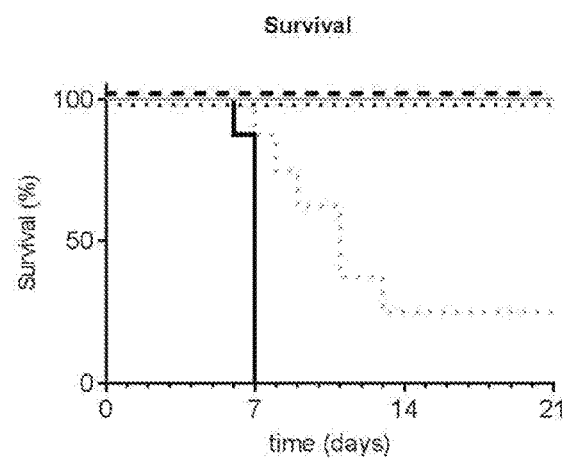
Fig. 23B ically infected neurons (Koelle, et al., *J. Clin. Invest.* 101:1500-8
RECOMBINANT HERPES SIMPLEX VIRUS-2 EXPRESSING GLYCOPROTEIN B AND D ANTIGENS

CROSS-REFERENCE TO RELATED APPLICATIONS

This application is a 35 U.S.C. § 371

Viral Vaccines

It is well documented that live viral vaccines capable of de novo synthesis of immunogens in the host induce a broader and more durable immune response than vaccines consisting of only peptides or proteins. Various forms of replication-defective HSV and neuro-attenuated, replication-competent mutants have been developed and tested as potential vaccines against HSV infection (U.S. Pat. No. 7,223,411; Dudek, et al., *Virology* 344:230-9 (2006)). However, because both replication-defective viruses and neuro-attenuated mutants can co-replicate with wild-type virus or become replication-competent in the context of wild-type virus, their use as a vaccine in humans poses a safety concern, particularly in individuals who harbor latent HSV infection (Koelle, et al., *Curr. Eye Res.* 30:929-42 (2005)). The observation that replication-defective HSV-1 mutants can reactivate the latent HSV-1 immediate-early promoter in the rodent brain has raised additional safety concerns about the possibility of such recombinants triggering outbreaks of productive viral infections in latently infected individuals (Starr, et al., *Gene Ther.* 3:615-23 (1996)).

To minimize the risk of activating latent wild-type infections, an HSV-2 vaccine that expresses a dominant-negative HSV replication initiating polypeptide, UL9 mutant (UL9-C535C), was generated (U.S. Pat. No. 8,809,047; Akhrameyeva et al, *J. Virol.* 85(10): 5036-5047 (2011); Zhang et al, PLoS ONE 9(6): e101373. doi: 10.1371). This replication defective HSV-2 recombinant vaccine, also referred to as CJ2-gD2, encodes 2 copies of the HSV-2 gD2, and is more effective than the gD2 subunit vaccines. Immunization with CJ2-gD2 elicits effective HSV-2 specific neutralizing antibody and T-cell response, as well as inhibits wild-type latent infections.

While significant progress has been made with respect to potential HSV-2 vaccination for clinical use, there continues to be a need in the art for vaccines that can achieve a robust immune response, that minimize the potential of activation of latent wild-type virus, and that are easy to produce.

SUMMARY OF THE INVENTION

In general, the present invention makes use of tetracycline gene-switch technology (T-REx, Invitrogen/ThermoFisher Scientific) (Yao, et al., *Hum. Gene Ther.* 9:1939-50 (1998)) and uses deletion of essential genes or a dominant-negative mutant form of the HSV-1 or HSV-2 UL9 polypeptide, e.g., UL9-C535C to make the virus replication-defective and safe for immunization against HSV-2.

More specifically, one aspect of the present invention described herein provides a replication-defective, Herpes simplex virus-2 (HSV-2) recombinant viruses that lacks the sequences encoding functional ICP0 protein and gG2 protein and which comprise within the HSV-2 genome: (a) a first coding sequence, wherein said first coding sequence encodes HSV-2 glycoprotein B (gB2); wherein said first coding sequence is operably linked to a first immediate-early promoter, (b) a second coding sequence, wherein said second coding sequence encodes HSV-2 glycoprotein D (gD2) and is operably linked to a second immediate-early promoter, and (c) a third coding sequence, wherein said third coding sequence encodes HSV-2 glycoprotein D (gD2) and is operably linked to a third immediate-early promoter.

In some embodiments, said first promoter is an HSV-1 or HSV-2 immediate early promoter that is optionally operably linked to a first tetracycline operator (tet-O) sequence; said second promoter is an HSV-1 or HSV-2 immediate early promoter that is optionally operably linked to a second tetracycline operator (tet-O) sequence; and said third promoter is an HSV-1 or HSV-2 immediate early promoter that is optionally operably linked to a third tetracycline operator (tet-O) sequence. In one embodiment, at least one promoter is operably linked to a tetracycline operator (tet-O) sequence.

In another aspect of the invention described herein is a replication-defective HSV-2 recombinant virus, comprising within its genome (a) a first coding sequence, wherein said first coding sequence encodes HSV-2 glycoprotein B (gB2), wherein said first coding sequence is operably linked to a first promoter, and said first promoter is an HSV-1 or HSV-2 immediate early promoter that is operably linked to a first tetracycline operator (tet-O) sequence; (b) a second coding sequence, wherein said second coding sequence encodes HSV-2 glycoprotein D (gD2) and is operably linked to a second immediate early promoter, wherein said second promoter is operably linked to a second tet-O sequence; and (c) a third coding sequence, wherein said third coding sequence encodes HSV-2 glycoprotein D (gD2) and is operably linked to a third immediate early promoter, wherein said third promoter is operably linked to a third tet-O sequence. In one embodiment, the second promoter and third promoter are a HSV-1 or HSV-2 immediate early promoter.

In one aspect of the invention, the genome of the replication defective recombinant virus does not encode functional ICP0 and functional gG2. In certain embodiments, the genome of the replication defective recombinant virus does not encode functional ICP0 and functional gG2, and further does not encode functional UL19 (VP5 protein).

In still another aspect of the invention described herein is a replication-defective HSV-2 recombinant virus, comprising within its genome: (a) a first coding sequence, wherein said first coding sequence encodes HSV-2 glycoprotein B (gB2), wherein said first coding sequence is operably linked to a first promoter, and said first promoter is an HSV-1 or HSV-2 immediate early promoter that is operably linked to a first tetracycline operator (tet-O) sequence; (b) a second coding sequence, wherein said second coding sequence encodes HSV-2 glycoprotein D (gD2) and is operably linked to a second HSV-1 or HSV-2 immediate early promoter, wherein said second promoter is operably linked to a second tet-O sequence; and (c) a third coding sequence, wherein said third coding sequence encodes HSV-2 glycoprotein D (gD2) and is operably linked to a third HSV-1 or HSV-2 immediate early promoter, wherein said third promoter is operably linked to a third tet-O sequence.

In certain preferred embodiments, a non-essential gene encoding HSV-2 glycoprotein G (gG2), has been disrupted by the insertion of an HSV-2 glycoprotein B (gB2) sequence. In one embodiment, the first coding sequence is located at the gG2 locus of the HSV-2 genome and gG2 is not expressed. This preferred embodiment is counter-intuitive, as insertion at this location removes expression of the gG2 antigen, and thus this antigen can no longer contribute to overall immunogenicity of the vector. However, we have demonstrated that the recombinant viruses of the invention provide surprisingly strong and protective immune responses even in the absence of gG2 antigen. One advantage of this is that, since the loss of gG2 does not prevent HSV-2 viral replication (Liljeqvist, et al., *J. Virol.* 73:9796-802 (1999); Harland, et al., *J. Gen. Virol.* 69(Pt 1):113-24 (1988)), one can produce gG2 deletion mutants in cells that do not need to be engineered to produce compensatory gG2. An additional advantage is that assays, e.g., by PCR or serological tests, can be performed to determine whether gG2 is being expressed in the vaccinated host in order to differentiate between infection with wild type HSV-2 and with the vaccine vector. This ability may be important in serological differentiation for breakthrough HSV-2 infections in clinical settings.

In some embodiments, a dominant-negative mutant form of the HSV-1 or HSV-2 UL9 polypeptide, e.g., UL9-C535C, is used to develop a safe recombinant viral vaccine against HSV-2 infection. A reference providing guidance on how to make and use HSV-2 vaccines based on this technology is provided by U.S. Pat. No. 8,809,047 (incorporated herein by reference in its entirety).

In certain embodiments of various aspects, the recombinant virus is a dominant-negative virus that further comprises a fourth coding sequence, wherein said fourth coding sequence encodes a dominant negative mutant HSV-1 or HSV-2 UL9 protein, and is operably linked to a fourth promoter, wherein said fourth promoter is operably linked to a fourth tet-O sequence.

In certain embodiments of various aspects, the recombinant dominant-negative virus further comprises a fifth coding sequence, wherein said fifth coding sequence encodes a dominant negative mutant HSV-1 or HSV-2 UL9 protein, and is operably linked to a fifth promoter, wherein said fifth promoter is operably linked to a fifth tet-O sequence.

In one aspect of any of the embodiments, described herein is a replication-defective Herpes simplex virus 2 (HSV-2) recombinant virus, comprising within its genome: a) a first coding sequence, wherein said first coding sequence encodes HSV-2 glycoprotein B (gB2), wherein said first coding sequence is operably linked to a first immediate-early promoter; b) a second coding sequence, wherein said second coding sequence encodes HSV-2 glycoprotein D (gD2), and is operably linked to a second immediate-early promoter; c) a third coding sequence, wherein said third coding sequence encodes HSV-2 glycoprotein D (gD2); and is operably linked to a third immediate-early promoter; and wherein said genome does not comprise a sequence encoding a functional ICP0 protein, and does not comprise a sequence encoding functional HSV-2 gG2 protein.

In one aspect of any of the embodiments, described herein is a replication-defective Herpes simplex virus 2 (HSV-2) recombinant virus, comprising within its genome: a) a first coding sequence, wherein said first coding sequence encodes HSV-2 glycoprotein B (gB2), wherein said first coding sequence is operably linked to a first immediate-early promoter, and said first promoter is an HSV-1 or HSV-2 immediate early promoter that is operably linked to a first tetracycline operator (tet-O) sequence; b) a second coding sequence, wherein said second coding sequence encodes HSV-2 glycoprotein D (gD2) and is operably linked to a second immediate-early promoter, wherein said second promoter is operably linked to a second tet-O sequence; c) a third coding sequence, wherein said third coding sequence encodes HSV-2 glycoprotein D (gD2) and is operably linked to a third immediate-early promoter, wherein said third promoter is operably linked to a third tet-O sequence; and wherein said genome does not comprise a sequence encoding a functional ICP0 protein, and does not comprise a sequence encoding functional HSV-2 gG2 protein.

In some embodiments of any of the aspects, said second promoter and third promoter are a HSV-1 or HSV-2 immediate early promoter operably linked to a tetracycline operator (tet-O) sequence.

In some embodiments of any of the aspects, the first coding sequence is located at the gG2 locus of the HSV-2 genome.

In some embodiments of any of the aspects, said genome further does not comprise a sequence encoding a functional UL19 (VP5) protein.

In some embodiments of any of the aspects, the recombinant virus further comprises a fourth coding sequence, wherein said fourth coding sequence encodes a dominant negative mutant HSV-1 or HSV-2 UL9 protein, and is operably linked to a fourth promoter, wherein said fourth promoter is operably linked to a fourth tet-O sequence.

In some embodiments of any of the aspects, the recombinant virus further comprises a fifth coding sequence, wherein said fifth coding sequence encodes a dominant negative mutant HSV-1 or HSV-2 UL9 protein, and is operably linked to a fifth promoter, wherein said fifth promoter is operably linked to a fifth tet-O sequence.

In some embodiments of any of the aspects, said fourth sequence encodes UL9-C535C.

In some embodiments of any of the aspects, the recombinant virus comprises said fifth sequence, wherein said fifth sequence encodes UL9-C535C.

In some embodiments of any of the aspects, each of said first, second and third promoters are HSV-1 or HSV-2 immediate early promoters.

In some embodiments of any of the aspects, each of said first, second and third promoters are selected from the group consisting of an ICP0 promoter, an ICP27 promoter, and an ICP4 promoter.

In some embodiments of any of the aspects, the first promoter is a HSV-1 or HSV-2 ICP0 promoter.

In some embodiments of any of the aspects, the first promoter is a modified HSV-1 or HSV-2 ICP0 promoter comprising a human cytomegalovirus (hCMV) TATA element.

In some embodiments of any of the aspects, the first promoter comprises SEQ ID NO: 08.

In some embodiments of any of the aspects, the fourth and fifth promoters are hCMV immediate-early promoters.

In some embodiments of any of the aspects, said first sequence is a codon optimized sequence.

In one aspect of any of the embodiments, described herein is a replication-defective Herpes simplex virus 2 (HSV-2) recombinant virus, comprising within its genome: a) a first coding sequence, wherein said first coding sequence encodes HSV-2 glycoprotein B (gB2), wherein said first coding sequence is operably linked to a first immediate-early promoter, and said first promoter is an HSV-1 or HSV-2 immediate early promoter that is operably linked to a first tetracycline operator (tet-O) sequence; b) a second coding sequence, wherein said second coding sequence encodes HSV-2 glycoprotein D (gD2) and is operably linked to a second HSV-1 or HSV-2 immediate-early promoter, wherein said second promoter is operably linked to a second tet-O sequence; c) a third coding sequence, wherein said third coding sequence encodes HSV-2 glycoprotein D (gD2) and is operably linked to a third HSV-1 or HSV-2 immediate-early promoter, wherein said third promoter is operably linked to a third tet-O sequence; and wherein said genome does not comprise a sequence encoding a functional ICP0 protein, and does not comprise a sequence encoding functional HSV-2 gG2 protein.

In one aspect of any of the embodiments, described herein is a replication-defective HSV-2 recombinant virus, comprising within its genome: a) a first coding sequence, comprising a codon optimized HSV-2 gB2 sequence operably linked to a first promoter, wherein said first promoter is an HSV-1 or HSV-2 ICP0 or ICP4 promoter that is operably linked to a first tet-O sequence; b) a second coding sequence, comprising a codon-optimized HSV gD2 sequence operably linked to a second promoter, wherein said second promoter is an HSV-1 ICP4 promoter that is operably linked to a second tet-O sequence and wherein the second coding sequence operably linked to the second promoter is located at the UL26/UL27 intergenic region; c) a third coding sequence, comprising a codon optimized HSV gD2 sequence operably linked to a third promoter, wherein said third promoter is an HSV-1 ICP27 promoter that is operably linked to a third tet-O sequence, wherein the third coding sequence operably linked to the third promoter displaces the UL19 gene; and wherein said genome does not comprise a sequence encoding a functional ICP0 protein, and does not comprise a sequence encoding functional HSV-2 gG2 protein.

In one aspect of any of the embodiments, described herein is a replication-defective HSV-2 recombinant virus, comprising within its genome: a) a first coding sequence, comprising a codon optimized HSV-2 gB2 sequence operably linked to a first promoter, wherein said first promoter is an HSV-1 or HSV-2 ICP0 or ICP4 promoter that is operably linked to a first tet-O sequence; b) a second coding sequence, comprising an HSV-2 gD2 sequence operably linked to a second promoter, wherein said second promoter is an HSV-1 or HSV-2 ICP0, ICP4, or ICP27 promoter that is operably linked to a second tet-O sequence; c) a third coding sequence, comprising an HSV-2 gD2 sequence operably linked to a third promoter, wherein said third promoter is an HSV-1 or HSV-2 ICP0, ICP4, or ICP27 promoter that is operably linked to a third tet-O sequence; and wherein said genome does not comprise a sequence encoding a functional ICP0 protein, and does not comprise a sequence encoding HSV-2 gG2 protein.

In some embodiments of any of the aspects, the first coding sequence is located at the gG2 locus of the HSV-2 genome.

In some embodiments of any of the aspects, said genome does not comprise a sequence encoding a functional UL19 (VP5) protein.

In some embodiments of any of the aspects, the replication-defective HSV-2 recombinant virus further comprises i) a fourth coding sequence, encoding a dominant negative UL9-C535C protein, and operably linked to a third promoter, wherein said third promoter is an hCMV immediate early promoter that is operably linked to a third tet-O sequence; and ii) a fifth sequence, encoding a dominant negative UL9-C535C protein, operably linked to a fifth promoter, wherein said fifth promoter is an hCMV immediate early promoter that is operably linked to a fifth tet-O sequence.

In some embodiments of any of the aspects, the first promoter is an HSV-1 or HSV-2 ICP0 promoter.

In some embodiments of any of the aspects, the first promoter is a modified HSV-1 or HSV-2 ICP0 promoter comprising a human cytomegalovirus (hCMV) TATA element.

In some embodiments of any of the aspects, the first promoter comprises SEQ ID NO: 08.

In some embodiments of any of the aspects, at least one of the second and third promoters is a HSV-1 or HSV-2 ICP27 promoter operably linked to a tet-O sequence.

In some embodiments of any of the aspects, at least one of the second and third promoters is a HSV-1 or HSV-2 ICP4 promoter operably linked to a tet-O sequence.

In some embodiments of any of the aspects, each of the second and third promoters are the same, and wherein the same promoter is an HSV-1 or HSV-2 promoter selected from the group consisting of: an ICP4 promoter, an ICP27 promoter.

In some embodiments of any of the aspects, each of the second and third promoters are different, and wherein one of these promoters is an HSV-1 or HSV-2 ICP4 promoter, and wherein the other of these promoters is an HSV-1 or HSV-2 ICP27 promoter.

In one aspect of any of the embodiments, described herein is a replication defective HSV recombinant virus, comprising a modified HSV-1 or HSV-2 ICP0 promoter comprising a human cytomegalovirus (hCMV) TATA element, wherein said modified promoter is operably linked to a transgene.

In some embodiments of any of the aspects, the transgene encodes HSV-2 glycoprotein B (gB).

In some embodiments of any of the aspects, said modified promoter comprises SEQ ID NO: 08.

In one aspect of any of the embodiments, described herein is a vaccine comprising a recombinant virus described herein in unit dose form.

In one aspect of any of the embodiments, described herein is a method of immunizing a subject against HSV-1 or HSV-2 infection, comprising administering to said subject a vaccine described herein.

In some embodiments of any of the aspects, said subject is seropositive for HSV-1.

In some embodiments of any of the aspects, said subject is seropositive for HSV-2.

In some embodiments of any of the aspects, said subject is seronegative for HSV-1 and HSV-2.

In one aspect of any of the embodiments, described herein is a method for producing a virus described herein, the method comprising; a) infecting complementing cells with the virus, wherein the complementing cells express a functional gene product or products that are needed for replication of the virus and for which sequences encoding such are lacking from the virus genome; b) culturing the complementing cells such that the virus replicates; and c) harvesting said replicated virus from the complementing cells.

In some embodiments of any of the aspects, the complementary cells further express TetR.

In some embodiments of any of the aspects, the complementary cells express ICP0 functional gene product.

In some embodiments of any of the aspects, the complementary cells express UL19 (VP5) functional gene product.

In one aspect of any of the embodiments, described herein is a composition comprising a vaccine comprising a recombinant virus described herein for use in unit dose form in the treatment of an infection with HSV-1 or HSV-2.

In one aspect of any of the embodiments, described herein is a composition comprising a virus for use in the treatment of an infection with HSV-1 or HSV-2, the composition comprising; a) infecting complementing cells with the virus, wherein the complementing cells express a functional gene product or products that are needed for replication of the virus and for which sequences encoding such are lacking from the virus genome; b) culturing the complementing cells such that the virus replicates; and c) harvesting said replicated virus from the complementing cells.

Definitions

As described above, the genome of the HSV-2 virus according to the invention has a first coding sequence which codes for gB2 and which is operably linked to a first promoter (e.g. an HSV-1 or HSV-2 immediate early promoter) that is under the control of (operably linked to) a first tetracycline operator (tet-O) nucleotide segment. The genome also includes two sequences encoding HSV-2 gD (gD2), a "second coding sequence" and a "third coding sequence". In one embodiment, at least one sequence encoding HSV-2 gD2 is operably linked to a promoter under control of a tet-O nucleotide segment. In one embodiment, the second coding sequence is operably linked to a second promoter under the control of a second tet-O nucleotide segment and the third coding sequence is operably linked to a third promoter under the control of a third tet-O nucleotide segment.

In one embodiment of various aspects, in order to control viral replication, the genome comprises a fourth coding sequence and that codes for a dominant negative mutant HSV-1 or HSV-2 UL9 protein. In some embodiment, there is also a fifth coding sequence that codes for a dominant negative mutant HSV-1 or HSV-2 UL9 protein. In some embodiments, the dominant negative mutant of the fourth and/or fifth sequence is UL9-C535C. When this sequence is expressed, the mutant protein produced acts in trans to inhibit the replication of HSV-2. The fourth coding sequence is operably linked to a fourth promoter, and this is operably linked to a fourth tet-O sequence. A second copy of a dominant negative mutant HSV-1 or HSV-2 UL9 protein (a "fifth coding sequence," e.g., UL9-C535C) may also be present and is operably linked to a fifth promoter under the control of a fifth tet-O nucleotide segment.

In certain embodiments of various aspects, in order to control viral replication, the genome of the HSV-2 recombinant virus lacks the sequence encoding the essential UL19 (VP5) protein. In such embodiments, it is not necessary to have a dominant negative UL9 protein for replication incompetency.

Each of the tet operators allows transcription to proceed from its associated promoter when free of tet repressor (tetR) but represses transcription when bound by repressor.

In addition, the genome of the virus is characterized by the absence of a sequence encoding a functional ICP0 protein.

In order to enhance its antigenicity, the genome may in certain embodiments also express recombinant immunomodulating genes, such as IL-12, IL-15 or may express other HSV-1 or HSV-2 major antigens in levels comparable to, or higher than, the levels expressed by wild type HSV-1 or HSV-2 viruses.

The genome of the HSV-2 virus according to the invention lacks a sequence encoding a functional ICP0 protein. In certain embodiments, the second and third coding sequences (encoding HSV-2 gD, also referred to as gD2 herein) are inserted into the position where ICP0 genes are present in wild-type HSV-2, therewith disrupting the ICP0 genes (e.g. as in FIGS. 2 and 3 herein, see also e.g. U.S. Pat. No. 8,809,047 for a description of such embodiments, incorporated by reference herein).

In some embodiments of various aspects, the genome of the HSV-2 virus according to the invention also lacks a sequence encoding a functional UL19 protein. In certain embodiments, the second and/or third coding sequences are inserted at the UL19 locus. In certain embodiments, the second and/or third coding sequences are inserted at the UL26/UL27 intergenic region. Insertion of a coding sequence into an intergenic region of the HSV genome, e.g., UL26 and UL27 intergenic region, does not disrupt or delete other HSV genes; this is an advantageous strategy.

In certain embodiments of various aspects, gD2 is in a bidirectional expression cassette, e.g. with UL9-C535C (e.g. as in FIG. 2 herein), as for instance described in more detail in U.S. Pat. No. 8,809,047, incorporated by reference herein.

In certain embodiments of various aspects, gD2 is in a one-directional expression cassette, e.g. positioned at the UL19 locus, or at the UL26/UL27 intergenic region. In certain embodiments, one gD2 expression cassette is positioned at the UL19 locus and another gD2 expression cassette is positioned at the UL26/UL27 intergenic region, and preferably the nucleotide sequences of these two gD2 expression cassettes are different, while the gD2 protein sequences encoded by these two expression cassettes may be different but preferably are the same.

As used herein, the term "operably linked" refers to genetic elements that are joined together in a manner that enables them to carry out their normal functions. For example, a gene is operably linked to a promoter when its transcription is under the control of the promoter and this transcription results in the production of the product normally encoded by the gene. A tet operator sequence is operably linked to a promoter when the operator blocks transcription from the promoter in the presence of bound tet repressor but allows transcription in the absence of the repressor. The term "recombinant" refers to a virus that has nucleic acid sequences that are the result of recombining nucleic acid sequences and sequence elements and introducing these recombined sequences into the wildtype virus or into a recombinant ancestor virus.

In certain embodiments of various aspects, the first coding sequence of HSV-2 gB (also referred to as gB2 herein) is a codon optimized sequence. For the purposes of the present invention, a "codon optimized", or "codon diversified" sequence is one in which one or more codons in the wild type sequence are replaced with an alternative codon that codes for the same amino acid and that results in increased protein production. In a preferred embodiment, the nucleic acid encoding HSV-2 gB2 is codon optimized for expression in mammalian cells, preferably human cells. Methods of codon-optimization are known and have been described previously (e.g. WO 96/09378). A sequence is considered codon optimized if at least one non-preferred codon as compared to a wild type sequence is replaced by a codon that is more preferred. Herein, a non-preferred codon is a codon that is used less frequently in an organism than another codon coding for the same amino acid, and a codon that is more preferred is a codon that is used more frequently in an organism than a non-preferred codon. The frequency of codon usage for a specific organism can be found in codon frequency tables, such as in http://www.kazusa.or.jp/codon. Preferably more than one non-preferred codon, e.g. more than 10%, 40%, 60%, 80% of non-preferred codons, preferably most (e.g. at least 90%) or all non-preferred codons, are replaced by codons that are more preferred. Preferably the most frequently used codons in an organism are used in a codon-optimized sequence. Replacement by preferred codons generally leads to higher expression. A non-limiting example of a codon-optimized sequence for HSV2 gB2 is provided herein in SEQ ID NO: 07. Optionally other coding sequences, e.g. one or more of the gD2 coding sequences, may also be codon-optimized.

In one embodiment of various aspects, at least one of the first, second and third promoters are HSV-1 or HSV-2 immediate early promoters. ICP0 and ICP4 promoters are particularly preferred. In one embodiment, each of the first, second and third promoters are HSV-1 or HSV-2 immediate early promoters, e.g. ICP0 and ICP4. In certain embodiments, the second and third promoters operably linked to HSV-2 gD are tetO-containing ICP4 promoters. In certain embodiments of various aspects, at least one of the second and third promoters operably linked to HSV-2 gD2 is a tetO-containing HSV ICP27 promoter.

In one embodiment of various aspects, the first promoter, second promotor, or third promoter are a human cytomegalovirus (hCMV) immediate early promoter.

In embodiments of various aspects where the fourth coding sequence is present, this fourth coding sequence preferably encodes UL9-C535C. In a further embodiment, the fifth coding sequence is present and encodes UL9-C535C. As with the other coding sequences, the fourth and fifth coding sequences may be operably linked to an HSV-1 or HSV-2 immediate early promoter, but in these cases, hCMV immediate early promoters are most preferred.

In one aspect, the replication defective HSV-2 of the invention does not comprise a dominant negative UL9 mutant and is rendered replication incompetent by deletion of the essential expression of UL19, i.e. the replication defective HSV-2 does not express functional UL19 (VP5), does not express functional ICP0, and does not express functional gG2. In one embodiment of this aspect, recombinant gD2 is located in a one directional expression cassette and positioned at the UL19 locus and/or positioned in the UL26/27 intergenic region. In another embodiment, recombinant gD2 is located in a first one directional expression cassette positioned at the UL19 locus and in a second one directional expression cassette positioned in the UL26/27 intergenic region. In yet another embodiment, recombinant gD2 is located in a first one directional expression cassette positioned at the UL19 locus and is operably linked to a first promoter, wherein said first promoter is an HSV-1 or HSV-2 ICP0 or ICP4 promoter that is operably linked to a first tet-O sequence, and recombinant gD2 is located in a second one directional expression cassette positioned in the UL26/27 intergenic region and is operably linked to a second promoter, wherein said second promoter is an HSV-1 or HSV-2 ICP0 or ICP4 promoter that is operably linked to a second tet-O sequence.

In another embodiment of this aspect, at least one of the second and third promoters that are operably linked to gD2 in a tetO-containing HSV-1 or HSV-2 ICP27 promoter. In one embodiment both the second and the third promoter are a tetO-containing HSV-1 or HSV-2 ICP27 promoter.

In one embodiment of various aspects, the first coding sequence is operably linked to an ICP0 promoter which may optionally be modified so that the TATA element normally present (TATAAGTT (SEQ ID NO: 12)) corresponds to the hCMV TATA element (TATATAAG (SEQ ID NO: 13)), the second and third coding sequences are operably linked to ICP4 promoters, and the fourth and fifth (if present) coding sequences are operably linked to hCMV immediate early promoters, and each promoter is operably linked to a tetO sequence.

In order to obtain optimal results, the promoters used should have a TATA element and the tet operator sequences linked to the promoters should preferably have two op2 repressor binding sequences. The positioning of the operator sequence is important in achieving effective control over the promoter. Specifically, the first nucleotide in the operator sequence is located between six and twenty-four nucleotides 3' to the last nucleotide in the TATA element (see e.g., U.S. Pat. No. 6,444,871 or 5,972,650). Structural sequences encoding, for example gB2, gD2 or UL9-C535C, are positioned 3' to the operator.

Accordingly, in certain embodiments of various aspects, a) the first, second, third, and optionally the fourth and fifth promoters of the replication-defective dominant negative HSV-2 virus each have a TATA element; b) each of the first, second, third, and optional fourth and fifth tet-O sequences comprise two op2 repressor binding sites, wherein the first nucleotide in said tet operator is between 6 and 24 nucleotides 3' to the last nucleotide in said TATA element; c) the first sequence, encoding HSV-2 gB, lies 3' to said first tet-O sequence, and said first tet-O sequence is operably linked to said first promoter; d) the second sequence, encoding HSV-2 gD, lies 3' to the second tet-O sequence and said second tet-O sequence is operably linked to the second promoter; e) the third sequence, encoding HSV-2 gD, lies 3' to said third tet-O sequence and said third tet-O sequence is operably linked to the third promoter; and in some embodiments, f) a fourth sequence, encoding a dominant negative mutant HSV-1 or HSV-2 UL9 protein, lies 3' to said fourth tet-O sequence and the fourth tet-O sequence is operably linked to said fourth promoter; and, in some embodiments, a fifth sequence, encoding a dominant negative mutant HSV-1 or HSV-2 UL9 protein, lies 3' to said fifth tet-O sequence, and said fifth tet-O sequence is operably linked to said fifth promoter.

In one specific aspect of the invention, a replication-defective HSV-2 recombinant virus, is provided that comprises within its genome: (a) a first coding sequence, comprising a codon optimized HSV-2 gB2 sequence operably linked to a first promoter, wherein said first promoter is an HSV-1 or HSV-2 ICP0 or ICP4 promoter that is operably linked to a first tet-O sequence and wherein said first coding sequence is preferably displaces the gG2 gene; (b) a second coding sequence, comprising a codon-optimized HSV gD2 sequence operably linked to a second promoter, wherein said second promoter is an HSV-1 ICP4 promoter that is operably linked to a second tet-O sequence and wherein said second coding sequence is located at the UL26/UL27 intergenic region; (c) a third coding sequence, comprising a codon-diversified HSV gD2 sequence operably linked to a third promoter, wherein said third promoter is an HSV-1 ICP27 promoter or an HSV-1 ICP4 promoter that is operably linked to a third tet-O sequence, wherein the third coding sequence displaces the UL19 gene; and wherein said genome does not comprise a sequence encoding a functional ICP0 protein, and does not comprise a sequence encoding HSV-2 gG2 protein.

In one specific aspect, a replication-defective, dominant-negative HSV-2 recombinant virus, is provided that comprises within its genome: (a) a first coding sequence, comprising a codon optimized HSV-2 gB2 sequence operably linked to a first promoter, wherein said first promoter is an HSV-1 or HSV-2 ICP0 or ICP4 promoter that is operably linked to a first tet-O sequence; (b) a second coding sequence, comprising an HSV-2 gD2 sequence operably linked to a second promoter, wherein said second promoter is an HSV-1 or HSV-2 ICP0 or ICP4 promoter that is operably linked to a second tet-O sequence; (c) a third coding sequence, comprising an HSV-2 gD2 sequence operably linked to a third promoter, wherein said third promoter is an HSV-1 or HSV-2 ICP0 or ICP4 promoter that is operably linked to a third tet-O sequence; (d) a fourth coding sequence, encoding a UL9-C535C protein, and operably linked to a fourth promoter, wherein said fourth promoter is an hCMV immediate early promoter that is operably linked to a fourth tet-O sequence; (d) a fifth sequence, encoding a UL9-C535C protein, and operably linked to a fifth promoter, wherein said fifth promoter is an hCMV immediate early promoter that is operably linked to a fifth tet-O sequence; and wherein said genome does not comprise a sequence encoding a functional ICP0 protein. In certain embodiments, i) said first, second, third, fourth and fifth promoters each have a TATA element; ii) each of said first, second, third, fourth and fifth tet-O sequences comprise two op2 repressor binding sites, wherein the first nucleotide in said tet operator is between 6 and 24 nucleotides 3' to the last nucleotide in said TATA element; and iii) said first, second, third, fourth and fifth coding sequences each lie 3' to their respective tet-O sequences, and said tet-O sequences are operably linked to their respective promoters.

In another aspect of the invention, a replication defective HSV recombinant virus (e.g. HSV-1 or HSV-2) is provided that comprises a modified HSV-1 or HSV-2 ICP0 promoter comprising a hCMV TATA element, wherein said modified promoter is operably linked to a transgene. In one embodiment, the modified promoter comprises SEQ ID NO: 08. In one embodiment, the transgene encodes HSV-2 glycoprotein B (gB2). Replication-defective genomic HSV vectors are known in the art and are described in, e.g., Burton et al, *Current Opinion in Molecular Therapeutics* 7(4):326-336 (2005); Mundle et al. *PLoS ONE* 8(2): e57224, (2013); Akhrameyeva et al. *J. Virol.* 85(10): 5036-5047 (2011); and Johnston et al., *Vaccine* 32 (14):1553-1560 (2014). Such recombinant viruses may be used in both vaccine applications and in gene therapy applications to express a transgene of interest.

In still another aspect, the invention is directed to a vaccine that can be used prophylactically or therapeutically against HSV-2 infection and which comprises one or more of the recombinant viruses described above in unit dose form. The term "unit dose form" refers to a single drug administration entity, e.g., as a syringe, tablet, or capsule. Preferably the "unit dose form" will be a solution in which the drug (e.g., a vaccine virus described herein) is suspended at a concentration that provides a therapeutic or prophylactic effect when a selected volume (unit dose) is administered to a patient by injection and will be found within an injection vial. It is believed that the minimum effective dose in a human should be between about $1 \times 10^6$ and $1 \times 10^8$ plaque-forming units (PFU). Thus, a unit dose should have at least this amount of virus, with $1 \times 10^6$-$1 \times 10^9$ PFU or $1 \times 10^7$-$1 \times 10^9$ PFU being typical. Vaccines may be stored in a lyophilized form and reconstituted in a pharmaceutically acceptable carrier prior to administration. Alternatively, preparations may be stored in the vehicle itself. The volume of a single dose of the vaccine will vary but, in general, should be between about 0.1 mL and 10 mL and, more typically, between about 0.2 mL and 5 mL, e.g., about 0.5 mL, 1 mL or 2 mL.

The invention also includes methods of immunizing subjects against HSV-1 or HSV-2 infection and the conditions resulting from such infection (e.g., genital herpes ulcers) by administering to the subjects the vaccines described above. The vaccines may also be given to patients that have been infected to prevent or reduce outbreaks of the virus. Any method for administering a vaccine to a patient which does not result in the destruction of vaccine virus is compatible with the present invention. Generally, administration will be by parenteral means such as by intramuscular or intradermal injection. The dosage and scheduling of administration of vaccines can be determined using methods that are routine in the art. The preparations may be administered in either single or multiple injections.

In another aspect, the invention relates to a method for producing any of the viruses described herein comprising: (a) infecting complementing cells with the virus, wherein the complementing cells express a functional gene product or products that are needed for replication of the virus and for which sequences encoding such are lacking from the virus genome; (b) culturing the complementing cells such that the virus replicates; and (c) harvesting said replicated virus from the complementing cells.

In one embodiment, the complementing cells further express a tetR to repress expression from the tetO-regulated promoters. In certain embodiments, the complementing cells express at least one functional gene product selected from ICP0, UL9, or UL19 (VP5). In certain embodiments, the complementing cells express tetR and ICP0. In certain embodiments, the complementing cells express tetR, ICP0 and UL19 (VP5).

As used herein, a "functional gene product or products that are needed for replication of the virus" refers to any gene product or products required for, e.g., the genetic replication of the virus in a host cell. These gene product(s) include, but are not limited to, gene products required for transcription of immediate-early, early, or late gene products (e.g., α-TIF); immediate-early, early, or late gene products; gene products required for virion host shutoff (e.g., VHS, and UL41); and gene products required for production of, e.g., the capsid, viral envelope, or viral surface receptors. One skilled in the art will be able to determine those gene product(s) required for replication of the viruses described herein.

As used herein, a "subject" means a human or animal. In one embodiment, the animal is a vertebrate such as a primate, rodent, domestic animal, or game animal. In one embodiment, the subject is human. The terms, "patient", "individual" and "subject" are used interchangeably herein.

BRIEF DESCRIPTION OF THE DRAWINGS

FIGS. 23A and 23B present results indicating that purified CJ2-gD2/gB2 is as effective as crude CJ2-gD2/gB2 in protecting against HSV-2 genital disease. Female Balb/cAnNCrl mice were intra-muscularly either sham-immunized with formulation buffer (black solid line, in clinical score [CS] graph with additional triangular point markers) or immunized with purified CJ2-gD2/gB2 at a dose of $1.8 \times 10^5$ (grey dotted line, with squares for CS), $1.8 \times 10^6$ (black dotted line, with squares for CS) or $1.8 \times 10^7$ PFU (black dashed line, with squares for CS) or crude CJ2-gD2/gB2 at $1.43 \times 10^6$ PFU/mouse (grey solid line, with circles for CS). Individual groups of mice were boosted with the same vaccine virus and at the same dose 2 weeks later. Mice were pre-treated with medroxyprogesterone at 2 weeks post boost immunization followed by intravaginal challenge with $5 \times 10^5$ PFU of HSV-2 strain G 5 days later. After challenge with wild-type HSV-2, individual mice were observed during a 21-day follow-up period (A) for the incidence of genital and disseminated HSV-2 disease using the following clinical score scale: 0=no sign, 1=slight genital erythema and edema, 2=moderate genital inflammation, 3=purulent genital lesions and/or systemic illness, and 4=hind-limb paralysis, and (B) for percent survival.

DETAILED DESCRIPTION OF THE INVENTION

Figure 1:
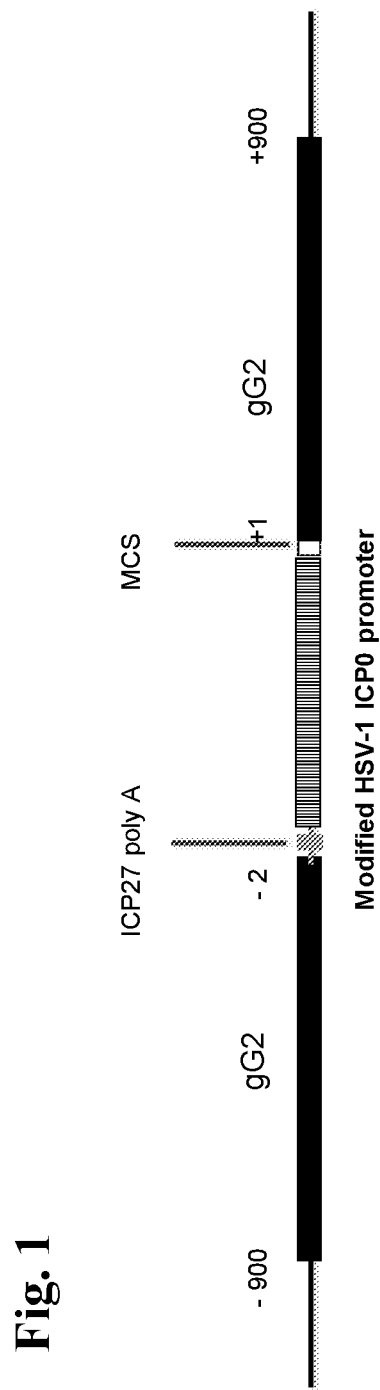
FIG. 1 shows a schematic of an HSV-2 gG2 locus-specific vector sequences plus a tetO-bearing HSV-1 ICP0 promoter sequence modified to replace the ICP0 TATA element with the hCMV TATA element. The elements are presented as follows along the sequence: the sequence from −900 to −2 bp upstream of the gG2 open reading frame (black box); the poly A signal sequence of HSV-1 ICP27 (gray box); the tetO-bearing modified HSV-1 ICP0 promoter plus part of 5' untranslated region of ICP0 gene (striped box), a sequence containing multiple cloning sites (open box), and the sequence from +1 to +900 bp downstream of the gG2 ORF stop codon (black box).

The present invention makes use of the concept of using tetracycline gene-switch technology together with essential gene deletions and/or a dominant-negative mutant polypeptide of HSV-1 UL9 to develop an HSV recombinant virus which is replication-incompetent and capable of inhibiting wild-type HSV infections. The methods described herein may be used to make vectors that recombinantly express two sequences encoding HSV-2 gD2 and, at least one sequence encoding gB2.

The Tet Operator/Repressor Switch and Recombinant DNA

Methods for making recombinant DNA molecules with genes whose expression is regulated by the tetracycline operator and repressor protein have been previously described (see U.S. Pat. Nos. 6,444,871; 6,251,640; and 5,972,650) and plasmids which contain the tetracycline-inducible transcription switch are commercially available (T-REx™, Invitrogen, CA).

An essential feature of the DNA of the present invention is the presence of genes that are operably linked to a promoter, preferably having a TATA element. A tet operator sequence is located between 6 and 24 nucleotides 3' to the last nucleotide in the TATA element of the promoter and 5' to the gene. Virus may be grown in cells that express the tet repressor to block gene transcription and allow viral replication. The effectiveness of the tet repressor in blocking gene expression from the tetO sequence-containing promoter is enhanced by using a form of operator which contains two op2 elements each having the nucleotide sequence: TCCCTATCAGTGATAGAGA (SEQ ID NO: 11) linked by a sequence of, preferably, 1-3 nucleotides. When repressor is bound to this operator, very little or no transcription of the associated gene will occur. If DNA with these characteristics is present in a cell that also expresses the tetracycline repressor, transcription of the gene that can prevent viral infection and that is operably linked to the tet operator sequence (e.g., a dominant negative mutant such as UL9-C535C) will be blocked by the repressor binding to the operator and e.g. replication of the virus will occur.

Selection of Promoters and Genes

During productive infection, HSV gene expression falls into three major classes based on the temporal order of expression: immediate-early (α), early (β), and late (γ), with late genes being further divided into two groups, γ1 and γ2. The expression of immediate-early genes does not require de novo viral protein synthesis and is activated by the virion-associated protein VP16 together with cellular transcription factors when the viral DNA enters the nucleus. The protein products of the immediate-early genes are designated infected cell polypeptides ICP0, ICP4, ICP22, ICP27, and ICP47 and it is the promoters of these genes that are preferably used in directing the expression of the recombinant genes discussed herein.

ICP0 plays a major role in enhancing the reactivation of HSV from latency and confers a significant growth advantage on the virus at low multiplicities of infection. ICP4 is the major transcriptional regulatory protein of HSV, which activates the expression of viral early and late genes. ICP27 is essential for productive viral infection and is required for efficient viral DNA replication and the optimal expression of viral γ genes and a subset of viral P genes. The function of ICP47 during HSV infection appears to be to down-regulate the expression of the major histocompatibility complex (MHC) class I on the surface of infected cells.

The HSV-1 UL9-C535C sequence consists of UL9 amino acids 1-10, a Thr-Met-Gly tripeptide, and amino acids 535 to 851 of UL9 (Yao, et al., *Hum. Gene Ther.* 10:419-27 (1999)). An example of a sequence coding for UL9-C535C is provided in SEQ ID NO: 14. The other sequences described for use in recombinant viruses are all well known in the art. For example, the full length genomic sequence for HSV-1 may be found as GenBank sequence X14112. The HSV-1 ICP4 sequence may be found as GenBank number X06461; HSV-1 glycoprotein D may be found as GenBank sequence J02217; HSV-2 glycoprotein D may be found as GenBank number K01408; the HSV-1 UL 9 gene as GenBank sequence M19120; and gB2 as GenBank sequence M15118.1. All of these references are incorporated by reference herein in their entirety. Examples of gD2 and gB2 amino acid sequences are provided as SEQ ID NOs: 23 and 24 respectively.

Inclusion of Tet Repressor and Making of Virus Sequences for the HSV ICP0 and ICP4 promoters and for the genes whose regulation they endogenously control are well known in the art (McGeoch et al., *J. Gen. Virol.* 72:3057-3075 (1991); McGeoch et al., *Nucl. Acid Res.* 14:1727-1745 (1986); Perry, et al., *J. Gen. Virol.* 67:2365-2380 (1986)) and procedures for making viral vectors containing these elements have been previously described (see US 2005/0266564). These promoters are not only very active in promoting gene expression, they are also specifically induced by VP16, a virus-associated transactivator released when HSV-1 or HSV-2 infects a cell.

Once appropriate DNA constructs have been produced, they may be incorporated into HSV-2 virus using methods that are well known in the art (Akhrameyeva, *J. Virol.* 85:5036-47 (2011); Lu, et al., *J. Invest. Dermatol.* 129:1174-84 (2009); Yao, et al., *Hum. Gene Ther.* 10:1811-8 (1999)).

In one embodiment, viruses described herein are replicated using complementing cells. A complementing cell expresses the gene or genes missing in the genome of a replication-defective virus (e.g., ICP0 and VP5), and are commonly used to propagate replication-defective viruses. Complementary cells are further reviewed in Dudek and Knipe. *Virology* 2006 January; 344(1): 230-239. One skilled in the art will be capable of determining the appropriate complementary cell for use in replicating a given virus described herein. Preferably, the complementary cell further expresses TetR in order to repress expression from the TetO-regulated promoters. In one embodiment, the complementing cells express UL9. In another embodiment, the complementing cells express ICP0 and UL9.

Immunization Methods

The viruses described herein will be used to immunize individuals and/or patients, typically by injection as a vaccine. Other routes of administration, e.g. oral administration, could also be used. The vaccine may be used either prophylactically to prevent HSV-1 or HSV-2 infection or therapeutically to reduce the severity of symptoms if an HSV-1 or HSV-2 infection has already occurred. In order to make a vaccine, the viruses are suspended in a pharmaceutically acceptable solution such as sterile isotonic saline, water, phosphate buffered saline, 1,2-propylene glycol, polyglycols mixed with water, Ringer's solution, etc. The exact number of viruses to be administered is not crucial to the invention but should be an "effective amount," i.e., an amount sufficient to elicit an immunological response strong enough to inhibit HSV infection. In general, it is expected that the number of viruses (PFU) initially administered will be between $1 \times 10^7$ and $1 \times 10^9$.

The effectiveness of a dosage, as well as the effectiveness of the overall treatment can be assessed using standard immunological methods to test for the presence of antibodies effective at attacking HSV. Immunizing injections or administrations can be repeated as many times as desired. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The practice of embodiments of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, *Current Protocols in Immunology* (J. E. Coligan et al., eds., 1999, including supplements through 2016); *Current Protocols in Molecular Biology* (F. M. Ausubel et al., eds., 1987, including supplements through 2016); Short Protocols in Molecular Biology, F. M. Ausubel et al., eds., fifth edition 2002, including supplements through 2016; *Molecular Cloning: A Laboratory Manual*, third edition (Sambrook and Russel, 2001); *PCR: The Polymerase Chain Reaction*, (Mullis et al., eds., 1994); *The Immunoassay Handbook* (D. Wild, ed., Stockton Press NY, 1994); Bioconjugate Techniques (Greg T. Hermanson, ed., Academic Press, 1996); *Methods of Immunological Analysis* (R. Masseyeff, W. H. Albert, and N. A. Staines, eds., Weinheim: VCH Verlags gesellschaft mbH, 1993), Harlow and Lane *Using Antibodies: A Laboratory Manual* (Cold Spring Harbor Laboratory Press, Cold Spring Harbor, N.Y., 1999; and Beaucage et al. eds., Current Protocols in Nucleic Acid Chemistry John Wiley & Sons, Inc., New York, 2000, including supplements through 2016).

As used herein the term "herpes simplex virus" (HSV) refers to both HSV type 1 and HSV type 2 (See e.g. Fatahzadeh ZM1, Schwartz R A. Human herpes simplex virus infections: epidemiology, pathogenesis, symptomatology, diagnosis, and management, *J Am Acad Dermatol.* 2007 November; 57(5):737-63, ATCC holdings (Manassas, Va. 20110 USA) include a number of HSV-1 and HSV-2 strains, including for example: HSV-1 HF; HSV-1 MacIntyre; HSV-1 KOS; HSV-1 GHSV-UL46; HSV-1 ATCC-2011-9; HSV-2 MS; HSV-2 G; HSV-2 ATCC-2011-2). As used herein, the term "ICP0 protein" refers to the HSV protein that is an immediate-early protein which possesses E3 ubiquitin ligase activity. ICP0 activates HSV-1 gene expression, disrupts nuclear domain (ND) 10 structures, mediates the degradation of cellular proteins, and enables evasion of the host's antiviral defenses. As used herein the term "ICP0 deficient HSV" refers to a recombinant HSV vector whose genome does not encode active ICP0 or fully functional ICP0, i.e. ICP0 with normal wild type function. Activity of ICP0 can be monitored using any of the means known to those in the art (See e.g. Miles C Smith et al, HSV-1 ICP0: paving the way for viral replication *Future Virol.* 2011 April; 6(4): 421-429; Mirna P Lanfranca et al., HSV-1 ICP0: An E3 Ubiquitin Ligase that counteracts host intrinsic and immunity, *Cells* 2014 3:438-454).

There are many variants of HSV ICP0 protein, e.g. some of HSV-1 ICP0, strain KOS variants are: Genebank Accession: P08393.1 GI: 124134; Accession: AFI23590.1 GI: 384597746; Accession: AFI23649.1 GI: 384597805; Accession: AFE62827.1 GI: 380776964; Accession: AFE62886.1 GI: 380777023; Accession: ADM22381.1 GI: 304318198; Accession: ALO18731.1 GI: 952947655; Accession: ALO18672.1 GI: 952947596; Accession: ALO18655.1 GI: 952947578; Accession: ALO18596.1 GI: 952947519; Accession: AKH80472.1 GI: 822581062; Accession: AKH80399.1 GI: 822580988; Accession: AKG61929.1 GI: 820021112; Accession: AKG61857.1 GI: 820021035; etc. and the like. Each strain of HSV1 or of HSV2 have multiple variants, all with functional ICP0. These variants are well known in the art and can be found in protein databases. Such variants may be used in methods of the invention. Examples of HSV-2 ICP0 variants, include but are not limited to: Accession: YP_009137210; YP_009137210.1 GI: 820945210; Accession: YP_009137151.1 GI: 820945151; Accession: AEV91397.2 GI: 556197555; Accession: AEV91338.2 GI: 556197550; Accession: ADG01890.1 GI:

295322885; Accession: ADG01889.1 GI: 295322883; Accession: ADG01888.1 GI: 295322881; Accession: ADG01887.1 GI: 295322879; Accession: ADG01885.1 GI: 295322875; Accession: ADG01886.1 GI: 295322877; etc, and the like.

As used herein, the term "gG2 protein" refers to an antigenic envelope glycoprotein that is specific for HSV-2 virus (See Gorander, S. et al, Glycoprotein G of HSV-2 as a novel vaccine antigen for immunity to genital and neurological disease). The protein has been mapped to the US segment of HSV-2 genome (See Mardsen et al. *J. Virol.* 1984, 50(2): 547-554 and Roizman et al. *Virology,* 1984, 133: 242-247). gG2 protein is cleaved intracellularly into a membrane bound portion and a secreted portion. Both the membrane bound portion and the secreted portion of gG2 function as antigens (Staffan et al. *J. Clin. Microbiol.* 2003, 41(8):3681-3686; Staffan et al. *Clin. Vaccine Immunol.* 2006, 13(6):633-639). The secreted portion of gG2 is also known to modify NGF-TrkA signaling to attract free nerve endings to the site of infection (Cabrera, et al. *PLoS Pathog.* 2015 January; 11(1): e100457). Alternative names for HSV gG2 protein are: HSV2 gG, HSV2 gG antigen, HSV gG-2 protein, HSV gG 2, Herpes Simplex Virus 2 glycoprotein G protein, HSV-2 gG protein, HSV gG-2.

HSV gG2 gene is also known as US4. The complete nucleotide sequence can be found at GenBank Accession: KF588470. In certain embodiments, gB2 is located at the gG2 (US4) locus of the HSV-2 genome thereby generating a gG2 deficient HSV-2.

As used herein the term "gG2 deficient HSV-2" or "gG2-" refers to a recombinant HSV vector whose genome does not encode active or functional gG2, i.e. gG2 with wild type function, e.g. antigenic function. Serologic antigenic activity of gG2 can be monitored using any of the means known to those in the art (See e.g. Sulaiman et al, *Clin Vaccine Immunol.* 2009 June; 16(6): 931-934). It should be understood that there are many variants of HSV gG2 protein, all with functional gG2. These variants are well known in the art and can be found in protein databases.

As used herein the term "UL19 deficient HSV-2" or "UL19-" refers to a recombinant HSV vector whose genome does not encode active or functional UL19 open reading frame protein, i.e. VP5 protein with wild type function. VP5 is non-functional if it cannot form HSV-2 viral capsid and therefore virus. VP5 is a major capsid protein of HSV-2. It should be understood that there are many variants of HSV UL19, all with functional VP5. These variants are well known in the art and can be found in protein databases. The genome of HSV-2 and UL19 open reading frame is described, e.g., in *J Virol.* 1998 March; 72(3): 2010-2021.

As used herein, "displaces" refers to the removal of a gene (e.g., G2, or UL19), or fragment thereof, from its endogenous location in the vector genome by the localization of an exogenous sequence (e.g., an indicated coding sequence) into such endogenous location. "Displacing" a gene can result in the depletion of the gene such that a genome no longer encodes the active or functional gene, or hinders the function of the gene.

As used herein, the term "variant" in the context of polypeptides or proteins refers to a polypeptide or protein that comprises an amino acid sequence which has been altered by the introduction of amino acid residue substitutions, deletions and/or additions. Typically, substitutions are conservative amino acid substitutions, however non-conservative substitutions can be made that do not destroy the functionality of the protein, e.g. HSV gB2 or gD2 proteins. "Conservative amino acid substitutions" refers to replacing one amino acid with another having similar structural and/or chemical properties, e.g. such as the replacement of a leucine with an isoleucine or valine, an aspartate with a glutamate, or a threonine with a serine, or glycine with another small amino acid residue. Conservative substitution tables providing functionally similar amino acids are well known in the art. As used herein, the term "non-conservative" refers to substituting an amino acid residue for a different amino acid residue that has different chemical properties. The non-conservative substitutions include, but are not limited to aspartic acid (D) being replaced with glycine (G); asparagine (N) being replaced with lysine (K); or alanine (A) being replaced with arginine (R). For purposes of embodiments of the invention non-conservative substitutions may reduce but does not destroy the proteins normal function.

As used herein the term "comprising" or "comprises" is used in reference to compositions, methods, and respective component(s) thereof, that are essential to the invention, yet open to the inclusion of unspecified elements, whether essential or not.

As used herein the terms, "consisting essentially of," or variations such as "consists essentially of", or "consist essentially of" refer to the inclusion of any recited elements, or group of elements, and the optional inclusion of other elements, of similar or different nature than the recited elements, that do not materially change the basic properties of the claimed elements. For example, a nucleotide sequence that consists essentially of a recited sequence may also include additional one or more nucleic acid additions, deletions, or substitutions that do not materially change, by a statistically significant amount, the function of the protein prior to the additions, deletions, or substitutions. For example, substitutions may correlate to the degenerative amino acid code.

The term "consisting of" refers to compositions, methods, and respective components thereof as described herein, which are exclusive of any element not recited in that description of the embodiment. For example, the nucleotide sequence has no additions, deletions or substitutions.

As used herein, the term "protein" or "polypeptide" refers to a polymer or oligomer of consecutive amino acid residues. As used herein, the term "nucleotide sequence" refers to DNA molecule sequences (e.g., cDNA or genomic DNA).

As used herein, the term "promoter" refers to regulatory control nucleic acid sequences involved in transcription of nucleotide coding sequences, which may or may not include enhancer elements. Such a promoter may be inducible or constitutive. The term "operably linked" refers to a juxtaposition wherein the components described are in a relationship permitting them to function in their intended manner. A promoter "operably linked" to a coding sequence is ligated in such a way that expression of the coding sequence is achieved.

Other than in the operating examples, or where otherwise indicated, all numbers expressing quantities of ingredients or reaction conditions used herein should be understood as modified in all instances by the term "about." The term "about" when used in connection with percentages may mean±10%, or even e.g. ±20%, preferably ±10%, more preferably ±5%, still more preferably ±1%. In addition, the singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. The abbreviation, "e.g." is derived from the Latin exempli gratia, and is used herein to indicate a non-limiting example. Thus, the abbreviation "e.g." is synonymous with the term "for example."

The term "statistically significant" or "significantly" refers to statistical significance and generally means a two-standard deviation (2SD) above or below a normal or reference level. The term refers to statistical evidence that there is a difference. The decision is often made using the p-value. If within two standard deviations than there is not a statistically significant difference.

It should be understood that this invention is not limited to the particular methodology, protocols, and reagents, and etc., described herein in the examples. The terminology used herein is for the purpose of describing particular embodiments only, and is not intended to limit the scope of the present invention, which is defined solely by the claims All references, publications and patents described herein, in the Examples and throughout the Specification, are incorporated herein by reference in their entirety. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. A replication-defective Herpes simplex virus 2 (HSV-2) recombinant virus, comprising within its genome:
   a) a first coding sequence, wherein said first coding sequence encodes HSV-2 glycoprotein B (gB2), wherein said first coding sequence is operably linked to a first immediate-early promoter;
   b) a second coding sequence, wherein said second coding sequence encodes HSV-2 glycoprotein D (gD2), and is operably linked to a second immediate-early promoter;
   c) a third coding sequence, wherein said third coding sequence encodes HSV-2 glycoprotein D (gD2); and is operably linked to a third immediate-early promoter; and wherein said genome does not comprise a sequence encoding a functional ICP0 protein, and does not comprise a sequence encoding functional HSV-2 gG2 protein.

2. A replication-defective Herpes simplex virus 2 (HSV-2) recombinant virus, comprising within its genome:
   a) a first coding sequence, wherein said first coding sequence encodes HSV-2 glycoprotein B (gB2), wherein said first coding sequence is operably linked to a first immediate-early promoter, and said first promoter is an HSV-1 or HSV-2 immediate early promoter that is operably linked to a first tetracycline operator (tet-O) sequence;
   b) a second coding sequence, wherein said second coding sequence encodes HSV-2 glycoprotein D (gD2) and is operably linked to a second immediate-early promoter, wherein said second promoter is operably linked to a second tet-O sequence;
   c) a third coding sequence, wherein said third coding sequence encodes HSV-2 glycoprotein D (gD2) and is operably linked to a third immediate-early promoter, wherein said third promoter is operably linked to a third tet-O sequence; and wherein said genome does not comprise a sequence encoding a functional ICP0 protein, and does not comprise a sequence encoding functional HSV-2 gG2 protein.

3. The recombinant virus of paragraph 1, wherein said second promoter and third promoter are a HSV-1 or HSV-2 immediate early promoter operably linked to a tetracycline operator (tet-O) sequence.

4. The recombinant virus of any of paragraphs 1-3, wherein the first coding sequence is located at the gG2 locus of the HSV-2 genome.

5. The recombinant virus of any one of paragraphs 1-4, wherein said genome further does not comprise a sequence encoding a functional UL19 (VP5) protein.

6. The recombinant virus of any one of paragraphs 1-4, further comprising a fourth coding sequence, wherein said fourth coding sequence encodes a dominant negative mutant HSV-1 or HSV-2 UL9 protein, and is operably linked to a fourth promoter, wherein said fourth promoter is operably linked to a fourth tet-O sequence.

7. The recombinant virus of paragraph 6, further comprising a fifth coding sequence, wherein said fifth coding sequence encodes a dominant negative mutant HSV-1 or HSV-2 UL9 protein, and is operably linked to a fifth promoter, wherein said fifth promoter is operably linked to a fifth tet-O sequence.

8. The recombinant virus of any one of paragraphs 6-7, wherein said fourth sequence encodes UL9-C535C.

9. The recombinant virus of any one of paragraphs 7-8, comprising said fifth sequence, wherein said fifth sequence encodes UL9-C535C.

10. The recombinant virus of any one of paragraphs 1-9, wherein each of said first, second and third promoters are HSV-1 or HSV-2 immediate early promoters.

11. The recombinant virus of any one of paragraphs 1-10, wherein each of said first, second and third promoters are selected from the group consisting of an ICP0 promoter, an ICP27 promoter, and an ICP4 promoter.

12. The recombinant virus of any one of paragraphs 1-11, wherein the first promoter is a HSV-1 or HSV-2 ICP0 promoter.

13. The recombinant virus of any one of paragraphs 1-12, wherein the first promoter is a modified HSV-1 or HSV-2 ICP0 promoter comprising a human cytomegalovirus (hCMV) TATA element.

14. The recombinant virus of paragraph 13, wherein the first promoter comprises SEQ ID NO: 08.

15. The recombinant virus of any one of paragraphs 1-14, wherein said the fourth and fifth promoters are hCMV immediate-early promoters.

16. The recombinant virus of any one of paragraphs 1-15, wherein said first sequence is a codon optimized sequence.

17. A replication-defective Herpes simplex virus 2 (HSV-2) recombinant virus, comprising within its genome:
   a) a first coding sequence, wherein said first coding sequence encodes HSV-2 glycoprotein B (gB2), wherein said first coding sequence is operably linked to a first immediate-early promoter, and said first promoter is an HSV-1 or HSV-2 immediate early promoter that is operably linked to a first tetracycline operator (tet-O) sequence;
   b) a second coding sequence, wherein said second coding sequence encodes HSV-2 glycoprotein D (gD2) and is operably linked to a second HSV-1 or HSV-2 immediate-early promoter, wherein said second promoter is operably linked to a second tet-O sequence;

c) a third coding sequence, wherein said third coding sequence encodes HSV-2 glycoprotein D (gD2) and is operably linked to a third HSV-1 or HSV-2 immediate-early promoter, wherein said third promoter is operably linked to a third tet-O sequence; and wherein said genome does not comprise a sequence encoding a functional ICP0 protein, and does not comprise a sequence encoding functional HSV-2 gG2 protein.

18. A replication-defective HSV-2 recombinant virus, comprising within its genome:
    a) a first coding sequence, comprising a codon optimized HSV-2 gB2 sequence operably linked to a first promoter, wherein said first promoter is an HSV-1 or HSV-2 ICP0 or ICP4 promoter that is operably linked to a first tet-O sequence;

b) a second coding sequence, comprising a codon-optimized HSV gD2 sequence operably linked to a second promoter, wherein said second promoter is an HSV-1 ICP4 promoter that is operably linked to a second tet-O sequence and wherein the second coding sequence operably linked to the second promoter is located at the UL26/UL27 intergenic region;

c) a third coding sequence, comprising a codon optimized HSV gD2 sequence operably linked to a third promoter, wherein said third promoter is an HSV-1 ICP27 promoter that is operably linked to a third tet-O sequence, wherein the third coding sequence operably linked to the third promoter displaces the UL19 gene; and wherein said genome does not comprise a sequence encoding a functional ICP0 protein, and does not comprise a sequence encoding functional HSV-2 gG2 protein.

19. A replication-defective HSV-2 recombinant virus, comprising within its genome:

a) a first coding sequence, comprising a codon optimized HSV-2 gB2 sequence operably linked to a first promoter, wherein said first promoter is an HSV-1 or HSV-2 ICP0 or ICP4 promoter that is operably linked to a first tet-O sequence;

b) a second coding sequence, comprising an HSV-2 gD2 sequence operably linked to a second promoter, wherein said second promoter is an HSV-1 or HSV-2 ICP0, ICP4, or ICP27 promoter that is operably linked to a second tet-O sequence;

c) a third coding sequence, comprising an HSV-2 gD2 sequence operably linked to a third promoter, wherein said third promoter is an HSV-1 or HSV-2 ICP0, ICP4, or ICP27 promoter that is operably linked to a third tet-O sequence; and wherein said genome does not comprise a sequence encoding a functional ICP0 protein, and does not comprise a sequence encoding HSV-2 gG2 protein.

20. The replication-defective HSV-2 recombinant virus of any one of paragraphs 17-19, wherein the first coding sequence is located at the gG2 locus of the HSV-2 genome.

21. The replication-defective HSV-2 recombinant virus of any one of paragraphs 17-20, wherein said genome does not comprise a sequence encoding a functional UL19 (VP5) protein.

22. The replication-defective HSV-2 recombinant virus of any one of paragraphs 17-20, further comprising i) a fourth coding sequence, encoding a dominant negative UL9-C535C protein, and operably linked to a third promoter, wherein said third promoter is an hCMV immediate early promoter that is operably linked to a third tet-O sequence; and ii) a fifth sequence, encoding a dominant negative UL9-C535C protein, operably linked to a fifth promoter, wherein said fifth promoter is an hCMV immediate early promoter that is operably linked to a fifth tet-O sequence.

23. The recombinant virus of any one of paragraphs 17-22, wherein the first promoter is an HSV-1 or HSV-2 ICP0 promoter.

24. The recombinant virus of any one of paragraphs 17-23, wherein the first promoter is a modified HSV-1 or HSV-2 ICP0 promoter comprising a human cytomegalovirus (hCMV) TATA element.

25. The recombinant virus of paragraph 24, wherein the first promoter comprises SEQ ID NO: 08.

26. The recombinant virus of any one of paragraphs 17-25, wherein at least one of the second and third promoters is a HSV-1 or HSV-2 ICP27 promoter operably linked to a tet-O sequence.

27. The recombinant virus of any one of paragraphs 17-26, wherein at least one of the second and third promoters is a HSV-1 or HSV-2 ICP4 promoter operably linked to a tet-O sequence.

28. The recombinant virus of any one of paragraphs 17-28, wherein each of the second and third promoters are the same, and wherein said same promoter is an HSV-1 or HSV-2 promoter selected from the group consisting of: an ICP4 promoter, an ICP27 promoter.

29. The recombinant virus of any one of paragraphs 17-27, wherein each of the second and third promoters are different, and wherein one of these promoters is an HSV-1 or HSV-2 ICP4 promoter, and wherein the other of these promoters is an HSV-1 or HSV-2 ICP27 promoter.

30. A replication defective HSV recombinant virus, comprising a modified HSV-1 or HSV-2 ICP0 promoter comprising a human cytomegalovirus (hCMV) TATA element, wherein said modified promoter is operably linked to a transgene.

31. The replication defective virus of paragraph 30, wherein the transgene encodes HSV-2 glycoprotein B (gB).

32. The replication defective virus of paragraph 30 or 31, wherein said modified promoter comprises SEQ ID NO: 08.

33. A vaccine comprising the recombinant virus of any one of paragraphs 1-32 in unit dose form.

34. A method of immunizing a subject against HSV-1 or HSV-2 infection, comprising administering to said subject the vaccine of paragraph 33.

35. The method of paragraph 34, wherein said subject is seropositive for HSV-1.

36. The method of paragraph 34, wherein said subject is seropositive for HSV-2.

37. The method of paragraph 34, wherein said subject is seronegative for HSV-1 and HSV-2.

38. A method for producing the virus of any one of paragraphs 1-32, the method comprising;

a) infecting complementing cells with the virus, wherein the complementing cells express a functional gene product or products that are needed for replication of the virus and for which sequences encoding such are lacking from the virus genome;

b) culturing the complementing cells such that the virus replicates; and c) harvesting said replicated virus from the complementing cells.

39. The method of paragraph 38, wherein the complementary cells further express TetR.

40. The method of paragraph 38 or 39, wherein the complementary cells express ICP0 functional gene product.

41. The method of any one of paragraphs 37-40, wherein the complementary cells express UL19 (VP5) functional gene product.

42. A composition comprising a vaccine comprising the recombinant virus of any of paragraphs 1-32 for use in unit dose form in the treatment of an infection with HSV-1 or HSV-2.

43. A composition comprising the virus of any one of paragraphs 1-32 for use in the treatment of an infection with HSV-1 or HSV-2, the composition comprising;
a) infecting complementary cells with the virus, wherein the complementing cells express a functional gene product or products that are needed for replication of the virus and for which sequences encoding such are lacking from the virus genome;
b) culturing the complementing cells such that the virus replicates; and
c) harvesting said replicated virus from the complementing cells.

EXAMPLES

Example 1

Construction and Characterization of CJ2-gD2/gB2(UL9) and CJ2-gD2/gB2, and Testing the Vaccine Efficacy of CJ2-gD2/gB2.

Figure 2:
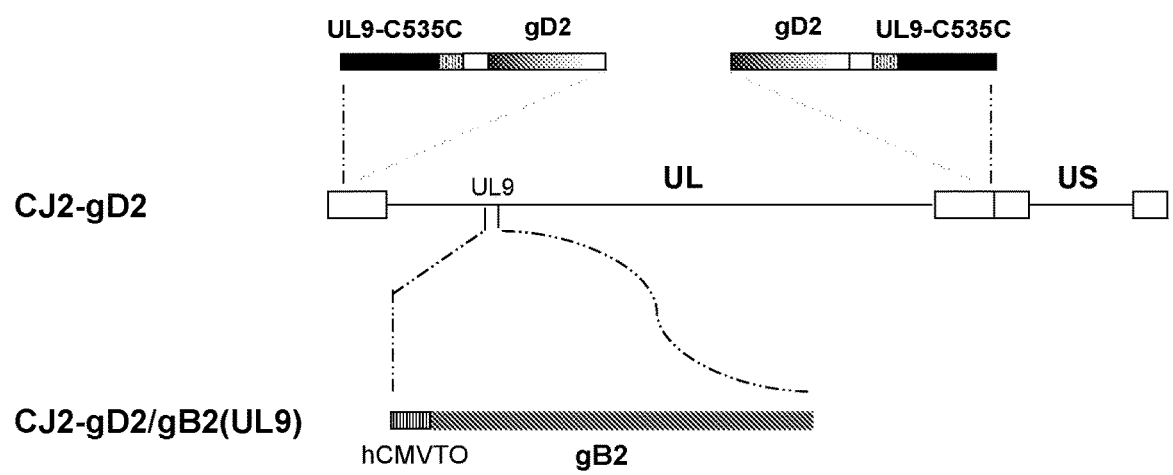
FIG. 2 is a schematic of genomes of non-replicating dominant-negative HSV-2 recombinant viral vaccine construct, CJ2-gD2, and a CJ2-gD2-derived viral recombinant, CJ2-gD2/gB2(UL9). UL and US represent the unique long and unique short regions of the HSV-2 genome, respectively, which are flanked by their corresponding inverted repeat regions (open boxes). The replacements of both copies of the ICP0 coding sequences with DNA sequences encoding UL9-C535C under control of the tetO-bearing hCMV major immediate-early promoter and gD2 under the tetO-bearing HSV-1 ICP4 promoter in CJ2-gD2 are shown expanded above the ICP0 coding sequences of the HSV-2 genome. The replacement of the HSV-2 UL9 DNA sequence encoding UL9 amino acids 285-742 with DNA sequence encoding gB2 under control of the tetO-bearing hCMV major immediate-early promoter is shown expanded below the UL9 coding sequences of the HSV-2 genome.
Figure 3:
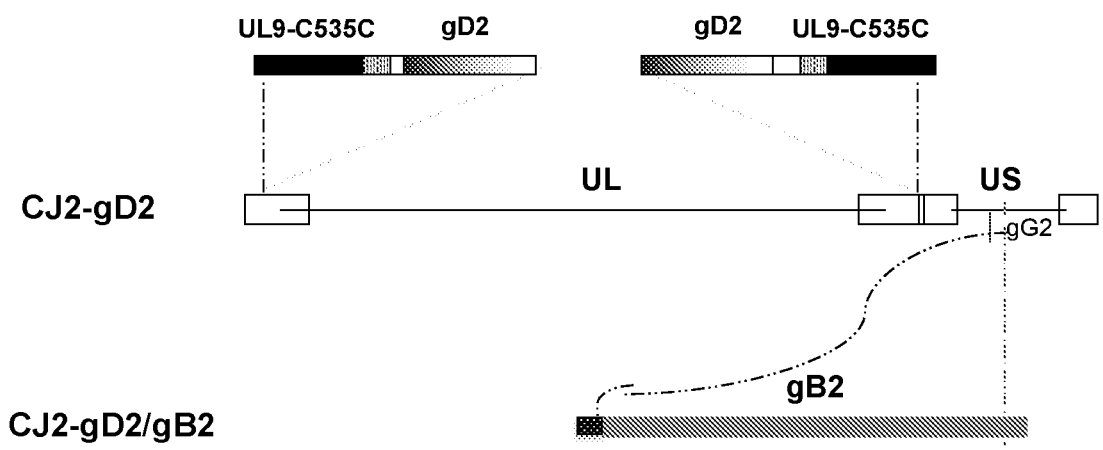
FIG. 3 is a schematic drawing of the genome of a non-replicating dominant-negative HSV-2 recombinant viral vaccine construct, named CJ2-gD2/gB2, in which the HSV-2 gG2 coding sequence in CJ2-gD2 is replaced with a codon-optimized gB2 sequence under control of the tetO-bearing modified HSV-1 ICP0 promoter plus part of 5' untranslated region of ICP0 gene described in FIG. 21. Again, the replacements of both copies of the ICP0 coding sequences with DNA sequences encoding UL9-C535C under control of the tetO-bearing hCMV major immediate-early promoter and gD2 under the tetO-bearing HSV-1 ICP4 promoter in CJ2-gD2 are shown expanded above the ICP0 coding sequences of the HSV-2 genome.

The current example describes 1) the construction and in vitro characterization of a CJ2-gD2-derived recombinant virus, CJ2-gD2/gB2(UL9), in which the gB2 gene is inserted at a site encoding a gene needed for viral replication (the UL9 gene) and is operably linked to a tetO-bearing hCMV immediate-early promoter (see FIG. 2), and 2) the construction and in vitro characterization of a CJ2-gD2-derived recombinant virus, CJ2-gD2/gB2, in which the codon-optimized gB2 gene is inserted at a site encoding HSV-2 glycoprotein G (gG2) and is operably linked to a tetO-bearing HSV-1 ICP0 promoter (see FIG. 3).

Materials and Methods

Cells: African Green Monkey Kidney (Vero) cells and the human osteosarcoma line U2OS cells were grown and maintained in Dulbecco's Modified Eagle's Medium (DMEM; Sigma Aldrich) supplemented with 10% fetal bovine serum (FBS) in the presence of 100 U/ml penicillin G and 100 µg/ml streptomycin sulfate (GIBCO, Carlsbad, Calif.) (Yao, et al., *J. Virol.* 69:6249-58 (1995)). U2OS cells are able to complement functionally for the HSV-1 ICP0 deletion (Yao, et al., *J. Virol.* 69:6249-58 (1995)). U2CEP4R11 cells are tetR-expressing U2OS cells that were maintained in DMEM plus 10% FBS and hygromycin B at 50 µg/ml (Yao, et al., *Hum. Gene Ther.* 9:1939-50 (1998)). RUL9 cells are HSV-1 UL9-expressing U2CEP4R-11 cells that were maintained in DMEM plus 10% FBS supplemented with hygromycin and G418 (Yao, et al., *Mol. Ther.* 13:1133-41 (2006)).

Plasmids: Plasmid p2UL9-V is a pUC19 based plasmid that encodes the PCR amplified HSV-2 UL9 sequences covering 31 bp upstream of the HSV-2 UL9 open reading frame (ORF) to 216 bp downstream of the stop codon of UL9 ORF. p2UL9-lacZ is a p2UL9-V derived plasmid encoding the lacZ gene under the control of the HSV-1 ICP6 promoter. Plasmid p2UL9-TO was created by replacing the PstI-MluI fragment of p2UL9-V, which encodes UL9 amino acids 285-742, with the MtuI-PvuII DNA fragment of pCDNA4-TO, which consists of the tetO-hCMV-MCS-poly A transcription unit of pCDNA4-TO. p2UL9TO-gB2 expresses the HSV-2 gB under control of the tetO-containing hCMV major immediate-early promoter (hCMVTO), which was constructed by inserting the HindIII-BamHI-HSV-2 gB ORF-encoding fragment of pMM245 (the kind gift of Martin I. Muggeridge, Louisiana State University Health Sciences Center) into p2UL9-TO at the EcoRV and HindIII sites.

Plasmid pgG2-TO is an HSV-2 gG2 locus-specific shuttle plasmid, that contains a synthesized ~2.7 kb DNA fragment (GeneArt, Invitrogen) consisting of a) an HSV-2 DNA sequence covering 900 bp to 2 bp upstream of the gG2 ORF; b) an HSV-1 ICP27 poly A signal sequence, which ensures that expression of HSV-2 US3 gene is properly terminated; c) a modified tetO-bearing HSV-1 ICP0 promoter; d) a multiple cloning region; and e) HSV-2 DNA sequences spanning 1 bp downstream of the stop codon of the gG2 ORF to 900 bp downstream of the gG2 stop codon. pgG2-TO/gB2 is a pgG2-TO vector-derived plasmid encoding a codon optimized gB2 under the control of the modified tetO-containing HSV-1 ICP0 promoter. Plasmid pgG2-vector was constructed with the deletion of the tetO sequence in pgG2-TO. The lacZ gene was then inserted into the pgG2-vector at the Hind III and Eco RI sites within the multiple cloning region of the pgG2-vector, resulting in plasmid pgG2-lacZ.

Viruses: Wild-type HSV-2 strain G, strain 186, and strain MS, and HSV-1 strain mP were propagated and plaque assayed in Vero cells (Brans, et al., *J. Invest. Dermatol.* 129:2470-79 (2009); Zhang, et al., *PLOS ONE,* 9:e101373 (2014)). CJ2-gD2 is an HSV-2 ICP0-deletion mutant-based non-replicating dominant-negative HSV-2 recombinant virus in which both copies of the HSV-2 ICP0 gene were replaced by DNA sequences encoding the gD2 gene driven by the tetO-bearing HSV-1 major immediate-early ICP4 promoter, while the gene encoding UL9-C535C is under the control of the tetO-containing hCMV major immediate-early promoter in an opposite orientation of the inserted gD2 gene (Akhrameyeva, *J. Virol.* 85:5036-47 (2011); U.S. Pat. No. 8,809,047). CJ2-gD2 was propagated and plaque assayed in U2CEP4R11 cells or in Vero cells that express tetR and ICP0, e.g. VOR-124 cells (See e.g. U.S. Application Ser. No. 62/515,260, Filed on Jun. 5, 2017 entitled Vero cell lines Stably Expressing HSV ICP0 protein).

CJ2-gD2/lacZ(UL9) is a CJ2-gD2-derived recombinant virus that encodes the lacZ gene under control of the HSV-1 ICP6 promoter at the HSV-2 UL9 locus, which was generated by transfecting U2CEP4R-11 cells with NheI-linearized p2UL9-lacZ and pcDNA-UL9 (Yao, et al., *Mol. Ther.* 13:1133-41 (2006)) followed by superinfection with CJ2-gD2 as previously described (Lu, et al., *J. Invest. Dermatol.* 129:1174-84 (2009)). The replacement of the UL9 gene with the lacZ gene at the UL9 locus was confirmed by PCR analysis of CJ2-gD2/lacZ(UL9) viral DNA with the primers that flank the UL9 gene and primers specific for the lacZ gene (Lu, et al., *J. Invest. Dermatol.* 129:1174-84 (2009)). CJ2-gD2/lacZ was propagated and titered in RUL9 cells.

CJ2-gD2/gB2(UL9) is a derivative of CJ2-gD2/lacZ (UL9), in which the lacZ gene in CJ2-gD2/lacZ(UL9) is replaced with DNA sequences encoding gB2 under control of hCMVTO in plasmid p2UL9TO-gB2. In brief, U2CEP4R11 cells were co-transfected with Nhe-linearized p2UL9TO-gB2 and pcDNA-UL9 followed by superinfection with CJ2-gD2/lacZ(UL9) at an MOI of 5 PFU/cell. Progeny of the superinfection were screened for the recombinational replacement of the lacZ gene of CJ2-gD2/lacZ (UL9) with the DNA sequence containing CMVTO/gB2 by standard plaque assays. Plaques were stained with 5-bromo-4-chloro-3-indolyl-b-D-galactopyranoside (X-Gal) at 72 hr post-infection. White plaques, reflecting the replacement of the lacZ gene by the gB2 DNA-encoding sequence, were isolated. One of the isolates, designated CJ2-gD2/gB2 (UL9), yielded uniformly white plaques after four rounds of plaque purification in RUL9 cells.

CJ2-gD2/lacZ is a CJ2-gD2-derived recombinant virus that encodes the lacZ gene under control of the HSV-1 ICP0 promoter at the HSV-2 gG2 locus, which was generated by transfecting U2CEP4R-11 cells with PstI-linearized pgG2-lacZ (Yao, et al., *Mol. Ther.* 13:1133-41 (2006)) followed by superinfection with CJ2-gD2 as previously described (Lu, et al., *J. Invest. Dermatol.* 129:1174-84 (2009)). CJ2-gD2/lacZ was propagated and titered in U2CEP4R-11 cells. CJ2-gD2/lacZ was a fourth round plaque-purified CJ2-gD2-derived recombinant virus that exhibits uniform blue plaques in U2CEP4R-11 cells. The plaque-forming efficiency of CJ2-gD2/lacZ in U2CEP4R-11 cells in the absence of tetracycline is 6550-fold higher than in the presence of tetracycline, indicating that like CJ2-gD2, CJ2-gD2/lacZ is capable of expressing high-level of UL9-C535C in the absence of tetracycline repressor, tetR. Additionally, like CJ2-gD2, CJ2-gD2/lacZ replicates efficiently in U2CEP4R-11 cells in the absence of tetracycline.

CJ2-gD2/gB2 is a CJ2-gD2/lacZ-derived recombinant virus, which was generated by super-infection of AscI-linearized pgG2-TO/gB2-transfected U2CEP4R11 cells with CJ2-gD2/lacZ. Progeny of the superinfection were screened for the recombinational replacement of the lacZ gene of CJ2-gD2/lacZ with the gB2-containing DNA sequence by standard plaque assays. Plaques were stained with 5-bromo-4-chloro-3-indolyl-b-D-galactopyranoside (X-Gal) at 72 hours post-infection. White plaques, reflecting the replacement of the lacZ gene by the gB2 DNA-encoding sequence, were isolated. CJ2-gD2/gB2 is a CJ2-gD2/lacZ-derived recombinant that was obtained after four rounds of plaque purification in U2CEP4R-11 cells that express higher levels of gB2 in infected Vero cells compared with cells infected with CJ2-gD2, and CJ2-gD2/lacZ. The genomic location of gB2 in CJ2-gD2/gB2 at the gG2 locus was verified by PCR analysis with gG2-specific primers that flank the insert and primers specific for gB2.

Animal Experiments in Mice

Mice: Female BALB/c mice 6-7 weeks of age were purchased from Charles River Laboratories (Wilmington, Mass.). Mice were housed in metal cages at four mice per cage and maintained on a 12 h-light/dark cycle. Mice were allowed to acclimatize to the housing conditions for 1 week prior to experimentation. All animal experiments were conducted according to the protocols approved by Harvard Medical Area Standing Committee on Animals and the American Veterinary Medical Association. The Harvard Medical School animal management program is accredited by the Association for Assessment and Accreditation of Laboratory Animal Care (AAALAC) and meets National Institutes of Health standards as set forth in "The Guide for the Care and Use of Laboratory Animals" (National Academy Press, 1996).

Immunization and challenges: Female BALB/c mice 7- to 8-week-old were randomly divided into several groups and the hair on their left rear upper leg area was trimmed. Mice were either sham-immunized with DMEM (n=6) or immunized with CJ2-gD2/gB2 (n=8), or CJ2-gD2 (n=7) at a dose of $2 \times 10^6$ PFU/mouse or with CJ2-gD2/gB2 (n=8), or CJ2-gD2 (n=8) at a dose of $5 \times 10^5$ PFU/mouse in a volume of 50 µl intramuscular injection into the left rear calf muscle (gastrocnemius) using a 1-ml syringe fitted with a 25 G5/8-gauge needle. Individual groups of mice were boosted with the same virus and at the same dose 2 weeks later. Mice were challenged with wild-type HSV-2 strain G three weeks after secondary immunization. Five days prior to challenge, mice were injected subcutaneously in the neck ruff with medroxy-progesterone (SICOR Pharmaceuticals, Inc., Irvine, Calif.) at 3 mg per mouse in a volume of 20 µl (Akhrameyeva, *J. Virol.* 85:5036-47 (2011)). For intravaginal challenge, mice in all groups were anesthetized, pre-swabbed with a calcium alginate swab (Sterile urethro-genital calcium alginate tipped applicator, Puritan Medical Products company LLC, Guilford, Me. USA) and inoculated intravaginally with 20 µl of culture medium containing $5 \times 10^5$ PFU (50 $LD_{50}$) of HSV-2 strain G (Morrison, et al., *Virology* 243:178-87 (1998)). Animals were kept on their backs with their rear part elevated under the influence of anesthesia for 30-45 min post-infection. The CJ2-gD2 and CJ2-gD2/gB2 stocks used in the described animal experiments were prepared and titered on Vero cells that express tetR and ICP0.

Acute infection assays and clinical observations: On days 1, 2, 3, 5, and 7 post-challenge, vaginal mucosae were swabbed with calcium alginate (Brans, et al., *J. Invest. Dermatol.* 129:2470-9 (2009)). Infectious viruses in swab materials were assessed by standard plaque assay on Vero cell monolayers.

Following challenge with wild-type HSV-2, mice were assessed daily during a 21-day follow-up period for signs of genital lesions and systemic illness. The severity of disease was scored as follows: 0=no sign of herpetic infection, 1=slight genital erythema and edema, 2=moderate genital inflammation, 3=purulent genital lesions and/or systemic illness, 4=hind-limb paralysis, and 5=death (Brans, et al., *J. Invest. Dermatol.* 129:2470-9 (2009)).

Detection of HSV-2-specific neutralizing antibodies: Blood was collected from tail veins of immunized and mock-immunized mice 4 weeks after primary immunization. Neutralizing serum antibody titers were determined as previously described in the presence of complement (Bourne, et al., *Vaccine* 14:1230-4 (1996); Brans, et al., *J. Invest. Dermatol.* 129:2470-9 (2009)) with 250 PFU of wild-type HSV-2 strain 186. The neutralizing titer was expressed as the final serum dilution required to achieve a 50% reduction in HSV PFU relative to the HSV PFU obtained in medium plus complement alone.

Animal Experiment in Guinea Pigs

Preparation of gD2-alum/MPL. Purified recombinant gD2 protein was produced (at U-Protein-Express B.V., Utrecht, the Netherlands) from CHO cells expressing a His-tagged truncated form of gD2 polypeptide consisting of amino acids 1-306 of the mature gD2. The gD2 coding sequence is derived from HSV-2 strain G. The gD2-alum/MPL subunit vaccine was freshly prepared prior to each immunization in a formulation similar to that described by Bourne et al. (Bourne, et al., *J. Infect. Dis.* 192:2117-23 (2005)). In brief, 50 µg of the recombinant gD2 protein was first mixed with 1250 µg of alum (Imject Alum, Thermo Scientific, Rockford, Ill.) in a volume of 850 µl on a rotating platform. After 30 minutes of incubation at room temperature, 125 µg of Monophosphoryl Lipid A (MPL) (Avanti Polar Lipids, Inc., Alabaster, Ala.) was added to gD2-alum solution followed by gentle mixing. MPL stock solution was prepared at a concentration of 500 µg/ml containing 10% DMSO (Sigma Aldrich) and stored at −20° C. (InvivoGen, San Diego, Calif.).

Immunization and challenge. Female Hartley guinea pigs (300-350 g) were obtained from Charles River Laboratories (Wilmington, Mass.). Animals were randomly assigned to three groups of six animals each. Each of the groups was either sham-immunized with DMEM, immunized with gD2-alum/MPL at a dose of 5 µg of gD2/animal, or immunized with CJ2-gD2/gB2 at a dose of $5 \times 10^6$ PFU/animal. Each vaccine was administered by intramuscular injection into the quadriceps of the left and right hind limbs in a volume of 50 µl per injection (Bourne, et al., *J. Infect. Dis.* 192:2117-23 (2005); Zhang, et al., *PLOS ONE*, 9:e101373 (2014)). Guinea pigs were boosted with gD2-alum/MPL or CJ2-gD2/gB2 on days 14 and 28 post primary immunization. Anesthetized sham-immunized and immunized animals were pre-swabbed with a moist sterile calcium alginate swab (Calgiswab type 2, Puritan Medical Products Company LLC, Maine USA) and challenged intravaginally with $5 \times 10^5$ PFU of HSV-2 strain MS at 3 weeks after the third immunization (Zhang, et al., *PLOS ONE*, 9:e101373 (2014)).

Clinical observations. After challenge with wild-type HSV-2, the animals were examined daily until day 60 post-challenge. The number of lesions for individual animals was counted and the disease was scored non-blindly as previously described (Zhang, et al., *PLOS ONE*, 9:e101373 (2014)). The severity of disease were scored as follows: 0=no disease; 1=redness or swelling; 2=a few small vesicles; 3=several large vesicles; 4=several large ulcers with maceration; 5=paralysis; and 6=death.

Analysis of acute and recurrent vaginal shedding of challenge virus. Animals were anesthetized and vaginal mucosae were swabbed on days 1, 2, 3, 5, 7, and 9 post-challenge. Materials on individual swabs were suspended in 1 ml of DMEM containing 10% FBS in the presence of 100 U/ml penicillin G and 100 µg/ml of streptomycin sulfate (Gibco, Carlsbad, Calif.). Infectious virus on swab materials was assessed by standard plaque assay in 60-mm dishes of Vero cells. The minimum titer of challenge virus that could be detected was 1 PFU per original vaginal swab materials.

Statistical analysis: For statistical analysis, un-paired Student's t-tests were performed. Results are considered as statistically significant when the P value is less than 0.05.

Results

In Vitro Characterization of CJ2-gD2/gB2

Figure 4:
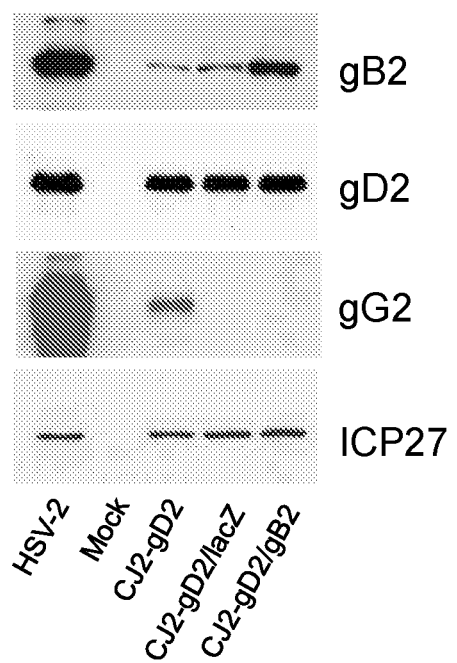
FIG. 4 shows the expression of gB2 and gD2, as well as the absence of gG2 expression following infection of Vero cells with CJ2-gD2/gB2. Vero cells in duplicate were either mock-infected or infected with wild-type HSV-2, CJ2-gD2, CJ2-gD2/lacZ, a CJ2-gD2 derived virus that encodes the lacZ gene in the HSV-2 gG2 locus, or CJ2-gD2/gB2 at an MOI of 5 PFU/cell. Infected cell extracts were prepared at 16 h post-infection. Proteins in infected cell extracts were resolved on SDS-PAGE, followed by immunoblotting with monoclonal antibodies against gB2, HSV-1/2 gD, gG2, or ICP27 (HSV-specific input control). In contrast to wild-type HSV-2, which can replicate as early as 6 hours post-infection, CJ2-gD2, CJ2-gD2/lacZ and CJ2-gD2/gB2 do not replicate or amplify genome following infection.

CJ2-gD2/gB2 expresses gB2 efficiently and is incapable of expressing gG2 in infected Vero cells. The CJ2-gD2, CJ2-gD2/lacZ, and CJ2-gD2/gB2 stocks used in experiments described in this section were prepared and titered on U2CEP4R11 cells. To examine expression of gB2, Vero cells were either mock-infected or infected with wild-type HSV-2, CJ2-gD2, CJ2-gD2/lacZ, or CJ2-gD2/gB2 at an MOI of 5 PFU/cell. Infected cell extracts were prepared at 16 h post-infection. Proteins in infected cell extracts were resolved on SDS-PAGE, followed by immunoblotting with monoclonal antibody against HSV-1/2 gD, or monoclonal antibodies specific for ICP27, gB, and gG2. The results in FIG. 4 showed that while similar levels of ICP27 and gD2 were expressed in cells infected with the indicated viruses, CJ2-gD2/gB2 expressed higher levels of gB2 than CJ2-gD2 and CJ2-gD2/lacZ. As expected, the results showed that CJ2-gD2/gB2 and CJ2-gD2/lacZ are incapable of expressing gG2. This allows convenient discrimination between wild-type HSV infection and presence of CJ2-gD2/gB2 in vaccinated individuals.

Figure 5:
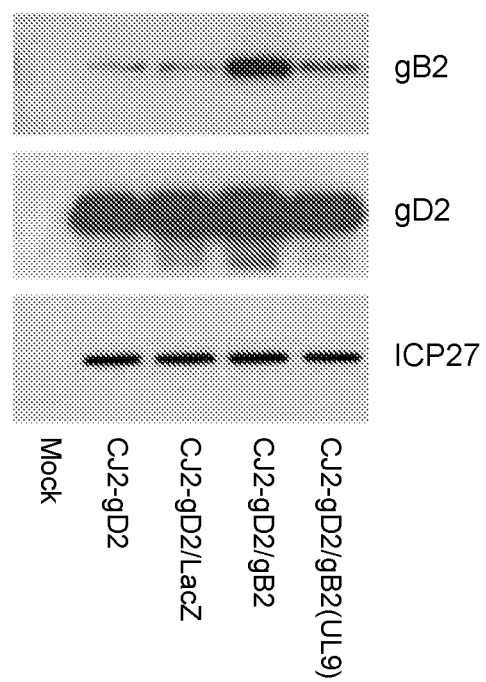
FIG. 5 shows that CJ2-gD2/gB2 expresses gB2 more efficiently than CJ2-gD2/gB2(UL9) in Vero cells. Vero cells in duplicate were either mock-infected or infected with wild-type HSV-2, CJ2-gD2, CJ2-gD2/lacZ, CJ2-gD2/gB2, or CJ2-gD2/gB2(UL9) at an MOI of 5 PFU/cell. Infected cell extracts were prepared at 16 h post-infection. Proteins in infected cell extracts were resolved on SDS-PAGE, followed by immunoblotting with monoclonal antibodies against gB2, HSV-1/2 gD, or ICP27 (HSV-specific input control).

To determine the level of expression of gB2 from CJ2-gD2/gB2 and CJ2-gD2/gB2(UL9), we carried out an additional experiment, in which 60 mm dishes of Vero cells in duplicate were either mock-infected or infected with CJ2-gD2, CJ2-gD2/lacZ, CJ2-gD2/gB2, or CJ2-gD2/gB2(UL9) at an MOI of 5 PFU/cell. Infected cell extracts were prepared at 16 h post-infection followed by western blot analyses with monoclonal antibodies against gD2, ICP27 and gB2, respectively. Surprisingly, the results in FIG. 5 showed that levels of gB2 detected in CJ2-gD2/gB2-infected cells were markedly higher than in cells infected by CJ2-gD2/gB2(UL9). The levels of gB2 detected in CJ2-gD2/gB2-infected cells were also markedly higher than in cells infected by CJ2-gD2, as well as CJ2-gD2/lacZ. Comparable levels of ICP27 and gD2 were detected among cells infected with these four indicated viruses. Taken together, the data indicates that CJ2-gD2/gB2, where gB2 is located at the gG2 locus expresses gB2 more efficiently than CJ2-gD2 and CJ2-gD2/gB2(UL9), where the gB2 is located at the UL9 locus.

Figure 6:
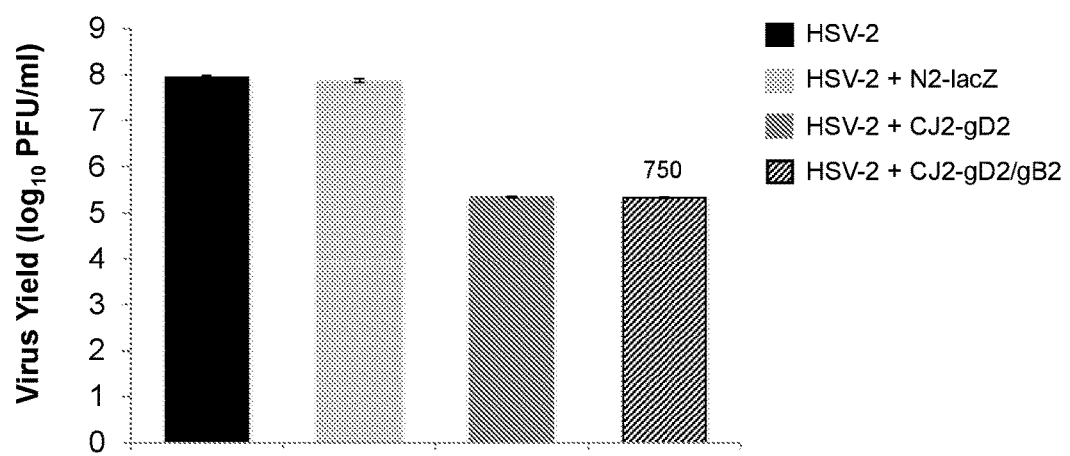
FIG. 6 shows a trans-dominant-negative effect of CJ2-gD2/gB2 on replication of wild-type HSV-2. Vero cells were infected in triplicate with either wild-type HSV-2 strain 186 alone at an MOI of 2 PFU/cell; with wild-type HSV-2 (MOI 2) and N2-lacZ, a HSV-2 ICP0 deletion mutant that does not express UL9-C535C, at an MOI of 5 PFU/cell; with wild-type HSV-2 (MOI 2) and CJ2-gD2 at an MOI of 5 PFU/cell; or with wild-type HSV-2 (MOI 2) and CJ2-gD2/gB2 at an MOI of 5 PFU/cell. Infected cells were harvested at 18 h post-infection and viral titers were determined on Vero cell monolayers. Viral titers are expressed as the mean+/−SD. Number on the top of the graph indicates the fold reduction in wild-type virus yield between single infection and co-infection.

Inhibition of wild-type HSV-2 replication by CJ2-gD2/gB2. To examine the effectiveness of CJ2-gD2/gB2 in blocking wild-type HSV-2 infection in co-infected cells, Vero cells in triplicate were infected with either wild-type HSV-2 at an MOI of 2 PFU/cell, wild-type HSV-2 at an MOI of 2 PFU/cell and CJ2-gD2 at an MOI of 5 PFU/cell, wild-type HSV-2 at an MOI of 2 PFU/cell and CJ2-gD2/gB2 at an MOI of 5 PFU/cell, or wild-type HSV-2 at an MOI of 2 PFU/cell and the HSV-2 ICP0 deletion mutant, N2-lacZ at an MOI of 5 PFU/cell. Infected cells were harvested at 18 h post-infection and viral titers were determined on Vero cell monolayers. The data presented in FIG. 6 show that CJ2-gD2/gB2 is as effective as CJ2-gD2 in blocking wild-type HSV-2 infection in co-infected cells. Specifically, yields of wild-type HSV-2 in cells co-infected with CJ2-gD2/gB2 was more than 750-fold lower than in cells singly infected by wild-type HSV-2. Little reduction in wild-type virus yield was detected when a similar co-infection experiment was performed with N2-lacZ.

Figure 7:
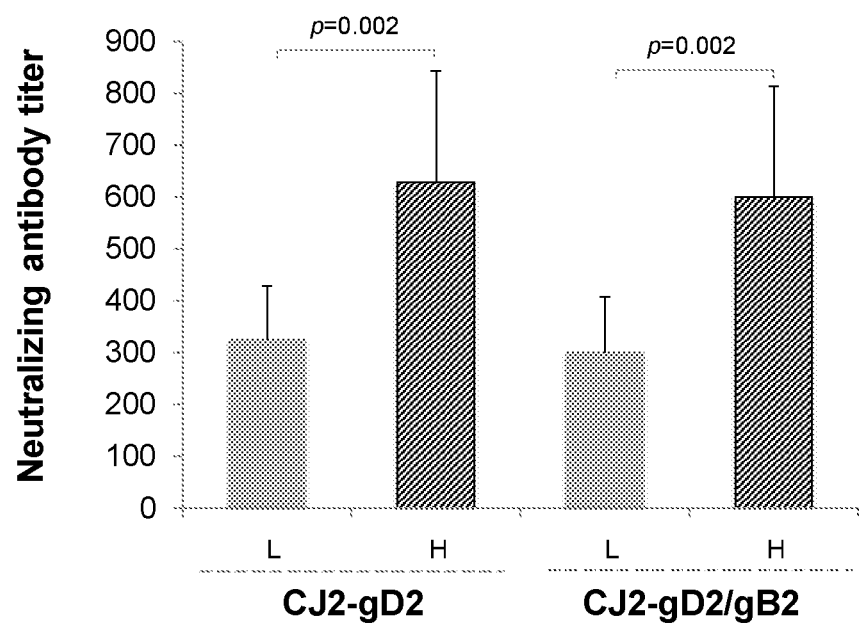
FIG. 7 shows the induction of HSV-2-neutralizing antibody responses. 7- to 8-week-old female BALB/c mice were either immunized with CJ2-gD2/gB2 (n=8) or CJ2-gD2 (n=7) at a dose of $2 \times 10^6$ PFU/mouse (H) or with CJ2-gD2/gB2 (n=8) or CJ2-gD2 (n=8) at a dose of $5 \times 10^5$ PFU/mouse (L). Mice were boosted 2 weeks later with the same vaccine virus at the same dose as used for prime immunization. Blood was obtained from the tail veins of mice 2 weeks after boost immunization. Serum from each immunized animal were heat-inactivated. HSV-2-specific neutralizing antibody titers were determined. The results represent average titers f SEM (SEM, un-paired Student's t-tests).

Investigating the Vaccine Efficacy of CJ2-gD2/gB2 Against HSV-2 Genital Infection in Mice CJ2-gD2/gB2 is as effective as CJ2-gD2 in eliciting HSV-2-specific neutralizing antibodies in immunized mice. The ability of CJ2-gD2/gB2 to elicit anti-HSV-2-specific neutralizing antibodies was determined in mice immunized with CJ2-gD2/gB2 or CJ2-gD2 at a dose of $2 \times 10^6$ PFU or $5 \times 10^5$ PFU. As shown in FIG. 7, the HSV-2-specific neutralization antibody titer in mice immunized with CJ2-gD2/gB2 were on average of 300 at a low dose ($5 \times 10^5$ PFU) and 600 at the high dose ($2 \times 10^6$ PFU), while the HSV-2-specific neutralization antibody titer in mice immunized with CJ2-gD2 was on average of 629 at a high dose, and 325 at a low dose.

Figure 8A:
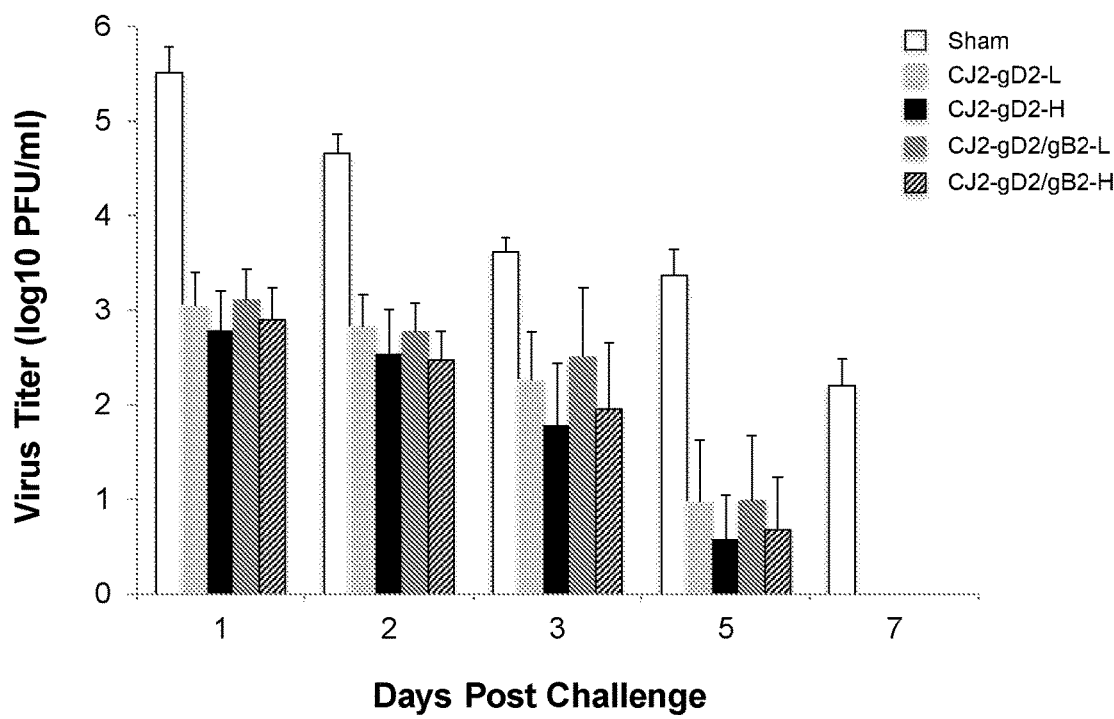
FIGS. 8A-8C present results indicating that CJ2-gD2/gB2 is as effective as CJ2-gD2 in protecting against HSV-2 genital infection and disease. This is unexpected, given that CJ2-gD2/gB2 lacks the antigen gG2. Female BALB/c mice treated as described for FIG. 7 were pre-treated with medroxyprogesterone at 2 weeks post boost immunization followed by intravaginal challenge with $5 \times 10^5$ PFU of HSV-2 strain G 5 days later. (A) Vaginal swabs were taken on days 1, 2, 3, 5, and 7 post-challenge. Infectious virus titers in swab materials were assessed by standard plaque assay on Vero cell monolayers. Viral titers are expressed as the mean±SEM in individual vaginal swabs. (B and C) After challenge with wild-type HSV-2, individual mice were observed during a 21-day follow-up period for the incidence of genital and disseminated HSV-2 disease using the following scale: 0=no sign, 1=slight genital erythema and edema, 2=moderate genital inflammation, 3=purulent genital lesions and/or systemic illness, 4=hind-limb paralysis, and 5=death (B), and percent survival (C).
Figure 8B:
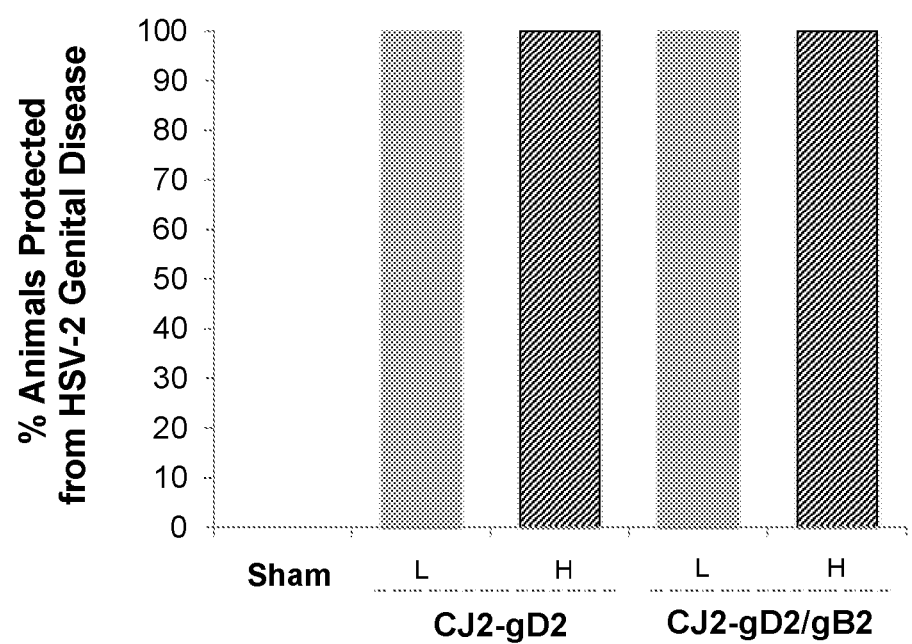
Figure 8C:
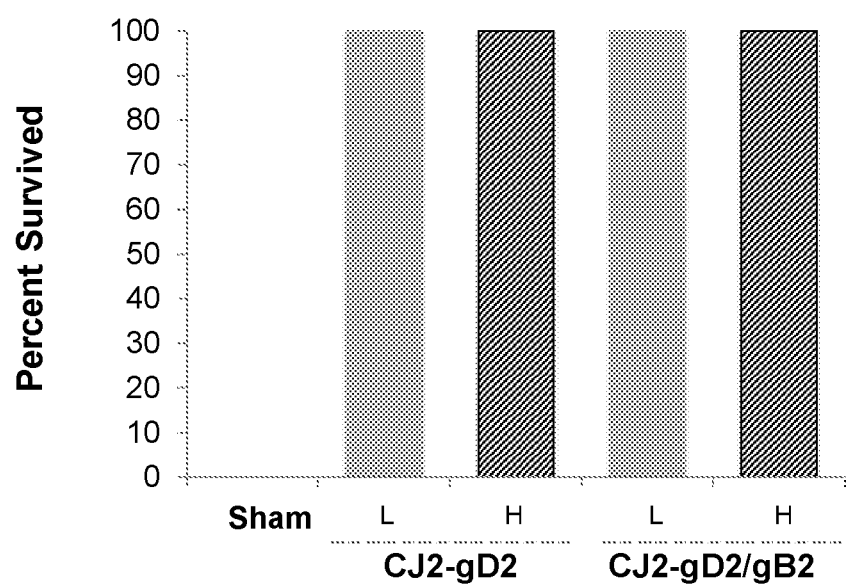
Figure 9A:
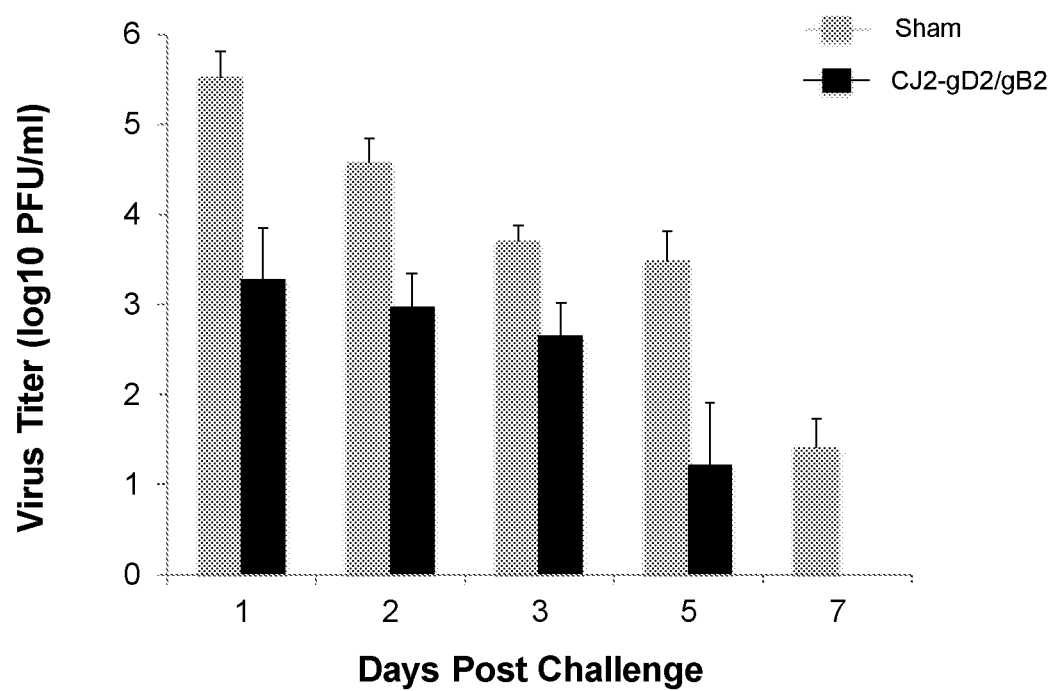
FIGS. 9A-9C present results showing that immunization with CJ2-gD2/gB2 can elicit durable protective immunity against HSV-2 genital infection and disease, and that this occurs even in the absence of gG2. Seven to eight week old female BALB/c mice were either sham-immunized (n=8) or immunized with CJ2-gD2/gB2 (n=8) at a dose of $1 \times 10^6$ PFU/mouse as described earlier. Mice were boosted with the same dose of CJ2-gD2/gB2 on days 14 and 28 post primary immunization. Five months after the third immunization, mice were challenged intravaginally with HSV-2 strain G at $5 \times 10^5$ PFU/mouse. (A) Vaginal swabs were taken on days 1, 2, 3, 5, and 7 post-challenge. Infectious viruses in swab materials were assessed by standard plaque assay on Vero cell monolayers. Viral titers are expressed as the mean±SEM in individual vaginal swabs. (B and C) After challenge with wild-type HSV-2, individual mice were observed during a 21-day follow-up period for the incidence of genital and disseminated HSV-2 disease (using a scale described in FIG. 8) (B) and percent survival (C).
Figure 9B:
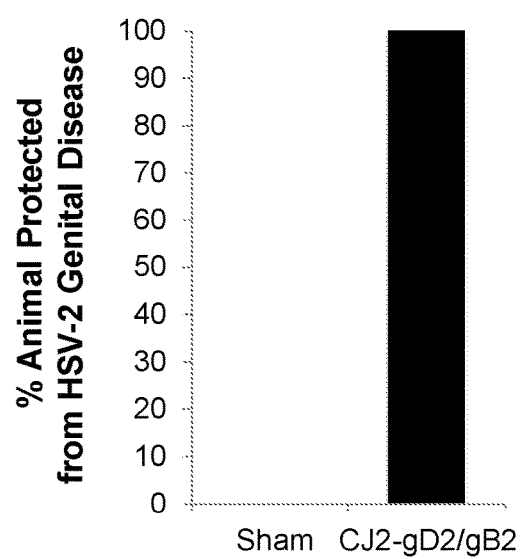
Figure 9C:
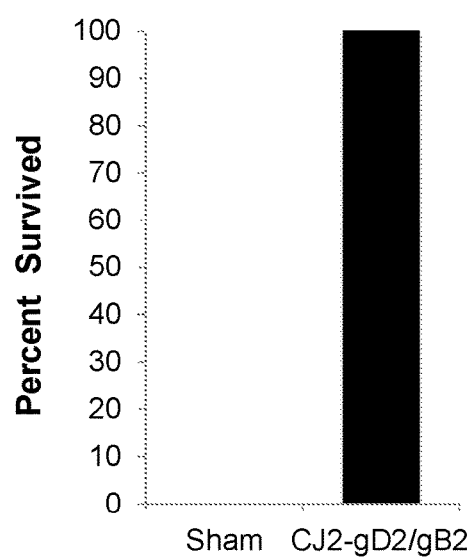
Figure 10:
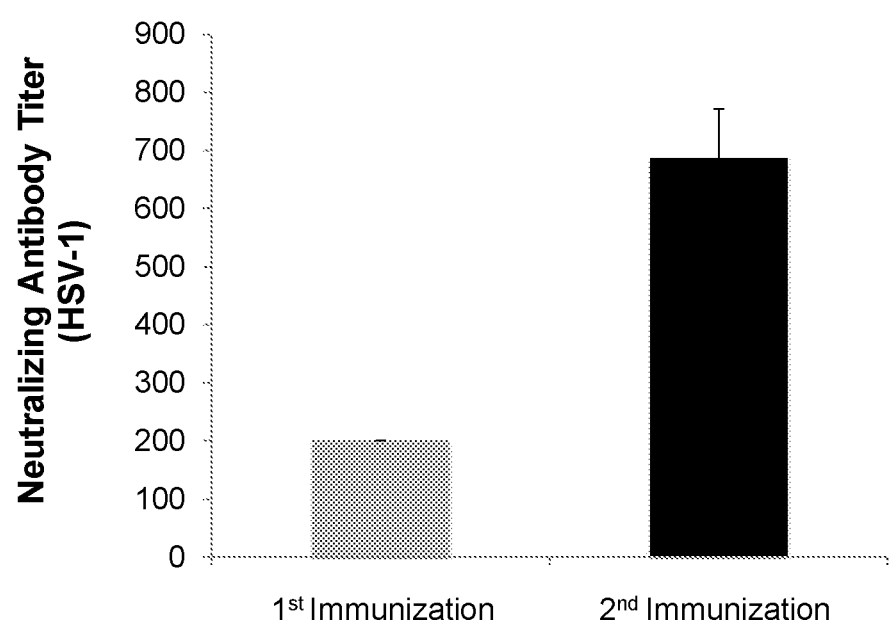
FIG. 10 shows the induction of HSV-1-neutralizing antibody responses. 7- to 8-week-old female BALB/c mice were immunized with CJ2-gD2/gB2 at a dose of $2 \times 10^6$ PFU/mouse (n=7). Individual groups of mice were boosted with CJ2-gD2/gB2 at the same dose 2 weeks later. Blood was obtained from the tail veins of mice 2 weeks after primary immunization (gray bar) as wells as 2 weeks after boost immunization (black bar). Heat-inactivated serum from each CJ2-gD2/gB2-immunized mouse after boost immunization was assayed individually for HSV-1-specific neutralizing antibody titers on Vero cell monolayers. Heat-inactivated pooled serum was used for determining HSV-1-specific neutralizing antibody response after primary immunization. The results represent average titers f SEM.
Figure 11A:
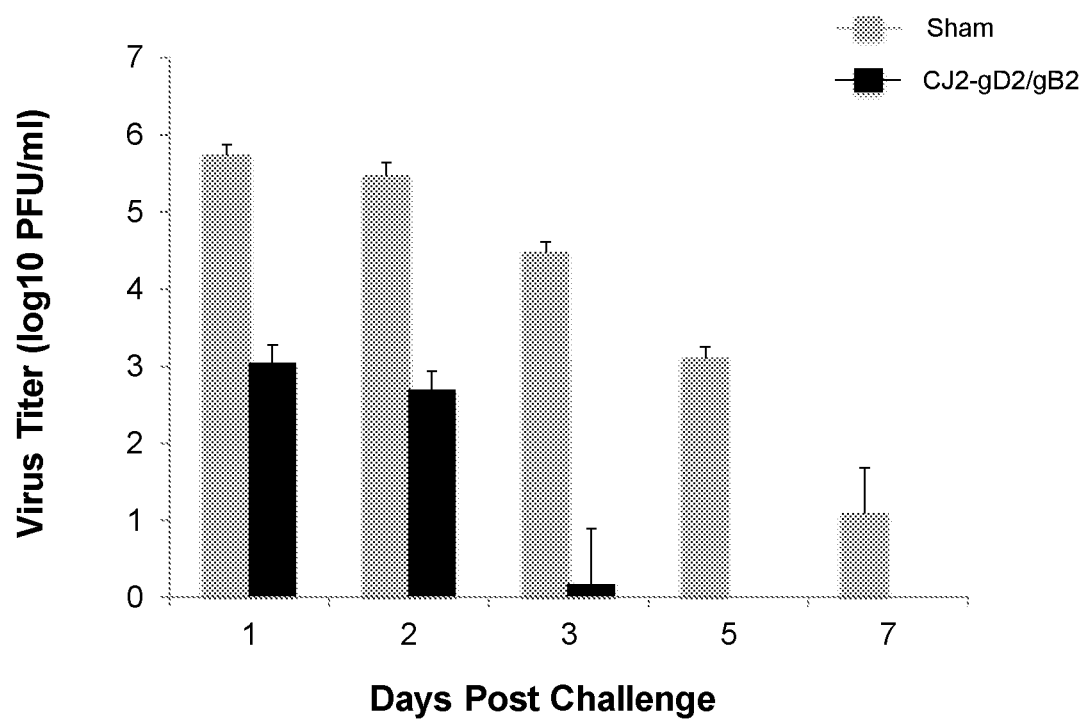
FIGS. 11A-11C present results indicating that immunization with CJ2-gD2/gB2 can effectively protect mice against HSV-1 genital infection and disease. Female BALB/c mice described for FIG. 10 were pre-treated with medroxyprogesterone at 2 weeks post boost immunization followed by intravaginal challenge with $5 \times 10^5$ PFU of HSV-1 strain mP 5 days later. (A) Vaginal swabs were taken on days 1, 2, 3, 5, and 7 post-challenge. Infectious virus titers in swab materials were assessed by standard plaque assay on Vero cell monolayers. Viral titers are expressed as the mean±SEM in individual vaginal swabs. (B and C) After challenge with wild-type HSV-1, individual mice were observed during a 21-day follow-up period for the incidence of genital and disseminated HSV-1 disease (using scale in FIG. 8) (B) and percent survival (C).
Figure 11B:
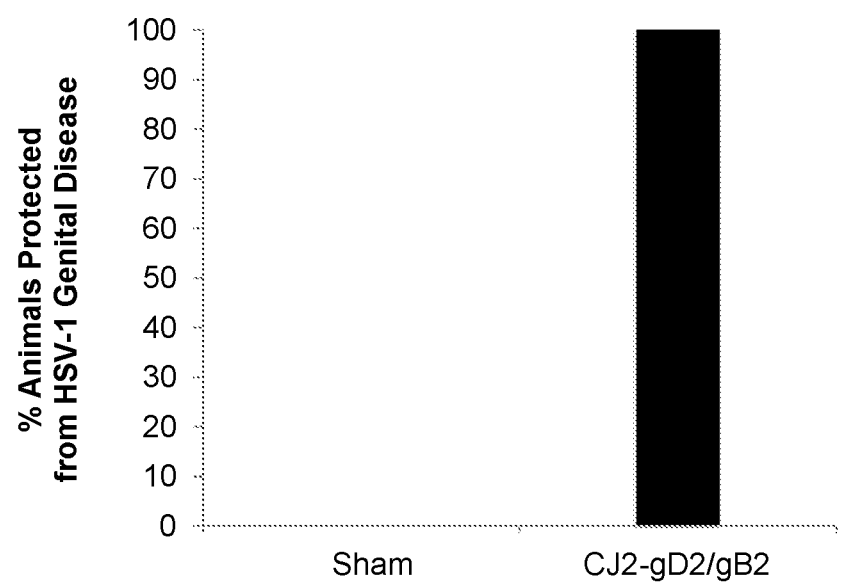
Figure 11C:
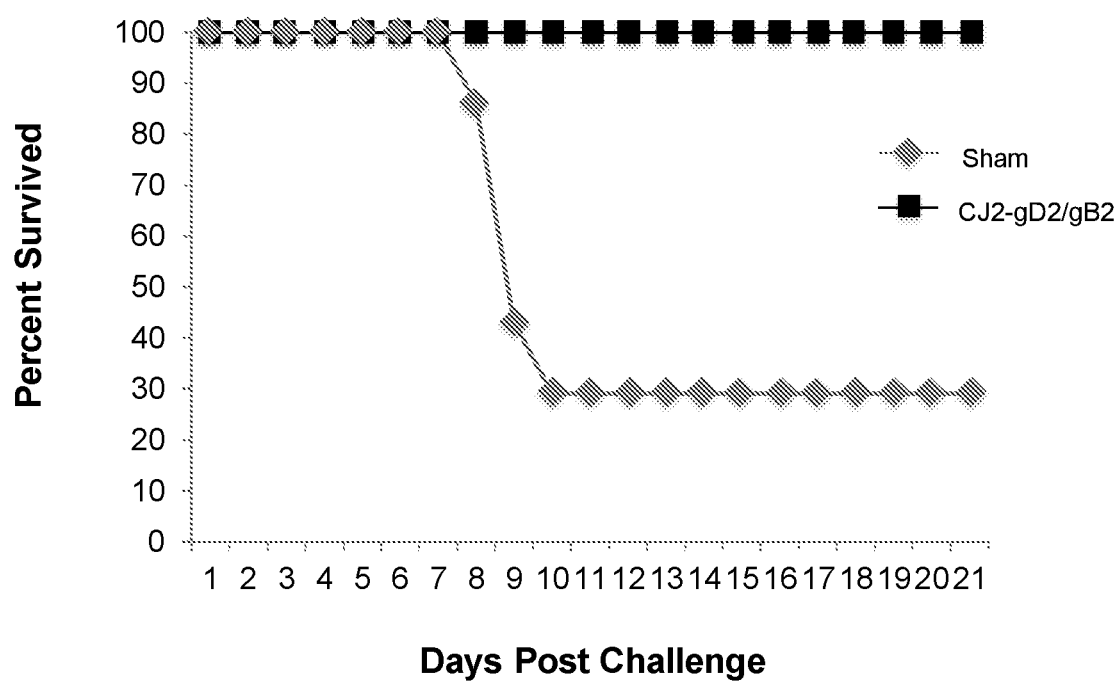
Figure 12:
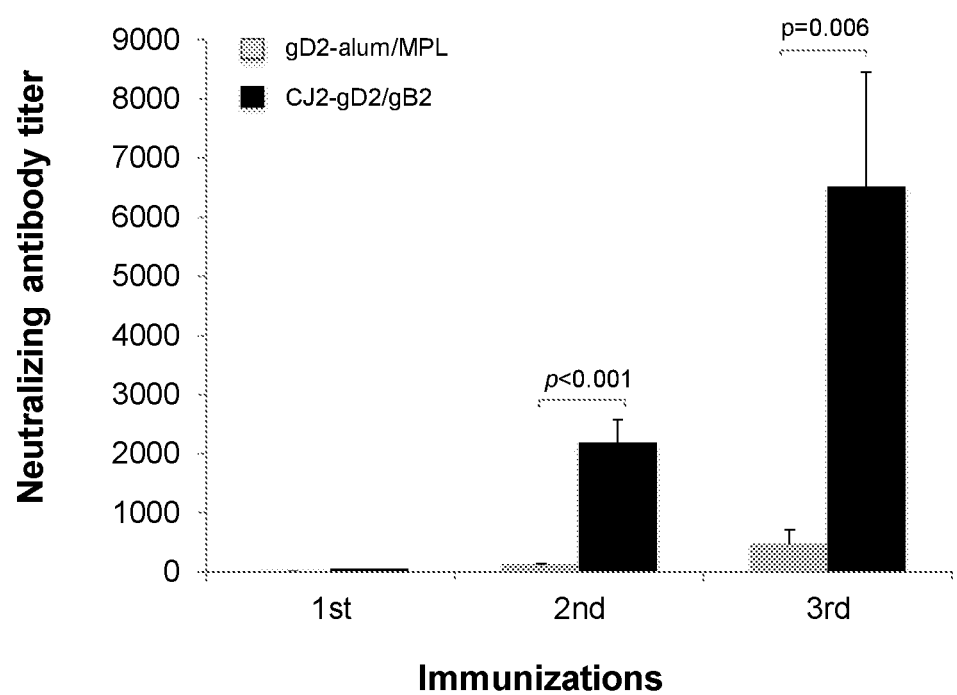
FIG. 12 presents results indicating that CJ2-gD2/gB2 is significantly more effective than gD2-alum/MPL subunit vaccine in eliciting an HSV-2-specific neutralizing antibody response in immunized guinea pigs. Female Hartley guinea pigs were randomly assigned to three groups of six animals each in the first experimental group and three groups of six to eight each in the second experimental group. They were either immunized with 5 µg of purified recombinant gD2 freshly formulated with 12.5 µg of MPL and 125 µg of alum or immunized with CJ2-gD2/gB2 at a dose of $5 \times 10^6$ PFU on days 0, 14, and 28. Blood was taken at 2 weeks after the first, second, and third immunizations. Heat inactivated serum from each animal was assayed individually for HSV-2-specific neutralizing antibody titers on Vero cell monolayers. The results represent average titers±SEM.
Figure 13A:
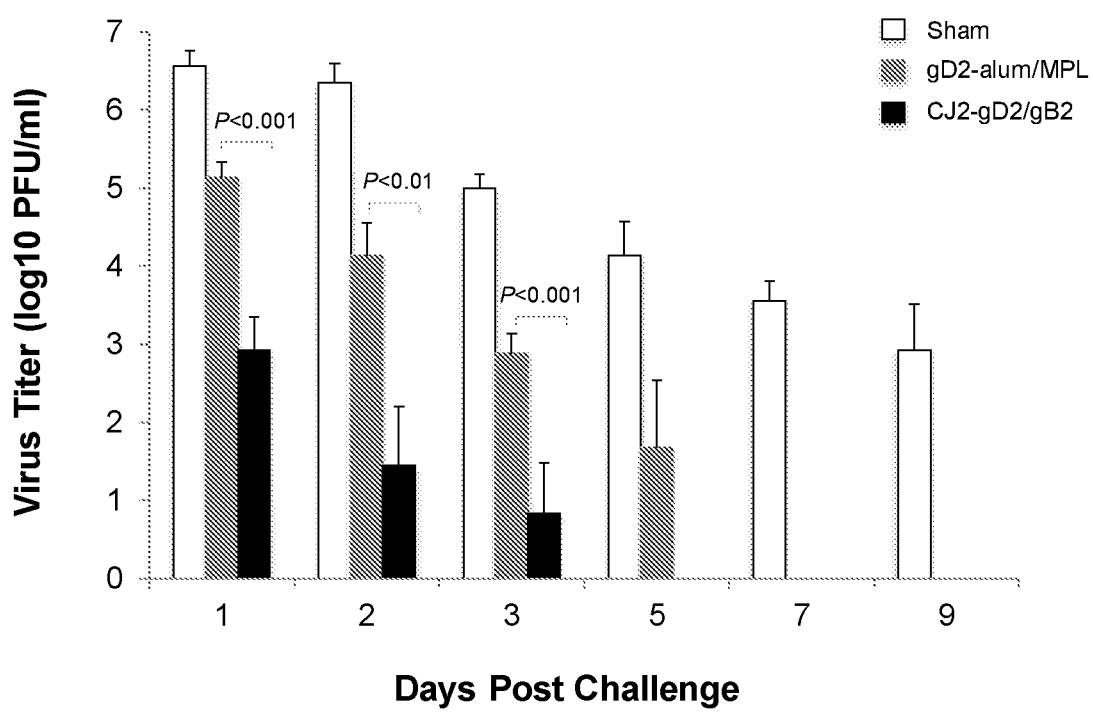
FIGS. 13A and 13B present results demonstrating that CJ2-gD2/gB2 is significantly superior to gD2-alum/MPL subunit vaccine in protecting against intravaginal wild-type HSV-2 infection in guinea pigs. Female guinea pigs sham-immunized with DMEM or immunized with gD2-alum/MPL or CJ2-gD2/gB2 described in FIG. 12 were challenged intravaginally with $5 \times 10^5$ PFU of HSV-2 strain MS. Vaginal swabs were taken on days 1, 2, 3, 5, 7, and 9 post-challenge. Infectious virus on swab materials was determined by standard plaque assay in Vero cells. Viral yields are expressed as the means f SEM for individual swabs (A). The duration of viral shedding is represented as the mean number of days during which infectious virus was detected in vaginal swabs±SEM (B). Statistical method (SEM, un-paired Student's t-tests) used for comparisons. P-value equal to or greater than 0.05 is significant.
Figure 13B:
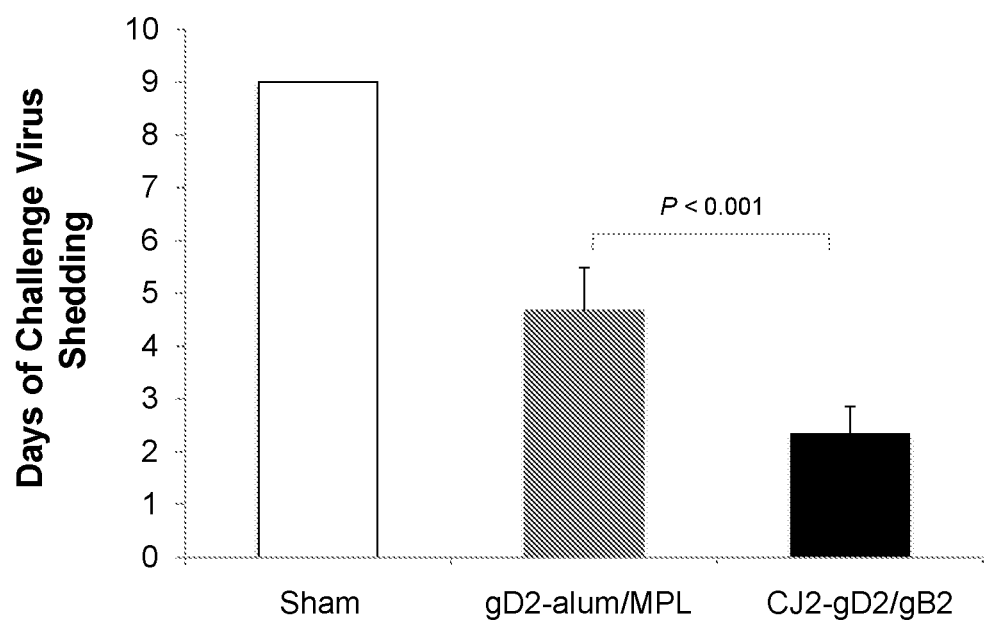

CJ2-gD2/gB2 is as effective as CJ2-gD2 in induction of protective immunity against HSV-2 genital infection and disease in mice. The results in FIG. 8 show that immunization with CJ2-gD2/gB2 or CJ2-gD2 at both high and low doses completely protects mice from development of local genital lesions (FIG. 8B) and these mice exhibit no signs of systemic disease after challenge with wild-type HSV-2, whereas 100% of mock-vaccinated mice developed severe genital lesions and succumbed to wild-type HSV-2 infection by day 9 post-challenge (FIG. 8C). The yields of challenge virus were 418-, 155-, and 495-fold lower in mice immunized with a high dose of CJ2-gD2/gB2 compared with those in mock-immunized mice on day 1 (P<0.001), day 2 (P<0.001), and day 5 (p=0.002) post challenge, respectively (FIG. 8A). The HSV-2 viral shedding was reduced 542-, 134-fold, and 634-fold in mice immunized with CJ2-gD2 at the same dose on day 1 (p=0.002), day 2 (p<0.001), and day 5 (p<0.001) post challenge than mock-immunized mice, respectively.

Immunization with CJ2-gD2/gB2 at a low dose also led to 251-, 77- and 241-fold reduction in the viral titer of challenge virus recovered from vaginal swabs on day 1 (P<0.001), day 2 (P<0.001), and day 5 (p<0.001) compared with those from mock-immunized mice, respectively. Similar results were observed in mice immunized with a low dose of CJ2-gD2.

Figure 14A:
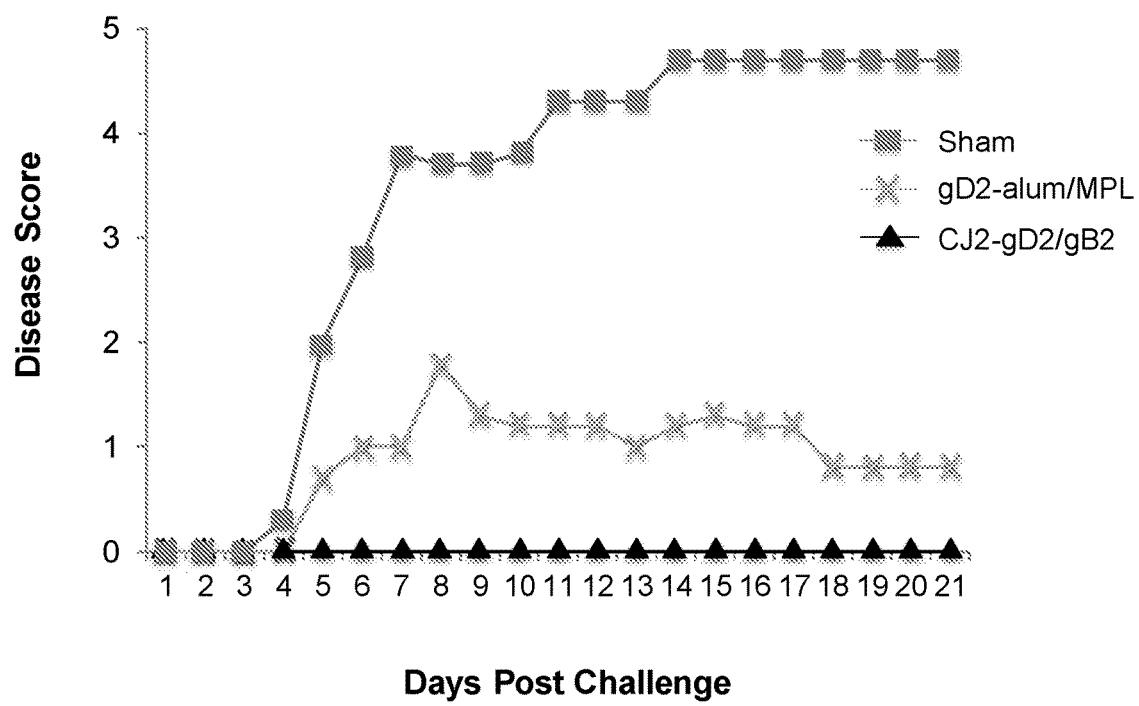
FIGS. 14A-14C present results indicating that immunization with CJ2-gD2/gB2 can provide a full protection against primary HSV-2 genital disease in guinea pigs. Sham-immunized, gD2-alum/MPL- or CJ2-gD2/gB2-immunized guinea pigs described in FIG. 13 were monitored daily during the first 21-day follow-up period for the incidence of genital and disseminated HSV-2 disease. The severity of disease was scored as follows: 0, no sign of disease; 1, redness or swelling; 2, a few small vesicles; 3, several large vesicles; 4, several large ulcers with maceration; 5, paralysis; and 6, death. Presented are the average disease scores for the first 21 days after challenge (A), the percent of animals that experienced primary herpetic disease (B), and the percent of survival until day 60 after challenge (C).
Figure 14B:
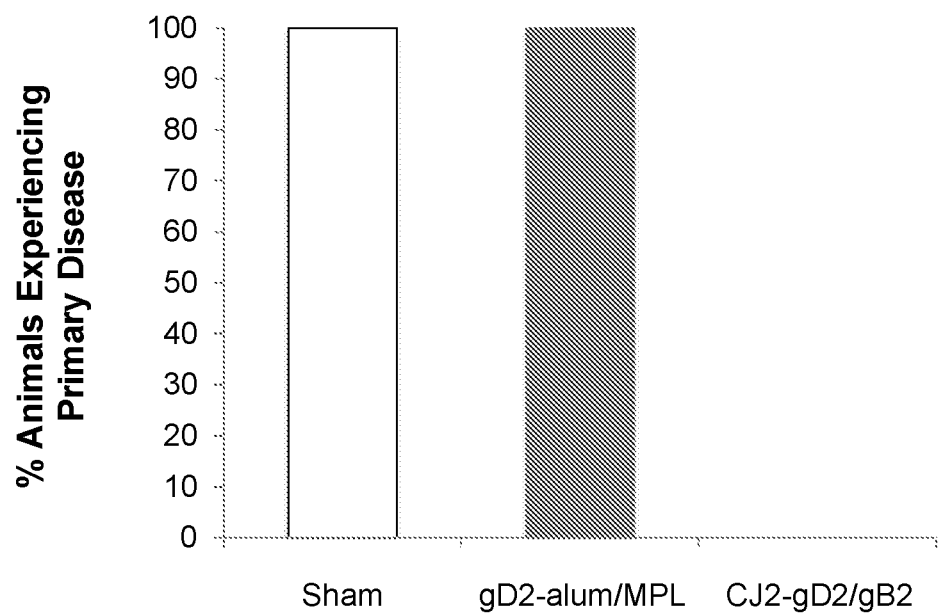
Figure 14C:
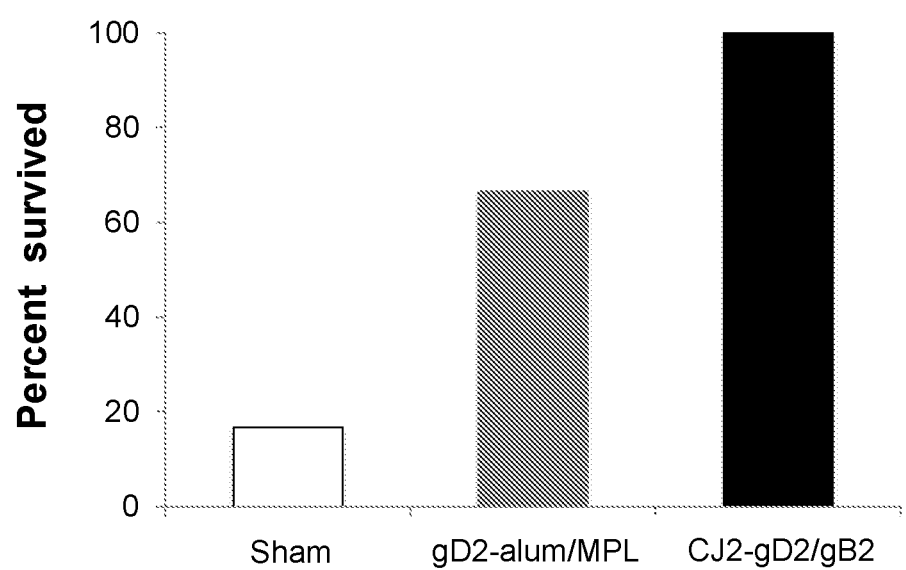

The experimental results described above show that the vaccine efficacy of CJ2-gD2/gB2 and CJ2-gD2 is essentially the same at the tested immunization doses. Whether CJ2-gD2/gB2 at a lower immunization dose would offer a better protective immunity than CJ2-gD2 remains to be investigated. Similarly, whether the purified CJ2-gD2/gB2 vaccine construct, free of contamination with infected cell proteins, such as gB2, would provide superior vaccine efficacy to similarly purified CJ2-gD2 remains to be determined. In any case, we have determined that the absence of gG2 expression from the novel CJ2-gD2/gB2 vaccine does not remove its capacity to induce protective immunity to HSV2 infections and thus, we have generated a novel efficacious vaccine that also enables serological monitoring in a clinical setting to differentiate between infection with wild type HSV-2 and with the vaccine vector. This is a significant advancement in the field of HSV vaccines.

Immunization with CJ2-gD2/gB2 elicits long-term protective immune response against HSV-2 genital infection. Sixteen 7-8 week old female BALB/c mice were divided into 2 groups of 8 mice each. Mice were either sham-immunized or immunized with CJ2-gD2/gB2 at a dose of $1\times10^6$ PFU/mouse as described earlier. Mice were boosted with the same dose of CJ2-gD2/gB2 twice on days 14 and 28 post primary immunization, respectively. Five months after the third immunization, mice were challenged intravaginally with HSV-2 strain G at $5\times10^5$ PFU/mouse. Vaginal swabs were taken on days 1, 2, 3, 5, and 7 after challenge. Mice were observed during a 21-day follow-up period for the incidence of genital and disseminated HSV-2 disease.

The results presented in FIG. 9 show that immunization with CJ2-gD2/gB2 can offer an effective protective immune response against HSV-2 vaginal infection at 5 months post last immunization. Yields of challenge HSV-2 were reduced 178-fold on day 1 ($p<0.001$), 40-fold on day 2 ($p<0.001$), and 185-fold on day 5 ($p<0.001$) post-challenge in the immunized animals compared to the sham-immunized mice (FIG. 9A). No HSV-2 was detected in the vaginal swabs collected on day 7 post-challenge in the CJ2-gD2/gB2 vaccinated groups. While all sham-immunized mice died by day 9 post-challenge, none of CJ2-gD2/gB2-immunized animals experienced any signs of HSV-2 genital disease or neurological complications associated with HSV-2 infection (FIG. 9B, FIG. 9C).

Investigating the Vaccine Efficacy of CJ2-gD2/gB2 Against HSV-1 Genital Infection in Mice CJ2-gD2/gB2 can elicit a strong HSV-1-specific neutralizing antibody response in immunized mice. Results in FIG. 10 show that the HSV-1-specific neutralization antibody titer in mice immunized with CJ2-gD2/gB2 were on average 200 following primary immunization and reached an average of 686 at 2 weeks after boost immunization.

CJ2-gD2/gB2 is highly effective in induction of cross-protective immunity against HSV-1 genital infection and disease in mice. The results in FIG. 11 show that immunization with CJ2-gD2/gB2 completely protects mice from development of local genital lesions and systemic disease after challenge with wild-type HSV-1, whereas 100% of mock-vaccinated mice developed genital lesions (FIG. 11B) and 5 of 7 mice died from wild-type HSV-1 challenge infection (FIG. 11C). The yields of challenge virus were about 510-, 610-, and 20500-fold lower in CJ2-gD2/gB2-immunized mice than those mock-immunized mice on day 1 ($P<0.0001$), day 2 ($P<0.0001$), and day 3 ($p<0.0001$) post challenge, respectively (FIG. 11A). None of CJ2-gD2/gB2-immunized mice had detectable virus shedding on day 5 post-infection, while all mock-immunized animals continued to shed virus at an overall average yield of 1,270 PFU/ml.

Investigating the Vaccine Efficacy of CJ2-gD2/2B2 Against HSV-2 Genital Infection in Guinea Pigs CJ2-gD2/gB2 is significantly more efficient than gD2-subunit vaccine in eliciting HSV-2-specific neutralizing antibody response. Adjuvanted gD2 protein has previously been used by others in advanced clinical trials, as described above. The results presented in FIG. 12 show that the neutralizing antibody titers detected in the CJ2-gD2/gB2-immunized animals are 20- and 14-fold higher than those detected in the gD2-alum/MPL-immunized animals after the second and third immunizations, respectively ($p<0.0001$). There was a significant increase in the HSV-2 neutralizing antibody titers from the first to the second vaccination with an average titer of ~2,167 after the second immunization and 6,500 after the third immunization. The average HSV-2 neutralizing antibody titer in gD2-alum/MPL-immunized animals was 108 after the second immunization and ~467 after the third immunization. No HSV-2-specific neutralizing antibody was detected in serum from the sham-immunized animals at 1:10-dilution.

CJ2-gD2/gB2 is significantly more effective than gD2-alum/MPL in protecting against acute replication of challenge HSV-2 as well as primary and recurrent HSV-2 genital disease. The sham-immunized and immunized animals described in FIG. 12 were challenged intravaginally with wild-type HSV-2 as detailed in the Materials and Methods. The results in FIG. 13A showed that the yields of challenge virus in sham-immunized controls were ~$4.2\times10^6$ PFU/ml, ~$4.1\times10^6$ PFU/ml, and ~$1.6\times10^5$ PFU/ml on days 1, 2, and 3 post-challenge, respectively. The yields of challenge virus in the CJ2-gD2/gB2-immunized animals were 4,396- ($p<0.0001$), 80,059- ($p<0.0001$), and ~14,700 ($p<0.0001$)-fold lower than the sham-immunized animals on days 1, 2, and 3 post-challenge, respectively, and 166- ($p<0.0001$), 493- ($P<0.005$), and 113 ($p<0.0004$)-fold lower than in the gD2-alum/MPL-immunized animals on days 1, 2, and 3 post-challenge. By day 5, none of CJ2-gD2/gB2-immunized animals had detectable virus shedding, while all gD2-alum/MPL-immunized animals continued to shed virus. The duration of detectable challenge virus shedding was 2.3 days in the CJ2-gD2/gB2-immunized animals compared with 4.6 days in the gD2-alum/MPL group ($p=0.001$) and 9 days in the sham-immunized control ($p<0.0001$) (FIG. 13B).

The impact of immunization with CJ2-gD2/gB2 and gD2-alum/MPL in protecting against primary skin lesions as well as recurrent disease is summarized in FIG. 14. As shown in FIG. 14A, all the sham-immunized animals developed multiple genital herpetic lesions following challenge with wild-type HSV-2 and five of six animals succumbed to HSV-2 infection by day 14 post-challenge. None of CJ2-gD2/gB2 immunized animals exhibited signs of primary genital disease, while all gD2-alum/MPL-immunized animals experienced primary herpetic skin lesions with a total of 30 lesions detected between days 5 and 8 (FIG. 14B). Moreover, one of the gD2-alum/MPL immunized animals died on day 11 post-challenge and an additional animal had to be sacrificed on day 26 post-challenge due to the severity of local and systemic herpetic disease (FIG. 14C). Collectively, the results demonstrate that CJ2-gD2/gB2 is significantly superior to gD2-alum/MPL in protecting against HSV-2 primary genital disease in guinea pigs (FIG. 14B, p<0.0001).

Figure 15A:
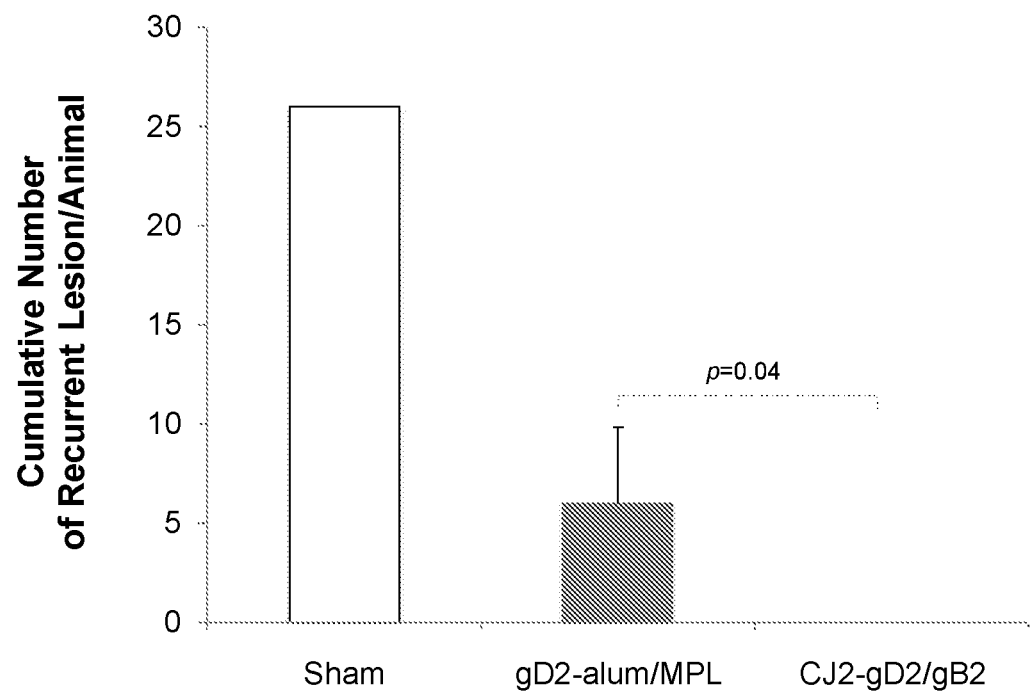
FIGS. 15A-C present results showing that immunization with CJ2-gD2/gB2 is highly effective in protecting against recurrent HSV-2 disease in guinea pigs. After challenge with wild-type HSV-2, individual guinea pigs described in the legend of FIG. 13 were monitored daily from days 21 to 60 post challenge for the incidence of recurrent genital and disseminated HSV-2 disease. Presented are the cumulative numbers of recurrent lesions per animal (A), average number of days that recurrent disease was experienced per animal (B), and the percent of animals that experienced recurrent disease between days 21 to 60 after challenge (C). Statistical method (SEM, un-paired Student's t-tests) used for comparisons. P-value equal to or greater than 0.05 is significant.
Figure 15B:
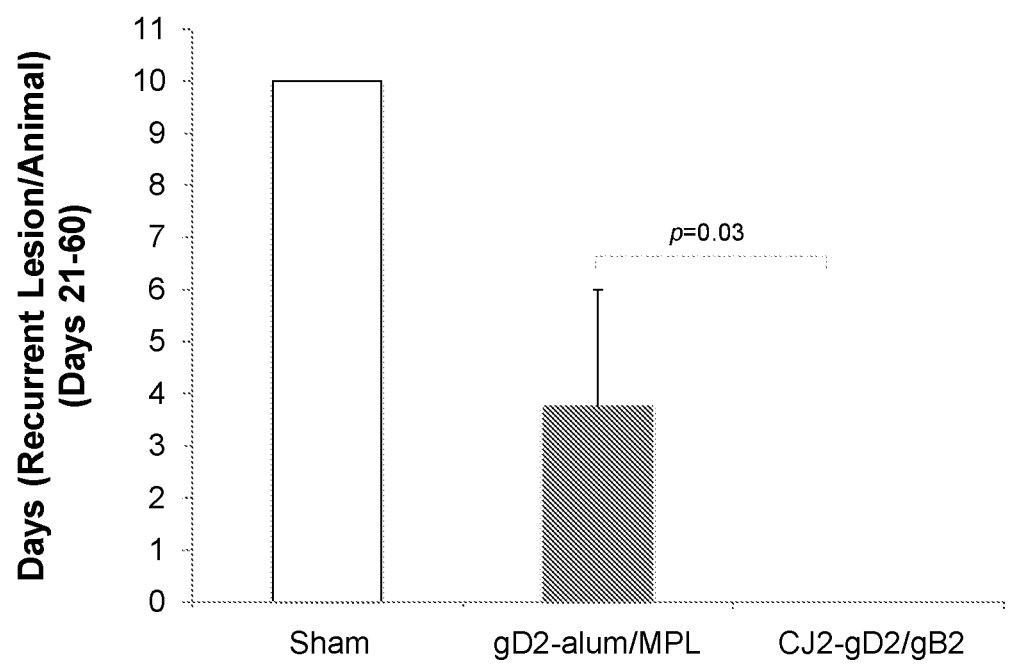
Figure 15C:
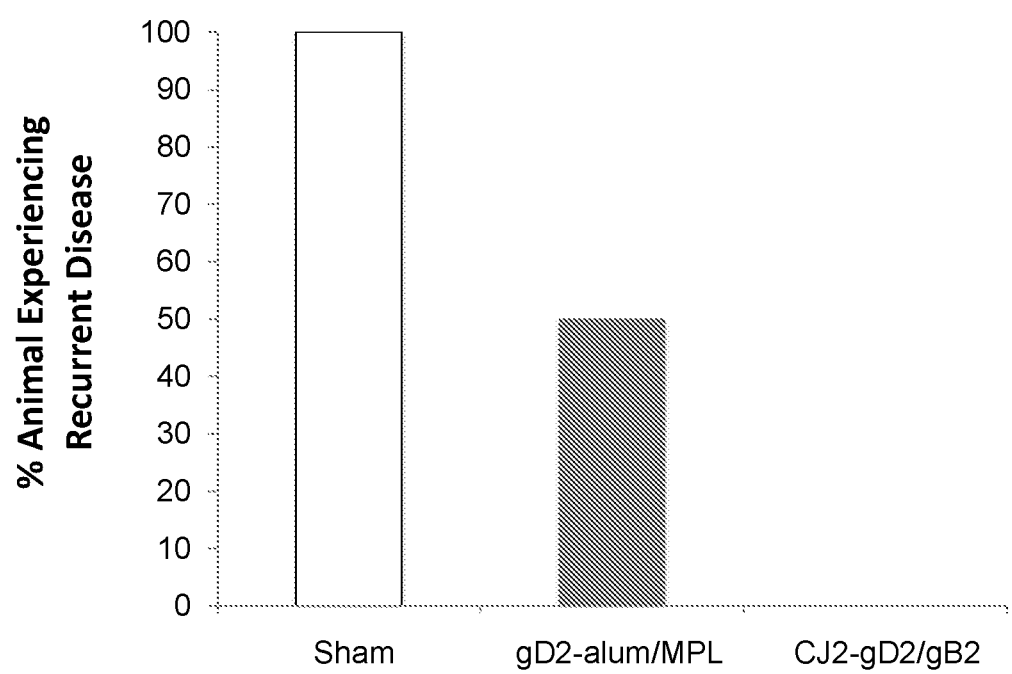

The results in FIG. 15 showed that immunization with CJ2-gD2/gB2 is significantly more effective than immunization with gD2-alum/MPL in protecting against recurrent HSV-2 genital disease in terms of cumulative recurrent lesions per animal (0 vs. 6, p=0.04) and days on which animals exhibited recurrent disease (0 vs. 3.75, p=0.03). In this experiment, none of the CJ2-gD2/gB2-immunized animals (e.g., guinea pigs) experienced detectable recurrent disease compared with 50% observed in the gD2-alum/MPL subunit vaccine group.

Example 2

Evaluation of CJ2-gD2/gB2 as a Therapeutic Vaccine Against HSV-2 Genital Herpes in Guinea Pigs Experimental Design Twenty-eight female Hartley guinea pigs were intravaginally infected with $5 \times 10^5$ PFU of HSV-2 strain MS/wp28 on day 0 as previously described (Zhang, et al., *PLOS ONE*, 9:e101373 (2014)). On day 21 post-intravaginal infection, the surviving animals (27 of 28) were divided into 2 groups based on the disease scores as well as titers of virus shedding on days 2 and 5. Animals in group 1 (n=13) were sham-immunized with DMEM, while animals in group 2 (n=14) were immunized with CJ2-gD2/gB2 at a dose of $5 \times 10^6$ PFU/animal in 50 µl. Animals were boosted with DMEM or CJ2-gD2/gB2 two weeks later. All animals were examined for clinical scores daily until day 70 post-challenge. The number of lesions for individual animals was counted and the disease was scored non-blindly as previously described: 0=no disease; I=redness or swelling; 2=a few small vesicles; 3=several large vesicles; 4=several large ulcers with maceration; 5=paralysis; and 6=death. Blood sample was collected from the saphenous veins on day 21, day 35 and day 49 post-intravaginal infection. On day 2 and 5 post-intravaginal infection, the vaginal mucosae were swabbed under anesthesia.

Materials and Methods

Intravaginal infection. Twenty-eight female Hartley guinea pigs were anesthetized and pre-swabbed followed by intravaginal infection with $5 \times 10^5$ PFU of HSV-2 strain MS/wp28 (A gift of Nigel Bourne, University of Texas Medical Branch, Tex.).

Analysis of acute vaginal shedding of wild-type HSV-2. Animals were anesthetized and vaginal mucosae were swabbed on days 2 and 5 post-intravaginal infection. Infectious virus on swab materials was assessed by standard plaque assay in 60-mm dishes of Vero cells. The minimum titer of challenge virus that could be detected was 1 PFU per original vaginal swab materials. For analysis of recurrent virus shedding, swabs were taken daily from days 27 to 52 post challenge. DNA was isolated from swab materials with the DNeasy tissue kit (Qiagen, Santa Clarita, Calif.), and stored at −20° C.

Clinical observations. After infection with wild-type HSV-2, the animals were examined daily until day 70 post-challenge. The number of lesions for individual animals was counted and the disease was scored non-blindly as previously described: 0=no disease; 1=redness or swelling; 2=a few small blisters; 3=several large vesicles; 4=several large ulcers with maceration; 5=paralysis; and 6=death.

Immunization. On day 21 post-intravaginal infection, surviving animals (27 of 28) were divided into 2 groups based on the disease scores as well as titers of virus shedding on days 2 and 5 such that animals in both groups experienced similar degrees of primary infection and disease (Table 1). Animals in group 1 (n=13) were sham-immunized with DMEM, while animals in group 2 (n=14) were immunized with CJ2-gD2/gB2 at a dose of $5 \times 10^6$ PFU/animal. Vaccine was administered i.m. into the quadriceps of the left and right hind limbs in a volume of 50 µl per injection. Guinea pigs were boosted with CJ2-gD2/gB2 two weeks later.

Neutralizing antibody assay. Blood was obtained from the saphenous veins on day 21 post-intravaginal infection, prior to immunization and 14 days after primary immunization as well as boost immunization. HSV-2-specific neutralizing antibody titers in serum collected from each animal were determined in the presence of complement as previously described (Zhang, et al., *PLOS ONE*, 9:e101373 (2014)).

Quantitative real-time PCR. For analysis of recurrent virus shedding, swabs were taken daily from days 27 to 52 post-intravaginal infection. DNA was isolated from swab materials with the DNeasy tissue kit (Qiagen, Santa Clarita, Calif.), and stored at −20° C. (see protocol in Attachment VII). The presence of HSV-2 DNA was quantified by real-time PCR (Applied Biosystems 7300 Real-Time PCR System) with 10 µl of 200-400 ng vaginal swab DNA and primers specific to the HSV DNA polymerase (Forward: 5' GCT CGA GTG CGA AAA AAC GTT C, Reverse: 5' CGG GGC GCT CGG CTA AC) as previously described (see protocol in Attachment VIII). The minimal copies of HSV-2 viral DNA that could reliably be detected were 2.5 to 5 copies per reaction.

Statistical analysis. For statistical analysis, un-paired Student's t-tests and un-paired Fisher's exact test were performed. Results are considered to be statistically significant when the P value is less than 0.05.

Results

Figure 16A:
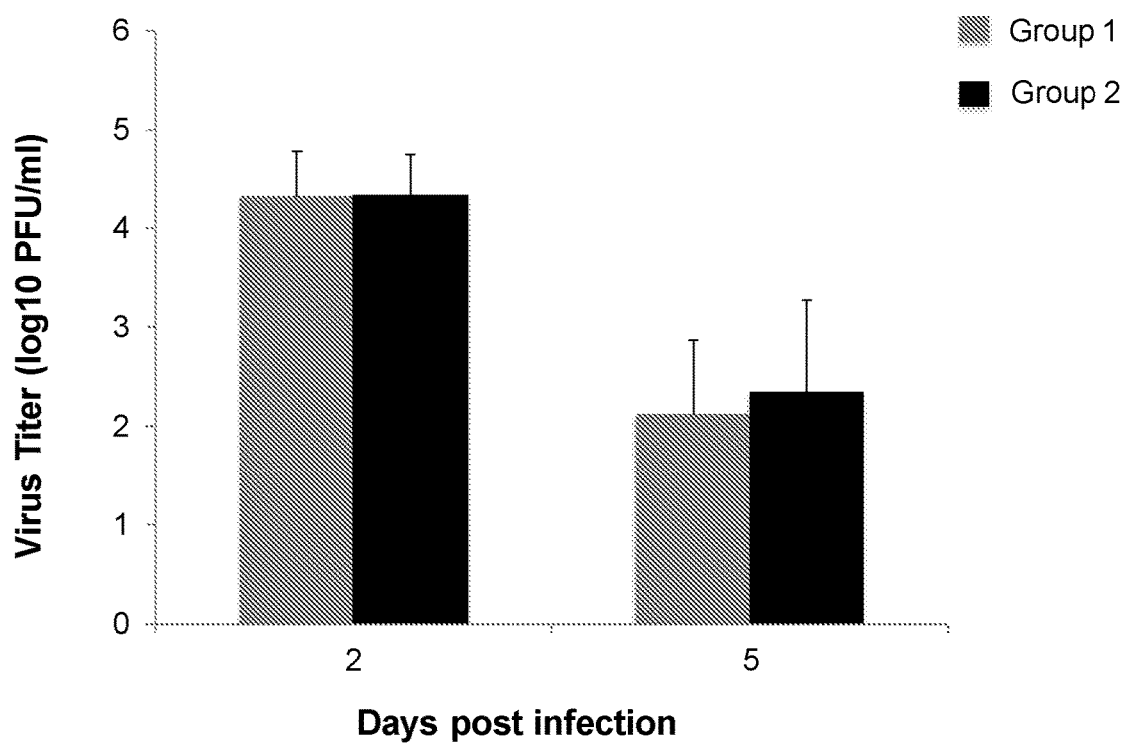
FIGS. 16A and 16B present results showing that intravaginal infection of guinea pigs with wild-type HSV-2 strain MS, wp/28 (displayed per two groups assigned for subsequent immunization as described in FIG. 17). Twenty-eight female Hartley guinea pigs were challenged with $5 \times 10^5$ PFU of HSV-2 strain MS/wp28. The intra-vaginal mucosae were swabbed on day 2 and 5 post infection and clinical symptoms were examined daily until day 70 post-challenge. (A) Mean infectious titers of swab samples at day 2 and 5 post infection, respectively, where the error bars represent the standard deviations (SD), (B) Mean clinical scores from day 1 to day 20 after challenge (before prime immunization at day 21).
Figure 16B:
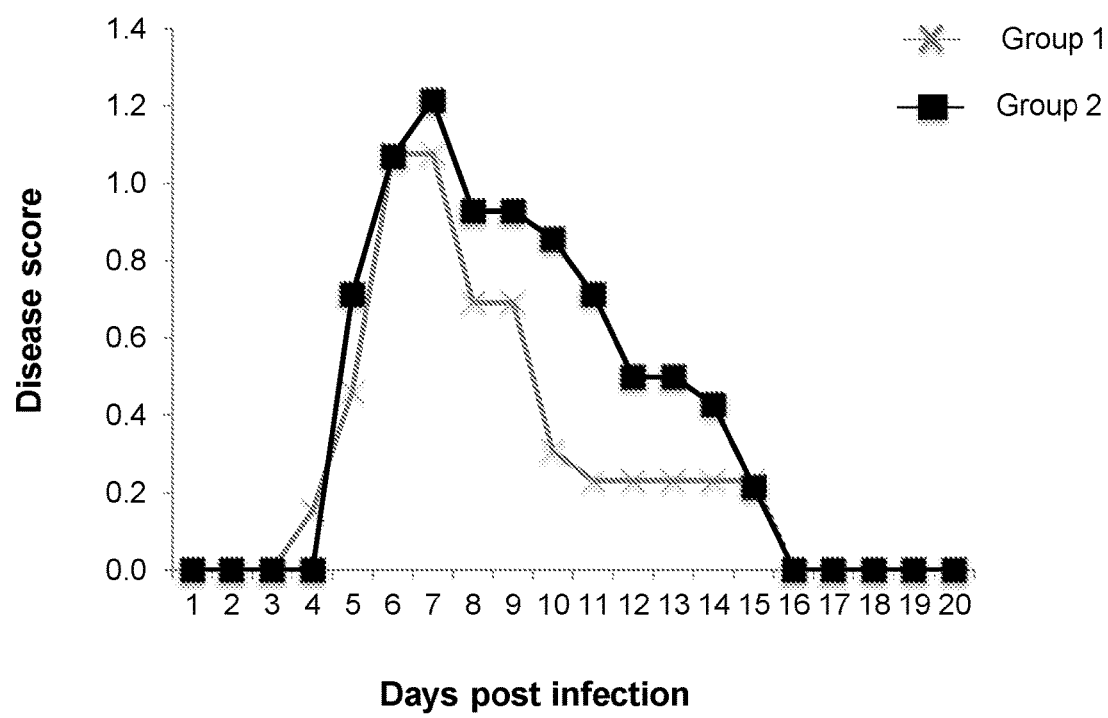

Intravaginal infection of guinea pigs with wild-type HSV-2 strain MS, wp/28. Of 28 intravaginally infected animals, 19 experienced primary herpetic disease and one animal was euthanized on day 8 post-intravaginal infection due to severity of disease. Nine animals did not experience primary HSV-2 genital disease with vaginal titers ranging from $4.4 \times 10e3$ PFU to $2.1 \times 10e4$ PFU/ml on day 2 post-challenge. The lowest vaginal titer for animals experiencing primary genital disease was $4.8 \times 10e3$ PFU/ml on day 2 post-intravaginal infection. On day 21 post-intravaginal infection, the 27 surviving animals were divided into 2 groups based on the disease scores as well as titers of virus shedding on days 2 and 5 (FIG. 16 and Table 1). Group 1 (n=13) was subsequently sham-immunized with DMEM, while animals in group 2 (n=14) were immunized with CJ2-gD2/gB2 at a dose of 5×10⁶ PFU/animal.

TABLE 1

Intravaginal infection of guinea pigs with wildtype HSV-2 strain MS, wp/28.

| | No. of guinea pigs[a] | Virus titer, mean ± SD (log10 PFU/ml) | | Primary disease | |
|---|---|---|---|---|---|
| | | Day 2 | Day 5 | Incidence[b] | severity[c] |
| All | 27/28 | 4.32 ± 0.44 | 2.25 ± 0.84 | 19/28 | 6.89 |
| Group 1 | 13/13 | 4.32 ± 0.47 | 2.12 ± 0.75 | 9/13 | 5.62 |
| Group 2 | 14/14 | 4.33 ± 0.43[d] | 2.34 ± 0.93[e] | 9/14 | 8.07[f] |

[a]No. of guinea pigs that were analyzed for virus titers on day 2 and 5/total no. of guinea pigs inoculated.
[b]No. of guinea pigs with clinical signs/total no. of guinea pigs inoculated.
[c]Cumulative mean clinical scores from day 1 to day 20 after challenge (before prime immunization at day 21)
[d]group 1 vs group 2 p = 0.98;
[e]group 1 vs group 2 p = 0.53;
[f]group 1 vs group 2 p = 0.33

Figure 17:
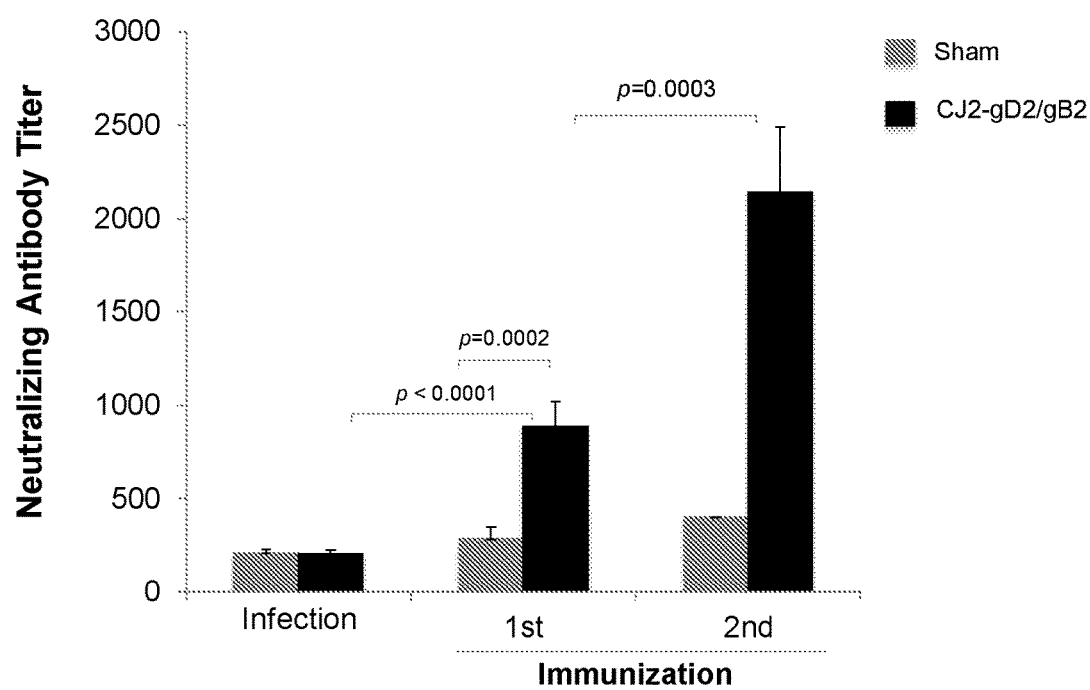
FIG. 17 presents results showing that CJ2-gD2/gB2 immunization induced HSV-2-specific neutralizing antibody responses in immunized guinea pigs. On day 21 post-intravaginal infection, 27 surviving animals were divided into 2 groups based on the disease scores as well as titers of virus shedding on days 2 and 5. Animals in group 1 (n=13, gray bars) were sham-immunized with DMEM, while animals in group 2 (n=14, black bars) were immunized with CJ2-gD2/gB2 at a dose of $5 \times 10^6$ PFU/animal. Blood samples were obtained from the saphenous veins on day 21 post-intravaginal infection and 14 days after primary immunization (day 35) and 14 days after boost immunization (day 49). Data represents the mean HSV-2-specific neutralizing antibody titers in corresponding groups where error bars represent the standard deviations.

Induction of HSV-2-specific neutralizing antibody response by CJ2-gD2/gB2 in the immunized animals. Anti-HSV-2 neutralizing antibody titers on day 21 post-intravaginal challenge are about the same in both groups, sham- and CJ2-gD2/gB2 immunized, while the neutralizing antibody titers detected in the CJ2-gD2/gB2 immunized animals are 3.12- and 5.36-fold higher than in sham-immunized animals after the first and second immunization, respectively (FIG. 17). There was a 2.42-fold increase in the HSV-2 neutralizing antibody titers from the first to the second vaccination (p<0.0003) with an average titer of 886 two weeks after the first immunization and 2183 two weeks after the second immunization. These results demonstrate that therapeutic immunization can significantly enhance the HSV-2-specific neutralizing antibody response in the immunized animals.

Figure 18A:
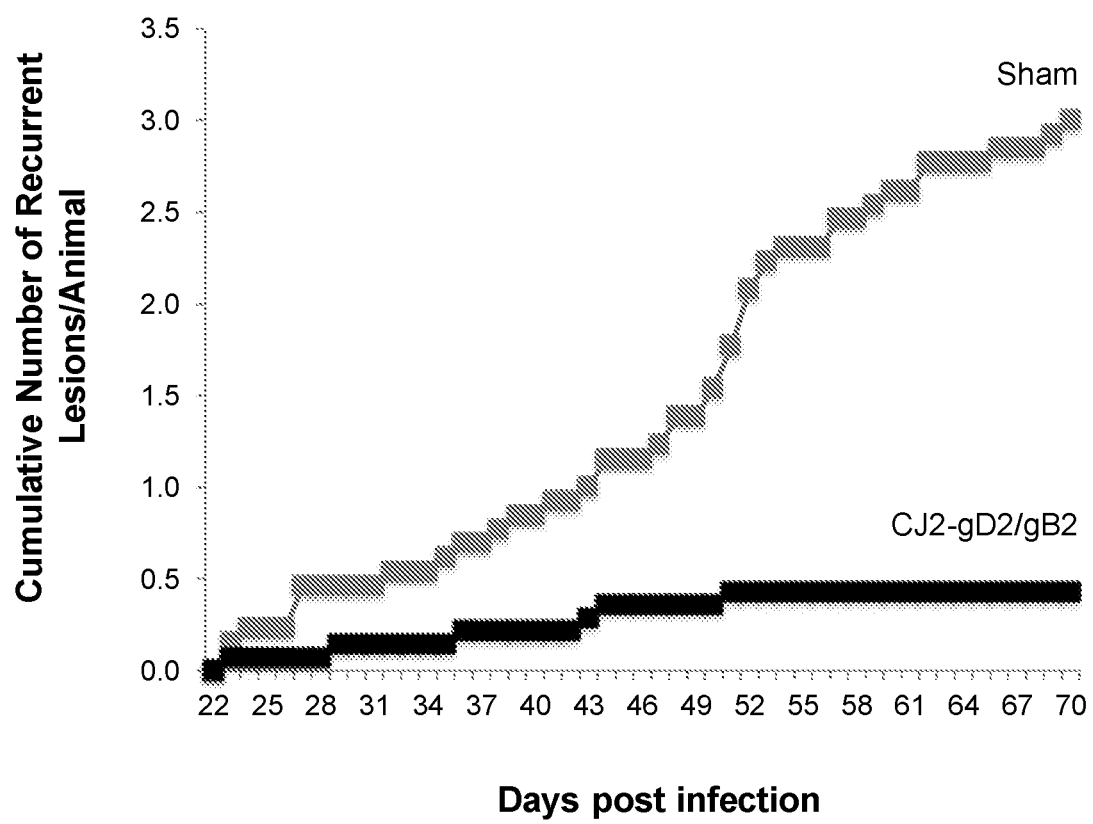
FIGS. 18A and 18B present results showing that CJ2-gD2/gB2 immunization effectively protects guinea pigs against recurrent genital disease. Recurrent genital skin lesions were monitored during days 21 to 70 post-intravaginal infection. (A) Data represent the percentage of animals experiencing recurrent disease in each group. (B) percent of animal experiencing recurrent disease.
Figure 18B:
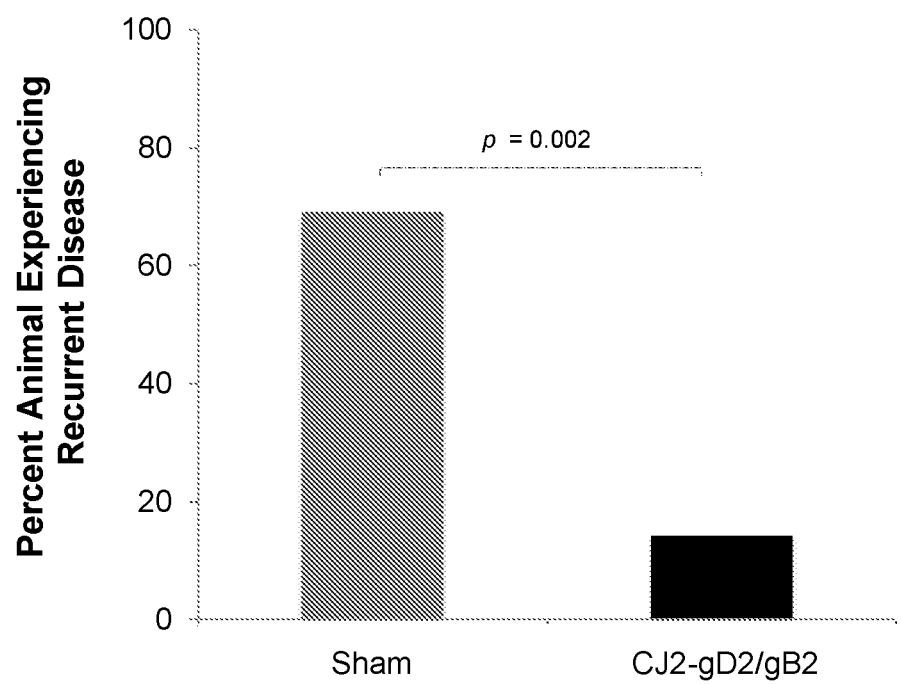
Figure 19A:
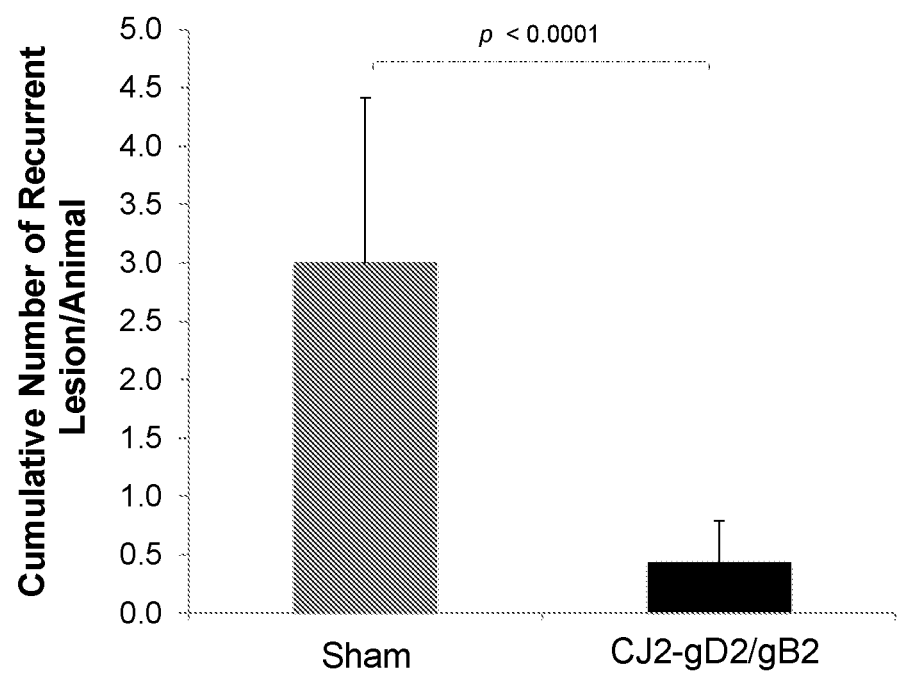
FIGS. 19A and 19B present results showing that CJ2-gD2/gB2 immunization effectively reduced recurrent genital lesions in guinea pigs. Animals' recurrent genital skin lesions were monitored daily during day 21 to 70 post-intravaginal infection. (A) Mean cumulative numbers of recurrent lesions per animal. (B) Mean frequency (days) of animal experiencing recurrent genital disease, where error bars represent the standard deviations.

Immunization with CJ2-gD2/gB2 is effective in protecting against recurrent genital disease in the immunized animals. The impact of immunization with CJ2-gD2/gB2 in protecting against recurrent genital skin lesions was monitored after prime immunization. Among sham-immunized animals, 9 of 13 animals (69%) experienced episodic recurrences during the 50 days follow-up (FIG. 18 and Table 2), while only 2 of 14 immunized animals (14%) had detectable recurrent skin lesions during this period (p=0.0063). The average of cumulative number of recurrent lesions per animal in the sham-immunized animals from days 21 to 70 post-intravaginal infection was 3/animal compared with 0.43/animal seen in the CJ2-gD2/gB2 immunized animals (p<0.0001) (FIG. 19A).

Figure 19B:
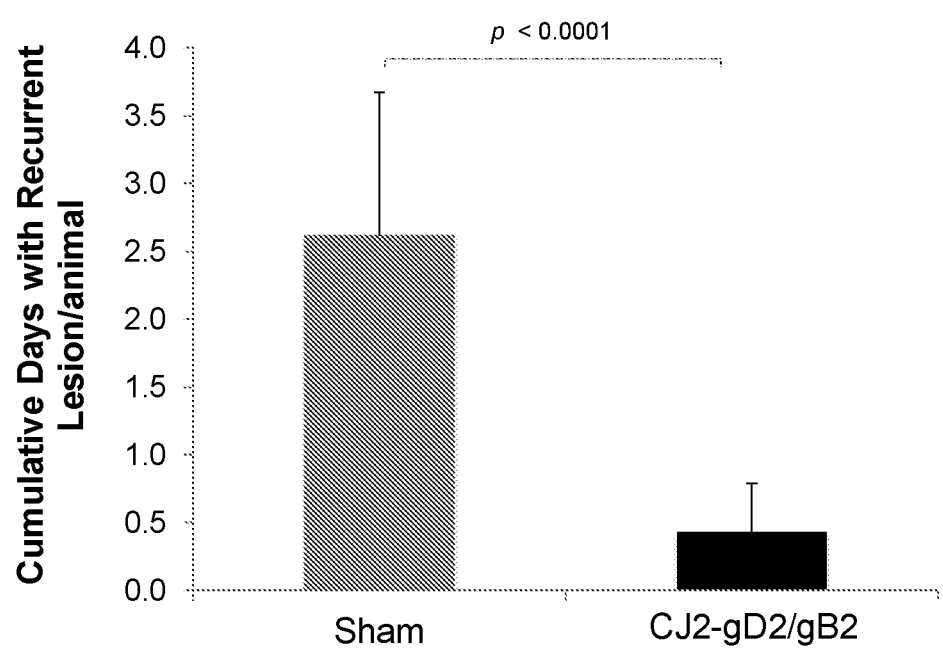

The frequency of recurrent genital disease was 2.62 days/animal in the sham-immunized animals compared with 0.43 days/animal in the CJ2-gD2/gB2 immunized animals (p<0.0001) (FIG. 19B). No recurrent disease was detected in CJ2-gD2/gB2 immunized animals until 9 days after the second immunization. Collectively, the results show that therapeutic immunization with CJ2-gD2/gB2 is effective in protecting against recurrent HSV-2 genital disease, i.e. the number of animals experiencing episodic recurrences, the cumulative number of recurrent lesions and the duration of recurrent disease were reduced significantly.

Figure 20A:
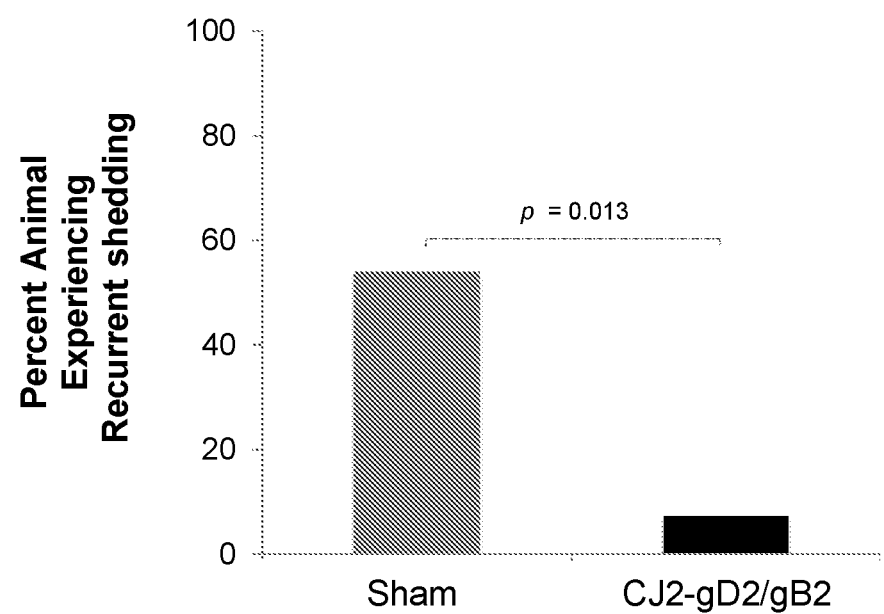
FIGS. 20A and 20B present results showing that CJ2-gD2/gB2 immunization effectively reduced recurrent viral shedding. Animals' intra-vaginal mucosae were swabbed daily from day 27 to 52 post-intravaginal infection. HSV-2 viral DNA copies in swabbing samples were detected by Real-time PCR analysis. (A) Percentage of the animals that experienced recurrent virus shedding within each group. (B) Mean cumulative days of recurrent viral shedding per animal within each group, where error bars represent the standard deviations.
Figure 20B:
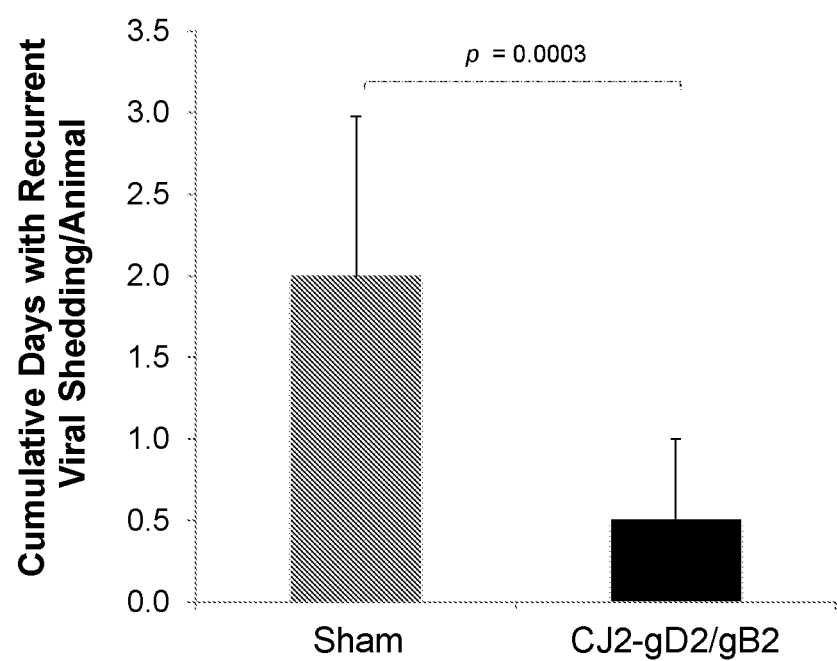
Figure 21:
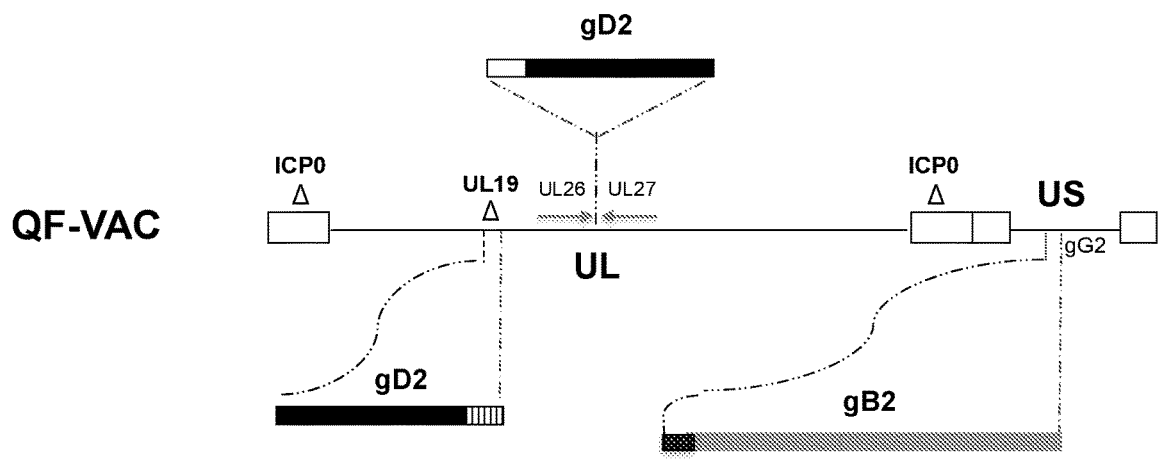
FIG. 21 shows a schematic of QF-VAC, an exemplary replication incompetent HSV, made incompetent by essential gene deletion. The replication incompetent HSV is a UL19 (VP5) deletion mutant comprising 1 of 2 recombinant copies of gD2 under tetO-containing HSV-1 ICP27 promoter at the UL19 locus; and the second copy of recombinant gD2 in a one directional expression cassette in a UL26/UL27 intergenic region. The replication incompetent HSV is an ICP0 and a gG2 deletion mutant with two copies of gD2 under tetO-containing immediate-early promotes (and at least one copy is under tet-O)-containing HSV-1 ICP4 promoter. The gG2 gene is replaced by the codon-optimized gB2 gene under the control of the tetO-bearing HSV-1 ICP0 promoter, as described in FIG. 3 legend.

Immunization with CJ2-gD2/gB2 is effective in reducing recurrent virus shedding. One of fourteen CJ2-gD2/gB2 immunized animals (7%) had detectable virus shedding for a total of 7 days, while seven of thirteen sham-immunized animals (53.8%) experienced detectable virus shedding for a total of 26 days (FIG. 20 and Table 2). These results indicate that therapeutic immunization with CJ2-gD2/gB2 is also effective in protecting against recurrent virus shedding in the immunized animals compared to sham-immunized control in terms of percent of animals experiencing detectable virus shedding (p=0.013) and frequency (p=0.0003) in recurrent virus shedding.

TABLE 2

Overview of effects of CJ2-gD2/gB2 vaccine on recurrent disease and viral shedding in the genital tract.

| | Recurrent disease | | | Viral shedding | | |
|---|---|---|---|---|---|---|
| Immunized Group | Incidence[a] | Frequency, mean ± SD[b] | Quantity, mean[c] | Incidence[d] | Frequency, mean ± SD[e] | Quantity, mean[f] |
| Sham | 9/13 | 2.62 ± 3.82 | 3 | 7/3 | 2.0 ± 3.51 | 2 |
| CJ2-gD2/gB2 | 2/14[g] | 0.43 ± 5.10[h] | 0.43[i] | 1/14[k] | 0.5 ± 1.87[m] | 0.5 |

[a]No. of guinea pigs with recurrent lesions/total no. of infected guinea pigs that could be evaluated.
[b]Days with recurrent lesions between days 21 and 70 post-intravaginal infection (days/animal).
[c]Cumulative no. of recurrent lesions between days 21 and 70 post-intravaginal infection (lesions/animal)
[d]No. of guinea pigs shedding virus into the genital tract/total no. of infected guinea pigs evaluated.
[e]Days on which viral DNA was detected in vaginal swabs between days 27 and 52 post-intravaginal infection (days/animal).
[f]No. of viral genomes equivalents detected by qPCR in vaginal swap samples.
[g]p = 0.0063;
[h]p < 0.0001;
[i]p < 0.0001;
[k]p = 0.013;
[m]p = 0.0003.

CONCLUSIONS

Therapeutic immunization of guinea pigs, previously infected with wild-type HSV-2, with CJ2-gD2/gB2 significantly elevated levels of HSV-2-specific neutralizing antibody responses. Importantly, therapeutic immunization led to a significant reduction in recurrent HSV-2 genital disease and recurrent virus shedding compared with sham-immunized control. The observed therapeutic vaccine efficacy in this study is considerably higher than previously reported with other HSV-2 vaccine candidates [1, 2, 3, and 4].

REFERENCES

1. Hoshino Y, Dalai S K, Wang K, Pesnicak L, Lau T Y, Knipe D M, Cohen J I, Straus S E. Comparative efficacy and immunogenicity of replication-defective, recombinant glycoprotein, and DNA vaccines for herpes simplex virus 2 infections in mice and guinea pigs. J Virol. 2005 January; 79(1):410-8. Erratum in: J Virol. 2005 April; 79(7):4554.
2. Awasthi S, Zumbrun E E, Si H, Wang F, Shaw C E, Cai M, Lubinski J M, Barrett S M, Balliet J W, Flynn J A, Casimiro D R, Bryan J T, Friedman H M. Live attenuated herpes simplex virus 2 glycoprotein E deletion mutant as a vaccine candidate defective in neuronal spread. J Virol. 2012 April; 86(8):4586-98.
3. Skoberne M, Cardin R, Lee A, Kazimirova A, Zielinski V, Garvie D, Lundberg A, Larson S, Bravo F J, Bernstein D I, Flechtner J B, Long D. An adjuvanted herpes simplex virus 2 subunit vaccine elicits a T cell response in mice and is an effective therapeutic vaccine in Guinea pigs. J Virol. 2013 April; 87(7):3930-42.
4. Veselenak R L, Shlapobersky M, Pyles R B, Wei Q, Sullivan S M, Bourne N. A Vaxfectin(®)-adjuvanted HSV-2 plasmid DNA vaccine is effective for prophylactic and therapeutic use in the guinea pig model of genital herpes. Vaccine. 2012 Nov. 19; 30(49):7046-51.

Example 3

Evaluation of Purified CJ2-gD2/gB2 Virus as a Prophylactic Vaccine Against HSV-2 Genital Herpes Infection in Mice Materials and Methods Virus purification. Purification of CJ2-gD2 and CJ2-gD2/gB2 viruses can be done using a chromatography-based purification as described in Mundle, S. T., et al. PLOS One. February 2013; 8(2):e57224, which is incorporated herein in its entirety. This purification requires a viral harvest method that utilizes a chemical treatment of infected cells by the sulfated polymeric anion dextran sulfate (DS) to elute the virus from the surface of the cells. The purification procedure led to a >3 log and >5 log reduction of host cell protein and host cell DNA, respectively, in the CJ2-gD2/gB2 virus batch.

Animal experiments in mice. Female Balb/cAnNCrl mice were purchased from Charles River Laboratories (Sulzfeld, Germany) and kept at the AAALAC-certified institutional animal facility under specified pathogen-free conditions. Animals were co-housed per group in IVC cages using compressed sawdust as bedding, under controlled conditions of temperature, humidity and light (12-hour light, 12-hour dark cycles). Mice were allowed to acclimatize to the housing conditions for 12 days prior to experimentation. Experimental procedures were approved by the local animal experiments ethical committee and conducted according to the Dutch Experiments on Animals Act and the Council of Europe.

Immunization and challenges: Female Balb/cAnNCrl mice 7- to 8-week-old were randomly divided into three groups (n=8 each). Mice were either sham-immunized with formulation buffer or immunized with purified CJ2-gD2/gB2 at a dose of $1.8 \times 10^5$, $1.8 \times 10^6$ or $1.8 \times 10^7$ PFU or crude CJ2-gD2/gB2 at $1.43 \times 10^6$ PFU/mouse in a volume of 50 µl by intramuscular injection into both quadriceps muscles of the hind legs. Individual groups of mice were boosted with the same virus and at the same dose 2 weeks later. Mice were challenged with wild-type HSV-2 strain G three weeks after secondary immunization. Five days prior to challenge, mice were injected subcutaneously in the neck ruff with medroxyprogesterone (Depo-Provera, Pfizer) at 3 mg per mouse in a volume of 100 µl. For intravaginal challenge, mice in all groups were anesthetized, pre-swabbed with a calcium alginate swab and inoculated intravaginally with 20 µl of culture medium containing $5 \times 10^5$ PFU of HSV-2 strain G (Morrison, et al., Virology 243:178-87 (1998)). Animals were kept on their backs with their rear part elevated under the influence of anesthesia for 30-45 min post-infection.

Acute infection assays and clinical observations: On days 1, 2, 4, and 7 post-challenge, vaginal mucosae were swabbed with calcium alginate to assess viral shedding. Infectious viruses in swab materials were assessed by standard plaque assay on Vero cell monolayers. HSV-2 plaque assays were performed to measure the virus titer in mouse vaginal swabs. Briefly, Vero cells were seeded in 6-well cell-culture plates one day prior to infection. On the day of infection, culture medium was discarded and 300 µl serially diluted mouse vaginal swabs and controls were added to each well, and incubated for 1.5 hr at 37° C. Subsequently, 3 mL of agarose mix was added to the virus and cells. After the agarose solidified the plates were incubated at 37° C. for 3 days. At day 3, cells were fixed and stained, dried at room temperature before counting of plaques. Following challenge with wild-type HSV-2, mice were assessed daily during a 21-day follow-up period for signs of genital lesions and systemic illness. The severity of disease was scored as follows: 0=no sign of herpetic infection, 1=slight genital erythema and edema, 2=moderate genital inflammation, 3=purulent genital lesions and/or systemic illness, and 4=hind-limb paralysis (Brans, et al., J. Invest. Dermatol. 129:2470-9 (2009)).

Detection of HSV-2-specific neutralizing antibodies: Blood was collected from the saphenous veins of immunized and mock-immunized mice at days 0 (before prime), 13 (before boost), and 34 (before challenge) and stored after heat inactivation for measurements of immunological parameters. Neutralizing serum antibody titers were determined in the ELVIS reporter assay on BHKICP6-lacZ cells. These cells stably express lacZ under the HSV-1 ICP6 promoter. ICP0 acts as a major activator of this promoter after successful HSV infection. Consequently, cells that are infected with HSV-2 express beta-galactosidase (β-gal). β-gal is subsequently detected using a chemiluminescent reporter gene assay. In the presence of complement, a serial dilution of serum was added to the reporter cells prior to addition of virus. The 50% neutralization titer (IC50) was calculated by non-linear regression using a 4-parameter logistic curve fit per sample. This assay was adapted from Blevins et al. PLoS One. 2015; 10(12):e0144738, which is incorporated herein by reference in its entirety.

Exploratory detection of cellular immunity: Mice immunized with either sham-immunized with formulation buffer (n=2) or immunized with purified CJ2-gD2/gB2 at a dose of $1.8 \times 10^6$ PFU/mouse (n=6) as described above were sacrificed 3 weeks after boost. The mice received medroxyprogesterone (MPG) 5 days before sacrifice. Cellular immune responses were determined by stimulating splenocytes with pools of 15mer peptides (>90% pure, with 11 AA overlap) spanning gB2 and gD2 proteins, i.e. a gD2 pool of 96 peptides covering all gD2, a gB2 pool (#1) of peptides 1-95 of the gB2 extracellular region, a gB2 pool (#2) of peptides 96-192 of the gB2 extracellular region, and a gB2 pool (#3) of peptides 193-224 covering the gB2 transmembrane and intracellular region. In addition, a previously described 13-mer VP11/12 peptide (AFLTGADRSVRLA; (SEQ ID NO: 41)); as described in, e.g., Muller et al. Journal of General Virology. 2009; 90: 1153-1163, which is incorporated herein by reference in its entirety, and a 9-mer ICP27 peptide (HGPSLYRTF; (SEQ ID NO: 42)), as described in, e.g., Haynes et al. Vaccine 2006; 24: 5016-5026, which is incorporated herein by reference in its entirety) were used as stimulants. The induction of IFNγ-producing cells was measured by ELISPOT.

Results

Figure 22:
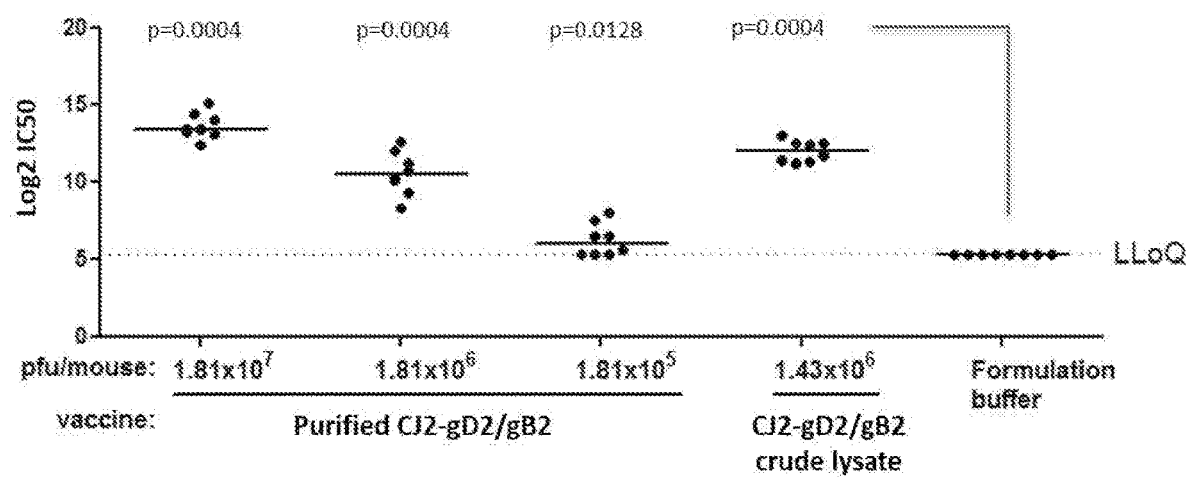
FIG. 22 shows results demonstrating that immunization with purified CJ2-gD2/gB2 induces HSV-2-neutralizing antibody titers comparable to responses induced by crude CJ2-gD2/gB2 (clarified cell lysate). Groups of 7- to 8-week-old female Balb/cAnNCrl mice (n=8 each) were either immunized with purified or crude CJ2-gD2/gB2 at the doses indicated. Mice were boosted 2 weeks later with the same vaccine virus at the same dose as used for prime immunization. Blood was obtained from the saphenous vein of mice 20 days after boost immunization. Serum from each immunized animal was heat-inactivated and HSV-2-specific neutralizing antibody titers were determined. HSV-2 neutralizing antibody titers (IC50) are shown for individual mice (dots), group medians are indicated with a solid line. P values of vaccine groups versus formulation buffer are indicated, when significant. The dotted line indicates the estimated lower limit of detection (LLoQ) of the assay used.

Purified CJ2-gD2/gB2 is as effective as CJ2-gD2/gB2 in crude cell lysate in eliciting HSV-2-specific neutralizing antibodies in immunized mice. The ability of purified CJ2-gD2/gB2 to elicit anti-HSV-2-specific neutralizing antibodies was determined in mice immunized with purified CJ2-gD2/gB2 at a dose of $1.8 \times 10^5$, $1.8 \times 10^6$ or $1.8 \times 10^7$ PFU or crude CJ2-gD2/gB2 at $1.43 \times 10^6$ PFU or formulation buffer. As shown in FIG. 22, all vaccine groups showed a significant increase in HSV-2 neutralizing antibody titers compared to the formulation buffer group (Mann-Whitney). The indicated p values for the purified vaccine were obtained via a stepwise comparison of vaccinated groups (from high to low vaccine dose) with the formulation buffer group. The HSV-2-specific neutralization antibody titer three weeks after boost immunization in mice immunized with a medium and high dose of purified CJ2-gD2/gB2 were comparable to titers induced by crude vaccine.

Figure 24:
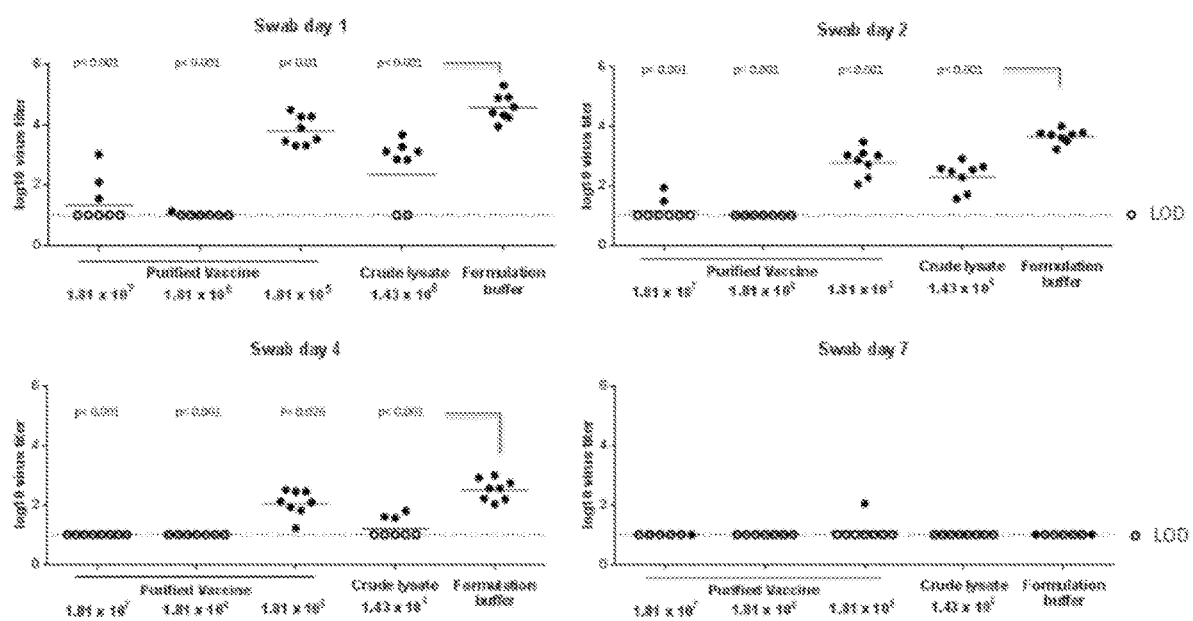
FIG. 24 presents results indicating that purified CJ2-gD2/gB2 is as effective as crude CJ2-gD2/gB2 in reducing vaginal virus shedding, i.e. protecting mice against HSV-2 genital infection. Female Balb/cAnNCrl mice treated and challenged as described for FIG. 23. On days 1, 2, 4, and 7 post-challenge, vaginal mucosae were swabbed with calcium alginate to assess viral shedding. HSV-2 virus titers of individual mice vaginal swabs are shown as dots, group means are indicated with a solid line. When compared with the sham immunization group, vaccine immunized groups showed significant decrease in virus shedding titers in day 1, 2 and 4 post challenge swabs. No significant differences in shedding titers were observed between groups on day 7.

Purified CJ2-gD2/gB2 is as effective as CJ2-gD2/gB2 in crude cell lysate in induction of protective immunity against HSV-2 genital infection and disease in mice. The results in FIG. 23 show that comparable to immunization with crude CJ2-gD2/gB2, immunization with purified CJ2-gD2/gB2 at high and medium doses completely protects mice from development of local genital lesions and that these mice exhibit no signs of systemic disease after challenge with wild-type HSV-2, whereas 100% of sham-vaccinated mice developed severe genital lesions (FIG. 23A) and succumbed to wild-type HSV-2 infection by day 7 post-challenge (FIG. 23B). As shown in FIG. 24, compared with the sham-immunization group, high and mid dose ($1.81 \times 10^7$, $1.81 \times 10^6$ pfu/mouse) purified CJ2-gD2/gB2 as well as crude vaccine immunized groups showed significant decrease in virus shedding titers on day 1, 2 and 4 post challenge ($p<0.001$, Wilcoxon, stepwise approach, if applicable, starting from the highest dose). The low dose ($1.81 \times 10^5$ pfu/mouse) purified CJ2-gD2/gB2 immunized group also showed significant decrease in virus shedding titers on day 1, 2 and 4 post challenge ($p<0.01$, $p<0.001$ and $p=0.026$, respectively). No significant differences in shedding titers were observed on day 7. Mouse vaginal virus shedding in the mock immunized group reduced over time to below the limit of detection on day 7.

Figure 25:
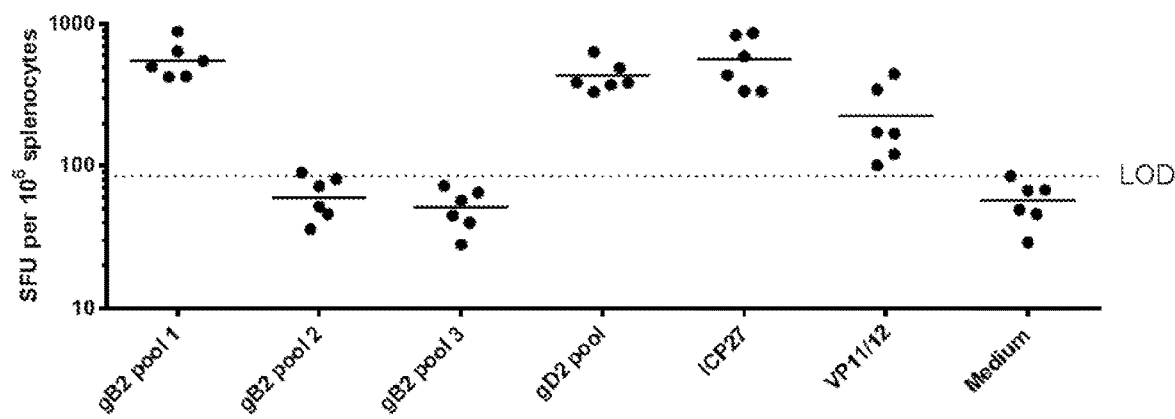
FIG. 25 shows that CJ2-gD2/gB2 induces T cell responses (IFNγ+) against gB2, gD2 and other vaccine components. ELISPOT counts (SFU per $10^6$ splenocytes) for individual mice immunized with purified CJ2-gD2/gB2 vaccine are presented by dots and group geometric means are indicated with a solid line. IFNγ release was detected after stimulation with the gD2 peptide pool and gB2 peptide pool #1. Culture medium (negative control) and PMA (positive control, data not shown) gave negative and positive IFNγ response, respectively. In addition, ICP27 and VP11/12 peptides showed positive responses. Responses of mice receiving formulation buffer were all below the limit of detection (LOD) (data not shown).

Purified CJ2-gD2/gB2 elicits HSV-2-specific cellular immune responses in immunized mice. As shown in FIG. 25, CJ2-gD2/gB2 induces T cell responses (IFNγ+) against gB2, gD2 and other vaccine components. IFNγ release was detected after stimulation with the peptide pool covering the N-terminal extracellular part of gB2, with the complete gD2 peptide pool, and with peptides specific for the viral proteins ICP27 and VP11/12.

Example 4

Vero Cell Lines Stably Expressing ICP0 Protein

We were able to successfully minimize the cytotoxic effect of ICP0 by using a minimal promoter pMF-3. To establish the ICP0-expressing stable cell lines, we constructed an ICP0-expressing plasmid, pMF3-ICP0. Linearized pMF3-ICP0 plasmid was then transfected into CCL-81 Vero cells along with linearized pcDNA3 by Lipofectamine 2000 (Invitrogen Inc.). At 30 hours post-transfection, cells were seeded into 100 mm dishes at various cell density and were grown in DMEM growth medium containing G418 at 400 µg/ml. G418 resistant colony cells were assayed by its ability to complement the growth of HSV-2 ICP0 null mutant, N2-lacZ, benchmarked against U2OS cells. Among more than 1000 G418-resistant colonies that were selected, V0-584 cells represented the only G418-resistant and ICP0-expressing stable cell line that can complement the plaque-formation of N2-lacZ at level comparable to U2OS cells. The plaque-forming efficacy of N2-lacZ in passage 7 V0-584 cells is ~2-fold lower than that of U2OS cells and ~120-fold higher than that of normal CCL-81 cells. The complementing efficiency of V0-584 cells for N2-lacZ remained 2-3 fold lower than that of U2OS cells at passage 33. These cells are further described in U.S. Application Ser. No. 62/515,260, filed on Jun. 5, 2017.

We also generated a tetR- and ICP0-expressing Vero cell line that can complement the plaque forming efficiency. To establish tetR- and ICP0-expressing stable CCL-81 Vero cells, V0-584 cells were transfected with linearized pMF-tetR along with linearized pCDNA4/TO (Invitrogen) by Lipofectamine 2000. Transfected cells were then seeded into 100 mm dishes at various cell density and were grown in DMEM growth medium containing G418 at 400 µg/ml and Zeocin at 200 µg/ml. G418- and Zeocin-resistant colony cells were assayed for their ability to complement the growth of CJ2-gD2, benchmarked against U2CEP4R-11 cells. VOR-124 cells represent a G418/Zeocin-resistant stable cell line that can complement the plaque-formation of a control virus CJ2-gD2 efficiently even at passage 41. The plaque-forming efficacy of control CJ2-gD2 in VOR-124 cells is ~4.5-fold lower than that of U2CEP4R-11 cells and is 3,378-fold higher than that of V0-584 cells. The plaque-forming efficiency of N2-lacZ on VOR-124 cells is similar to that of V0-584 cells (data not shown). Notably, VOR-124 cells are morphologically similar to CCL-81 cells and exhibit similar growth kinetics as CCL-81 cells. These cells are further described further in U.S. Application Ser. No. 62/515,260, Filed on Jun. 5, 2017.

These cells are for instance also used to similarly generate a tetR, ICP0 and VP5-expressing Vero cell line by transfection in VOR-124 cells of a VP5 expression cassette along with DNA encoding hygromycin-B resistant gene. The resulting cells can be used to complement recombinant HSV viruses that do not express ICP0 and UL19 (VP5), such as QF-VAC that is described in the following experiment.

Example 5

QF-VAC, a Further HSV-2 Virus that Over-Expresses gB2, gD2 and does not Express ICP0 and gG2.

Herein, a vaccine candidate is described that possesses the key immunogenicity features of CJ2-gD2/gB2, such as overexpression of gD2 and gB2 at the immediate-early stage of viral infection, and deletions of ICP0 and gG2, while ensuring its inability to produce infectious virus particles through deletion of the HSV-2 essential gene UL19, which encodes the HSV-2 major capsid protein VP5.

Specifically, QF-VAC represents a novel HSV-2 ICP0-, gG2-, and UL19-minus recombinant virus, that encodes:

1) a codon-optimized gD2 gene under the control of the tetO-containing HSV-1 ICP4 promoter at the UL26/UL27 intergenic region, and 2) a codon-diversified gD2 gene under the control of the tetO-containing HSV-1 immediate-early ICP27 promoter at the UL19 locus displacing the UL19 gene.

Because 1) deletion of UL19 has no effect on de novo viral DNA replication, the resulting recombinant virus will express all HSV-2 genes except ICP0, gG2, and VP5, and 2)

QF-VAC encodes 2 recombinant copies of the gD2 gene controlled by immediate-early promoters, in addition to one recombinant copy of gB2 under control of the tetO-containing immediate-early HSV-1 ICP0 promoter at the gG2 locus, we expect that overall vaccine efficacy of QF-VAC is at least comparable to and may actually be further enhanced compared to CJ2-gD2/gB2. Unlike CJ2-gD2/gB2, QF-VAC does not express dominant-negative HSV UL9-C535C protein.

Construction of CJ2-gD2/gB2-lacZ, a CJ2-gD2/gB2-Derived Recombinant Virus, in which the lacZ Gene Cassette is Inserted at the Intergenic Region Between the UL26 and UL27 Genes Description of Plasmids p2UL2627-v and p2UL2627-lacZ p2UL26.27-v contains a synthesized DNA fragment consisting of 1) HSV-2 DNA sequence consisting of 900 bp upstream of HSV-2 UL26 poly A signal to 110 bp downstream of UL26 poly A signal sequence, 2) DNA sequence containing a modified ICP27 promoter in which the ICP27 TATA element is changed to HCMV TATATAA followed by part of 5' untranslated region of HSV-1 ICP4 and ICP27, MCS and a synthetic poly A signal sequence, and 3) HSV-2 DNA sequence consisting of 121 bp downstream of the HSV-2 UL26 poly A signal to 873 bp upstream of UL27 poly A signal. p2UL2627-lacZ is a p2UL2627-v-derived plasmid that encodes the lacZ gene under the control of the modified HSV-1 ICP27 promoter.

CJ2-gD2/gB2-lacZ is a CJ2-gD2/gB2-derived recombinant virus, in which the lacZ gene under the control of HSV-1 ICP27 promoter is inserted into the intergenic region of UL26 and UL27 genes. CJ2-gD2/gB2-lacZ was generated by co-transfecting U2OS cells with XhoI/XmnI-linearized p2UL2627-lacZ and pcDNA-3-tetR (Yao, et al., Mol. Ther. 13:1133-41 (2006)) followed by superinfection with CJ2-gD2/gB2 as previously described (Lu, et al., J. Invest. Dermatol. 129:1174-84 (2009)). The lacZ-expressing viruses were then selected and plaque-purified on U2CEP4R-11 cells.

CJ2-gD2/gB2-lacZ was a third-round plaque-purified CJ2-gD2/gB2-derived recombinant virus that exhibits uniform blue plaques in U2CEP4R-11 cells. The plaque-forming efficiency of CJ2-gD2/gB2-lacZ in U2CEP4R-11 cells in the absence of tetracycline is 39,200-fold higher than in the presence of tetracycline, indicating that like CJ2-gD2/gB2, CJ2-gD2/gB-lacZ can express high-level of UL9-C535C in the absence of tetracycline repressor, tetR. Additionally, like CJ2-gD2/gB2, CJ2-gD2/gB2-lacZ replicates efficiently in U2CEP4R-11 cells in the absence of tetracycline. CJ2-gD2/gB2-lacZ was propagated and titered in U2CEP4R-11 cells.

Construction of QON-lacZ, a CJ2-gD2/gB2-lacZ-Derived Recombinant Virus, in which the UL9-C535C/gD2 Cassette at the ICP0 Loci Will be Deleted Description of Plasmid p2ICP0-V p2ICP0-V is an HSV-2 ICP0 locus-specific shuttle plasmid, which contains 1) a PCR amplified HSV-2 ICP0 DNA fragment covering −762 bp to −21 bp upstream of HSV-2 ICP0 ORF, 2) a multiple cloning site, and 3) a PCR-amplified HSV-2 DNA sequence containing +14 bp to +1406 bp downstream of the HSV-2 ICP0 stop codon. The amplified 5' and 3' ICP0 flanking sequences exhibit 99% sequence homology compared to the corresponding ICP0 flanking sequences from HSV-2 strain SD90e (GenBank: KF781518.1). The annotated sequence is provided as SEQ ID NO: 36.

Generation and Testing of QON-lacZ Virus Clones

QON-lacZ virus will be generated by co-transfection of linearized p2ICP0-V and infectious, early passage CJ2-gD2/gB2-lacZ viral DNA into VOR-124 or U2CEP4R-11 cells as previously described. The progeny virus will be first amplified in V0-584 cells, an HSV-1 ICP0-expressing Vero cell line, followed by first-round plaque purification on V0-584 cells. Individual single large plaques will be picked and amplified in V0-584 cells. Following viral DNA isolation, PCR analysis will be performed with primers specific to the 5' and 3' ICP0 flanking sequence. p2ICP0-V plasmid and CJ2-gD2/gB2-lacZ viral DNA will be used as control. QON-lacZ will not contain any sequence that overlaps with the HSV-1 ICP0 ORF sequence in VOR-124 cells.

Viruses with the confirmed complete deletion of UL9-C535C/gD2 cassette will be further analyzed by 1) X-Gal staining to confirm their ability to efficiently express the lacZ gene located in the UL26/UL27 intergenic region, 2) PCR analysis to confirm the presence of the codon-optimized gB2 gene at the gG2 locus, 3) their replication-efficiency in V0-584 cells as compared with N2-lacZ, and 4) Western blot analysis to examine their efficiency in expressing gB2 using N2-lacZ and CJ2-gD2/gB2-lacZ and CJ2-gD2/gB2 controls. In addition, Western blots will be also performed with gD2- and ICP27-specific antibodies as previously described. The final QON-lacZ virus clone will be subjected to a third round of plaque purification.

Generation of Q0N-gD2, a Q0N-lacZ Derived Virus in which the lacZ Gene in the UL26/UL27 Intergenic Region Will be Replaced with a Codon-Optimized gD2 Under Control of the HSV-1 ICP4-tetO Promoter Construction of plasmid p2UL2627TO-gD2 p2UL2627TO-gD2 will be a p2UL2627-v-derived plasmid that encodes the codon-optimized gD2 gene (derived from strain 333) under the control of the wild-type HSV-1 ICP4-tetO promoter with the BGH poly-A signal sequence at the 3' end of the gD2 gene. The annotated sequence is provided as SEQ ID NO: 24.

Generation and Testing of QON-gD2 Virus Clones.

QON-gD2 will be generated by co-transfection of U2CEP4R-11 cells or U2OS cells with linearized p2UL2627TO-gD2 and infectious QON-lacZ viral DNA. Transfected cells will be harvested at 72 h post-transfection.

X-Gal selection. Progeny viruses will be screened for the recombinational replacement of the lacZ gene of QON-lacZ with the gD2-containing DNA sequence of p2UL2627TO-gD2 by standard plaque assays on U2OS cells followed by X-Gal staining of plaques at 72 h post-infection. White plaques, reflecting the replacement of the lacZ gene by the gD2-containing DNA sequence of p2UL2627TO-gD2, will be isolated. The isolated individual (white) plaques will be amplified in VOR-124 cells and subjected to three rounds of plaque purification.

Viruses derived from amplification/plaque purification of individual (white) plaques will be tested for their ability to efficiently express gD2 and gB2 in Vero cells by Western-blot analyses with antibodies specific for gD2, gB2, and ICP27 as previously describe. N2-lacZ, QON-lacZ, CJ2-gD2/gB2 and wild-type HSV-2 will be included in these studies as controls.

Verification of genomic location. The genomic location of the codon-optimized gD2 gene at the UL26/UL27 intergenic region in QON-gD2 will be verified by PCR analysis with UL26 and UL27 locus-specific primers that flank the gD2 insert and primers specific for codon-optimized gD2.

Replication in VOR-124 cells as compared to CJ2-gD2/gB2. Upon confirming the insertion of codon-optimized gD2 at the UL26/UL27 intergenic region, the replication efficiency of these viruses in VOR-124 cells will be examined by plaque assays. As control, QON-lacZ, CJ2-gD2/gB2 will be included in these studies. QON-gD2 is expected to exhibit similar replication efficiency as QON-lacZ and CJ2-gD2/gB2 in VOR-124 cells.

Construction of QF5-lacZ, a QON-gD2-Derived Recombinant Virus, in which the HSV-2 UL19 Gene Will be Replaced with the lacZ Gene Under the Control of the HSV-1 ICP27 Promoter Construction of p2UL19-V and p2UL19-lacZ p2UL19-V will be an HSV-2 UL19 (VP5) locus-specific shuttle plasmid, which will contain 1) a PCR-amplified DNA sequence covering 1465 bp upstream of the HSV-2 VP5 TATA element to 1 bp downstream of the VP5 TATA box, 2) the modified HSV-1 ICP27 promoter followed by a multiple cloning region, and 3) a PCR amplified DNA sequences covering 16 bp to 1256 bp downstream of the VP5 stop codon. The viral DNA used for PCR-amplification of described HSV-2 VP5 flanking sequences was isolated from CJ2-gD2/gB2-infected VOR-124 cells. The amplified 5' and 3' HSV-2 VP5 flanking sequences will be sequenced and compared with the corresponding HSV-2 strain SD90e VP5 flanking sequence (GenBank: KF781518.1).

p2UL19-lacZ will be a p2UL19-V-derived plasmid that encodes the lacZ gene under the control of the HSV-1 ICP27 promoter.

Construction and Testing of QF5-lacZ Virus Clones

The linearized p2UL19-lacZ vector and infectious QON-gD2 viral DNA will be co-transfected into V0R5 cells, a VOR-124-derived HSV-2 VP5-expressing cell line, with Lipofectamine 2000 mediated transfection. The transfected cells will be harvested at 72 h post-transfection.

X-Gal selection. Progeny viruses will be screened for the recombinational replacement of the VP5 ORF-containing fragment at the VP5 locus of QON-gD2 with the lacZ gene by standard plaque assays. Plaques will be stained with X-Gal at 72 h post-infection. Blue plaques, reflecting the replacement of the VP5 ORF at the VP5 locus by the lacZ gene of p2UL19-lacZ, will be isolated and amplified in V0R5 cells. The isolated individual (blue) plaques will be amplified in RVP-5 and/or V0R5 cells and subjected to three rounds of plaque purification.

Viruses derived from amplification/plaque purification of individual (blue) plaques will be tested for their ability to efficiently express gD2, gB2, and HSV-2 late gene gC2 in Vero cells by Western-blot analyses with antibodies specific for gD2, gB2, gC2, and ICP27 as previously described. QON-gD2, CJ2-gD2/gB2 and wild-type HSV-2 will be included in these studies.

Replication in V0R5 cells as compared to N2-lacZ and CJ2-gD2/gB2. Upon confirming the insertion of lacZ in the UL19 locus, the replication efficiency (PFU/mL) of these viruses in V0R5 cells will be examined by plaque assay. As controls, CJ2-gD2/gB2 and QON-lacZ will be included. In addition, the growth kinetics and the replication efficiency of QF5-lacZ will be compared with QON-gD2 in V0R5 cells. QF5-lacZ is expected to exhibit similar replication efficiency as QON-gD2 in V0R5 cells.

Replication deficiency testing. The replication-incompetency of QF5-lacZ will be determined by standard plaque assay on monolayers of the non-complementing cell lines, Vero and VOR-124. We expect that no replication competent virus/plaques will be detected in Vero cells and VOR-124 cells.

Construction and Characterization of QF-VAC, a QF5-lacZ-Derived Recombinant Virus in which the lacZgene at the HSV-2 UL19 Locus Will be Replaced with a HSV-2 gD2 Gene Under the Control of the HSV-1 ICP27-tetO Promoter Construction of Plasmid p2UL19-gD2 p2UL19-gD2 will be a p2UL19-V derived plasmid that encodes the gD2 gene under the control of the HSV-1 ICP27-tetO promoter. Alternatively, p2UL19-gD2 will be a p2UL19-V derived plasmid that encodes the gD2 gene under the control of the HSV-1 ICP4-tetO promoter.

Construction and Testing of QF-VAC Virus Clones

QF-VAC will be generated by co-transfection of V0R5 cells with linearized p2UL19-gD2 and infectious QF5-lacZ viral DNA. Transfected cells will be harvested at 72 h post-transfection.

X-Gal selection. Progeny viruses will be screened for the recombinational replacement of the lacZ gene at the VP5 locus of QF5-lacZ with the codon-diversified gD2 gene by standard plaque assays. Plaques will be stained with X-Gal at 72 h post-infection. White plaques, reflecting the replacement of the lacZ gene at the VP5 locus by the gD2 gene of p2UL19-gD2, will be isolated and amplified in V0R5 cells and subjected to three rounds of plaque purification.

Viruses derived from amplification/plaque purification of individual (white) plaques will be tested for their ability to efficiently express gD2 and gB2, and HSV-2 late gene gC2 in Vero cells using Western blot analyses with antibodies specific for gD2, gB2, gC2, UL19 and ICP27 as previously described (13). QON-gD2, QF5-lacZ, CJ2-gD2/gB2, and wild-type HSV-2 will be included in these studies. QF-VAC is expected to express gD2 and gB2 to at least similar levels as CJ2-gD2/gB2 in infected Vero cells.

Verification of genomic location. The genomic location of the inserted gD2 gene at the UL19 locus in QF-VAC will be verified by PCR analysis with UL19 locus-specific primers that flank the inserted gD2 gene and primers specific for this particular gD2 gene.

Replication in V0R5 cells as compared to QON-lacZ and CJ2-gD2/gB2. Upon confirming the insertion of gD2 in the UL19 locus, the replication efficiency (PFU/mL) of these viruses in V0R5 cells will be examined by plaque assays. CJ2-gD2/gB2 and QON-lacZ will be included as controls. In addition, the growth kinetics and the replication efficiency of QF-VAC will be compared with QF5-LacZ in V0R5 cells. QF-VAC is expected to exhibit similar replication efficiency as QF5-LacZ in V0R5 cells.

Replication deficiency testing. The replication-defective nature of QF-VAC will be determined by standard plaque assay on monolayers of non-complementing Vero and VOR-124 cells. We expect that no replication competent virus/plaques will be detected in Vero cells and VOR-124 cells.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

SEQUENCES 1. gG2 Sequence: −900 to −2 bp Upstream of gG2 ORF
CGTCAAGGCGGGGTGGTACGCCAGCACGAGC-
CACGAGGCGCGGCTGCTGAGACGCCTGAACC
ACCCCGCGATCCTACCCCTCCTGGACCTGCAC-
GTCGTTTCTGGGGTCACGTGTCTGGTCCTC
CCCAAGTATCACTGCGACCTGTATACCTATCT-
GAGCAAGCGCCCGTCTCCGTTGGGCCACCT ACA-
GATAACCGCGGTCTCCCGGCAGCTCTTGAGCGC-
CATCGACTACGTCCACTGCAAAGGCA TCATCCA-
CCGCGATATTAAGACCGAGAACATCTTCATCAACA-
CCCCCGAGAACATCTGTCTG GGGGACTT- TGGGG-
CGGCGTGCTTTGTGCGCGGGTGTCGATCGAGCCCC- 1. TTCCATTACGGGAT CGCAGGCACCATCGATA-CAAACGCCCCCGAGGTCCTGGCCGGGGATCCGTA-CACCCAGGTAA TCGACATCTGGAGCGCCGGCC-TGGTGATCTTTGAGACCGCCGTCCACACCGCGT-CCTTGTTC TCGGCCCCGCGCGACCCCGAAAGGCG-GCCGTGCGACAACCAGATCGCGCGCATCATCCG-ACA GGCCCAGGTACACGTCGACGAGTTTCCGA-CGCACGCGGAATCGCGCCTCACCGCGCACTACC GCTCGCGGGCGGCCGGGAACAATCGTCCGGCGTG-GACCCGACCGGCGTGGACCCGCTACTAC AAGATC-CACACAGACGTCGAATATCTCATATGCAAAGCCCT-TACCTTTGACGCGGCGCTCCG CCCAAGCGCCGCG-GAGTTGCTGCGCCTGCCGCTATTTCACCCTAAGTG-ACCCCGCTCCCCCC GGGGGGCGTGGAGGGGG-GGGCTGGTTGGATGTTTTTGCACAAAAAGACG-CGGCCCTCGGGCT TTGGTGTTTTTGGCACCTTG-CCGCCCGGCGT (SEQ ID NO: 01)

2. Poly A Signal of HSV-1 ICP27 Sequence: CAAATATTTTTATTGCAACTCCCTGTTTTAGGTA-CAATAAAAACAAAACATTTCAAA CAAATC-
GCCCCTCGTGTTGTCCTTCTTTGCTCATGGCC-
GGCGG (SEQ ID NO: 02)

3. TetO-Bearing Modified HSV-1 ICP0 Promoter Plus Part of 5' Untranslated Region of ICP0 Gene:
TAATGGGCAACCCCGGTATTCCCCGCCTCCC-
GCGCCGCGCGTAACCACTCCCCTGGGGTTCC
GGGTTATGCTAATTGCTTTTTTGGCGGAACACA-
CGGCCCCTCGCGCATTGGCCCGCGGGTCG CTCAAT-
GAACCCGCATTGGTCCCCTGGGGTTCCGGGTATG-
GTAATGAGTTTCTTCGGGAAGG CGGGAAGCCC-
CGGGGCACCGACGCAGGCCAAGCCCCTGTTG-
CGTCGGCGGGAGGGGCATGCT AATGGGGTTCT-
TTGGGGGACACCGGGTTGGGCCCCCAAATCGG-
GGGCCGGGCCGTGCATGCT AATGATATTCTTTG-
GGGGCGCCGGGTTGGTCCCCGGGGACGGGGCCG-
CCCCGCGGTGGGCCT GCCTCCCCTGGGACGC-
GCGGCCATTGGGGGAATCGTCACTGCCGCCCCTT-
TGGGGAGGGGAA AGGCGTGGGGTATATAAGC-
AGAGCTCTCCCTATCAGTGATAGAGATCTCCCTAT-
CAGTGATAGAGATCGTCGACGAGCTCGCGTGTCG-
CATTTGCACCTCGGCACTCGGAGCGAGACGCA-
GCAG CCAGGCAGACTCGGGCCGCCCCCTCTCCG-
CATCACCACAGAAGCCCCGCCTACGTTGCGACC
CCCAGGG (SEQ ID NO: 03)

4. gG2 Sequence: +1 to +900 bp Downstream of gG2 ORF Stop Codon
GGGGTGGGGGTGGGGGGCGAGAAACGATGAAGG-
ACGGGAAAGGGAACAGCGACCAAATGTCA CGA-
TAAGAACAATAAACCTGTGACGTCAATCAGATAT-
GTGAGTTTGGTTGTGTTTTGTGGGA CTGGGGGC-
GGGGGGTGGGAGGTATCAGTGGGTGACAGAGT-
CTTTTAAAAGACGTGTCCCGGG GCCCTCGA-
GATGCGCAACTTTTGGCCACACAGAGAAAGGCC-
CCCAGACGAAGTCACCCGGGT CCCCGAAC-
AAAAACAAAAACCTTGACCGCCGCCGGGGGGCG-
TGCCTGTTGTTTTGGTCTCAA TGGATCGGTA-
TGCCGTTCGGACCTGGGGGATTGTGGGAATCCT-
CGGGTGTGCTGCTGTTGGG GCCGCACCCACCG-
GCCCCGCGTCCGATACAACAAACGCGACCGCACG-
CCTCCCCACGCACCC CCCACTCATCCGTTCCG-
GGGGCTTTGCCGTCCCCCTCATCGTGGGGGGG-
CTGTGTCTCATGA TTCTGGGGATGGCGTGTCTACT-
CGAGGTCCTGCGTCGCCTGGGTCGCGAGTTGGCG-
AGGTGC TGCCCCCACGCGGGCCAATTTGCCCCAT-
GATTTTTCGCCTTTCTGGCCTTGCCCCCACCCCA
TCGCCCCGATTGTGTGTCGGGTGCCCGGGGTA-
CAGCAGCTATGGAGCGGTCGGTAATATAAC TTTGG-
TTGTCGCCACACGCCCCGTGCCGGGCATGGGTTG-
TGCGGGAAGGACGAAATAATCCG GCGATCCC-
CAAGCGTACCAACTGGGGGGGGGGGGGGGG-
GAAAAGAAACTAAAAACACATC AAGCCCACA-
ACCCATCCCACAATGGGGGTTATGGCGGACC-
CACCGCACCACCATACTCCGAT TCGACCA-
CATATGCAACCAAATCACCCCCAGA (SEQ ID NO: 04)

5. Multiple Cloning Sites of pCDNA3
AAGCTTGGTCGATATCTATCGGAGCTGTGCTAGC-
GCCACTGGCGGCCGCTGCAGCGAGCGGA ATTCT
(SEQ ID NO: 05)

6. HSV-2 gG2 Locus-Specific Vector Sequences Plus the Modified tetO-Bearing HSV-1 ICP0 Promoter Sequences in pgG2-TO.
CAGCTGcgtcaaggcggggtggtacgccagcacgagccacgaggcgcg-
gctgctgagacgcc tgaaccaccccgcgatcctacccctcctggacctgcac-
gtcgtttctggggtcacgtgtctg gtcctccccaagtatcactgcgacctgtatacc-
tatctgagcaagcgcccgtctccgttggg ccacctacagataaccgcggtct-
cccggcagctcttgagcgccatcgactacgtccactgca aaggcatcatc-
caccgcgatattaagaccgagaacatcttcatcaacacccccgagaacatc tgt-
ctgggggactttggggcggcgtgctttgtgcgcgggtgtcgatcgagcccc ttc-
catta cgggatcgcaggcaccatcgatacaaacgcccccgaggtcctggcc-
ggggatccgtacaccc aggtaatcgacatctggagcgccggcctggtgatcttt-
gagaccgccgtccacaccgcgtcc ttgttctcggccccgcgcgaccccg-
aaaggcggccgtgcgacaaccagatcgcgcgcatcat ccgacaggccca-
ggtacacgtcgacgagtttccgacgcacgcggaatcgcgcctcaccgcgc act-
accgctcgcgggcggccgggaacaatcgtccggcgtggacccgaccggc-
gtggacccgc tactacaagatccacacagacgtcgaatatctcatatgcaa-
agcccttacctttgacgcggc gctccgcccaagcgccgcggagttgctgc-
gcctgccgctatttcaccctaagtgaccccgct ccccccgggggggcgtg-
gagggggggctggttggatgtttttgcacaaaaagacgcggccct cgggcttt-
ggtgtttttggcaccttgccgcccggcgtACCGGTACTAGTCAATTG
CAAATAT TTTTATTGCAACTCCCTGTTTTAGGTA-
CAATAAAAACAAAACATTTCAAACAAATCGCCCCT
CGTGTTGTCCTTCTTTGCTCATGGCCGGCGG
GGTACCGTTAACATACGTAACGCGTAATGGG CAAC-
CCCGGTATTCCCCGCCTCCCGCGCCGCGCGTAAC-
CACTCCCCTGGGGTTCCGGGTTAT GCTAATTGCT-
TTTTTGGCGGAACACACGGCCCCTCGCGCATTGGC-
CCGCGGGTCGCTCAATG AACCCGCATTGGTCCC-
CTGGGGTTCCGGGTATGGTAATGAGTTTCTTCGG-
GAAGGCGGGAAG CCCCGGGGCACCGACGCAGGC-
CAAGCCCCTGTTGCGTCGGCGGGAGGGGCATGCT-
AATGGGG TTCTTTGGGGGACACCGGGTTG-
GGCCCCCAAATCGGGGGCCGGGCCGTGCAT-
GCTAATGATA TTCTTTGGGGGCGCCGGGTTGGTC-
CCCGGGGACGGGGCCGCCCCGCGGTGGGCCT-
GCCTCCC CTGGGACGCGCGGCCATTGGGG-
GAATCGTCACTGCCGCCCCTTTGGGGAGGG-
GAAAGGCGTG GGGTATATAAGCAGAGCTCTCCC-
TATCAGTGATAGAGATCTCCCTATCAGTGATAGA-
GATCG TCGACGAGCTCGCGTGTCGCATTTGCAC-
CTCGGCACTCGGAGCGAGACGCAGCAGCCAGGCA
GACTCGGGCCGCCCCCTCTCCGCATCAC-
CACAGAAGCCCCGCCTACGTTGCGACCCCCAGGG
AAGCTTGGTCGATATCTATCGGAGCTGTGCTAGCG-
CCACTGGCGGCCGCTGCAGCGAGCGGAATTCTggg-
gtgggggtgggggcgagaaacgatgaaggacgggaaagggaacagcgac-
caaa tgtcacgataagaacaataaacctgtgacgtcaatcagatatgt-
gagtttggttgtgttttg tgggactgggggcgggggggtgggaggtatcagtgg-
gtgacagagtcttttaaaagacgtgtc ccgggggccctcgagatgcgcaacttttg-
gccacacagagaaaggcccccagacgaagtcacc cgggtccccgaaca-
aaaacaaaaaccttgaccgccgccgggggggcgtgcctgttgttttggt ctcaatg-
gatcggtatgccgttcggacctgggggattgtgggaatcctcgggtgtgctgctg
ttggggccgcacccaccggccccgcgtccgatacaacaaacgcgaccgcac-
gcctccccacg cacccccactcatccgttccgggggctttgccgtccccctcat-
cgtgggggggctgtgtct catgattctggggatggcgtgtctactcgaggtcctgcgtcgcctgggtcgcgagttggcga ggtgctgccccacgcgggccaat-
ttgccccatgattttttcgcctttctggccttgccccca ccccatcgccccgat-
tgtgtgtcgggtgcccggggtacagcagctatggagcggtcggtaat
ataactttggttgtcgccacacgccccgtgccgggcatgggttgtgcgg-
gaaggacgaaata atccggcgatccccaagcgtaccaactggggggggggg-
gggggggggaaaagaaactaaaaac acatcaagcccacaacccatcc-
cacaatggggggttatggcggacccaccgcaccaccatact ccgattcgacca-
catatgcaaccaaatcaccccccaga<u>TCTAGA</u> (SEQ ID NO: 06)

In SEQ ID NO: 06, the elements shown are highlighted as follows along the sequence: a) a first restriction site (bold and underlined); b) the sequence from −900 to −2 bp upstream of the gG2 open reading frame (ordinary lower case text); c) a second restriction site sequence containing one or more restriction enzyme sites (bold and underlined); d) the poly A signal sequence of HSV-1 ICP27 (capitalized text in italics); e) a third restriction site sequence containing one or more restriction enzyme sites (bold and italics); f) the tetO-bearing modified HSV-1 ICP0 promoter plus part of 5' untranslated region of ICP0 gene (in ordinary capitalized text) with the TATA element shown in bold, underlined and in italics; g) a fourth sequence consisting of multiple restriction sites (bold and underlined); h) the sequence from +1 to +900 bp downstream of the gG2 ORF stop codon (ordinary lower case text); and h) a final restriction site (bold and underlined).

7. Codon-Optimized gB2 Codon Sequence Plus Kozak Consensus Sequence (Indicated by Low and Uppercase Letters)
acttAAGCTTgccaccATGAGAGGCGGCGGCCTGATCT-
GCGCCCTGGTGGTGGGCGCCCTGG TGGCCGCCG-
TGGCCAGCGCCGCCCCCGCCGCCCCGCCGCCCC-
CAGAGCCAGCGGCGGCGTG GCCGCCACCGTGG-
CCGCCAACGGCGGCCCCGCCAGCAGACCCCCC-
CCCGTGCCCAGCCCCGC CACCACCAAGGCCAGAA-
AGAGAAAGACCAAGAAGCCCCCCAAGAGACCC-
GAGGCCACCCCCC CCCCCGACGCCAACGCCACC-
GTGGCCGCCGGCCACGCCACCCTGAGAGCC-
CACCTGAGAGAG ATCAAGGTGGAGAACGC-
CGACGCCCAGTTCTACGTGTGCCCCCCCCCC-
CACCGGCGCCACCGT GGTGCAGTTCGAGCAGC-
CCAGAAGATGCCCCACCAGACCCGAGGG-
CCAGAACTACACCGAGG GCATCGCCGTGGTGTT-
CAAGGAGAACATCGCCCCCTACAAGTTCAAGGC-
CACCATGTACTAC AAGGACGTGACCGTGAGCCAG-
GTGTGGTTCGGCCACAGATACAGCCAGTTCATGGG-
CATCTT CGAGGACAGAGCCCCCGTGCCCTTCGAG-
GAGGTGATCGACAAGATCAACGCCAAGGGCGTGT
GCAGAAGCACCGCCAAGTACGTGAGAAACAA-
CATGGAGACCACCGCCTTCCACAGAGACGAC
CACGAGACCGACATGGAGCTGAAGCCCGC-
CAAGGTGGCCACCAGAACCAGCAGAGGCTGGCA
CACCACCGACCTGAAGTACAACCCCAGCAGAGTG-
GAGGCCTTCCACAGATACGGCACCACCG
TGAACTGCATCGTGGAGGAGGTGGACGCC-
AGAAGCGTGTACCCCTACGACGAGTTCGTGCTG
GCCACCGGCGACTTCGTGTACATGAGCCCCTTC-
TACGGCTACAGAGAGGGCAGCCACACCGA
GCACACCAGCTACGCCGCCGACAGATTCAAGCA-
GGTGGACGGCTTCTACGCCAGAGACCTGA CCAC-
CAAGGCCAGAGCCACCAGCCCCACCACCAGAAA-
CCTGCTGACCACCCCCAAGTTCACC GTGGCCTGG-
GACTGGGTGCCCAAGAGACCCGCCGTGTGCAC-
CATGACCAAGTGGCAGGAGGT GGACGAGATGCT-
GAGAGCCGAGTACGGCGGCAGCTTCAGAT-
TCAGCAGCGACGCCATCAGCA CCACCTTCAC-
CACCAACCTGACCCAGTACAGCCTGAGCAGAG-
TGGACCTGGGCGACTGCATC GGCAGAGACGCC-
AGAGAGGCCATCGACAGAATGTTCGCCAGAAA-
GTACAACGCCACCCACAT CAAGGTGGGCC-
AGCCCCAGTACTACCTGGCCACCGGCGGCTTCCT-
GATCGCCTACCAGCCCC TGCTGAGCAACACC-
CTGGCCGAGCTGTACGTGAGAGAGTACATGAGA-
GAGCAGGACAGAAAG CCCAGAAACGCCACCCC-
CGCCCCCCTGAGAGAGGCCCCCAGCGCCAACGCC-
AGCGTGGAGAG AATCAAGACCACCAGCAG-
CATCGAGTTCGCCAGACTGCAGTTCACCTACAAC-
CACATCCAGA GACACGTGAACGACATGCTGGG-
CAGAATCGCCGTGGCCTGGTGCGAGCTGCAGAAC-
CACGAG CTGACCCTGTGGAACGAGGCCAGAA-
AGCTGAACCCCAACGCCATCGCCAGCGCCACC-
GTGGG CAGAAGAGTGAGCGCCAGAATGCTGGG-
CGACGTGATGGCCGTGAGCACCTGCGTGCCCGTGG
CCCCCGACAACGTGATCGTGCAGAACAGCAT-
GAGAGTGAGCAGCAGACCCGGCACCTGCTAC
AGCAGACCCCTGGTGAGCTTCAGATACGAGGA-
CCAGGGCCCCCTGATCGAGGGCCAGCTGGG
CGAGAACAACGAGCTGAGACTGACCAGAGACG-
CCCTGGAGCCCTGCACCGTGGGCCACAGAA
GATACTTCATCTTCGGCGGCGGCTACGTGTA-
CTTCGAGGAGTACGCCTACAGCCACCAGCTG
AGCAGAGCCGACGTGACCACCGTGAGCACCTT-
CATCGACCTGAACATCACCATGCTGGAGGA CC-
ACGAGTTCGTGCCCCTGGAGGTGTACACCAGACA-
CGAGATCAAGGACAGCGGCCTGCTGG ACTACAC-
CGAGGTGCAGAGAAGAAACCAGCTGCACGACCT-
GAGATTCGCCGACATCGACACC GTGATCAGA-
GCCGACGCCAACGCCGCCATGTTCGCCGGCCT-
GTGCGCCTTCTTCGAGGGCAT GGGCGACCTGG-
GCAGAGCCGTGGGCAAGGTGGTGATGGGCGT-
GGTGGGCGGCGTGGTGAGCG CCGTGAGCGGCGT-
GAGCAGCTTCATGAGCAACCCCTTCGGCGCCCT-
GGCCGTGGGCCTGCTG GTGCTGGCCGGCCTGG-
TGGCCGCCTTCTTCGCCTTCAGATACGTGCT-
GCAGCTGCAGAGAAA CCCCATGAAGGCCCT-
GTACCCCCTGACCACCAAGGAGCTGAAGACCA-
GCGACCCCGGCGGCG TGGGCGGCGAGGGCGAG-
GAGGGCGCCGAGGGCGGCGGCTTCGACGAGGC-
CAAGCTGGCCGAG GCCAGAGAGATGATCAGATA-
CATGCCCTGGTGAGCGCCATGGAGAGAACCGAG-
CACAAGGC CAGAAAGAAGGGCACCAGCGCC-
CTGCTGAGCAGCAAGGTGACCAACATGGTGCT-
GAGAAAGA GAAACAAGGCCAGATACAGCCCCCT-
GCACAACGAGGACGAGGCCGGCGACGAGGACGA-
GCTG TAGaggagctagcGAATTCtgc (SEQ ID NO: 07)

8. Modified HSV-1 ICP0 Promoter with hCMV TATA Element Plus Part of 5'
Untranslated Region of ICP0 Gene: hCMV TATA Element Underlined. TAATGGGCAACCCCGGTATTCCCC-
GCCTCCCGCGCCGCGCGTAACCACTCCCCT-
GGGGTTCC GGGTTATGCTAATTGCTTTTTTGGCG-
GAACACACGGCCCCTCGCGCATTGGCCCGCG-
GGTCG CTCAATGAACCCGCATTGGTCCCCTGGGGT-
TCCGGGTATGGTAATGAGTTTCTTCGGGAAGG
CGGGAAGCCCCGGGGCACCGACGCAGGC-
CAAGCCCCTGTTGCGTCGGCGGGAGGGGCATGCT
AATGGGGTTCTTTGGGGGACACCGGGTTGGGCCCC-
CAAATCGGGGGCCGGGCCGTGCATGCT AATGATAT-
TCTTTGGGGGCGCCGGGTTGGTCCCCGGGGACGG-
GGCCGCCCCGCGGTGGGCCT GCCTCCCCTGG-
GACGCGCGGCCATTGGGGGAATCGTCACTGCCGC-
CCCTTTGGGGAGGGGAA AGGCGTGGGG
<u>TATATAAGCAGAGCTCGTCGCATTTGCACCTCGGC-
ACTCGGAGCGAGACGCA</u> GCAGCCAGGCA-

GACTCGGGCCGCCCCCTCTCCGCATCACCACAGAAGCCCCGCCTACGTTGC GACCCCCAGGG (SEQ ID NO: 08)

9. TetO-Containing DNA Sequence (Underlined Sequence Represents Two Tandem Tet Operators)
TCCCTATCAGTGATAGAGATCTCCCTATCAGTGATAGAGATCGTCGACGAGCTCGCGT (SEQ ID NO: 09)

10. Two Tandem Tet Operator Sequence
TCCCTATCAGTGATAGAGATCTCCCTATCAGTGATAGAGA (SEQ ID NO: 10)

SEQ ID NO's 11-13 are in text of specification: SEQ ID NO: 11 is a Tet operator op2 element; SEQ ID NO: 12 and 13 are TATA elements.

11. HSV-1 UL9-C535C Coding Sequence (SEQ ID NO: 14)
ATGGGAGAGG CGTCGCTGCC GGCCCAGGCC GCCGAGACGG AGGAGGTGGG TCTTTTGTCG AAAAATACCT CCGGTCCGAT GTCGCGCCGG CGGAAATTGT CGCGCTCATG CGCAACCTCA ACAGCCTGAT GGGACGCACG CGGTTTATTT ACCTGGCGTT GCTGGAGGCC TGTCTCCGCG TTCCCATGGC CACCCGCAGC AGCGCCATAT TTCGGCGGAT CTATGACCAC TACGCCACGG GCGTCATCCC CACGATCAAC GTCACCGGAG AGCTGGAGCT CGTGGCCCTG CCCCCCACCC TGAACGTAAC CCCCGTCTGG GAGCTGTTGT GCCTGTGCAG CACCATGGCC GCGCGCCTGC ATTGGGACTC GGCGGCCGGG GGATCTGGGA GGACCTTCGG CCCCGATGAC GTGCTGGACC TACTGACCCC CCACTACGAC CGCTACATGC AGCTGGTGTT CGAACTGGGC CACTGTAACG TAACCGACGG ACTTCTGCTC TCGGAGGAAG CCGTCAAGCG CGTCGCCGAC GCCCTAAGCG GCTGTCCCCC GCGCGGGTCC GTTAGCGAGA CGGACCACGC GGTGGCGCTG TTCAAGATAA TCTGGGGCGA ACTGTTTGGC GTGCAGATGG CCAAAAGCAC GCAGACGTTT CCCGGGGCGG GGCGCGTTAA AAACCTCACC AAACAGACAA TCGTGGGGTT GTTGGACGCC CACCACATCG ACCACAGCGC CTGCCGGACC CACAGGCAGC TGTACGCCCT GCTTATGGCC CACAAGCGGG AGTTTGCGGG CGCGCGCTTC AAGCTACGCG TGCCCGCGTG GGGGCGCTGT TTGCGCACGC ACTCATCCAG CGCCAACCCC AACGCTGACA TCATCCTGGA GGCGGCGCTG TCGGAGCTCC CCACCGAGGC CTGGCCCATG ATGCAGGGGG CGGTGAACTT TAGCACCCTA TAA (SEQ ID NO: 14)

12. HSV-2 gD2 Genbank Number K01498 (SEQ ID NO: 15)
CTTGGGGGGG GGGGGGAAGA AACTAAAAAC ACATCAAGCC CACAACCCAT CCCACAAGGG GGGTTATGGC GGACCCACCG CACCACCATA CTCCGATTCG ACCACATATG CAACCAAATC ACCCCCAGAG GGGAGGTTCC ATTTTTACGA GGAGGAGGAG TATAATAGAG TCTTTGTGTT TAAAACCCGG GGTCGGTGTG GTGTTCGGTC ATAAGCTGCA TTGCGAACCA CTAGTCGCCG TTTTTCGTGT GCATCGCGTA TCACGGCATG GGGCGTTTGA CCTCCGGCGT CGGGACGGCG GCCCTGCTAG TTGTCGCGGT GGGACTCCGC GTCGTCTGCG CCAAATACGC CTTAGCAGAC CCCTCGCTTA AGATGGCCGA TCCCAATCGA TTTCGCGGGA AGAACCTTCC GGTTTTGGAC CAGCTGACCG ACCCCCCCGG GGTGAAGCGT GTTTACCACA TTCAGCCGAG CCTGGAGGAC CCGTTCCAGC CCCCCAGCAT CCCGATCACT GTGTACTACG CAGTGCTGGA ACGTGCCTGC CGCAGCGTGC TCCTACATGC CCCATCGGAG GCCCCCCAGA TCGTGCGCGG GGCTTCGGAC GAGGCCCGAA AGCACACGTA CAACCTGACC ATCGCCTGGT ATCGCATGGG AGACAATTGC GCTATCCCCA TCACGGTTAT GGAATACACC GAGTGCCCCT ACAACAAGTC GTTGGGGGTC TGCCCCATCC GAACGCAGCC CCGCTGGAGC TACTATGACA GCTTTAGCGC CGTCAGCGAG GATAACCTGG GATTCCTGAT GCACGCCCCC GCCTTCGAGA CCGCGGGTAC GTACCTGCGG CTAGTGAAGA TAAACGACTG GACGGAGATC ACACAATTTA TCCTGGAGCA CCGGGCCCGC GCCTCCTGCA AGTACGCTCT CCCCCTGCGC ATCCCCCCGG CAGCGTGCCT CACCTCGAAG GCCTACCAAC AGGGCGTGAC GGTCGACAGC ATCGGGATGT ACCCCGCTT ATCCCCGAA AACCAGCGCA CCGTCGCCCT ATACAGCTTA AAAATCGCCG GGTGGCACGG CCCCAAGCCC CCGTACACCA GCACCCTGCT GCCGCCGGAG CTGTCCGACA CCACCAACGC CACGCAACCC GAACTCGTTC CGGAAGACCC CGAGGACTCG GCCCTCTTAG AGGATCCCGC CGGGACGGTG TCTTCGCAGA TCCCCCCAAA CTGGCACATC CCGTCGATCC AGGACGTCGC GCCGCACCAC GCCCCGCCG CCCCCAGCAA CCCGGGCCTG ATCATCGGCG CGCTGGCCGG CAGTACCCTG GCGGCGCTGG TCATCGGCGG TATTGCGTTT TGGGTACGCC GCCGCGCTCA GATGGCCCCC AAGCGCCTAC GTCTCCCCCA CATCCGGGAT GACGACGCGC CCCCCTCGCA CCAGCCATTG TTTTACTAGA GGAGTTTCCC CGTTCCCGTG TACCTCTGGG CCCGTGTGGG AGGGTGGCCG GGGTATTTGG GTGGGACTTG GACTCCGCAT AAAGGGAGTC TCGAAGGAGG GAAACTAGGA CAGTTCATAG GCCGGGAGCG TGGGGCGCGC ACCGCGTCCC GACGATTAGC CACCGCGCCC ACAGCCACCT CGACC (SEQ ID NO: 15)

13. HSV-1 ICP0 Promoter Sequence Plus 5' Untranslated Region of ICP0
TAATGGGCAACCCCGGTATTCCCCGCCTCCCGCGCCGCGCGTAACCACTCCCCTGGGGTTCCGGGTTATGCTAATTGCTTTTTTGGCGGAACACACGGCCCCTCGCGCATTGGCCCGCGGGTCG CTCAATGAACCCGCATTGGTCCCCTGGGGTTCCGGGTATGGTAATGAGTTTCTTCGGGAAGG CGGGAAGCCCCGGGGCACCGACGCAGGCCAAGCCCCTGTTGCGTCGGCGGGAGGGGCATGCT AATGGGGTTCTTTGGGGGACACCGGGTTGGGCCCCCAAATCGGGGGCCGGGCCGTGCATGCT AATGATATTCTTTGGGGGCGCCGGGTTGGTCCCCGGGGACGGGGCCGCCCCGCGGTGGGCCT GCCTCCCCTGGGACGCGCGGCCATTGGGGGAATCGTCACTGCCGCCCCTTTGGGGAGGGGAA AGGCGTGGG<u>G</u>TATAAGTTAGCCCTGGCCCGACAGTCTGGTCGCATTTGCACCTCGGCACTCG GAGCGAGACGCAGCAGCCAGGCAGACTCGGGCCGCCCCTCTCCGCATCACCACAGAAGCCCCGCCTACGTTGCGACCCCCAGGGACCCTCCGTCCGCGACCCTCCAGCCGCATACGACCCC (SEQ ID NO: 16)

In SEQ ID NO: 16, the underlined single G represents the transcription start site of ICP0 gene, and the TATA element for ICP0 gene is TATAAGT.

14. HSV2 gD Protein Sequence (HSV-2, Strain SD90e, GenBank: KF781518.1)
MGRLTSGVGTAALLVVAVGLRVVCAKYALADPSLK-MADPNRFRGKNLPVLDQLTDPPGVKRV YHIQP-SLEDPFQPPSIPITVYYAVLERACRSVLLHAPSEAPQI- VRGASDEARKHTYNLTIAW YRMGDNCAIPITVMEYTECPYNKSLGVCPIRTQPRWSYYDSFSAVSEDNLGFLMHAPAFETA GTYLRLVKINDWTEITQFILEHRARASCKYALPLRIPPAACLTSKAYQQGVTVDSIGMLPRF IPENQRTVALYSLKIAGWHGPKPPYTSTLLPPELSDTTNATQPELVPEDPEDSALLEDPAGTVSSQIPPNWHIPSIQDVAPHHAPAAPSNPGLIIGALAGSTLAVLVIGGIAFWVRRRAQMAPK RLRLPHIRDDDAPPSHQPLFY (SEQ ID NO: 17)

15. HSV2 gB Protein Sequence (HSV-2, Strain SD90e, GenBank: KF781518.1)
MRGGGLICALVVGALVAAVASAAPAAPRASGGVAATVAANGGPASRPPVPSPATTRARKRK TKKPPERPEATPPPDANATVAAGHATLRAHLREIKVENADAQFYVCPPPTGATVVQFEQPRR CPTRPEGQNYTEGIAVVFKENIAPYKFKATMYYKDVTVSQVWFGHRYSQFMGIFEDRAPVPF EEVIDKINAKGVCRSTAKYVRNNMETTAFHRDDHETDMELKPAKVATRTSRGWHTTDLKYNP SRVEAFHRYGTTVNCIVEEVDARSVYPYDEFVLATGDFVYMSPFYGYREGSHTEHTSYAADR FKQVDGFYARDLTTKARATSPTTRNLLTTPKFTVAWDWVPKRPAVCTMTKWQEVDEMLRAEY GGSFRFSSDAISTTFTTNLTQYSLSRVDLGDCIGRDAREAIDRMFARKYNATHIKVGQPQYY LATGGFLIAYQPLLSNTLAELYVREYMREQDRKPRNATPAPLREAPSANASVERIKTTSSIE FARLQFTYNHIQRHVNDMLGRIAVAWCELQNHELTLWNEARKLNPNAIASATVGRRVSARML GDVMAVSTCVPVAPDNVIQNSMRVSSRPGTCYSRPLVSFRYEDQGPLIEGQLGENNELRLT RDALEPCTVGHRRYFIFGGGYVYFEEYAYSHQLSRADVTTVSTFIDLNITMLEDHEFVPLEV YTRHEIKDSGLLDYTEVQRRNQLHDLRFADIDTVIRADANAAMFAGLCAFFEGMGDLGRAVG KVVMGVVGGVVSAVSGVSSFMSNPFGALAVGLLVLAGLVAAFFAFRYVLQLQRNPMKALYPL TTKELKTSDPGGVGGEGEEGAEGGGFDEAKLAEAREMIRYMALVSAMERTEHKARKKGTSAL LSSKVTNMVLRKRNKARYSPLHNEDEAGDEDEL (SEQ ID NO: 18)

16. HSV2 gG Protein Sequence (HSV-2, Strain SD90e, GenBank: KF781518.1)
MHAIAPRLLLLFVLSGLPGTRGGSGVPGPINPPNNDVVFPGGSPVAQYCYAYPRLDDPGPLG SADAGRQDLPRRVVRHEPLGRSFLTGGLVLLAPPVRGFGAPNATYAARVTYYRLTRACRQPI LLRQYGGCRGGEPPSPKTCGSYTYTYQGGGPPTRYALVNASLLVPIWDRAAETFEYQIELGG ELHVGLLWVEVGGEGPGPTAPPQAARAEGGPCVPPVPAGRPWRSVPPVWYSAPNPGFRGLRF RERCLPPQTPAAPSDLPRVAFAPQSLLVGITGRTFIRMARPTEDVGVLPPHWAPGALDDGPY APFPPRPRFRRALRTDPEGVDPDVRAPLTGRRLMALTEDASSDSPTSAPEKTPLPVSATAMA PSVDPSAEPTAPATTTPPDEMATQAATVAVTPEETAVASPPATASVESSPLPAAAATPGAGH TNTSSAPAAKTPPTTPAPTTPPPTSTHATPRPTTPGPQTTPPGPATPGPVGASAAPTADSPL TASPPATAPGPSAANVSVAATTATPGTRGTARTPPTDPKTHPHGPADAPPGSPAPPPPEHRG GPEEFEGAGDGEPPDDDDSATGLAFRTPNPNKPPPARPGPIRPTLPPGILGPLAPNTPRPPA QAPAKDMPSGPTPQHIPLFWFLTASPALDILFIISTTIHTAAFVCLVALAAQLWRGRAGRRR YAHPSVRYVCLPPERD (SEQ ID NO: 19)

17. HSV-1 UL9 Protein Sequence (HSV-1, Strain KOS, GenBank: JQ673480)
MPFVGGAESGDPLGAGRPIGDDECEQYTSSVSLARMLYGGDLAEWVPRVHPKTTIERQQHGP VTFPNASAPTARCVTVVRAPMGSGKTTALIRWLREAIHSPDTSVLVVSCRRSFTQTLATRFA ESGLVDFVTYFSSTNYIMNDRPFHRLIVQVESLHRVGPNLLNNYDVLVLDEVMSTLGQLYSP TMQQLGRVDALMLRLLRTCPRIIAMDATANAQLVDFLCGLRGEKNVHVVVGEYAMPGFSARR CLFLPRLGTELLQAALRPPGPPSGPSPDASPDARGATFFGELEARLGGGDNICIFSSTVSFA EIVARFCRQFTDRVLLLHSLTPLGDVTTWGQYRVVIYTTVVTVGLSFDPLHFDGMFAYVKPM NYGPDMVSVYQSLGRVRTLRKGELLIYMDGSGARSEPVFTPMLLNHVVSSCGQWPAQFSQVT NLLCRRFKGRCDASACDTSLGRGSRIYNKFRYKHYFERCTLACLSDSLNILHMLLTLNCIRV RFWGHDDTLTPKDFCLFLRGVHFDALRAQRDLRELRCRDPEASLPAQAAETEEVGLFVEKYL RSDVAPAEIVALMRNLNSLMGRTRFIYLALLEACLRVPMATRSSAIFRRIYDHYATGVIPTI NVTGELELVALPPTLNVTPVWELLCLCSTMAARLHWDSAAGGSGRTFGPDDVLDLLTPHYDR YMQLVFELGHCNVTDGLLLSEEAVKRVADALSGCPPRGSVSETDHAVALFKIIWGELFGVQM AKSTQTFPGAGRVKNLTKQTIVGLLDAHHIDHSACRTHRQLYALLMAHKREFAGARFKLRVP AWGRCLRTHSSSANPNADIILEAALSELPTEAWPMMQGAVNFSTL (SEQ ID NO: 20)

18. UL9-C535C Protein Sequence (MG Plus UL9 Amino Acid 537 to 851)
MGEASLPAQAAETEEVGLFVEKYLRSDVAPAEIVALMRNLNSLMGRTRFIYLALLEACLRVP MATRSSAIFRRIYDHYATGVIPTINVTGELELVALPPTLNVTPVWELLCLCSTMAARLHWDS AAGGSGRTFGPDDVLDLLTPHYDRYMQLVFELGHCNVTDGLLLSEEAVKRVADALSGCPPRG SVSETDHAVALFKIIWGELFGVQMAKSTQTFPGAGRVKNLTKQTIVGLLDAHHIDHSACRTH RQLYALLMAHKREFAGARFKLRVPAWGRCLRTHSSSANPNADIILEAALSELPTEAWPMMQG AVNFSTL (SEQ ID NO: 21)

19. HSV-1 ICP27 Promoter (Strain KOS):
CAACGACCCCGCCCATGGGTCCCAATTGGCCGTCCCGTTACCAAGACCAACCCAGCCAGCGT ATCCACCCCCGCCCGGGTCCCCGCGGAAGCGGAACGGGGTATGTGATATGCTAATTAAATAC ATGCCACGTACTTATGGTGTCTGATTGGTCCTTGTCTGTGCCGGAGGTGGGGCGGGGGCCCC GCCCGGGGGGCGGAACGAGGAGGGGTTTGGGAGAGCCGGCCCCGGCACCACGGGTATAAGGA CATCCACCACC (SEQ ID NO: 22)

20. HSV-2 ICP27 Promoter (Strain HG52):
GCCGATCCGG CCTCGGGTCT GCTTGCCCCT CCCCCGGCCC AGCACAGGCA GGCTCGTCCG ACTTCCGCAT ACACCCCACC CTACCGCGTG CTTCCGCACC CCCGCCTACG CGTGTACGCG AAGGCGGACC CAGACCTGCC GTATGCTAAT TAAATACATA AAACCCACCC TCGGTGTCCG ATTGGTTTCT GGGGACGGCG GGGGCGGGGG CGGTGACGCC CGACGGGGAG GGACAAGGAG GAGTTTCGGA AAGCCGGCCC CGGTCGTGCG GGTATAAGGG CAGCCACCGG CCCACTGGGC GC (SEQ ID NO: 23)

21. ICP4/TO Promoter, Codon-Optimized gD2, and BGH Poly A:
caatt-
gaagcttcgtacgGGGCCCCGCCCCCTGCCCGTTCCTCGTTAGCATGCGGAACGGAA GCGGAAACCGCCGGATCGGGCGGTAATGAGATGCCATGCGGGGCGGGGCGCGGACCCACCCG CCCTCGCGCCCCCGCCATGGCAGATGCGCGGATGGGCGGGGCCGGGGGTTCGACCAACGGG CCGCGGCCACGGGCCCCCGGCGTGCCGGCGTCGGGGCGGGGTCGTGCAT- AATGGAATTCCGT TCGGGGTGGGCCCGCCGGGGG-
GGCGGGGGGCCGGCGGCCTCCGCTGCTCCTCCTT-
CCCGCCG GCCCCTGGGACTATATGAGCCGAGCT-
CTCCCTATCAGTGATAGAGATCTCCCTATCAGTGAT
AGAGATCGTCGACGAGCTCGCGTGTGCATCGCG-
TATCACGGCgccaccATGGGCCGCCTGAC CAGCGGC-
GTGGGCACCGCCGCCCTGCTGGTGGTGGCCGTGG-
GCCTGCGCGTGGTGTGCGCCA AGTACGCCCTGG-
CCGACCCCAGCCTGAAGATGGCCGACCCCAACC-
GCTTCCGCGGCAAGAAC CTGCCCGTGCTGGACC-
AGCTGACCGACCCCCCGGCGTGAAGCGCGTGT-
ACCACATCCAGCC CAGCCTGGAGGACCCCTTCCA-
GCCCCCCAGCATCCCCATCACCGTGTACTACGCCG-
TGCTGG AGCGCGCCTGCCGCAGCGTGCTGCTG-
CACGCCCCCAGCGAGGCCCCCCAGATCGTGCG-
CGGC GCCAGCGACGAGGCCCGCAAGCACACCTA-
CAACCTGACCATCGCCTGGTACCGCATGGGCGA
CAACTGCGCCATCCCCATCACCGTGATGGAGTA-
CACCGAGTGCCCCTACAACAAGAGCCTGG GCG-
TGTGCCCCATCCGCACCCAGCCCCGCTGGAGCTAC-
TACGACAGCTTCAGCGCCGTGAGC GAGGACAAC-
CTGGGCTTCCTGATGCACGCCCCCGCCTTCGA-
GACCGCCGGCACCTACCTGCG CCTGGTGAAGAT-
CAACGACTGGACCGAGATCACCCAGTTCATCCTG-
GAGCACCGCGCCCGCG CCAGCTGCAAGTA-
CGCCCTGCCCCTGCGCATCCCCCCCGCCGCCTGCC-
TGACCAGCAAGGCC TACCAGCAGGGCGTGAC-
CGTGGACAGCATCGGCATGCTGCCCCGCTTCATCC-
CCGAGAACCA GCGCACCGTGGCCCTGTACAGCCT-
GAAGATCGCCGGCTGGCACGGCCCCAAGCCCCC-
TACA CCAGCACCCTGCTGCCCCCGAGCTGAGC-
GACACCACCAACGCCACCCAGCCCGAGCTGGTG
CCCGAGGACCCCGAGGACAGCGCCCTGCTG-
GAGGACCCCGCCGGCACCGTGAGCAGCCAGAT
CCCCCCCAACTGGCACATCCCCAGCATCCAGGA-
CGTGGCCCCCACCACGCCCCGCCGCCC CCAG-
CAACCCCGGCCTGATCATCGGCGCCCTGGCCGG-
CAGCACCCTGGCCGTGCTGGTGATC GGCGGCATC-
GCCTTCTGGGTGCGCCGCCGCGCCCAGATGGCCC-
CCAAGCGCCTGCGCCTGCC CCACATCCGCGACG-
ACGACGCCCCCCCCAGCCACCAGCCCCTGTTC-
TACTAAAGGAGTTTCC CCGCTCCCGTGTACCTCT-
GGGCCCGTGTGGGAGGGTGGCTGGGGTATTTGG-
GTGGGACTTGG ACTCCGCATAAAGGGAGTCTCG-
AAGGAGGGAACCGCTGATCAGCCTCGACTGTGC-
CTTCTAGTTGCCAGCCATCTGTTGTTTGCCCCTCC-
CCCGTGCCTTCCTTGACCCTGGAAGGTGCCACTC-
CCACTGTCCTTTCCTAATAAAATGAGGAAATTGCA-
TCGCATTGTCTGAGTAGGTGTCATTCTATTCTGGG-
GGGTGGGGTGGGGCAGGACAGCAAGGGGGAGG-
ATTGGGAAGACAATAGCAGGCATGCgatatctacgcaacg-
accccgcccatgggtccaattggatcctctaga (SEQ ID NO: 24)

In SEQ ID NO: 24, bold italic represents the codon-optimized gD2 coding sequence; italic represents a part of the 3' untranslated region of gD2; underlined italic represents BGH poly A signal sequence.

22. p2UL26.27-v:
tgccggccgcggggacggtggcctacggacaccccggcgccggcccgtc-
ccgcactacccg cctcctcccgcccacccgtacccgggtatgctgttcgcgg-
gccccagtccctggaggccca gatcgccgcgctggtgggggccatcgccg-
ccgaccgccaggcgggtgggcttccggcggccg ccggagaccacgg-
gatccggggtcggcgaagcgccgccgacacgaggtggagcagccggag
tacgactgcggccgtgacgagccggaccgggacttcccgtattacccgggc-
gaggcccgccc cgagccgcgcccggtcgactcccggcgccgcgcgccag-
ggcttccgggccccacgaaacca tcacggcgctggtggggcggtgacgtcc-
ctgcagcaggaactggcgcacatgcgcgcgcgt acccacgccccc-
tacgggccgtatccgccggtgggggcctaccaccaccccacgcagacac
ggagaccccgcccaaccaccccgctaccccgccaaggccgtctatctgccg-
ccgccgcaca tcgccccccgggccctcctctatccggggcggtcccc-
caccctcgtatccccagttgcg gttaccccggtcccgctcccccgcta-
catcagccctcccccgcacacgccacccccctcc gccgccgccgggacc-
cacgcctcccccgccgcgagcttacccccaacccgaggcgcccggcg
cggaggccggcgccttagttaacgccagcagcgcgggcccacgtgaacgt-
ggacacggcccgg gccgccgatcgtttgtgtcacagatgatggggtcccg-
ctaactcgcctccaggatccggac ttggggggggtgtgtgttttcatatattt-
taaataaacaaacaaccggacaaaagtatacc acttcgtgtgcttgtgttttgttt-
gagaggggggggtggagtggggggaaagtgggccga atgacacaaaaatt-
aggtcgtacgCAACGACCCCGCCCATGGGTCCCAATTG-
GCCGTCCCGT TACCAAGACCAACCCAGCCA-
GCGTATCCACCCCCGCCCGGGTCCCCGCGGAAGC-
GGAACGGG GTATGTGATATGCTAATTAAATA-
CATGCCACGTACTTATGGTGTCTGATTGGTCC-
TTGTCTG TGCCGGAGGTGGGGCGGGGGCCCCG-
CCCGGGGGGCGGAACGAGGAGGGGTTTGGGAGA-
GCCG GCCCCGGCACCACGGGTATATAAGCA-
ACCGGTgtcgacggcggggtcgtcggggtccgtgg gtctgccccctc-
ccccatcgagagtccgtaggtgacctaccgtTGCGCCACCACCA-
GAGG CCATATCCGACACCCCAGCCCCGACGGCA-
GCCGACAGCCCGAAGCTTGGTCGATATCTATCG
GAGCTGTGCTAGCGCCACTGGTACCCGAGCG-
GAATTCTGTCTAGAAATGGTTACAAATAAAAGA-
TCTTTATTTTCATTAGATCTGTGTGTTGGTTTTTTG-
TGTGttggttttcccgttagcaca tgtctgcatttgttttctagtcacacgccccc-
ccccccaaataaaaaccaaggcaaaaca ataccagaagtcatgtgtattttgaa-
catcggtgtcttttatttatacacaagcccagct cccctcccctccttagagctc-
gtcttcgtctccggcctcgtcctcgttgtggagcggagag tacctggctttgttg-
cgcttgcgcagaaccatgttggtgaccttggagctgagcagggcgct
cgtgccctctttctggccttgtgttccgtgcgctccatggccgacaccaaagc-
catatatc ggatcatttctcgggcctcggccaacttggcctcgtcaaacccgccc-
ccctccgcgccttcc tccccctccccgcccacgccccggggtcggaagtctt-
gagttccttggtggtgagcggata cagggccttcatgggattgcgttgcagttgc-
aggacgtagcggaaggcgaagaaggccgcga ccaggccggccag-
gaccagcagccccacggcaagcgccccgaaggggttggacataaaggag
gacacgcccgagacggccgacaccacgccccccactactcccatgac-
taccttgccgaccgc gcgccccaagtcccccatccctcgaagaacgcgcac-
agccccgcgaacatggcggcgttgg cgtcggcgcggatgaccgtgtc-
gatgtcggcaaagcgcaggtcgtgcagctggttgcggcgc tggacctccgtg-
tagtccagcaggccgctgtcttgatctcgtggcgcgtgtagacctccag gggca-
caaactcgtggtcctccagcatggtgatgttcaggtcgatgaaggtgctg-
acggtgg tgacgtcggcgcgactcagctggtgagagtacgcgtactcctcg-
aagtacacgtagcccccg ccgaagatgaagtagcgccggtggcc-
cacggtgcacggctcgagcgcgtc (SEQ ID NO: 25)

23. 900 bp Upstream of HSV-2 UL26 Poly A Signal to 110 bp Downstream of UL26 Poly A Signal:
tgccggccgcggggacggtggcctacggacaccccggcgccggcccgtc-
ccgcactacccg cctcctcccgcccacccgtacccgggtatgctgttcgcgg-
gccccagtccctgaggccca gatcgccgcgctggtgggggccatcgccg-
ccgaccgccaggcgggtgggcttccggcggccg ccggagaccacgg-
gatccggggtcggcgaagcgccgccgacacgaggtggagcagccggag
tacgactgcggccgtgacgagccggaccgggacttcccgtattacccgggcg-
aggcccgccc cgagccgcgcccggtcgactcccggcgccgcgcgccag-
gcttccgggccccacgaaac catcacggcgctggtggggcggtgac-
gtccctgcagcaggaactggcgcacatgcgcgc gcgtacccacgccccc-
tacgggccgtatccgccggtgggggcctaccaccaccccacgc agacacg
gagaccccgcccaaccaccccgctaccccgccaaggccgtctatctgccgcc
gccgcacatcgccccccgggggcctcctctatccggggcggtcccc-
caccctcgtatcc cccagttgcggttaccccggtcccgctcccccgcta-
catcagccctcccccgcacacgc cacccccctccgccgccgcgggacc-
cacgcctcccccgccgcgagcttacccccaacc cgaggcgcccggcgcgg
aggccggcgccttagttaacgccagcagcgcggcccacgtgaa cgtgg-
acacggcccgggccgccgatcgtttgtgtcacagatgatggggtcccgctaact
cgcctccaggatccggacttgggggggtgtgtgttttcatatatttaaataaacaaac aaccggacaaaagtatacccacttcgtgtgcttgtgtttttgttt-gagaggggggggtgg agtggggggggaaagtgggccgaatgacacaaaaatt-aggt (SEQ ID NO: 26)

24. 121 bp Downstream of HSV-2 UL27 Poly A Signal to 873 bp Upstream of UL27 Poly A Signal:
ttggttttcc cgttagcaca tgtctgcatt tgttttctta gtcacacgcc cccccccccc aaataaaaac caaggcaaaa caataccaga agtcatgtgt attttgaac atcggtgtct ttttatttat acacaagccc agctcccctc ccctcccta gagctcgtct tcgtctccgg cctcgtcctc gttgtggagc ggagagtacc tggctttgtt gcgcttgcgc agaaccatgt tggtgacctt ggagctgagc agggcgctcg tgcccttctt tctggccttg tgttccgtgc gctc-catggc cgacaccaaa gccatatatc ggatcatttc tcgggcctcg gccaacttgg cctcgtcaaa cccgccccc tccgcgcctt cctccccctc cccgcccacg ccccgggggt cggaagtctt gagttccttg gtggtgagcg gatacagggc cttcatggga ttgcgttgca gttgcaggac gtagcggaag gcgaagaagg ccgcgaccag gccggccagg accagcagcc ccacggcaag cgccccgaag gggttggaca taaaggagga cacgcccgag acggccgaca ccacgccccc cactactccc atgactacct tgccgaccgc gcgccccaag tccccccatcc cctcgaagaa cgcgcacagc cccgcgaaca tggcggcgtt ggcgtcggcg cggatgaccg tgtcgatgtc ggcaaagcgc aggtcgtgca gctggttgcg gcgctggacc tccgtgtagt ccagcaggcc gctgtccttg atctcgtggc gcgtgtagac ctccaggggc acaaactcgt ggtcctccag catggtgatg ttcaggtcga tgaaggtgct gacggtggtg acgtcggcgc gactcagctg gtgagagtac gcgtactcct cgaagtacac gtagccccg ccgaagatga agtagcgccg gtggcccacg gtgcacggct cgagcgcgtc (SEQ ID NO: 27)

25. A Modified HSV-1 ICP27 Promoter in which the ICP27 TATA Element is Changed to HCMV TATATAAG Followed by an Age I Site and Part of 5' Untranslated Region of HSV-1 ICP4 and ICP27, MCS and a Synthetic Poly A Signal Sequence:
CAACGACCCCGCCCATGGGTCCCAATTGGCCGTC-CCGTTACCAAGACCAACCCAGCCAGCGT ATC-CACCCCCGCCCGGGTCCCCGCGGAAGCGGAACG-GGGTATGTGATATGCTAATTAAATAC ATGCCACGTA-CTTATGGTGTCTGATTGGTCCTTGTCTGTGCCG-GAGGTGGGGCGGGGCCCC GCCCGGGGGGCG-GAACGAGGAGGGGTTTGGGAGAGCCGGCCC-CGGCACCACGGGTATATAAG CAACCGGTgtcgacg-gcggggtcgtcggggtccgtgggtctcgcccctcccccatcgag agtccgtaggtgacctaccgtTGCGCCACCACCAGAGGC-CATATCCGACACCCCAGCCCGA CGGCAGCC-GACAGCCCGAAGCTTGGTCGATATCTATCGGAGC-TGTGCTAGCGCCACTGGTAC CCGAGCGGAAT-TCTGTCTAGAAATGGTTACAAATAAAAGATCTTTAT-TTTCATTAGATCTGT GTGTTGGTTTTTTGTG TG (SEQ ID NO: 28)

26. A Newly Designed HSV-1 tetO-Bearing ICP27 Promoter in which the ICP27 TATA Element is Changed to HCMV TATATAA and tetO Sequence is Flanked with Age I Site Followed by Part of 5' Untranslated Region of HSV-1 ICP4 and ICP27, MCS and a Synthetic Poly A Signal Sequence:
cgtacgCAACGACCCCGCCCATGGGTCCCAATTGGCC-GTCCCGTTACCAAGACCAACCCAGC CAGCGTATC-CACCCCCGCCCGGGTCCCCGCGGAAGCGGAACG-GGGTATGTGATATGCTAATT AAATACATGCCACGT-ACTTATGGTGTCTGATTGGTCCTTGTCTGTGCCG-GAGGTGGGGCGGG GGCCCCGCCGGGGGGCG-GAACGAGGAGGGGTTTGGGAGAGCCGGCCC-CGGCACCACGGGTA TAAGCAACCGGTCTCCCT-ATCAGTGATAGAGATCTCCCTATCAGTGATAGAG-ATCGaccg gtgtcgacggcggggtcgtcggggtccgtgggtct-cgcccctcccccatcgagagtccg taggtgacctaccgtTGCGCCAC-CACCAGAGGCCATATCCGACACCCCAGCCC-CGACGGCAG CCGACAGCCCGAAGCTTGGTCGA-TATCTATCGGAGCTGTGCTAGCGCCACTGGTACC-CGAGC GGAATTCTGTCTAGAAATGGTTACA (SEQ ID NO: 29)

27. HSV-1 ICP27 Promoter:
CAACGACCCCGCCCATGGGTCCCAATTGGCCGTC-CCGTTACCAAGACCAACCCAGCCAGCGT ATCCAC-CCCCGCCCGGGTCCCCGCGGAAGCGGAACGGG-GTATGTGATATGCTAATTAAATAC ATGCCACGTACT-TATGGTGTCTGATTGGTCCTTGTCTGTGCCGGAG-GTGGGGCGGGGCCCC GCCCGGGGGCGGAAC-GAGGAGGGGTTTGGGAGAGCCGGCCCCGGCAC-CACGGGTATAAGGA CATCCACCACC (SEQ ID NO: 30)

28. 5' Untranslated Region of HSV-1 ICP27, −49 bp Upstream of ICP27 ATG:
TGCGCCACCACCAGAGGCCATATCCGACACCCCA-GCCCCGACGGCAGCCGACAGCCCG (SEQ ID NO: 31)

29. 5' Untranslated Region of HSV-1 ICP4, −126 to −64 bp Upstream of ICP4 ATG:
Gtcgacggcggggtcgtcggggtccgtgggtctcgcccctcccccatcg-agagtccgta ggtgacctaccgt (SEQ ID NO: 32)

30. Multiple Cloning Sites:
AAGCTTGGTCGATATCTATCGGAGCTGTGCTAGCG-CCACTGGTACCCGAGCGGAATTTCTG TCTAGA (SEQ ID NO: 33)

31. Synthetic Poly A:
AATAAAAGATCTTTATTTTCATTA-GATCTGTGTGTTGGTTTTTTGTGTG (SEQ ID NO: 34)

32. p2UL2627-LacZ:
tcgcgcgtttcggtgatgacggtgaaaacctctgacacatgcagctcccgga-gacggtcaca gcttgtctgtaagcggatgccgggagcagacaagcccgtca-gggcgcgtcagcgggtgttgg cgggtgtcggggctggcttaactatgcgg-catcagagcagattgtactgagagtgcaccata tgtgccggccgcggg-gacggtggcctacggacaccccggcgccggcccgtccccgcactacc cgcctcctcccgcccacccgtacccgggtatgctgttcgcgggcccagtccc-ctggaggcc cagatcgccgcgctggtggggccatgccgccgaccg-ccaggcgggtgggcttccggcggc cgccggagaccacgggatccggggt-cggcgaagcgccgccgacacgaggtggagcagccgg agtacgactgcgg-ccgtgacgagccggaccgggacttcccgtattacccgggcgaggcccgc ccc-gagccgcgcccggtcgactcccggcgcgccgcgcgccaggcttccgggccc-cacgaaac catcacggcgctggtggggcggtgacgtccctgcagcag-gaactggcgcacatgcgcgcgc gtacccacgcccctacgggccgtatcc-gccggtggggccctaccaccaccccacgcagac acggagacccccgcc-caaccaccccgctacccgccaaggccgtctatctgccgccgccgca catcg-ccccccggggcctcctctatccggggcggtccccccaccctcgtatcccca-gttg cggttaccccggtcccgctccccgctacatcagccctcccccgca-cacgcccaccccct ccgccgccgccgggacccacgcctccccccgccgcg-agcttacccaaccccgaggcgcccgg cgcggaggccggcgccttagt-taacgccagcagcgcggcccacgtgaacgtggacacggcc gggccgcc-gatcgtttgtgtcacagatgatggggtcccgctaactcgcctccaggatccgg acttggggggggtgtgtgttttcatatattttaaataaacaaacaaccggacaaa-agtatac ccacttcgtgtgcttgtgttttgtttgagaggggggggtggagtgggg-gggaaagtgggcc gaatgacacaaaaattaggtcgtacgcaacgaccccgcc-catgggtcccaattggccgtccc gttaccaagaccaacccagccagcgtatc-cacccccgcccgggtccccgcggaagcggaacg gggtatgtgatatgctaat-taaatacatgccacgtacttatggtgtctgattggtccttgtc tgtgccggaggtg-gggcgggggccccgcccgggggcggaacgaggagggggtttgggagagc cggccccggcaccacgggtataagcaaccggtgtcgacggcggggt-cgtcggggtccgt gggtctcgcccctcccccatcgagagtccgtaggtgacc-taccgttgcgccaccaccaga ggccatatccgacaccccagccccgacg-gcagccgacagcccgAGCTTACCATGGGGGGTTC TCAT-CATCATCATCATCATGGTATGGCTAGCATGACTGG-TGGACAGCAAATGGGTCGGGATC TGTACGACGAT-GACGATAAGGTACCTAAGGATCAGCTTGGAGTT- GATCCCGTCGTTTTACAA CGTCGTGACTGGGAAAACCCTGGCGTTACCCAACTTAATCGCCTTGCAGCACATCCCCCTTT CGCCAGCTGGCGTAATAGCGAAGAGGCCCGCACCGATCGCCCTTCCCAACAGTTGCGCAGCC TGAATGGCGAATGGCGCTTTGCCTGGTTTCCGGCACCAGAAGCGGTGCCGGAAAGCTGGCTG GAGTGCGATCTTCCTGAGGCCGATACTGTCGTCGTCCCCTCAAACTGGCAGATGCACGGTTA CGATGCGCCCATCTACACCAACGTAACCTATCCCATTACGGTCAATCCGCCGTTTGTTCCCACGGAGA- ATCCGACGGGTTGTTACTCGCTCACATTTAATGTTGATGAAAGCTGGCTACAGGAA GGCCAGACGCGAATTATTTTTGATGGCGTTAACTCGGCGTTTCATCTGTGGTGCAACGGGCG CTGGGTCGGTTACGGCCAGGACAGTCGTTTGCCGTCTGAATTTGACCTGAGCGCATTTTTAC GCGCCGGAGAAAACCGCCTCGCGGTGATGGTGCTGCGTTGGAGTGACGGCAGTTATCTGGAA GATCAGGATATGTGGCGGATGAGCGGCATTTTCCGTGACGTCTCGTTGCTGCATAAACCGAC TACACAAATCAGCGATTTCATGTTGCCACTCGCTTTAATGATGATTTCAGCCGCGCTGTAC TGGAGGCTGAAGTTCAGATGTGCGGCGAGTTGCGTGACTACCTACGGGTAACAGTTTCTTTA TGGCAGGGTGAAACGCAGGTCGCCAGCGGCACCGCGCCTTTCGGCGGTGAAATTATCGATGA GCGTGGTGGTTATGCCGATCGCGTCACACTACGTCTGAACGTCGAAAACCCGAAACTGTGGAGCGCCGAAATCCCGAATCTCTATCGTGCGGTGGTTGAACTGCACACCGCCGACGGCACGCTG ATTGAAGCAGAAGCCTGCGATGTCGGTTTCCGCGAGGTGCGGATTGAAAATGGTCTGCTGCT GCTGAACGGCAAGCCGTTGCTGATTCGAGGCGTTAACCGTCACGAGCATCATCCTCTGCATG GTCAGGTCATGGATGAGCAGACGATGGTGCAGGATATCCTGCTGATGAAGCAGAACAACTTT AACGCCGTGCGCTGTTCGCATTATCCGAACCATCCGCTGTGGTACACGCTGTGCGACCGCTA CGGCCTGTATGTGGTGGATGAAGCCAATATTGAAACCCACGGCATGGTGCCAATGAATCGTC TGACCGATGATCCGCGCTGGCTACCGGCGATGAGCGAACGCGTAACGCGAATGGTGCAGCGC GATCGTAATCACCCGAGTGTGATCATCTGGTCGCTGGGGAATGAATCAGGCCACGGCGCTAA TCACGACGCGTCTATCGCTGGATCAAATCTGTCGATCCTTCCCGCCCGGTGCAGTATGAAG GCGGCGGAGCCGACACCACGGCCACCGATATTATTTGCCCGATGTACGCGCGCGTGGATGAA GACCAGCCCTTCCCGGCTGTGCCGAAATGGTCCATCAAAAAATGGCTTTCGCTACCTGGAGA GACGCGCCCGCTGATCCTTTGCGAATACGCCCACGCGATGGGTAACAGTCTTGGCGGTTTCG CTAAATACTGGCAGGCGTTTCGTCAGTATCCCGTTTACAGGGCGGCTTCGTCTGGGACTGG GTGGATCAGTCGCTGATTAAATATGATGAAAACGGCAACCCGTGGTCGGCTTACGGCGGTGA TTTTGGCGATACGCCGAACGATCGCCAGTTCTGTATGAACGGTCTGGTCTTTGCCGACCGCA CGCCGCATCCAGCGCTGACGGAAGCAAAACACCAGCAGCAGTTTTTCCAGTTCCGTTTATCC GGGCAAACCATCGAAGTGACCAGCGAATACCTGTTCCGTCATAGCGATAACGAGCTCCTGCA CTGGATGGTGGCGCTGGATGGTAAGCCGCTGGCAAGCGGTGAAGTGCCTCTGGATGTCGCTC CACAAGGTAAACAGTTGATTGAACTGCCTGAACTACCGCACCGGACGGAGAGCGCCGGGCAACTC TGGCTCACAGTACGCGTAGTGCAACGAACGCGACCGCATGGTCAGAAGCCGGGCACATCAG CGCCTGGCAGCAGTGGCGTCTGGCGGAAAACCTCAGTGTGACGCTCCCCGCCGCGTCCCACG CCATCCCGCATCTGACCACCAGCGAAATGGATTTTTGCATCGAGCTGGGTAATAAGCGTTGG CAATTTAACCGCCAGTCAGGCTTTCTTTCACAGATGTGGATTGGCGATAAAAAACAACTGCT GACGCCGCTGCGCGATCAGTTCACCCGTGCACCGCTGGATAACGACATTGGCGTAAGTGAAG CGACCCGCATTGACCCTAACGCCTGGGTCGAACGCTGGAAGGCGGCGGGCCATTACCAGGCC GAAGCAGCGTTGTTGCAGTGCACGGCAGATACACTTGCTGATGCGGTGCTGATTACGACCGC TCACGCGTGGCAGCATCAGGGGAAAACCTTATTTATCAGCCGGAAAACCTACCGGATTGATG GTAGTGGTCAAATGGCGATTACCGTTGATGTTGAAGTGGCGAGCGATACACCGCATCCGGCG CGGATTGGCCTGAACTGCCAGCTGGCGCAGGTAGCAGAGCGGGTAAACTGGCTCGGATTAGG GCCGCAAGAAAACTATCCCGACCGCCTTACTGCCGCCTGTTTTGACCGCTGGGATCTGCCAT TGTCAGACATGTATACCCCGTACGTCTTCCCGAGCGAAAACGGTCTGCGCTGCGGGACGCGC GAATTGAATTATGGCCCACACCAGTGGCGCGGCGACTTCCAGTTCAACATCAGCCGCTACAG TCAACAGCAACTGATGGAAAACCAGCCATCGCCATCTGCTGCACGCGGAAGAAGGCACATGGC TGAATATCGACGGTTTCCATATGGGGATTGGTGGCGACGACTCCTGGAGCCCGTCAGTATCG GCGGAGTTCCAGCTGAGCGCCGGTCGCTACCATTACCAGTTGGTCTGGTGTCAAAAATAATA AAGCCGAATTCtgtctagaaatggttacaaataaaagatctttattttcattagatctgtgt gttggttttttgtgtgttggttttcccgttagcacatgtctgcatttgttttctagtcaca cgccccccccccccaaataaaaaccaaggcaaaacaataccagaagtcatgtgtattttga acatcggtgtcttttatttatacacaagccagctcccctccctcccttagagctcgtct tcgtctccggcctcgtcctcgttgtggagcggagagtacctggctttgttgcgcttgcgcag aaccatgttggtgaccttggagctgagcagggcgctcgtgcccttctttctggccttgtgtt ccgtgcgctccatgccgacaccaaagccatatatcggatcatttctcgggcctcggccaac ttggcctcgtcaaacccgccccccctccgcgccttcctccccctcccgcccacgcccccggg gtcggaagtcttgagttccttggtggtgagcggatacagggccttcatgggattgcgttgca gttgcaggacgtagcggaaggcgaagaaggccgcgaccaggccggccaggaccagcagcccc acggcaagcgccccgaaggggttggacataaaggaggacacgcccgagacggccgacaccac gccccccactactccatgactaccttgccgaccgcgcgccccaagtccccatccccctcga agaacgcgcacagccccgcgaacatgcggcgttggcgtcggcgcggatgaccgtgtcgatg tcggcaaagcgcaggtcgtgcagctggttgcggcgctggacctccgtgtagtccagcaggcc gctgtccttgatctcgtggcgcgtgtagacctccaggggcacaaactcgtggtcctccagca tggtgatgttcaggtcgatgaaggtgctgacggtggtgacgtcggcgcgactcagctggtga gagtacgcgtactcctcgaagtacacgtagccccgccgaagatgaagtagcgccggtggcc cacggtgcacggctcgagcttcctcgctcactgactcgctgcgctcggtcgttcggctgcgg cgagcggtatcagctcactcaaaggcggtaatacggttatccacagaatcaggggataacgc aggaaagaacatgtgagcaaaaggccagcaaaaggccaggaaccgtaaaaaggccgcgttgc tggcgtttttccataggctccgccccctgacgagcatcacaaaaatcgacgctcaagtcag aggtggcgaaacccgacaggactataaagataccaggcgtttccccctggaagctccctcgt gcgctctcctgttccgaccctgccgcttaccggatacctgtccgcctttctcccttcgggaa gcgtggcgctttctcatagctcacgctgtaggtatctcagttcggtgtaggtcgttcgctcc aagctgggctgtgtgcacgaaccccccgttcagcccgaccgctgcgccttatccggtaacta tcgtcttgagtccaacccggtaagacacgacttatcgccactggcagcagccactggtaaca ggattagcagagcgaggtatgtaggcggtgctacagagttcttgaagtggtggcctaactac ggctacactagaaggacagtatttggtatctgcgctctgctgaagccagttaccttcggaaa aagagttggtagctcttgatccggcaaacaaaccaccgctggtagcggtggtttttttgttt gcaagcagcagattacgcgcagaaaaaaaggatctcaagaagatcctttgatcttttctacg gggtctgacgctcagtggaacgaaaactcacgttaagggattttggtcatgagattatcaaa aaggatcttcacctagatccttttaaattaaaaatgaagttttaaatcaatctaaagtatat atgagtaaacttggtctgacagttaccaatgcttaatcagtgaggcacctatctcagcgatc tgtctatttcgttcatccatagttgcctgactccccgtcgtgtagataactacgatacggga gggcttaccatctggccccagtgctgcaatgataccgcgagacccacgctcaccggctccag atttatcagcaataaaccagccagccggaagggccgagcgcagaagtggtcctgcaacttta tccgcctccatccagtctattaattgttgccgggaagctagagtaagtagtt- cgccagttaa tagtttgcgcaacgttgttgccattgctacaggcatcgtggtgt- cacgctcgtcgtttggta tggcttcattcagctccggttcccaacgat- caaggcgagttacatgatcccccatgttgtgc aaaaaagcggt- tagctccttcggtcctccgatcgttgtcagaagtaagttggccgcagtgtt atcactcatggttatggcagcactgcataattctcttactgtcatgccatccgtaa- gatgct tttctgtgactggtgagtactcaaccaagtcattct- gagaatagtgtatgcggcgaccgagt tgctcttgcccggcgtcaatacggga- taataccgcgccacatagcagaactttaaaagtgct catcattggaaaacgtt- cttcggggcgaaaactctcaaggatcttaccgctgttgagatcca gttc- gatgtaacccactcgtgcacccaactgatcttcagcatcttttactttcaccagcgtt tctgggtgagcaaaaacaggaaggcaaaatgccgcaaaaaagggaataagg- gcgacacggaa atgttgaatactcatactcttccttttcaatattattgaagcatt- tatcaggggttattgtc tcatgagcggatacatatttgaatgtatttagaaaaata- aacaaatagggttccgcgcaca ttccccgaaaagtgccacctgacgtct- aagaaaccattattatcatgacattaacctataa aaataggcgtat- cacgaggcccttcgtc (SEQ ID NO: 35)

In SEQ ID NO: 35, the Italic sequence represents the Hind III/Eco RI-lacZ-containing DNA sequence inserted into p2UL2627-V.

33. Annotated Sequence of p2ICP0-V Plasmid:

tcgcgcgtttcggtgatgacggtgaaaacctctgacacatgcagctcccgga- gacggtcaca gcttgtctgtaagcggatgccgggagcagacaagcccgtca- gggcgcgtcagcgggtgttgg cgggtgtcggggctggcttaactatgcgg- catcagagcagattgtactgagagtgcacCATA TGGCCGCCGCC- CGCGCGGGCCCGGACTCCGCCCCGGCGACCGCC- CCGCGCCGGCTTCCCGGT ATGGTAATTAGAAA- CTTTTAATAGGCGGTCCGGCCGCCATCCCCGCT- CATGGCAATTAGCA ACTTTTAATGGGCCGGCC- TTCCCGCTCGCGGTAATTAGCAGCTTTTAACGGGC- CGCCATTCC CGCTTATGGTAATTAAAAACGTTCG- GACGGCCCCTCGCTCCCCGCGTAATTACTCCC- TCGGG GTTCCGGGTTATGCTGATTACTTTCTTGG- CAGAACACGCAGAGCCTCGCGCGCCGCCGGGTG GGTGGGCTGATCGGCCCCTATTGGTCCCCTGG- GCTTCCTAGTATGCTAATGAATTTCTCCCC GGGG- GCGGGCACCACTCAGGGCCGCGCCGGCGGGGCG- CCGGGGGGACTCCCATCTGCGTCGG CGGGG- GCGGCGCATGCTAATGGGGTTCTTGGAGTACACC- CGGTTGGTCCCCGGGGACGGGGC CGCCCCGAG- AGGGGGGGATTCCCTCCCTTCCGCCCCCGCCGGG- GCGCGGCTATTGGGGGAA TCGTAAAT- GCCGCCCCTTTGGGGGAGTGGATAGGCGCCG- GGTATAAGGCAGCCCCGTGTGAC GGTCGGGCCG- CATTCGCACCCCGGCACTGCGAGCGACG- GAGCGGCGGCCCGGCGGGAGGAGG AGACCCG- GAGAGACAGAGACTAAAACCCGGCAAGAGAGAG- AGACCGCGGGCCGCCGTCTCGAAGCTTggtcgatatcta- tcggagctgtgctagcgccactggtacccgagcggaattcGGCTT GCTGCCCGAAGGGAAGCCGCCCCCCCCGGAC- CACCGGCCGAGGCGCCTCGGGGGCAGGGGG AGGTGGGGGGGGGAAGACGGGGAGGAGACAG- GAAGTGGGGGTGGGAGTGGGGGGGACGGAC ACGGCCCCGAACAGCAACACACACCAGCAT- TTTGTTATGGACTTTCTGGCCTTGTTGAAAAC TTGAGGAAAAAAAACTTTATATTTATAAAAATTTTA- CAATAAAGTTTTGTGATGCTTTTGAC ACACTTTG- TTGTTGGCCTTTGATGCAGCTCCCCCGCGCA- GGGGGGCCGGGGATGGGGGGGAA AGGGAGGAG- GAGGAGGGGGGGCGGGCACGAGAAGCCGCCCC- CACCCCGAGGCCTGTTGGTC TTTATCAT- AGAACAGAGCCGGGGCCCGGCCTGCCGTTCTGGCT- CCCTGTCTTGGTGGGTGGGC GGGCTGGCG- GGTAAAAAAAGAGTGTGTCCGTGTTGACAGG- GAGGGGGGCCCGATCGTV CAGAGCACGC- ACGTCTGGCCGGCCAGACCCTGGGGGTG- GTGGGCAGGAGTGGGAGGGCGCCT GGCTCGGG- GAGGGAGGAGGGGGGGGGTCAGCCGCAC- CACCGGCGCGAAGCCAGGGGCCAGGG AACTTT- GATAGAGAGGGGGGAAAGTGGGGCGGGGGCGAG- GGCGGTTGAATCACAACGCATGC ACGCCCTCTG- CCCCCGGGGACGGGTGGGAGGAAGGAGGAGG- GAGAAG- AGAAGACCCGAGGCA TGCACCCGCACT- TACGCCCGTGCCCACCCCCGCCCCGGCGCCCAC- CCCGCCCGCACACCTGC CCGCCACGCCCGCC- CCTCCTCACCCTGGCTGGGAGAAAGGAGGAG- GAGCAGGAAGAGGAGAC CCGAGGCATGCAA- CCGCACTCACCCCACCCCGCCCGCACACCTG- CCCGCCACGCCCGCCCCT CCTTACCCTGGC- TGCGGGGAGACTCCCATCGGGGCGAGGGGGC- TCGCGCGTTCGCAACACCA CACCACAC- CACACGGCCCACCACAACACGGCCCACCACGAC- ACAACACGACACGACGCGTTT TGCGGGG- CATGCAAGTCGACACACCGCGCGCGTGCCTACCTT- TCCCTAGCGGCCCCGGCCCC CCGGCCCGTTT- CCTTCCGCCACCACTACCACCACCCCCCG- CCCGCGCCCACGCGGTAGAGG AAGGGGA- CGGGCGCCACACCCACGGCTGTGGCCGGGCACG- CGCCTTTGGGGTTGTTGGGGGG GGGTGACCGG- CGCGTGGGGCGGTGGGCGTATGGGCCCGACCCG- CGCCTGCCCCCCCTGGGA ACGACGCCCCC- GGACGACACCACGGGGGGGGGAAACGGG- GGTGGGTGGAAGGGAAGAGGAAG GAGAAA- GGGGGGGTGGATCCGAACACGCCGGActcgagcttcc- tcgctcactgactcgctgc gctcggtcgttcggctgcggcgagcggtatcagct- cactcaaggcggtaatacggttatcc acagaatcaggggataacgcag- gaaagaacatgtgagcaaaaggccagcaaaaggccaggaa ccgtaaaaag- gccgcgttgctggcgttttttccataggctccgcccccctgacgagcatcaca aaaatcgacgctcaagtcagaggtggcgaaacccgacaggactataaaga- taccaggcgttt cccctggaagctccctcgtgcgctctcctgttccgaccctgc- cgcttaccggatacctgtc cgcctttctcccttcgggaagcgtggcgctttctcat- agctcacgctgtaggtatctcagtt cggtgtaggtcgttcgctccaagctgggc- tgtgtgcacgaaccccccgttcagcccgaccgc tgcgccttatccggtaac- tatcgtcttgagtccaacccggtaagacacgacttatcgccact ggcagcagc- cactggtaacaggattagcagagcgaggtatgtaggcggtgctacagagttct tgaagtggtggcctaactacggctacactagaaggacagtatttggtatctgc- gctctgctg aagccagttaccttcggaaaaagagttggtagctcttgatccggc- aaacaaaccaccgctgg tagcggtggtttttttgtttgcaagcagcagat- tacgcgcagaaaaaaaggatctcaagaag atcctttgatcttttctacggggtct- gacgctcagtggaacgaaaactcacgttaagggatt ttggtcatgagattat- caaaaaggatcttcacctagatccttttaaattaaaaatgaagtttt taaat- caatctaaagtatatatgagtaaacttggtctgacagttaccaatgcttaatcagtg aggcacctatctcagcgatctgtctatttcgttcatccatagttgcctgactcc- ccgtcgtg tagataactacgatacgggagggcttaccatctggccccagt- gctgcaatgataccgcgaga cccacgctcaccggctccagatttatcagcaat- aaaccagccagccggaagggccgagcgca gaagtggtcctgcaacttt- tatccgcctccatccagtctattaattgttgccgggaagctaga gtaagtagttcg- ccagttaatagtttgcgcaacgttgttgccattgctacaggcatcgtggt gtcac- gctcgtcgtttgtatggcttcattcagctccggttcccaacgatcaaggcgagtta catgatccccatgttgtgcaaaaaagcggttagctccttcggtcctccgatcgtt- gtcaga agtaagttggccgcagtgttatcactcatggttatggcagcactgcat- aattctcttactgt catgccatccgtaagatgcttttctgtgactggtgagtactcaac- caagtcattctgagaat agtgtatgcggcgaccgagtgctcttgcccggcgt- caatacgggataataccgcgccacat agcagaactttaaaagtgctcatcattg- gaaaacgttcttcggggcgaaaactctcaaggat cttaccgctgttgagatc- cagttcgatgtaacccactcgtgcacccaactgatcttcagcat cttttactttt- caccagcgttctgggtgagcaaaaacaggaaggcaaaatgccgcaaaaaag gaataagggcgacacggaaatgttgaatactcatactcttccttttcaatattatt- gaag catttatcaggggttattgtctcatgagcggatacatatttgaatgtatt- tagaaaataaac aaatagggttccgcgcacatttcccgaaaagtgc- cacctgacgtctaagaaaccattatt atcatgacattaacctataaaaataggcgta- tcacgaggcccttcgtc (SEQ ID NO: 36)

In SEQ ID NO: 36, nucleotide (nt) 189-nt 929 represent 5' ICP0 flanking sequence; nt 988-nt 2388 represent 3' ICP0 flanking sequence; and nt 930-nt 987 represents multiple cloning region. The ICP0 TATA Element comprises the following sequence: TATAAGG (SEQ ID NO: 37). The ICP0 POLY A comprises the following sequence: AATAAA (SEQ ID NO: 38), which is 233 nt down stream of ICP0 stop codon TAA (SEQ ID NO: 39).

34. Annotated Sequence of p2UL19-V Plasmid tcgcgcgtttcggtgatgacggtgaaaacctctgacacatgcagctcccgagacggtcaca gcttgtctgtaagcggatgccgggagcagacaagcccgtcagggcgcgtcagcgggtgttgg cgggtgtcggggctggcttaactatgcggcatcagagcagattgtactgagagtgcaccata tgtgagaatcccgaggccgccctacggaataaacggacccccccgcacacaaagtaggcgcgg tttctgtctgccgtgacgtaaaacacaacgtcccggtggtgcagggtggtggcatagctgagctccatgccggcgagccacggggcggacttgggggggggggaatagtggggtggtgggaggagggtggtgggagcaagggctggcggtggcgcgaacgggacccgtgggttgctctcgcgcgtg ccgcccgcgcgtagggttgtggccggacggaggaactcccccactgtggatcgcgcgtcg gtgcttgggcaaacgacggcttccgtcacgcacggccggccttttaaggacaactccgggcg cattcccgacgtgccctctgggtgttttcttcgtttcctcccccaacccatctttccccctgccttccactgactaaccgccacgtcatcagcccgcggggagggcggacgcacggatgtg cggctcgcgaaccacatccacccatgatttgggcgtcagggcgtgggtgtgaatttcggggg ttccgggcccaacggccgaggttatatcctgctgggacgtgacttcgccaggcactcgcat ccgcggatactacccggggtggggttgtgtgtagaaccccgcgcggtgcttgtttgattttgg cctccgccccccatccctgaagcttgggtccgaccccgggcccgccgccagcactacttt cggtttcgctgcctcgccggctccccgcaccgaccatgacaatgcgggatgatgttccttttg ttggatcgcgagctggtagacgaggccgcgtgtggcgggaggacggcgaactgccgctcgatgaacagttttcgctgtcctcgtacggcacgtctgatttttttgtcagttcggcctactcgc gtcttccgcccacacccagccggtctttccaagcgggtggtgatgtttgcttggtcgttc ctggtcctcaagccgctggagctggtggccgcgggcatgtattacgggtggaccggacgggc ggtggcgccggcatgtattatagccgccgtcctcgcctactatgtcacgtggctggcacggg cgctcctcctgtacgtgaacatcaaacgggatcgcctgccgttgtcgccaccccgtgttttgg gggttgtgcgtgatcatgggcggcgcggccctgtgcgccctggtggcggccgcccatgagac gttcagtcccgacgggcttttccattggatcaccgccagccagctgctgccccgcacggatc ccctccgcgcccgttctctgggaatcgcctgcgcggccggccgccgccatgtgggtggcggcg gcggactgctttgccgccttaccaactttttctagcacgcttttggaccagggccatctt gaaggcaccgtcgcgttctaacgggggtgtggcgggggggggtatataaggcaattggccgtc ccgttaccaagaccaacccagccagcgtatccaccccgccccgggtccccgcgaagcggaa cggggtatgtgatatgctaattaaatacatgccacgtacttatggtgtctgattggtccttg tctgtgccggaggtggggcggggggccccgcccggggggcggaacgaggagggggttgggaga gccggccccggcaccacggtatataagcaaccggtgtcgacggcgggggtcgtcggggtcc gtgggtctcgcccccctcccccatcgagagtccgtaggtgacctaccgttgcgccaccacca gaggccatatccgacacccagccccgacggcagccgacagcccgaagcttggtcgatatct atcggagctgtgctagcgccactggtacccgagcggaattctgtctagacccagctttccct ccacccgcccgtcttttttttttcctgtttggggcattgggtttgattttccgacgttgctt ttaccacacacacccccctgtccccgcccccccggggggcttggactgggagccgcgattc cgagggcaggtcccaataaaacccagacccgagctccggggactgattctcacctggggct cctgcgcacgacagacctccccgtgcgtgctgctgagccctgccccgcccctctcccacac ggtcggtgcccccatctctgtttcatcatcgtcccggtg cgttgcgctttccggccctcc cgcaccccgcgttccggtgtctcgcggcccggcgccatgatcacggattgtttcgaagcag acatcgcgatcccctcgggtatctcgcgccccgatgccgcggcgctgcagcggtgcgagggt cgagtggtctttctgccgaccatccgccgccagctggcgctcgcggacgtggcgcacgaatc gttcgtctccggaggagttagtcccgacacgttggggttgttgctggcgtaccgcaggcgct tccccgcggtaatcacgcgggtgctgcccacgcgaatcgtcgcctgccccgtggacctgggg ctcacgcacgccggcaccgtcaatctccgcaacaccctccccgtcgaccctctgcaacggggatcccgtcagcctcgtccgcccgtcttcgagggccaggcgacggacgtgcgcctggagtcgc tggacctcacgctgcggtttccggtcccgctcccaacgccctggcccgcgagatagtcgcg cggctggtcgcccggggcatccgggacctcaaccccgaccccggacgcccggggagctccc cgacctcaacgtgctgtattacaacggggcccgtctctcgctcgtggccgacgtccagcaac tcgcctccgtaaacaccgagctgcggtcgctcgtcctcaacatggtctactccataaccgaa ggaaccaccctcatcctcacgctcatccccgctgctcgcgctaagcgcccaggacggata cgtgaacgcgctcctgcagatgcagagcgtcacgcgagaagccgcccagctcatccaccccg aagcccccatgctgatgcaggacgcgagcgcaggctgccgctttacgagcgctggtcgcc tggctggcgcacgcgggccaactcggggacatcctggccctgccccgctcgagcttcctc gctcactgactcgctgcgctcggtcgttcggctgcggcgagcggtatcagctcactcaaagg cggtaatacggttatccacagaatcaggggataacgcaggaaagaacatgtgagcaaaagge cagcaaaaggccaggaaccgtaaaaaggccgcgttgctggcgtttttccataggctccgccc cctgacgagcatcacaaaaatcgacgctcaagtcagaggtggcgaaacccgacaggactat aaagataccaggcgtttccccctggaagctccctcgtgcgctctcctgttccgaccctgccg cttaccggatacctgtccgcctttctcccttcgggaagcgtggcgctttctcatagctcacg ctgtaggtatctcagttcggtgtaggtcgttcgctcaagctgggctgtgtgcacgaaccccccgttcagcccgaccgctgcgccttatccggtaactatcgtcttgagtccaacccggtaaga cacgacttatcgccactggcagcagccactggtaacaggattagcagagcgaggtatgtagg cggtgctacagagttcttgaagtggtggcctaactacggctacactagaaggacagtattg gtatctgcgctctgctgaagccagttaccttcggaaaaagagttggtagctcttgatccggc aaacaaaccaccgctggtagcggtggtttttttgttgcaagcagcagattacgcgcagaaa aaaggatctcaagaagatcctttgatcttttctacggggtctgacgctcagtggaacgaaa actcacgttaagggattttggtcatgagattatcaaaaaggatcttcacctagatcctttta aattaaaaatgaagttttaaatcaatctaaagtatatatgagtaaacttggtctgacagtta ccaatgcttaatcagtgaggcacctatctcagcgatctgtctatttcgttcatccatagttg cctgactccccgtcgtgtagataactacgatacgggagggcttaccatctggccccagtgct gcaatgataccgcgagacccacgctcaccggctccagatttatcagcaataaaccagccagc cggaagggccgagcgcagaagtggtcctgcaactttatccgcctccatccagtctattaatt gttgccgggaagctagagtaagtagttcgccagttaatagtttgcgcaacgttgttgccatt gctacaggcatcgtggtgtcacgctcgtcgtttggtatggcttcattcagctccggttccca acgatcaaggcgagttacatgatccccatgttgtgcaaaaaagcggttagctccttcggtc ctccgatcgttgtcagaagtaagttggccgcagtgttatcactcatggttatggcagcactg cataattctcttactgtcatgccatccgtaagatgcttttctgtgactggtgagtactcaac caagtcattctgagaatagtgtatgcggcgaccgagttgctcttgcccggcgtcaatacgg gataataccgcgccacatagcagaactttaaaagtgctcatcattggaaaacgttcttcgggg cgaaaactctcaaggatcttaccgctgttgagatcagttcgatgtaacccactcgtgcacc caactgatcttcagcatcttttactttcaccagcgtttctgggtgagcaaaaacaggaaggc aaaatgccgcaaaaaaggaataagggcgacacggaaatgttgaatactcatactcttcctt tttcaatattatt gaagcatttatcaggttattgtctcatgagcggatacatatttgaatg tatttagaaaaataaacaataggggttccgcgcacatttccccgaaaagtgccacctgacg tctaagaaaccattattatcatgacattaacctataaaaataggcgtatcacgaggccctttcgtc (SEQ ID NO: 40)

In SEQ ID NO: 40, nt 189-nt 1661 represents 5' UL19 flanking sequence; nt 1663-nt 2029 represents a modified HSV-1 ICP27 promoter containing sequence; and nt 2095-nt 3336 represents a 3' UL19 flanking sequence.

What is claimed is:

1. A replication defective HSV recombinant virus, comprising a modified HSV-1 or HSV-2 ICP0 promoter comprising a human cytomegalovirus (hCMV) TATA element, wherein said modified promoter comprises SEQ ID NO: 08, and wherein said modified promoter is operably linked to a transgene.

2. The replication defective virus of claim 1, wherein the transgene encodes HSV-2 glycoprotein B (gB).

3. A vaccine comprising the recombinant virus of claim 1 unit dose form.

4. A method of immunizing a subject against HSV-1 or HSV-2 infection, comprising administering to said subject the vaccine of claim 3.

5. The method of claim 4, wherein said subject is seropositive for HSV-1.

6. The method of claim 4, wherein said subject is seropositive for HSV-2.

7. The method of claim 4, wherein said subject is seronegative for HSV-1 and HSV-2.

8. A composition comprising the virus of claim 1.

* * * * *

SEQUENCE LISTING

<160> NUMBER OF SEQ ID NOS: 44

<210> SEQ ID NO 1
<211> LENGTH: 899
<212> TYPE: DNA

<213> ORGANISM: Herpes simplex virus 2

<400> SEQUENCE: 1

```
cgtcaaggcg gggtggtacg ccagcacgag ccacgaggcg cggctgctga gacgcctgaa      60
ccaccccgcg atcctacccc tcctggacct gcacgtcgtt tctggggtca cgtgtctggt     120
cctccccaag tatcactgcg acctgtatac ctatctgagc aagcgcccgt ctccgttggg     180
ccacctacag ataaccgcgg tctcccggca gctcttgagc gccatcgact acgtccactg     240
caaaggcatc atccaccgcg atattaagac cgagaacatc ttcatcaaca cccccgagaa     300
catctgtctg ggggactttg gggcggcgtg ctttgtgcgc gggtgtcgat cgagcccctt     360
ccattacggg atcgcaggca ccatcgatac aaacgccccc gaggtcctgg ccggggatcc     420
gtacacccag gtaatcgaca tctggagcgc cggcctggtg atctttgaga ccgccgtcca     480
caccgcgtcc ttgttctcgg ccccgcgcga ccccgaaagg cggccgtgcg acaaccagat     540
cgcgcgcatc atccgacagg cccaggtaca cgtcgacgag tttccgacgc acgcggaatc     600
gcgcctcacc gcgcactacc gctcgcgggc ggccgggaac aatcgtccgg cgtggacccg     660
accggcgtgg acccgctact acaagatcca cacagacgtc gaatatctca tatgcaaagc     720
ccttaccttt gacgcggcgc tccgcccaag cgccgcggag ttgctgcgcc tgccgctatt     780
tcaccctaag tgaccccgct cccccgggg ggcgtggagg gggggctgg ttggatgttt      840
ttgcacaaaa agacgcggcc ctcgggcttt ggtgttttg gcaccttgcc gcccggcgt      899
```

<210> SEQ ID NO 2
<211> LENGTH: 100
<212> TYPE: DNA
<213> ORGANISM: Herpes simplex virus 1

<400> SEQUENCE: 2

```
caaatatttt tattgcaact ccctgtttta ggtacaataa aaacaaaaca tttcaaacaa      60
atcgcccctc gtgttgtcct tctttgctca tggccggcgg                            100
```

<210> SEQ ID NO 3
<211> LENGTH: 627
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
taatgggcaa ccccggtatt ccccgcctcc cgcgccgcgc gtaaccactc ccctgggtt       60
ccgggttatg ctaattgctt ttttggcgga acacacggcc cctcgcgcat tggcccgcgg     120
gtcgctcaat gaaccgcat tggtcccctg gggttccggg tatggtaatg agtttcttcg      180
ggaaggcggg aagccccggg gcaccgacgc aggccaagcc cctgttgcgt cggcgggagg     240
ggcatgctaa tggggttctt tggggacac cgggttgggc cccaaatcg ggggccgggc       300
cgtgcatgct aatgatattc tttgggggcg ccgggttggt cccgggac ggggccgccc      360
cgcggtgggc ctgcctcccc tgggacgcgc ggccattggg ggaatcgtca ctgccgcccc     420
tttggggagg ggaaaggcgt ggggtatata agcagagctc tccctatcag tgatagagat     480
ctccctatca gtgatagaga tcgtcgacga gctcgcgtgt cgcatttgca cctcggcact     540
cggagcgaga cgcagcagcc aggcagactc gggccgcccc ctctccgcat caccacagaa     600
gccccgccta cgttgcgacc cccaggg                                         627
```

<210> SEQ ID NO 4
<211> LENGTH: 900
<212> TYPE: DNA
<213> ORGANISM: Herpes simplex virus 2

<400> SEQUENCE: 4

```
ggggtggggg tgggggcga gaaacgatga aggacgggaa agggaacagc gaccaaatgt      60
cacgataaga acaataaacc tgtgacgtca atcagatatg tgagtttggt tgtgttttgt     120
gggactgggg gcgggggtg ggaggtatca gtgggtgaca gagtctttta aaagacgtgt     180 cccgggccc tcgagatgcg caacttttgg ccacacagag aaaggccccc agacgaagtc     240
acccgggtcc ccgaacaaaa acaaaaacct tgaccgccgc cggggggcgt gcctgttgtt     300
ttggtctcaa tggatcggta tgccgttcgg acctgggga ttgtgggaat cctcgggtgt      360
gctgctgttg gggccgcacc caccggcccc gcgtccgata aacaaacgc gaccgcacgc     420 ctccccacgc accccccact catccgttcc ggggctttg ccgtcccct catcgtgggg      480 gggctgtgtc tcatgattct ggggatggcg tgtctactcg aggtcctgcg tcgcctgggt     540
cgcgagttgg cgaggtgctg ccccacgcg ggccaatttg ccccatgatt tttcgccttt      600
ctggccttgc ccccaccca tcgccccgat tgtgtgtcgg gtgcccgggg tacagcagct     660
atggagcggt cggtaatata actttggttg tcgccacacg ccccgtgccg ggcatgggtt     720
gtgcgggaag gacgaaataa tccggcgatc ccaagcgta ccaactgggg ggggggggg      780 gggggaaaag aaactaaaaa cacatcaagc ccacaaccca tcccacaatg ggggttatgg     840
cggacccacc gcaccaccat actccgattc gaccacatat gcaaccaaat cacccccaga    900
```

<210> SEQ ID NO 5
<211> LENGTH: 67
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5

```
aagcttggtc gatatctatc ggagctgtgc tagcgccact ggcggccgct gcagcgagcg      60
gaattct                                                               67
```

<210> SEQ ID NO 6
<211> LENGTH: 2647
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 6

```
cagctgcgtc aaggcggggt ggtacgccag cacgagccac gaggcgcggc tgctgagacg      60
cctgaaccac cccgcgatcc taccctcct ggacctgcac gtcgtttctg gggtcacgtg     120
tctggtcctc cccaagtatc actgcgacct gtatacctat ctgagcaagc gcccgtctcc     180
gttgggccac ctacagataa ccgcggtctc ccggcagctc ttgagcgcca tcgactacgt     240
ccactgcaaa ggcatcatcc accgcgatat taagaccgag aacatcttca tcaacacccc     300
cgagaacatc tgtctggggg actttggggc ggcgtgcttt gtgcgcgggt gtcgatcgag     360 cccttccat tacgggatcg caggcaccat cgatacaaac gccccgagg tcctggccgg      420 ggatccgtac acccaggtaa tcgacatctg gagcgccggc ctggtgatct tgagaccgc     480
```

```
cgtccacacc gcgtccttgt tctcggcccc gcgcgacccc gaaaggcggc cgtgcgacaa      540
ccagatcgcg cgcatcatcc gacaggccca ggtacacgtc gacgagtttc cgacgcacgc      600
ggaatcgcgc ctcaccgcgc actaccgctc gcgggcggcc gggaacaatc gtccggcgtg      660
gacccgaccg cgtggacccc gctactacaa gatccacaca gacgtcgaat atctcatatg      720
caaagccctt acctttgacg cggcgctccg cccaagcgcc gcggagttgc tgcgcctgcc      780
gctatttcac cctaagtgac cccgctcccc cggggggcg tggaggggg ggctggttgg       840 atgttttgc acaaaagac gcggccctcg ggctttggtg ttttggcac cttgccgccc        900 ggcgtaccgg tactagtcaa ttgcaaatat ttttattgca actccctgtt ttaggtacaa      960
taaaaacaaa acatttcaaa caaatcgccc ctcgtgttgt ccttctttgc tcatggccgg     1020
cggggtaccg ttaacatacg taacgcgtaa tgggcaaccc cggtattccc cgcctcccgc     1080
gccgcgcgta accactcccc tggggttccg ggttatgcta attgctttt tggcggaaca      1140 cacgcccct cgcgcattgg cccgcgggtc gctcaatgaa cccgcattgg tcccctgggg      1200
ttccgggtat ggtaatgagt tcttcggga aggcgggaag ccccggggca ccgacgcagg      1260
ccaagcccct gttgcgtcgg cgggaggggc atgctaatgg ggttctttgg gggacaccgg     1320
gttgggcccc caaatcgggg gccgggccgt gcatgctaat gatattcttt ggggcgccg      1380 ggttggtccc cggggacggg gccgccccgc ggtgggcctg cctcccctgg gacgcgcggc     1440
cattggggga atcgtcactg ccgccccttt ggggagggga aaggcgtggg gtatataagc     1500
agagctctcc ctatcagtga tagagatctc cctatcagtg atagagatcg tcgacgagct     1560
cgcgtgtcgc atttgcacct cggcactcgg agcgagacgc agcagccagg cagactcggg     1620 ccgcccctc tccgcatcac cacagaagcc ccgcctacgt tgcgaccccc agggaagctt      1680
ggtcgatatc tatcggagct gtgctagcgc cactggcggc cgctgcagcg agcggaattc     1740
tggggtgggg gtgggggggcg agaaacgatg aaggacggga aagggaacag cgaccaaatg     1800
tcacgataag aacaataaac ctgtgacgtc aatcagatat gtgagtttgg ttgtgttttg     1860
tgggactggg ggcggggggt gggaggtatc agtgggtgac agagtctttt aaaagacgtg     1920 tccccggggcc ctcgagatgc gcaacttttg gccacacaga gaaaggcccc cagacgaagt     1980
cacccgggtc cccgaacaaa aacaaaaacc ttgaccgccg ccgggggggcg tgcctgttgt     2040 tttggtctca atggatcggt atgccgttcg gacctggggg attgtgggaa tcctcggtg      2100 tgctgctgtt ggggccgcac ccaccggccc cgcgtccgat acaacaaacg cgaccgcacg     2160 cctcccacg cacccccac tcatccgttc cgggggcttt gccgtccccc tcatcgtggg      2220
ggggctgtgt ctcatgattc tggggatggc gtgtctactc gaggtcctgc gtcgcctggg     2280
tcgcgagttg gcgaggtgct gccccacgc gggccaattt gccccatgat ttttcgcctt     2340
tctggccttg cccccacccc atcgccccga ttgtgtgtcg ggtgcccggg gtacagcagc     2400
tatggagcgg tcggtaatat aactttggtt gtcgccacac gccccgtgcc gggcatgggt     2460
tgtgcgggaa ggacgaaata atccggcgat ccccaagcgt accaactggg ggggggggg     2520 gggggaaaa gaaactaaaa acacatcaag cccacaaccc atcccacaat ggggggttatg    2580 gcggacccac cgcaccacca tactccgatt cgaccacata tgcaaccaaa tcaccccag     2640 atctaga                                                              2647

<210> SEQ ID NO 7
<211> LENGTH: 2750
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 7

| | |
|---|---|
| acttaagctt gccaccatga gaggcggcgg cctgatctgc gccctggtgg tgggcgccct | 60 |
| ggtggccgcc gtggccagcg ccgccccgc cgccccgcc gccccagag ccagcggcgg | 120 |
| cgtggccgcc accgtggccg ccaacggcgg ccccgccagc agaccccccc ccgtgcccag | 180 |
| ccccgccacc accaaggcca gaaagagaaa gaccaagaag ccccccaaga gacccgaggc | 240 |
| caccccccc cccgacgcca acgccaccgt ggccgccggc cacgccaccc tgagagccca | 300 |
| cctgagagag atcaaggtgg agaacgccga cgcccagttc tacgtgtgcc ccccccccac | 360 |
| cggcgccacc gtggtgcagt tcgagcagcc cagaagatgc cccaccagac cgagggcca | 420 |
| gaactacacc gagggcatcg ccgtggtgtt caaggagaac atcgccccct acaagttcaa | 480 |
| ggccaccatg tactacaagg acgtgaccgt gagccaggtg tggttcggcc acagatacag | 540 |
| ccagttcatg ggcatcttcg aggacagagc ccccgtgccc ttcgaggagg tgatcgacaa | 600 |
| gatcaacgcc aagggcgtgt gcagaagcac cgccaagtac gtgagaaaca catggagac | 660 |
| caccgccttc cacagagacg accacgagac cgacatggag ctgaagcccg ccaaggtggc | 720 |
| caccagaacc agcagaggct ggcacaccac cgacctgaag tacaacccca gcagagtgga | 780 |
| ggccttccac agatacggca ccaccgtgaa ctgcatcgtg gaggaggtgg acgccagaag | 840 |
| cgtgtaccc tacgacgagt tcgtgctggc caccggcgac ttcgtgtaca tgagccctt | 900 |
| ctacggctac agagagggca gccacaccga gcacaccagc tacgccgccg acagattcaa | 960 |
| gcaggtggac ggcttctacg ccagagacct gaccaccaag gccagagcca ccagccccac | 1020 |
| caccagaaac ctgctgacca cccccaagtt caccgtggcc tgggactggg tgcccaagag | 1080 |
| acccgccgtg tgcaccatga ccaagtggca ggaggtggac gagatgctga gagccgagta | 1140 |
| cggcggcagc ttcagattca gcagcgacgc catcagcacc accttcacca ccaacctgac | 1200 |
| ccagtacagc ctgagcagag tggacctggg cgactgcatc ggcagagacg ccagagaggc | 1260 |
| catcgacaga atgttcgcca gaaagtacaa cgccacccac atcaaggtgg ccagccccca | 1320 |
| gtactacctg gccaccggcg gcttcctgat cgcctaccag cccctgctga gcaacaccct | 1380 |
| ggccgagctg tacgtgagag agtacatgag agagcaggac agaaagccca gaaacgccac | 1440 |
| ccccgccccc ctgagagagg cccccagcgc caacgccagc gtggagagaa tcaagaccac | 1500 |
| cagcagcatc gagttcgcca gactgcagtt cacctacaac cacatccaga gacacgtgaa | 1560 |
| cgacatgctg ggcagaatcg ccgtggcctg gtgcgagctg cagaaccacg agctgaccct | 1620 |
| gtggaacgag gccagaaagc tgaaccccaa cgccatcgcc agcgccaccg tgggcagaag | 1680 |
| agtgagcgcc agaatgctgg gcgacgtgat ggccgtgagc acctgcgtgc ccgtggcccc | 1740 |
| cgacaacgtg atcgtgcaga acagcatgag agtgagcagc agacccggca cctgctacag | 1800 |
| cagacccctg gtgagcttca gatacgagga ccagggcccc ctgatcgagg ccagctggg | 1860 |
| cgagaacaac gagctgagac tgaccagaga cgccctggag ccctgcaccg tgggccacag | 1920 |
| aagatacttc atcttcggcg gcggctacgt gtacttcgag gagtacgcct acagccacca | 1980 |
| gctgagcaga gccgacgtga ccaccgtgag caccttcatc gacctgaaca tcaccatgct | 2040 |
| ggaggaccac gagttcgtgc ccctggaggt gtacaccaga cacagagatca aggacagcgg | 2100 |
| cctgctggac tacaccgagg tgcagagaag aaaccagctg cacgacctga gattcgccga | 2160 |

```
catcgacacc gtgatcagag ccgacgccaa cgccgccatg ttcgccggcc tgtgcgcctt    2220
cttcgagggc atgggcgacc tgggcagagc cgtgggcaag gtggtgatgg gcgtggtggg    2280
cggcgtggtg agcgccgtga gcggcgtgag cagcttcatg agcaacccct cggcgccct    2340 ggccgtgggc ctgctggtgc tggccggcct ggtggccgcc ttcttcgcct tcagatacgt    2400
gctgcagctg cagagaaacc ccatgaaggc cctgtacccc ctgaccacca aggagctgaa    2460
gaccagcgac cccggcggcg tgggcggcga gggcgaggag ggcgccgagg gcggcggctt    2520
cgacgaggcc aagctggccg aggccagaga gatgatcaga tacatggccc tggtgagcgc    2580
catggagaga accgagcaca aggccagaaa gaagggcacc agcgccctgc tgagcagcaa    2640
ggtgaccaac atggtgctga gaaagagaaa caaggccaga tacagccccc tgcacaacga    2700
ggacgaggcc ggcgacgagg acgagctgta gaggagctag cgaattctgc                2750

<210> SEQ ID NO 8
<211> LENGTH: 569
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
taatgggcaa ccccggtatt ccccgcctcc cgcgccgcgc gtaaccactc ccctggggtt      60
ccgggttatg ctaattgctt ttttggcgga acacacggcc cctcgcgcat tggcccgcgg     120
gtcgctcaat gaacccgcat tggtcccctg gggttccggg tatggtaatg agtttcttcg    180
ggaaggcggg aagccccggg gcaccgacgc aggccaagcc cctgttgcgt cggcgggagg    240
ggcatgctaa tggggttctt tggggacac cgggttgggc ccccaaatcg ggggccgggc     300
cgtgcatgct aatgatattc tttggggcg ccgggttggt ccccggggac ggggccgccc      360
cgcggtgggc ctgcctcccc tgggacgcgc ggccattggg ggaatcgtca ctgccgcccc    420
tttggggagg ggaaaggcgt ggggtatata agcagagctc gtcgcatttg cacctcggca    480
ctcggagcga gacgcagcag ccaggcagac tcgggccgcc ccctctccgc atcaccacag    540
aagccccgcc tacgttgcga cccccaggg                                       569

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tccctatcag tgatagagat ctccctatca gtgatagaga tcgtcgacga gctcgcgt       58

<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tccctatcag tgatagagat ctccctatca gtgatagaga                           40

<210> SEQ ID NO 11
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tccctatcag tgatagaga                                                  19

<210> SEQ ID NO 12
<211> LENGTH: 8
<212> TYPE: DNA
<213> ORGANISM: Herpes simplex virus

<400> SEQUENCE: 12 tataagtt                                                               8

<210> SEQ ID NO 13
<211> LENGTH: 8
<212> TYPE: DNA
<213> ORGANISM: Human cytomegalovirus

<400> SEQUENCE: 13 tatataag                                                               8

<210> SEQ ID NO 14
<211> LENGTH: 953
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atgggagagg cgtcgctgcc ggcccaggcc gccgagacgg aggaggtggg tcttttgtcg    60
aaaaatacct ccggtccgat gtcgcgccgg cggaaattgt cgcgctcatg cgcaacctca   120
acagcctgat gggacgcacg cggtttattt acctggcgtt gctggaggcc tgtctccgcg   180
ttcccatggc cacccgcagc agcgccatat ttcggcggat ctatgaccac tacgccacgg   240
gcgtcatccc cacgatcaac gtcaccggag agctggagct cgtggccctg ccccccaccc   300
tgaacgtaac cccgtctgg gagctgttgt gcctgtgcag caccatggcc gcgcgcctgc   360
attgggactc ggcggccggg ggatctggga ggaccttcgg ccccgatgac gtgctggacc   420
tactgacccc ccactacgac cgctacatgc agctggtgtt cgaactgggc cactgtaacg   480
taaccgacgg acttctgctc tcggaggaag ccgtcaagcg cgtcgccgac gccctaagcg   540
gctgtccccc gcgcgggtcc gttagcgaga cggaccacgc ggtggcgctg ttcaagataa   600
tctggggcga actgtttggc gtgcagatgg ccaaaagcac gcagacgttt cccggggcgg   660
ggcgcgttaa aaacctcacc aaacagacaa tcgtgggggtt gttggacgcc caccacatcg   720
accacagcgc ctgccggacc cacaggcagc tgtacgccct gcttatggcc cacaagcggg   780
agtttgcggg cgcgcgcttc aagctacgcg tgcccgcgtg ggggcgctgt ttgcgcacgc   840
actcatccag cgccaacccc aacgctgaca tcatcctgga ggcggcgctg tcggagctcc   900
ccaccgaggc ctggcccatg atgcaggggg cggtgaactt tagcacccta taa          953

<210> SEQ ID NO 15
<211> LENGTH: 1635
<212> TYPE: DNA
<213> ORGANISM: Herpes simplex virus 2
```

<400> SEQUENCE: 15

```
cttgggggggg ggggggaaga aactaaaaac acatcaagcc cacaacccat cccacaaggg        60
gggttatggc ggacccaccg caccaccata ctccgattcg accacatatg caaccaaatc       120
acccccagag gggaggttcc atttttacga ggaggaggag tataatagag tctttgtgtt       180
taaaacccgg ggtcggtgtg gtgttcggtc ataagctgca ttgcgaacca ctagtcgccg       240
tttttcgtgt gcatcgcgta tcacggcatg gggcgtttga cctccggcgt cgggacggcg       300
gccctgctag ttgtcgcggt gggactccgc gtcgtctgcg ccaaatacgc cttagcagac       360
ccctcgctta agatggccga tcccaatcga tttcgcggga agaaccttcc ggttttggac       420
cagctgaccg accccccggg ggtgaagcgt gtttaccaca ttcagccgag cctggaggac       480
ccgttccagc cccccagcat cccgatcact gtgtactacg cagtgctgga acgtgcctgc       540
cgcagcgtgc tcctacatgc cccatcggag gcccccagat cgtgcgcgg ggcttcggac        600
gaggcccgaa agcacacgta caacctgacc atcgcctggt atcgcatggg agacaattgc       660
gctatcccca tcacggttat ggaatacacc gagtgcccct acaacaagtc gttgggggtc       720
tgccccatcc gaacgcagcc ccgctggagc tactatgaca gctttagcgc cgtcagcgag       780
gataacctgg gattcctgat gcacgccccc gccttcgaga ccgcgggtac gtacctgcgg       840
ctagtgaaga taacgactg gacggagatc acacaattta tcctggagca ccgggccgc        900
gcctcctgca agtacgctct ccccctgcgc atccccccgg cagcgtgcct cacctcgaag       960
gcctaccaac agggcgtgac ggtcgacagc atcgggatgt acccccgctt tatccccgaa      1020
aaccagcgca ccgtcgccct atacagctta aaaatcgccg ggtggcacgg ccccaagccc      1080
ccgtacacca gcaccctgct gccgccggag ctgtccgaca ccaccaacgc cacgcaaccc      1140
gaactcgttc cggaagaccc cgaggactcg gccctcttag aggatccgc cgggacggtg       1200
tcttcgcaga tcccccccaaa ctggcacatc ccgtcgatcc aggacgtcgc gccgcaccac      1260
gcccccgccg cccccagcaa cccgggcctg atcatcggcg cgctggccgg cagtaccctg      1320
gcggcgctgg tcatcggcgg tattgcgttt tgggtacgcc gccgcgctca gatggccccc      1380
aagcgcctac gtctccccca catccgggat gacgacgcgc cccctcgca ccagccattg        1440
ttttactaga ggagtttccc cgttcccgtg tacctctggg cccgtgtggg agggtggccg      1500
gggtatttgg gtgggacttg gactccgcat aaagggagtc tcgaaggagg gaaactagga      1560
cagttcatag gccgggagcg tggggcgcgc accgcgtccc gacgattagc caccgcgccc      1620
acagccacct cgacc                                                     1635
```

<210> SEQ ID NO 16
<211> LENGTH: 618
<212> TYPE: DNA
<213> ORGANISM: Herpes simplex virus 1

<400> SEQUENCE: 16

```
taatgggcaa cccccggtatt ccccgcctcc cgcgccgcgc gtaaccactc ccctgggggtt        60
ccgggttatg ctaattgctt ttttggcgga acacacggcc cctcgcgcat ggcccgcgg       120
gtcgctcaat gaacccgcat tggtcccctg gggttccggg tatggtaatg agtttcttcg       180
ggaaggcggg aagccccggg gcaccgacgc aggccaagcc cctgttgcgt cggcgggagg       240
ggcatgctaa tggggttctt tgggggacac cgggttgggc cccaaatcg ggggccgggc        300
cgtgcatgct aatgatattc tttggggggcg ccggggttggt ccccggggac ggggccgccc     360
```

-continued

```
cgcggtgggc ctgcctcccc tgggacgcgc ggccattggg ggaatcgtca ctgccgcccc      420
tttggggagg ggaaaggcgt ggggtataag ttagccctgg cccgacagtc tggtcgcatt      480
tgcacctcgg cactcggagc gagacgcagc agccaggcag actcgggccg cccctctcc       540 gcatcaccac agaagccccg cctacgttgc gaccccagg gaccctccgt ccgcgaccct       600
ccagccgcat acgacccc                                                   618
```

<210> SEQ ID NO 17
<211> LENGTH: 393
<212> TYPE: PRT
<213> ORGANISM: Herpes simplex virus 2

<400> SEQUENCE: 17

| | | | | | | | | | | | | | | |
|---|---|---|---|---|---|---|---|---|---|---|---|---|---|---|
| Met | Gly | Arg | Leu | Thr | Ser | Gly | Val | Gly | Thr | Ala | Ala | Leu | Leu | Val | Val |
| 1 | | | | 5 | | | | | 10 | | | | | 15 | |

Ala Val Gly Leu Arg Val Val Cys Ala Lys Tyr Ala Leu Ala Asp Pro
         20                  25                  30

Ser Leu Lys Met Ala Asp Pro Asn Arg Phe Arg Gly Lys Asn Leu Pro
     35                  40                  45

Val Leu Asp Gln Leu Thr Asp Pro Pro Gly Val Lys Arg Val Tyr His
 50                  55                  60

Ile Gln Pro Ser Leu Glu Asp Pro Phe Gln Pro Ser Ile Pro Ile
65                  70                  75                  80

Thr Val Tyr Tyr Ala Val Leu Glu Arg Ala Cys Arg Ser Val Leu Leu
                 85                  90                  95

His Ala Pro Ser Glu Ala Pro Gln Ile Val Arg Gly Ala Ser Asp Glu
            100                 105                 110

Ala Arg Lys His Thr Tyr Asn Leu Thr Ile Ala Trp Tyr Arg Met Gly
        115                 120                 125

Asp Asn Cys Ala Ile Pro Ile Thr Val Met Glu Tyr Thr Glu Cys Pro
    130                 135                 140

Tyr Asn Lys Ser Leu Gly Val Cys Pro Ile Arg Thr Gln Pro Arg Trp
145                 150                 155                 160

Ser Tyr Tyr Asp Ser Phe Ser Ala Val Ser Glu Asp Asn Leu Gly Phe
                165                 170                 175

Leu Met His Ala Pro Ala Phe Glu Thr Ala Gly Thr Tyr Leu Arg Leu
            180                 185                 190

Val Lys Ile Asn Asp Trp Thr Glu Ile Thr Gln Phe Ile Leu Glu His
        195                 200                 205

Arg Ala Arg Ala Ser Cys Lys Tyr Ala Leu Pro Leu Arg Ile Pro Pro
    210                 215                 220

Ala Ala Cys Leu Thr Ser Lys Ala Tyr Gln Gln Gly Val Thr Val Asp
225                 230                 235                 240

Ser Ile Gly Met Leu Pro Arg Phe Ile Pro Glu Asn Gln Arg Thr Val
                245                 250                 255

Ala Leu Tyr Ser Leu Lys Ile Ala Gly Trp His Gly Pro Lys Pro Pro
            260                 265                 270

Tyr Thr Ser Thr Leu Leu Pro Pro Glu Leu Ser Asp Thr Thr Asn Ala
        275                 280                 285

Thr Gln Pro Glu Leu Val Pro Glu Asp Pro Glu Asp Ser Ala Leu Leu
    290                 295                 300

Glu Asp Pro Ala Gly Thr Val Ser Ser Gln Ile Pro Pro Asn Trp His
305                 310                 315                 320

Ile Pro Ser Ile Gln Asp Val Ala Pro His His Ala Pro Ala Ala Pro

```
                   325                 330                 335
Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Arg Ala Gln
            355                 360                 365

Met Ala Pro Lys Arg Leu Arg Leu Pro His Ile Arg Asp Asp Asp Ala
            370                 375                 380

Pro Pro Ser His Gln Pro Leu Phe Tyr
385                 390

<210> SEQ ID NO 18
<211> LENGTH: 901
<212> TYPE: PRT
<213> ORGANISM: Herpes simplex virus 2

<400> SEQUENCE: 18

Met Arg Gly Gly Gly Leu Ile Cys Ala Leu Val Val Gly Ala Leu Val
1               5                   10                  15

Ala Ala Val Ala Ser Ala Ala Pro Ala Ala Pro Arg Ala Ser Gly Gly
            20                  25                  30

Val Ala Ala Thr Val Ala Ala Asn Gly Gly Pro Ala Ser Arg Pro Pro
            35                  40                  45

Pro Val Pro Ser Pro Ala Thr Thr Arg Ala Arg Lys Arg Lys Thr Lys
        50                  55                  60

Lys Pro Pro Glu Arg Pro Glu Ala Thr Pro Pro Asp Ala Asn Ala
65              70                  75                  80

Thr Val Ala Ala Gly His Ala Thr Leu Arg Ala His Leu Arg Glu Ile
                85                  90                  95

Lys Val Glu Asn Ala Asp Ala Gln Phe Tyr Val Cys Pro Pro Pro Thr
            100                 105                 110

Gly Ala Thr Val Val Gln Phe Glu Gln Pro Arg Arg Cys Pro Thr Arg
            115                 120                 125

Pro Glu Gly Gln Asn Tyr Thr Glu Gly Ile Ala Val Val Phe Lys Glu
        130                 135                 140

Asn Ile Ala Pro Tyr Lys Phe Lys Ala Thr Met Tyr Tyr Lys Asp Val
145                 150                 155                 160

Thr Val Ser Gln Val Trp Phe Gly His Arg Tyr Ser Gln Phe Met Gly
                165                 170                 175

Ile Phe Glu Asp Arg Ala Pro Val Pro Phe Glu Glu Val Ile Asp Lys
            180                 185                 190

Ile Asn Ala Lys Gly Val Cys Arg Ser Thr Ala Lys Tyr Val Arg Asn
        195                 200                 205

Asn Met Glu Thr Thr Ala Phe His Arg Asp Asp His Glu Thr Asp Met
210                 215                 220

Glu Leu Lys Pro Ala Lys Val Ala Thr Arg Thr Ser Arg Gly Trp His
225                 230                 235                 240

Thr Thr Asp Leu Lys Tyr Asn Pro Ser Arg Val Glu Ala Phe His Arg
                245                 250                 255

Tyr Gly Thr Thr Val Asn Cys Ile Val Glu Glu Val Asp Ala Arg Ser
            260                 265                 270

Val Tyr Pro Tyr Asp Glu Phe Val Leu Ala Thr Gly Asp Phe Val Tyr
        275                 280                 285

Met Ser Pro Phe Tyr Gly Tyr Arg Glu Gly Ser His Thr Glu His Thr
290                 295                 300
```

-continued

Ser Tyr Ala Ala Asp Arg Phe Lys Gln Val Asp Gly Phe Tyr Ala Arg
305                 310                 315                 320

Asp Leu Thr Thr Lys Ala Arg Ala Thr Ser Pro Thr Thr Arg Asn Leu
            325                 330                 335

Leu Thr Thr Pro Lys Phe Thr Val Ala Trp Asp Trp Val Pro Lys Arg
            340                 345                 350

Pro Ala Val Cys Thr Met Thr Lys Trp Gln Glu Val Asp Glu Met Leu
            355                 360                 365

Arg Ala Glu Tyr Gly Gly Ser Phe Arg Phe Ser Ser Asp Ala Ile Ser
            370                 375                 380

Thr Thr Phe Thr Thr Asn Leu Thr Gln Tyr Ser Leu Ser Arg Val Asp
385                 390                 395                 400

Leu Gly Asp Cys Ile Gly Arg Asp Ala Arg Glu Ala Ile Asp Arg Met
            405                 410                 415

Phe Ala Arg Lys Tyr Asn Ala Thr His Ile Lys Val Gly Gln Pro Gln
            420                 425                 430

Tyr Tyr Leu Ala Thr Gly Gly Phe Leu Ile Ala Tyr Gln Pro Leu Leu
            435                 440                 445

Ser Asn Thr Leu Ala Glu Leu Tyr Val Arg Glu Tyr Met Arg Glu Gln
450                 455                 460

Asp Arg Lys Pro Arg Asn Ala Thr Pro Ala Pro Leu Arg Glu Ala Pro
465                 470                 475                 480

Ser Ala Asn Ala Ser Val Glu Arg Ile Lys Thr Thr Ser Ser Ile Glu
            485                 490                 495

Phe Ala Arg Leu Gln Phe Thr Tyr Asn His Ile Gln Arg His Val Asn
            500                 505                 510

Asp Met Leu Gly Arg Ile Ala Val Ala Trp Cys Glu Leu Gln Asn His
            515                 520                 525

Glu Leu Thr Leu Trp Asn Glu Ala Arg Lys Leu Asn Pro Asn Ala Ile
530                 535                 540

Ala Ser Ala Thr Val Gly Arg Arg Val Ser Ala Arg Met Leu Gly Asp
545                 550                 555                 560

Val Met Ala Val Ser Thr Cys Val Pro Val Ala Pro Asp Asn Val Ile
            565                 570                 575

Val Gln Asn Ser Met Arg Val Ser Ser Arg Pro Gly Thr Cys Tyr Ser
            580                 585                 590

Arg Pro Leu Val Ser Phe Arg Tyr Glu Asp Gln Gly Pro Leu Ile Glu
            595                 600                 605

Gly Gln Leu Gly Glu Asn Asn Glu Leu Arg Leu Thr Arg Asp Ala Leu
610                 615                 620

Glu Pro Cys Thr Val Gly His Arg Arg Tyr Phe Ile Phe Gly Gly Gly
625                 630                 635                 640

Tyr Val Tyr Phe Glu Glu Tyr Ala Tyr Ser His Gln Leu Ser Arg Ala
            645                 650                 655

Asp Val Thr Val Ser Thr Phe Ile Asp Leu Asn Ile Thr Met Leu
            660                 665                 670

Glu Asp His Glu Phe Val Pro Leu Glu Val Tyr Thr Arg His Glu Ile
            675                 680                 685

Lys Asp Ser Gly Leu Leu Asp Tyr Thr Glu Val Gln Arg Arg Asn Gln
            690                 695                 700

Leu His Asp Leu Arg Phe Ala Asp Ile Asp Thr Val Ile Arg Ala Asp
705                 710                 715                 720

Ala Asn Ala Ala Met Phe Ala Gly Leu Cys Ala Phe Phe Glu Gly Met

-continued

```
                725                 730                 735
Gly Asp Leu Gly Arg Ala Val Gly Lys Val Met Gly Val Val Gly
            740                 745                 750

Gly Val Val Ser Ala Val Ser Gly Val Ser Ser Phe Met Ser Asn Pro
        755                 760                 765

Phe Gly Ala Leu Ala Val Gly Leu Leu Val Leu Ala Gly Leu Val Ala
    770                 775                 780

Ala Phe Phe Ala Phe Arg Tyr Val Leu Gln Leu Gln Arg Asn Pro Met
785                 790                 795                 800

Lys Ala Leu Tyr Pro Leu Thr Thr Lys Glu Leu Lys Thr Ser Asp Pro
                805                 810                 815

Gly Gly Val Gly Gly Glu Gly Glu Gly Ala Glu Gly Gly Gly Phe
                820                 825             830

Asp Glu Ala Lys Leu Ala Glu Ala Arg Glu Met Ile Arg Tyr Met Ala
                835                 840                 845

Leu Val Ser Ala Met Glu Arg Thr Glu His Lys Ala Arg Lys Lys Gly
    850                 855                 860

Thr Ser Ala Leu Leu Ser Ser Lys Val Thr Asn Met Val Leu Arg Lys
865                 870                 875                 880

Arg Asn Lys Ala Arg Tyr Ser Pro Leu His Asn Glu Asp Glu Ala Gly
                885                 890                 895

Asp Glu Asp Glu Leu
            900

<210> SEQ ID NO 19
<211> LENGTH: 698
<212> TYPE: PRT
<213> ORGANISM: Herpes simplex virus 2

<400> SEQUENCE: 19

Met His Ala Ile Ala Pro Arg Leu Leu Leu Leu Phe Val Leu Ser Gly
1               5                   10                  15

Leu Pro Gly Thr Arg Gly Gly Ser Gly Val Pro Gly Pro Ile Asn Pro
            20                  25                  30

Pro Asn Asn Asp Val Val Phe Pro Gly Gly Ser Pro Val Ala Gln Tyr
        35                  40                  45

Cys Tyr Ala Tyr Pro Arg Leu Asp Asp Pro Gly Pro Leu Gly Ser Ala
    50                  55                  60

Asp Ala Gly Arg Gln Asp Leu Pro Arg Val Val Arg His Glu Pro
65                  70                  75                  80

Leu Gly Arg Ser Phe Leu Thr Gly Gly Leu Val Leu Ala Pro Pro
                85                  90                  95

Val Arg Gly Phe Gly Ala Pro Asn Ala Thr Tyr Ala Ala Arg Val Thr
            100                 105                 110

Tyr Tyr Arg Leu Thr Arg Ala Cys Arg Gln Pro Ile Leu Leu Arg Gln
        115                 120                 125

Tyr Gly Gly Cys Arg Gly Gly Glu Pro Pro Ser Pro Lys Thr Cys Gly
    130                 135                 140

Ser Tyr Thr Tyr Thr Tyr Gln Gly Gly Pro Pro Thr Arg Tyr Ala
145                 150                 155                 160

Leu Val Asn Ala Ser Leu Leu Val Pro Ile Trp Asp Arg Ala Ala Glu
                165                 170                 175

Thr Phe Glu Tyr Gln Ile Glu Leu Gly Gly Glu Leu His Val Gly Leu
            180                 185                 190
```

-continued

```
Leu Trp Val Glu Val Gly Gly Glu Gly Pro Gly Pro Thr Ala Pro Pro
        195                 200                 205

Gln Ala Ala Arg Ala Glu Gly Gly Pro Cys Val Pro Pro Val Pro Ala
        210                 215                 220

Gly Arg Pro Trp Arg Ser Val Pro Pro Val Trp Tyr Ser Ala Pro Asn
225                 230                 235                 240

Pro Gly Phe Arg Gly Leu Arg Phe Arg Glu Arg Cys Leu Pro Pro Gln
                245                 250                 255

Thr Pro Ala Ala Pro Ser Asp Leu Pro Arg Val Ala Phe Ala Pro Gln
                260                 265                 270

Ser Leu Leu Val Gly Ile Thr Gly Arg Thr Phe Ile Arg Met Ala Arg
                275                 280                 285

Pro Thr Glu Asp Val Gly Val Leu Pro Pro His Trp Ala Pro Gly Ala
        290                 295                 300

Leu Asp Asp Gly Pro Tyr Ala Pro Phe Pro Pro Arg Pro Arg Phe Arg
305                 310                 315                 320

Arg Ala Leu Arg Thr Asp Pro Glu Gly Val Asp Pro Asp Val Arg Ala
                325                 330                 335

Pro Leu Thr Gly Arg Arg Leu Met Ala Leu Thr Glu Asp Ala Ser Ser
                340                 345                 350

Asp Ser Pro Thr Ser Ala Pro Glu Lys Thr Pro Leu Pro Val Ser Ala
                355                 360                 365

Thr Ala Met Ala Pro Ser Val Asp Pro Ser Ala Glu Pro Thr Ala Pro
        370                 375                 380

Ala Thr Thr Thr Pro Pro Asp Glu Met Ala Thr Gln Ala Ala Thr Val
385                 390                 395                 400

Ala Val Thr Pro Glu Glu Thr Ala Val Ala Ser Pro Pro Ala Thr Ala
                405                 410                 415

Ser Val Glu Ser Ser Pro Leu Pro Ala Ala Ala Thr Pro Gly Ala
                420                 425                 430

Gly His Thr Asn Thr Ser Ser Ala Pro Ala Lys Thr Pro Pro Thr
        435                 440                 445

Thr Pro Ala Pro Thr Thr Pro Pro Thr Ser Thr His Ala Thr Pro
450                 455                 460

Arg Pro Thr Thr Pro Gly Pro Gln Thr Thr Pro Pro Gly Pro Ala Thr
465                 470                 475                 480

Pro Gly Pro Val Gly Ala Ser Ala Ala Pro Thr Ala Asp Ser Pro Leu
                485                 490                 495

Thr Ala Ser Pro Pro Ala Thr Ala Pro Gly Pro Ser Ala Ala Asn Val
                500                 505                 510

Ser Val Ala Ala Thr Thr Ala Thr Pro Gly Thr Arg Gly Thr Ala Arg
                515                 520                 525

Thr Pro Pro Thr Asp Pro Lys Thr His Pro His Gly Pro Ala Asp Ala
        530                 535                 540

Pro Pro Gly Ser Pro Ala Pro Pro Pro Glu His Arg Gly Gly Pro
545                 550                 555                 560

Glu Glu Phe Glu Gly Ala Gly Asp Gly Glu Pro Pro Asp Asp Asp
                565                 570                 575

Ser Ala Thr Gly Leu Ala Phe Arg Thr Pro Asn Pro Asn Lys Pro Pro
                580                 585                 590

Pro Ala Arg Pro Gly Pro Ile Arg Pro Thr Leu Pro Pro Gly Ile Leu
                595                 600                 605

Gly Pro Leu Ala Pro Asn Thr Pro Arg Pro Pro Ala Gln Ala Pro Ala
```

```
                    610                 615                 620
Lys Asp Met Pro Ser Gly Pro Thr Pro Gln His Ile Pro Leu Phe Trp
625                 630                 635                 640

Phe Leu Thr Ala Ser Pro Ala Leu Asp Ile Leu Phe Ile Ile Ser Thr
                    645                 650                 655

Thr Ile His Thr Ala Ala Phe Val Cys Leu Val Ala Leu Ala Ala Gln
                660                 665                 670

Leu Trp Arg Gly Arg Ala Gly Arg Arg Tyr Ala His Pro Ser Val
            675                 680                 685

Arg Tyr Val Cys Leu Pro Pro Glu Arg Asp
            690                 695

<210> SEQ ID NO 20
<211> LENGTH: 851
<212> TYPE: PRT
<213> ORGANISM: Herpes simplex virus 1

<400> SEQUENCE: 20

Met Pro Phe Val Gly Gly Ala Glu Ser Gly Asp Pro Leu Gly Ala Gly
1                   5                   10                  15

Arg Pro Ile Gly Asp Asp Glu Cys Glu Gln Tyr Thr Ser Ser Val Ser
                20                  25                  30

Leu Ala Arg Met Leu Tyr Gly Gly Asp Leu Ala Glu Trp Val Pro Arg
            35                  40                  45

Val His Pro Lys Thr Thr Ile Glu Arg Gln Gln His Gly Pro Val Thr
        50                  55                  60

Phe Pro Asn Ala Ser Ala Pro Thr Ala Arg Cys Val Thr Val Val Arg
65                  70                  75                  80

Ala Pro Met Gly Ser Gly Lys Thr Thr Ala Leu Ile Arg Trp Leu Arg
                85                  90                  95

Glu Ala Ile His Ser Pro Asp Thr Ser Val Leu Val Val Ser Cys Arg
                100                 105                 110

Arg Ser Phe Thr Gln Thr Leu Ala Thr Arg Phe Ala Glu Ser Gly Leu
            115                 120                 125

Val Asp Phe Val Thr Tyr Phe Ser Ser Thr Asn Tyr Ile Met Asn Asp
        130                 135                 140

Arg Pro Phe His Arg Leu Ile Val Gln Val Glu Ser Leu His Arg Val
145                 150                 155                 160

Gly Pro Asn Leu Leu Asn Asn Tyr Asp Val Leu Val Leu Asp Glu Val
                165                 170                 175

Met Ser Thr Leu Gly Gln Leu Tyr Ser Pro Thr Met Gln Gln Leu Gly
            180                 185                 190

Arg Val Asp Ala Leu Met Leu Arg Leu Leu Arg Thr Cys Pro Arg Ile
        195                 200                 205

Ile Ala Met Asp Ala Thr Ala Asn Ala Gln Leu Val Asp Phe Leu Cys
        210                 215                 220

Gly Leu Arg Gly Glu Lys Asn Val His Val Val Gly Glu Tyr Ala
225                 230                 235                 240

Met Pro Gly Phe Ser Ala Arg Arg Cys Leu Phe Leu Pro Arg Leu Gly
                245                 250                 255

Thr Glu Leu Leu Gln Ala Ala Leu Arg Pro Gly Pro Pro Ser Gly
            260                 265                 270

Pro Ser Pro Asp Ala Ser Pro Asp Ala Arg Gly Ala Thr Phe Phe Gly
        275                 280                 285
```

```
Glu Leu Glu Ala Arg Leu Gly Gly Asp Asn Ile Cys Ile Phe Ser
    290                 295                 300

Ser Thr Val Ser Phe Ala Glu Ile Val Ala Arg Phe Cys Arg Gln Phe
305                 310                 315                 320

Thr Asp Arg Val Leu Leu Leu His Ser Leu Thr Pro Leu Gly Asp Val
                    325                 330                 335

Thr Thr Trp Gly Gln Tyr Arg Val Val Ile Tyr Thr Val Val Thr
                340                 345                 350

Val Gly Leu Ser Phe Asp Pro Leu His Phe Asp Gly Met Phe Ala Tyr
                355                 360                 365

Val Lys Pro Met Asn Tyr Gly Pro Asp Met Val Ser Val Tyr Gln Ser
    370                 375                 380

Leu Gly Arg Val Arg Thr Leu Arg Lys Gly Glu Leu Leu Ile Tyr Met
385                 390                 395                 400

Asp Gly Ser Gly Ala Arg Ser Glu Pro Val Phe Thr Pro Met Leu Leu
                    405                 410                 415

Asn His Val Val Ser Ser Cys Gly Gln Trp Pro Ala Gln Phe Ser Gln
                420                 425                 430

Val Thr Asn Leu Leu Cys Arg Arg Phe Lys Gly Arg Cys Asp Ala Ser
    435                 440                 445

Ala Cys Asp Thr Ser Leu Gly Arg Gly Ser Arg Ile Tyr Asn Lys Phe
450                 455                 460

Arg Tyr Lys His Tyr Phe Glu Arg Cys Thr Leu Ala Cys Leu Ser Asp
465                 470                 475                 480

Ser Leu Asn Ile Leu His Met Leu Leu Thr Leu Asn Cys Ile Arg Val
                485                 490                 495

Arg Phe Trp Gly His Asp Asp Thr Leu Thr Pro Lys Asp Phe Cys Leu
                500                 505                 510

Phe Leu Arg Gly Val His Phe Asp Ala Leu Arg Ala Gln Arg Asp Leu
                515                 520                 525

Arg Glu Leu Arg Cys Arg Asp Pro Glu Ala Ser Leu Pro Ala Gln Ala
    530                 535                 540

Ala Glu Thr Glu Glu Val Gly Leu Phe Val Glu Lys Tyr Leu Arg Ser
545                 550                 555                 560

Asp Val Ala Pro Ala Glu Ile Val Ala Leu Met Arg Asn Leu Asn Ser
                565                 570                 575

Leu Met Gly Arg Thr Arg Phe Ile Tyr Leu Ala Leu Leu Glu Ala Cys
                580                 585                 590

Leu Arg Val Pro Met Ala Thr Arg Ser Ser Ala Ile Phe Arg Arg Ile
                595                 600                 605

Tyr Asp His Tyr Ala Thr Gly Val Ile Pro Thr Ile Asn Val Thr Gly
                610                 615                 620

Glu Leu Glu Leu Val Ala Leu Pro Pro Thr Leu Asn Val Thr Pro Val
625                 630                 635                 640

Trp Glu Leu Leu Cys Leu Cys Ser Thr Met Ala Ala Arg Leu His Trp
                    645                 650                 655

Asp Ser Ala Ala Gly Ser Gly Arg Thr Phe Gly Pro Asp Asp Val
                660                 665                 670

Leu Asp Leu Leu Thr Pro His Tyr Asp Arg Tyr Met Gln Leu Val Phe
                675                 680                 685

Glu Leu Gly His Cys Asn Val Thr Asp Gly Leu Leu Leu Ser Glu Glu
                690                 695                 700

Ala Val Lys Arg Val Ala Asp Ala Leu Ser Gly Cys Pro Pro Arg Gly
```

```
705                 710                 715                 720
Ser Val Ser Glu Thr Asp His Ala Val Ala Leu Phe Lys Ile Ile Trp
                725                 730                 735

Gly Glu Leu Phe Gly Val Gln Met Ala Lys Ser Thr Gln Thr Phe Pro
                740                 745                 750

Gly Ala Gly Arg Val Lys Asn Leu Thr Lys Gln Thr Ile Val Gly Leu
                755                 760                 765

Leu Asp Ala His His Ile Asp His Ser Ala Cys Arg Thr His Arg Gln
                770                 775                 780

Leu Tyr Ala Leu Leu Met Ala His Lys Arg Glu Phe Ala Gly Ala Arg
785                 790                 795                 800

Phe Lys Leu Arg Val Pro Ala Trp Gly Arg Cys Leu Arg Thr His Ser
                805                 810                 815

Ser Ser Ala Asn Pro Asn Ala Asp Ile Ile Leu Glu Ala Ala Leu Ser
                820                 825                 830

Glu Leu Pro Thr Glu Ala Trp Pro Met Met Gln Gly Ala Val Asn Phe
                835                 840                 845

Ser Thr Leu
        850

<210> SEQ ID NO 21
<211> LENGTH: 317
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Glu Ala Ser Leu Pro Ala Gln Ala Ala Glu Thr Glu Glu Val
1               5                   10                  15

Gly Leu Phe Val Glu Lys Tyr Leu Arg Ser Asp Val Ala Pro Ala Glu
                20                  25                  30

Ile Val Ala Leu Met Arg Asn Leu Asn Ser Leu Met Gly Arg Thr Arg
            35                  40                  45

Phe Ile Tyr Leu Ala Leu Leu Glu Ala Cys Leu Arg Val Pro Met Ala
        50                  55                  60

Thr Arg Ser Ser Ala Ile Phe Arg Arg Ile Tyr Asp His Tyr Ala Thr
65                  70                  75                  80

Gly Val Ile Pro Thr Ile Asn Val Thr Gly Glu Leu Glu Leu Val Ala
                85                  90                  95

Leu Pro Pro Thr Leu Asn Val Thr Pro Val Trp Glu Leu Leu Cys Leu
                100                 105                 110

Cys Ser Thr Met Ala Ala Arg Leu His Trp Asp Ser Ala Ala Gly Gly
                115                 120                 125

Ser Gly Arg Thr Phe Gly Pro Asp Asp Val Leu Asp Leu Leu Thr Pro
                130                 135                 140

His Tyr Asp Arg Tyr Met Gln Leu Val Phe Glu Leu Gly His Cys Asn
145                 150                 155                 160

Val Thr Asp Gly Leu Leu Leu Ser Glu Glu Ala Val Lys Arg Val Ala
                165                 170                 175

Asp Ala Leu Ser Gly Cys Pro Pro Arg Gly Ser Val Ser Glu Thr Asp
                180                 185                 190

His Ala Val Ala Leu Phe Lys Ile Ile Trp Gly Glu Leu Phe Gly Val
                195                 200                 205
```

```
Gln Met Ala Lys Ser Thr Gln Thr Phe Pro Gly Ala Gly Arg Val Lys
    210                 215                 220
Asn Leu Thr Lys Gln Thr Ile Val Gly Leu Leu Asp Ala His His Ile
225                 230                 235                 240
Asp His Ser Ala Cys Arg Thr His Arg Gln Leu Tyr Ala Leu Leu Met
                245                 250                 255
Ala His Lys Arg Glu Phe Ala Gly Ala Arg Phe Lys Leu Arg Val Pro
            260                 265                 270
Ala Trp Gly Arg Cys Leu Arg Thr His Ser Ser Ser Ala Asn Pro Asn
        275                 280                 285
Ala Asp Ile Ile Leu Glu Ala Ala Leu Ser Glu Leu Pro Thr Glu Ala
    290                 295                 300
Trp Pro Met Met Gln Gly Ala Val Asn Phe Ser Thr Leu
305                 310                 315
```

<210> SEQ ID NO 22
<211> LENGTH: 259
<212> TYPE: DNA
<213> ORGANISM: Herpes simplex virus 1

<400> SEQUENCE: 22

```
caacgacccc gcccatgggt cccaattggc cgtcccgtta ccaagaccaa cccagccagc      60
gtatccaccc ccgcccgggt ccccgcggaa gcggaacggg gtatgtgata tgctaattaa     120
atacatgcca cgtacttatg gtgtctgatt ggtccttgtc tgtgccggag gtggggcggg     180
ggccccgccc gggggggcgga acgaggaggg gtttgggaga gccggccccg gcaccacggg    240
tataaggaca tccaccacc                                                  259
```

<210> SEQ ID NO 23
<211> LENGTH: 302
<212> TYPE: DNA
<213> ORGANISM: Herpes simplex virus 2

<400> SEQUENCE: 23

```
gccgatccgg cctcgggtct gcttgcccct ccccgggcc agcacaggca ggctcgtccg      60
acttccgcat acaccccacc ctaccgcgtg cttccgcacc cccgcctacg cgtgtacgcg    120
aaggcggacc cagacctgcc gtatgctaat taaatacata aaacccaccc tcggtgtccg    180
attggttct ggggacggcg ggggcggggg cggtgacgcc cgacggggag ggacaaggag     240
gagtttcgga agccggccc cggtcgtgcg ggtataaggg cagccaccgg cccactgggc     300
gc                                                                   302
```

<210> SEQ ID NO 24
<211> LENGTH: 1974
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
caattgaagc ttcgtacggg gccccgcccc ctgcccgttc ctcgttagca tgcggaacgg      60
aagcggaaac cgccggatcg ggcggtaatg agatgccatg cggggcgggg cgcggaccca    120
cccgccctcg cgcccgccc atggcagatg gcgcggatgg gcggggcgg gggttcgacc      180
aacgggccgc ggccacgggc cccggccgtg ccggcgtcgg ggcggggtcg tgcataatgg    240
aattccgttc ggggtgggcc cgccgggggg gcgggggggcc ggcggcctcc gctgctcctc   300
```

```
cttcccgccg gcccctggga ctatatgagc cgagctctcc ctatcagtga tagagatctc      360
cctatcagtg atagagatcg tcgacgagct cgcgtgtgca tcgcgtatca cggcgccacc      420
atgggccgcc tgaccagcgg cgtgggcacc gccgccctgc tggtggtggc cgtgggcctg      480
cgcgtggtgt gcgccaagta cgccctggcc gaccccagcc tgaagatggc cgaccccaac      540
cgcttccgcg gcaagaacct gcccgtgctg accagctga ccgaccccc cggcgtgaag        600
cgcgtgtacc acatccagcc cagcctggag gaccccttcc agcccccag catccccatc       660
accgtgtact acgccgtgct ggagcgcgcc tgccgcagcg tgctgctgca cgcccccagc      720
gaggccccc agatcgtgcg cggcgccagc gacgaggccc gcaagcacac ctacaacctg       780
accatcgcct ggtaccgcat gggcgacaac tgcgccatcc ccatcaccgt gatggagtac      840
accgagtgcc cctacaacaa gagcctgggc gtgtgcccca tccgcaccca gccccgctgg      900
agctactacg acagcttcag cgccgtgagc gaggacaacc tgggcttcct gatgcacgcc      960
cccgccttcg agaccgccgg cacctacctg cgcctggtga agatcaacga ctggaccgag     1020
atcacccagt tcatcctgga gcaccgcgcc cgcgccagct gcaagtacgc cctgcccctg     1080
cgcatccccc ccgccgcctg cctgaccagc aaggcctacc agcagggcgt gaccgtggac     1140
agcatcggca tgctgccccg cttcatcccc gagaaccagc gcaccgtggc cctgtacagc     1200
ctgaagatcg ccggctggca cggccccaag ccccccctaca ccagcaccct gctgccccc      1260
gagctgagcg acaccaccaa cgccacccag cccgagctgg tgcccgagga ccccgaggac     1320
agcgccctgc tggaggaccc cgccggcacc gtgagcagcc agatcccccc caactggcac     1380
atccccagca tccaggacgt ggccccccac cacgccccg ccgccccag caaccccggc        1440
ctgatcatcg gcgccctggc cggcagcacc ctggccgtgc tggtgatcgg cggcatcgcc     1500
ttctgggtgc gccgccgcgc ccagatggcc cccaagcgcc tgcgcctgcc ccacatccgc     1560
gacgacgacg cccccccag ccaccagccc ctgttctact aaaggagttt ccccgctccc       1620
gtgtacctct gggcccgtgt gggagggtgg ctggggtatt tgggtgggac ttggactccg     1680
cataaaggga gtctcgaagg agggaaccgc tgatcagcct cgactgtgcc ttctagttgc     1740
cagccatctg ttgtttgccc ctccccgtg ccttccttga ccctggaagg tgccactccc      1800
actgtccttt cctaataaaa tgaggaaatt gcatcgcatt gtctgagtag gtgtcattct     1860
attctgggg gtggggtggg gcaggacagc aaggggagg attgggaaga caatagcagg      1920
catgcgatat ctacgcaacg accccgccca tgggtcccaa ttggatcctc taga           1974
```

<210> SEQ ID NO 25
<211> LENGTH: 2530
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 25

```
tgccggccgc ggggacggtg gcctacggac accccggcgc cggcccgtcc ccgcactacc       60
cgcctcctcc cgcccacccg taccgggta tgctgttcgc gggccccagt cccctggagg       120
cccagatcgc cgcgctggtg ggggccatcg ccgccgaccg ccaggcgggt gggcttccgg      180
cggccgccgg agaccacggg atccgggggt cggcgaagcg ccgccgacac gaggtggagc      240
agccggagta cgactgcggc cgtgacgagc cggaccggga cttcccgtat tacccgggcg      300
aggcccgccc cgagccgcgc ccggtcgact cccgcgcgcg cgcgcgccag gcttccgggc      360
```

```
cccacgaaac catcacggcg ctggtggggg cggtgacgtc cctgcagcag gaactggcgc    420
acatgcgcgc gcgtacccac gcccctacg ggccgtatcc gccggtgggg ccctaccacc    480
acccccacgc agacacggag accccgccc aaccacccg ctaccccgcc aaggccgtct    540
atctgccgcc gccgcacatc gccccccgg ggcctcctct atccggggcg gtcccccac    600 cctcgtatcc cccagttgcg gttaccccg gtcccgctcc cccgctacat cagccctccc    660
ccgcacacgc ccacccccct ccgcgccgc cgggacccac gctcccccc gccgcgagct    720 taccccaacc cgaggcgccc ggcgcggagg ccggcgcctt agttaacgcc agcagcgcgg    780
cccacgtgaa cgtggacacg gcccgggccg ccgatctgtt tgtgtcacag atgatggggt    840
cccgctaact cgcctccagg atccggactt ggggggggtg tgtgttttca tatattttaa    900
ataaacaaac aaccggacaa aagtatacc acttcgtgtg cttgtgtttt tgtttgagag    960 ggggggggtgg agtggggggg aaagtgggcc gaatgacaca aaaattaggt cgtacgcaac   1020
gaccccgccc atgggtccca attggccgtc ccgttaccaa gaccaaccca gccagcgtat   1080
ccacccccgc ccgggtcccc gcggaagcgg aacgggtat gtgatatgct aattaaatac   1140
atgccacgta cttatggtgt ctgattggtc cttgtctgtg ccggaggtgg ggcggggcc   1200 ccgcccgggg ggcggaacga ggaggggttt gggagagccg gccccggcac cacgggtata   1260
taagcaaccg gtgtcgacgg cggggtcgt cggggtccgt gggtctcgcc ccctcccccc   1320
atcgagagtc cgtaggtgac ctaccgttgc gccaccacca gaggccatat ccgacacccc   1380
agccccgacg gcagccgaca gcccgaagct tggtcgatat ctatcggagc tgtgctagcg   1440
ccactggtac ccgagcggaa ttctgtctag aaatggttac aaataaaaga tctttatttt   1500
cattagatct gtgtgttggt tttttgtgtg ttggttttcc cgttagcaca tgtctgcatt   1560
tgttttccta gtcacacgcc ccccccccc aaataaaaac caaggcaaaa caataccaga   1620
agtcatgtgt atttttgaac atcggtgtct ttttatttat acacaagccc agctccctc   1680 ccctccctta gagctcgtct tcgtctccgg cctcgtcctc gttgtggagc ggagagtacc   1740
tggctttgtt gcgcttgcgc agaaccatgt tggtgacctt ggagctgagc agggcgctcg   1800
tgcccttctt tctggccttg tgttccgtgc gctccatggc cgacaccaaa gccatatatc   1860
ggatcatttc tcgggcctcg gccaacttgg cctcgtcaaa cccgccccc tccgcgcctt   1920 cctccccctc cccgcccacg ccccccgggt cggaagtctt gagttccttg gtggtgagcg   1980
gatacagggc cttcatggga ttgcgttgca gttgcaggac gtagcggaag gcgaagaagg   2040
ccgcgaccag gccggccagg accagcagcc ccacggcaag cgcccgaag gggttggaca   2100 taaaggagga cacgcccgag acggccgaca ccacgcccc cactactccc atgactacct   2160
tgccgaccgc gcgcccaag tccccatcc cctcgaagaa cgcgcacagc cccgcgaaca   2220
tggcggcgtt ggcgtcggcg cggatgaccg tgtcgatgtc ggcaaagcgc aggtcgtgca   2280
gctggttgcg gcgctggacc tccgtgtagt ccagcaggcc gctgtccttg atctcgtggc   2340
gcgtgtagac ctccaggggc acaaactcgt ggtcctccag catggtgatg ttcaggtcga   2400
tgaaggtgct gacggtggtg acgtcggcgc gactcagctg gtgagagtac gcgtactcct   2460
cgaagtacac gtagccccg ccgaagatga agtagcgccg gtggcccacg gtgcacggct   2520
cgagcgcgtc                                                          2530
```

<210> SEQ ID NO 26
<211> LENGTH: 1010
<212> TYPE: DNA

<213> ORGANISM: Herpes simplex virus 2

<400> SEQUENCE: 26

```
tgccggccgc ggggacggtg gcctacggac accccggcgc cggcccgtcc ccgcactacc        60
cgcctcctcc cgcccacccg tacccgggta tgctgttcgc gggccccagt cccctggagg       120
cccagatcgc cgcgctggtg ggggccatcg ccgccgaccg ccaggcgggt gggcttccgg       180
cggccgccgg agaccacggg atccgggggt cggcgaagcg ccgccgacac gaggtggagc       240
agccggagta cgactgcggc cgtgacgagc cggaccggga cttcccgtat acccgggcg        300
aggcccgccc cgagccgcgc ccggtcgact cccggcgcgc cgcgcgccag gcttccgggc       360
cccacgaaac catcacggcg ctggtggggg cggtgacgtc cctgcagcag gaactggcgc       420
acatgcgcgc gcgtacccac gcccctacg ggccgtatcc gccggtgggg ccctaccacc       480
accccacgc agacacggag accccgccc aaccaccccg ctaccccgcc aaggccgtct         540
atctgccgcc gccgcacatc gcccccccgg ggcctcctct atccggggcg gtcccccac        600
cctcgtatcc cccagttgcg gttacccccg gtcccgctcc ccgctacat cagccctccc        660
ccgcacacgc ccaccccct cgccgccgc cgggacccac gcctccccc gccgcgagct          720
taccccaacc cgaggcgccc ggcgcggagg ccggcgcctt agttaacgcc agcagcgcgg       780
cccacgtgaa cgtggacacg gcccgggccg ccgatctgtt tgtgtcacag atgatggggt       840
cccgctaact cgcctccagg atccggactt ggggggggtg tgtgttttca tatattttaa       900
ataaacaaac aaccggacaa agtataccc acttcgtgtg cttgtgtttt tgtttgagag        960
gggggggtgg agtgggggggg aaagtgggcc gaatgacaca aaaattaggt                1010
```

<210> SEQ ID NO 27
<211> LENGTH: 1000
<212> TYPE: DNA
<213> ORGANISM: Herpes simplex virus 2

<400> SEQUENCE: 27

```
ttggttttcc cgttagcaca tgtctgcatt tgttttctta gtcacacgcc cccccccc         60
aaataaaaac caaggcaaaa caataccaga agtcatgtgt attttttgaac atcggtgtct     120
ttttatttat acacaagccc agctcccctc ccctccctta gagctcgtct tcgtctccgg      180
cctcgtcctc gttgtggagc ggagagtacc tggctttgtt gcgcttgcgc agaaccatgt     240
tggtgacctt ggagctgagc agggcgctcg tgcccttctt tctggccttg tgttccgtgc     300
gctccatggc cgacaccaaa gccatatatc ggatcatttc tcgggcctcg gccaacttgg     360
cctcgtcaaa cccgcccccc tccgcgcctt cctcccctc cccgcccacg ccccgggt        420
cggaagtctt gagttccttg gtggtgagcg gatacagggc cttcatggga ttgcgttgca     480
gttgcaggac gtagcggaag gcgaagaagg ccgcgaccag gccggccagg accagcagcc    540
ccacggcaag cgcccgaag gggttggaca taaggaggga cacgcccgag acggccgaca      600
ccacgccccc cactactccc atgactacct tgccgaccgc gcgccccaag tccccatcc      660
cctcgaagaa cgcgcacagc cccgcgaaca tggcggcgtt ggcgtcggcg cggatgaccg     720
tgtcgatgtc ggcaaagcgc aggtcgtgca gctggttgcg gcgctggacc tccgtgtagt    780
ccagcaggcc gctgtccttg atctcgtggc gcgtgtagac ctccaggggc acaaactcgt     840
ggtcctccag catggtgatg ttcaggtcga tgaaggtgct gacggtggtg acgtcggcgc     900
gactcagctg tgagagtac gcgtactcct cgaagtacac gtagccccg ccgaagatga      960
agtagcgccg gtgcccacg gtgcacggct cgagcgcgtc                           1000
```

<210> SEQ ID NO 28
<211> LENGTH: 514
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
caacgacccc gcccatgggt cccaattggc cgtcccgtta ccaagaccaa cccagccagc      60
gtatccaccc ccgcccgggt ccccgcggaa gcggaacggg gtatgtgata tgctaattaa    120
atacatgcca cgtacttatg gtgtctgatt ggtccttgtc tgtgccggag gtggggcggg    180
ggccccgccc gggggcgga acgaggaggg gtttgggaga gccggccccg gcaccacggg     240
tatataagca accggtgtcg acggcggggg tcgtcggggt ccgtgggtct cgcccctcc    300 ccccatcgag agtccgtagg tgacctaccg ttgcgccacc accagaggcc atatccgaca    360
ccccagcccc gacggcagcc gacagcccga agcttggtcg atatctatcg agctgtgct    420 agcgccactg gtacccgagc ggaattctgt ctagaaatgg ttacaaataa aagatcttta    480
ttttcattag atctgtgtgt tggttttttg tgtg                                514

<210> SEQ ID NO 29
<211> LENGTH: 521
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
cgtacgcaac gaccccgccc atgggtccca attggccgtc cgttaccaa gaccaaccca      60 gccagcgtat ccaccccgc ccgggtcccc gcggaagcgg aacggggtat gtgatatgct    120
aattaaatac atgccacgta cttatggtgt ctgattggtc cttgtctgtg ccggaggtgg    180
ggcgggggcc ccgccggggg ggcggaacga ggaggggttt gggagagccg gccccggcac    240
cacgggtata taagcaaccg gtctccctat cagtgataga gatctcccta tcagtgatag    300
agatcgaccg gtgtcgacgg cggggtcgt cggggtccgt gggtctcgcc cctcccccc     360 atcgagagtc cgtaggtgac ctaccgttgc gccaccacca gaggccatat ccgacacccc    420
agccccgacg gcagccgaca gcccgaagct tggtcgatat ctatcggagc tgtgctagcg    480
ccactggtac ccgagcggaa ttctgtctag aaatggttac a                       521

<210> SEQ ID NO 30
<211> LENGTH: 259
<212> TYPE: DNA
<213> ORGANISM: Herpes simplex virus 1

<400> SEQUENCE: 30
caacgacccc gcccatgggt cccaattggc cgtcccgtta ccaagaccaa cccagccagc      60
gtatccaccc ccgcccgggt ccccgcggaa gcggaacggg gtatgtgata tgctaattaa    120
atacatgcca cgtacttatg gtgtctgatt ggtccttgtc tgtgccggag gtggggcggg    180
ggccccgccc gggggcgga acgaggaggg gtttgggaga gccggccccg gcaccacggg     240
tataaggaca tccaccacc                                                  259

<210> SEQ ID NO 31

```
<211> LENGTH: 58
<212> TYPE: DNA
<213> ORGANISM: Herpes simplex virus 1

<400> SEQUENCE: 31
tgcgccacca ccagaggcca tatccgacac cccagccccg acggcagccg acagcccg    58

<210> SEQ ID NO 32
<211> LENGTH: 75
<212> TYPE: DNA
<213> ORGANISM: Herpes simplex virus 1

<400> SEQUENCE: 32
gtcgacggcg ggggtcgtcg gggtccgtgg gtctcgcccc ctccccccat cgagagtccg    60
taggtgacct accgt                                                     75

<210> SEQ ID NO 33
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aagcttggtc gatatctatc ggagctgtgc tagcgccact ggtacccgag cggaattctg    60
tctaga                                                               66

<210> SEQ ID NO 34
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
aataaaagat ctttattttc attagatctg tgtgttggtt ttttgtgtg                49

<210> SEQ ID NO 35
<211> LENGTH: 7841
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg    120
ttggcgggtg tcgggctgg  cttaactatg cggcatcaga gcagattgta ctgagagtgc    180
accatatgtg ccgccgcgg  ggacggtggc tacggacac  cccggcgccg gcccgtcccc    240
gcactacccg cctcctcccg cccacccgta cccgggtatg ctgttcgcgg gccccagtcc    300
cctggaggcc cagatcgccg cgctggtggg ggccatcgcc gccgaccgcc aggcgggtgg    360
gcttccggcg gccgccggag accacgggat cggggggtcg gcgaagcgcc gccgacacga    420
ggtggagcag ccggagtacg actgcggccg tgacgagccg gaccgggact cccgtatta    480 cccgggcgag gcccgccccg agccgcgccc ggtcgactcc cggcgcgccg cgcgccaggc    540
ttccgggccc cacgaaacca tcacggcgct ggtgggggcg gtgacgtccc tgcagcagga    600
```

```
actggcgcac atgcgcgcgc gtacccacgc cccctacggg ccgtatccgc cggtggggcc      660
ctaccaccac ccccacgcag acacggagac ccccgcccaa ccaccccgct accccgccaa      720
ggccgtctat ctgccgccgc cgcacatcgc ccccccgggg cctcctctat ccggggcggt      780
ccccccaccc tcgtatcccc cagttgcggt taccccccggt cccgctcccc cgctacatca    840
gccctccccc gcacacgccc accccctcc gccgccgccg ggaccacgc ctcccccgc         900 cgcgagctta ccccaacccg aggcgccggg cgcggaggcc ggcgccttag ttaacgccag      960
cagcgcggcc cacgtgaacg tggacacggc ccgggccgcc gatctgtttg tgtcacagat    1020
gatggggtcc cgctaactcg cctccaggat ccggacttgg gggggtgtg tgttttcata     1080 tattttaaat aaacaaacaa ccggacaaaa gtatacccac ttcgtgtgct tgtgtttttg    1140
tttgagaggg ggggtggag tggggggaa agtgggccga atgacacaaa aattaggtcg     1200
tacgcaacga ccccgcccat gggtcccaat tggccgtccc gttaccaaga ccaacccagc    1260
cagcgtatcc accccgccc gggtcccgc ggaagcggaa cggggtatgt gatatgctaa    1320
ttaaatacat gccacgtact tatggtgtct gattggtcct tgtctgtgcc ggaggtgggg    1380 cggggccc gcccgggggg cggaacgagg aggggtttgg gagagccggc cccggcacca     1440
cgggtatata agcaaccggt gtcgacgcg ggggtcgtcg gggtccgtgg gtctcgcccc    1500 ctcccccat cgagagtccg taggtgacct accgttgcgc caccaccaga ggccatatcc     1560
gacaccccag ccccgacggc agccgacagc ccgagcttac catgggggt tctcatcatc    1620 atcatcatca tggtatggct agcatgactg gtggacagca aatgggtcgg gatctgtacg    1680
acgatgacga taaggtacct aaggatcagc ttggagttga tcccgtcgtt ttacaacgtc    1740
gtgactggga aaaccctggc gttacccaac ttaatcgcct tgcagcacat ccccctttcg    1800
ccagctggcg taatagcgaa gaggcccgca ccgatcgccc ttcccaacag ttgcgcagcc    1860
tgaatggcga atggcgcttt gcctggtttc cggcaccaga agcggtgccg gaaagctggc    1920
tggagtgcga tcttcctgag gccgatactg tcgtcgtccc ctcaaactgg cagatgcacg    1980
gttacgatgc gcccatctac accaacgtaa cctatcccat tacggtcaat ccgccgtttg    2040
ttcccacgga gaatccgacg ggttgttact cgctcacatt taatgttgat gaaagctggc    2100
tacaggaagg ccagacgcga attattttg atggcgttaa ctcggcgttt catctgtggt    2160
gcaacgggcg ctgggtcggt tacgccagg acagtcgttt gccgtctgaa tttgacctga    2220
gcgcattttt acgcgccgga gaaaaccgcc tcgcggtgat ggtgctgcgt tggagtgacg    2280
gcagttatct ggaagatcag gatatgtggc ggatgagcgg catttccgt gacgtctcgt    2340 tgctgcataa accgactaca caaatcagcg atttccatgt tgccactcgc tttaatgatg    2400
atttcagccg cgctgtactg gaggctgaag ttcagatgtg cggcgagttg cgtgactacc    2460
tacgggtaac agtttcttta tggcagggtg aaacgcaggt cgccagcggc accgcgcctt    2520
tcggcggtga aattatcgat gagcgtggt gttatgccga tcgcgtcaca ctacgtctga    2580
acgtcgaaaa cccgaaactg tggagcgccg aaatcccgaa tctctatcgt gcggtggttg    2640
aactgcacac cgccgacggc acgctgattg aagcagaagc ctgcgatgtc ggtttccgcg    2700
aggtgcggat tgaaaatggt ctgctgctgc tgaacggcaa gccgttgctg attcgaggcg    2760
ttaaccgtca cgagcatcat cctctgcatg gtcaggtcat ggatgagcag acgatggtgc    2820
aggatatcct gctgatgaag cagaacaact ttaacgccgt gcgctgttcg cattatccga    2880
accatccgct gtggtacacg ctgtgcgacc gctacgccct gtatgtggtg atgaagccaa    2940
atattgaaac ccacggcatg gtgccaatga atcgtctgac cgatgatccg cgctggctac    3000
```

-continued

```
cggcgatgag cgaacgcgta acgcgaatgg tgcagcgcga tcgtaatcac ccgagtgtga    3060
tcatctggtc gctggggaat gaatcaggcc acggcgctaa tcacgacgcg ctgtatcgct    3120
ggatcaaatc tgtcgatcct tcccgcccgg tgcagtatga aggcggcgga gccgacacca    3180
cggccaccga tattatttgc ccgatgtacg cgcgcgtgga tgaagaccag cccttcccgg    3240
ctgtgccgaa atggtccatc aaaaaatggc tttcgctacc tggagagacg cgcccgctga    3300
tcctttgcga atacgcccac gcgatgggta acagtcttgg cggtttcgct aaatactggc    3360
aggcgtttcg tcagtatccc cgtttacagg gcggcttcgt ctgggactgg gtggatcagt    3420
cgctgattaa atatgatgaa aacggcaacc cgtggtcggc ttacggcggt gattttggcg    3480
atacgccgaa cgatcgccag ttctgtatga cggtctggt ctttgccgac cgcacgccgc     3540
atccagcgct gacggaagca aaacaccagc agcagttttt ccagttccgt ttatccgggc    3600
aaaccatcga agtgaccagc gaatacctgt tccgtcatag cgataacgag ctcctgcact    3660
ggatggtggc gctggatggt aagccgctgg caagcggtga agtgcctctg gatgtcgctc    3720
cacaaggtaa acagttgatt gaactgcctg aactaccgca gccggagagc gccgggcaac    3780
tctggctcac agtacgcgta gtgcaaccga acgcgaccgc atggtcagaa gccgggcaca    3840
tcagcgcctg gcagcagtgg cgtctggcgg aaaacctcag tgtgacgctc cccgccgcgt    3900
cccacgccat cccgcatctg accaccagcg aaatggattt tgcatcgag ctgggtaata     3960 agcgttggca atttaaccgc cagtcaggct ttctttcaca gatgtggatt ggcgataaaa    4020
aacaactgct gacgccgctg cgcgatcagt tcacccgtgc accgctggat aacgacattg    4080
gcgtaagtga agcgacccgc attgaccta acgcctgggt cgaacgctgg aaggcggcgg     4140
gccattacca ggccgaagca gcgttgttgc agtgcacggc agatacactt gctgatgcgg    4200
tgctgattac gaccgctcac gcgtggcagc atcagggaa aaccttattt atcagccgga     4260
aaacctaccg gattgatggt agtggtcaaa tggcgattac cgttgatgtt gaagtggcga    4320
gcgatacacc gcatccggcg cggattggcc tgaactgcca gctggcgcag gtagcagagc    4380
gggtaaactg gctcggatta gggccgcaag aaaactatcc cgaccgcctt actgccgcct    4440
gttttgaccg ctgggatctg ccattgtcag acatgtatac cccgtacgtc ttcccgagcg    4500
aaaacggtct gcgctgcggg acgcgcgaat tgaattatgg cccacaccag tggcgcggcg    4560
acttccagtt caacatcagc cgctacagtc aacagcaact gatggaaacc agccatcgcc    4620
atctgctgca cgcggaagaa ggcacatggc tgaatatcga cggtttccat atggggattg    4680
gtggcgacga ctcctggagc ccgtcagtat cggcggagtt ccagctgagc gccggtcgct    4740
accattacca gttggtctgg tgtcaaaaat aataaagccg aattctgtct agaaatggtt    4800
acaaataaaa gatctttatt ttcattagat ctgtgtgttg gttttttgtg tgttggtttt    4860
cccgttagca catgtctgca tttgtttttc tagtcacacg ccccccccc ccaaataaaa     4920 accaaggcaa acaataccaa gaagtcatgt gtattttga acatcggtgt cttttttattt    4980 atacacaagc ccagctcccc tcccctccct tagagctcgt cttcgtctcc ggcctcgtcc    5040
tcgttgtgga gcggagagta cctggctttg ttgcgcttgc gcagaaccat gttggtgacc    5100
ttggagctga gcagggcgct cgtgcccttc tttctggcct tgtgttccgt gcgctccatg    5160
gccgacacca aagccatata tcggatcatt tctcgggcct cggccaactt ggcctcgtca    5220
aacccgcccc cctccgcgcc ttcctccccc tcccgcccca cgcccccggg gtcggaagtc    5280
ttgagttcct tggtggtgag cggatacagg gccttcatgg gattgcgttg cagttgcagg    5340
```

```
acgtagcgga aggcgaagaa ggccgcgacc aggccggcca ggaccagcag ccccacggca      5400
agcgccccga aggggttgga cataaaggag gacacgcccg agacggccga caccacgccc      5460
cccactactc ccatgactac cttgccgacc gcgcgcccca agtcccccat ccctcgaag      5520 aacgcgcaca gccccgcgaa catggcgcg ttggcgtcgg cgcggatgac cgtgtcgatg       5580
tcggcaaagc gcaggtcgtg cagctggttg cggcgctgga cctccgtgta gtccagcagg      5640
ccgctgtcct tgatctcgtg gcgcgtgtag acctccaggg gcacaaactc gtggtcctcc      5700
agcatggtga tgttcaggtc gatgaaggtg ctgacggtgg tgacgtcggc gcgactcagc      5760
tggtgagagt acgcgtactc ctcgaagtac acgtagcccc cgccgaagat gaagtagcgc      5820
cggtggccca cggtgcacgg ctcgagcttc ctcgctcact gactcgctgc gctcggtcgt      5880
tcggctgcgg cgagcggtat cagctcactc aaaggcggta atacggttat ccacagaatc      5940
aggggataac gcaggaaaga acatgtgagc aaaaggccag caaaaggcca ggaaccgtaa      6000
aaaggccgcg ttgctggcgt ttttccatag gctccgcccc cctgacgagc atcacaaaaa      6060
tcgacgctca agtcagaggt ggcgaaaccc gacaggacta taaagatacc aggcgtttcc      6120
ccctggaagc tccctcgtgc gctctcctgt tccgaccctg ccgcttaccg gatacctgtc      6180
cgcctttctc ccttcgggaa gcgtggcgct ttctcatagc tcacgctgta ggtatctcag      6240
ttcggtgtag tcgttcgct ccaagctggg ctgtgtgcac gaaccccccg ttcagcccga       6300
ccgctgcgcc ttatccggta actatcgtct gagtccaac ccgtaagac acgacttatc       6360 gccactggca gcagccactg gtaacaggat tagcagagcg aggtatgtag gcggtgctac      6420
agagttcttg aagtggtggc ctaactacgg ctacactaga aggacagtat ttggtatctg      6480
cgctctgctg aagccagtta ccttcggaaa aagagttggt agctcttgat ccggcaaaca      6540
aaccaccgct ggtagcggtg gtttttttgt ttgcaagcag cagattacgc gcagaaaaaa      6600
aggatctcaa gaagatcctt tgatctttc tacggggtct gacgctcagt ggaacgaaaa       6660
ctcacgttaa gggattttgg tcatgagatt atcaaaaagg atcttcacct agatcctttt      6720
aaattaaaaa tgaagtttta aatcaatcta agtatatat gagtaaactt ggtctgacag       6780
ttaccaatgc ttaatcagtg aggcaccat ctcagcgatc tgtctatttc gttcatccat       6840
agttgcctga ctccccgtcg tgtagataac tacgatacgg gagggcttac catctggccc      6900
cagtgctgca atgataccgc gagacccacg ctcaccggct ccagatttat cagcaataaa      6960
ccagccagcc ggaagggccg agcgcagaag tggtcctgca actttatccg cctccatcca      7020
gtctattaat tgttgccggg aagctagagt aagtagttcg ccagttaata gtttgcgcaa      7080
cgttgttgcc attgctacag gcatcgtggt gtcacgctcg tcgtttggta tggcttcatt      7140
cagctccggt tcccaacgat caaggcgagt tacatgatcc cccatgttgt gcaaaaaagc      7200
ggttagctcc ttcggtcctc cgatcgttgt cagaagtaag ttggccgcag tgttatcact      7260
catggttatg gcagcactgc ataattctct tactgtcatg ccatccgtaa gatgcttttc      7320
tgtgactggt gagtactcaa ccaagtcatt ctgagaatag tgtatgcggc gaccgagttg      7380
ctcttgcccg gcgtcaatac gggataatac cgcgccacat agcagaactt taaaagtgct      7440
catcattgga aaacgttctt cggggcgaaa actctcaagg atcttaccgc tgttgagatc      7500
cagttcgatg taacccactc gtgcacccaa ctgatcttca gcatctttta ctttcaccag      7560
cgtttctggg tgagcaaaaa caggaaggca aaatgccgca aaaaagggaa taagggcgac      7620
acggaaatgt tgaatactca tactcttcct ttttcaatat tattgaagca tttatcaggg      7680
ttattgtctc atgagcggat acatatttga atgtatttag aaaaataaac aaataggggt      7740
```

-continued

| | |
|---|---|
| tccgcgcaca tttccccgaa aagtgccacc tgacgtctaa gaaaccatta ttatcatgac | 7800 |
| attaacctat aaaaataggc gtatcacgag gccctttcgt c | 7841 |

<210> SEQ ID NO 36
<211> LENGTH: 4389
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

| | |
|---|---|
| tcgcgcgttt cggtgatgac ggtgaaaacc tctgacacat gcagctcccg agacggtca | 60 |
| cagcttgtct gtaagcggat gccgggagca gacaagcccg tcaggcgcg tcagcgggtg | 120 |
| ttggcgggtg tcgggctgg cttaactatg cggcatcaga gcagattgta ctgagagtgc | 180 |
| accatatggc gcgccgccgc gcgggcccgg actccgcccc ggcgaccgcc ccgcgccggc | 240 |
| ttcccggtat ggtaattaga aacttttaat aggcggtccc ggccgccatc cccgctcatg | 300 |
| gcaattagca acttttaatg gccggcctt cccgctcgcg gtaattagca gcttttaacg | 360 |
| ggccgccatt cccgcttatg gtaattaaaa acgttcggac ggcccctcgc tccccgcgta | 420 |
| attactccct cggggttccg ggttatgctg attactttct tggcagaaca cgcagagcct | 480 |
| cgcgcgccgc cgggtgggtg ggctgatcgg cccctattgg tccctgggc ttcctagtat | 540 |
| gctaatgaat ttctccccgg gggcgggcac cactcagggc cgcgccggcg gggcgccggg | 600 |
| gggactccca tctgcgtcgg cggggggcgg gcatgctaat gggggttcttg gagtacaccc | 660 |
| ggttggtccc cggggacggg gccgcccga gagggggga ttcctccct ccgccccgc | 720 |
| cggggcgcgc ggctattggg ggaatcgtaa atgccgcccc tttggggag tggataggcg | 780 |
| ccgggtataa ggcagccccg tgtgacggtc gggccgcatt cgcaccccgg cactgcgagc | 840 |
| gacggagcgg cggcccggcg ggaggaggag acccggagag acagagacta aaacccggca | 900 |
| agagagagag accgcgggcc gccgtctcga agcttggtcg atatctatcg gagctgtgct | 960 |
| agcgccactg gtacccgagc ggaattcggc ttgctgcccg aagggaagcc gccccccccc | 1020 |
| ggaccaccgg ccgaggcgcc tcgggggcag ggggaggtgg ggggggaag acggggagga | 1080 |
| gacaggaagt gggggtggga gtgggggggg acggacacgg ccccgaacag caacacacac | 1140 |
| cagcattttg ttatggactt tctggccttg ttgaaaactt gaggaaaaaa aactttatat | 1200 |
| ttataaaaat tttacaataa agttttgtga tgcttttgac acactttgtt gttggccttt | 1260 |
| gatgcagctc ccccgcgcag gggggccggg gatgggggggg aaagggagga ggaggaggg | 1320 |
| gggcgggcac gagaagccgc ccccacccc gaggcctgtt ggtctttatc atagaacaga | 1380 |
| gccggggccc ggcctgcgtt ctggctccct gtcttggtgg gtgggcgggc tggctggcgg | 1440 |
| gtaaaaaaag agtgtgtccg tgttgacagg gagggggggcc cgatcgtgca gagcacgcac | 1500 |
| gtctggccgg ccagaccctg ggggtggtgg gcaggagtgg gagggcgcct ggctcgggga | 1560 |
| gggaggaggg gggggggtcag ccgcaccacc ggcgcgaagc caggggccag ggaactttga | 1620 |
| tagagagggg ggaaagtggg gcgggggcga gggcggttga atcacaacgc atgcacgccc | 1680 |
| tctgcccccg gggacgggtg ggaggaagga ggagggagaa gagaagaccc gaggcatgca | 1740 |
| cccgcactta cgcccgtgcc cacccccgcc ccggcgccca cccgcccgc acacctgccc | 1800 |
| gccacgcccg ccctcctca ccctggctgg gagaaaggag gaggagcagg aagaggagac | 1860 |
| ccgaggcatg caaccgcact cacccacc cgcccgcaca cctgcccgcc acgccgccc | 1920 |

```
ctccttaccc tggctgcggg gagactccca tcggggcgag ggggctcgcg cgttcgcaac      1980
accacaccac accacacggc ccaccacaac acggcccacc acgacacaac acgacacgac      2040
gcgttttgcg gggcatgcaa gtcgacacac cgcgcgcgtg cctacctttc cctagcggcc      2100
ccggcccccc ggcccgtttc cttccgccac cactaccacc acccccccgc ccgcgcccac      2160
gcggtagagg aagggacgg gcgccacacc cacggctgtg gccgggcacg cgcctttggg       2220
gttgttgggg ggggtgacc ggcgcgtggg ggcggtgggc gtatgggccc gacccgcgcc       2280
tgcccccct gggaacgacg ccccggacg acaccacggg ggggggaaac ggggtgggt         2340
ggaagggaag aggaaggaga aaggggggt ggatccgaac acgccggact cgagcttcct       2400
cgctcactga ctcgctgcgc tcggtcgttc ggctgcggcg agcggtatca gctcactcaa      2460
aggcggtaat acgttatcc acagaatcag gggataacgc aggaaagaac atgtgagcaa      2520
aaggccagca aaaggccagg aaccgtaaaa aggccgcgtt gctggcgttt ttccataggc      2580
tccgcccccc tgacgagcat cacaaaaatc gacgctcaag tcagaggtgg cgaaacccga      2640
caggactata aagataccag gcgtttcccc ctggaagctc cctcgtgcgc tctcctgttc      2700
cgaccctgcc gcttaccgga tacctgtccg ccttctccc ttcgggaagc gtggcgcttt       2760
ctcatagctc acgctgtagg tatctcagtt cggtgtaggt cgttcgctcc aagctgggct      2820
gtgtgcacga accccccgtt cagcccgacc gctgcgcctt atccggtaac tatcgtcttg      2880
agtccaaccc ggtaagacac gacttatcgc cactggcagc agccactggt aacaggatta      2940
gcagagcgag gtatgtaggc ggtgctacag agttcttgaa gtggtggcct aactacggct      3000
acactagaag gacagtattt ggtatctgcg ctctgctgaa gccagttacc ttcggaaaaa      3060
gagttggtag ctcttgatcc ggcaaacaaa ccaccgctgg tagcggtggt ttttttgttt      3120
gcaagcagca gattacgcgc agaaaaaaag gatctcaaga agatcctttg atcttttcta      3180
cggggtctga cgctcagtgg aacgaaaact cacgttaagg gattttggtc atgagattat      3240
caaaaaggat cttcacctag atccttttaa attaaaaatg aagttttaaa tcaatctaaa      3300
gtatatatga gtaaacttgg tctgacagtt accaatgctt aatcagtgag gcacctatct      3360
cagcgatctg tctatttcgt tcatccatag ttgcctgact ccccgtcgtg tagataacta      3420
cgatacggga gggcttacca tctggcccca gtgctgcaat gataccgcga gacccacgct      3480
caccggctcc agatttatca gcaataaacc agccagccgg aagggccgag cgcagaagtg      3540
gtcctgcaac tttatccgcc tccatccagt ctattaattg ttgccgggaa gctagagtaa      3600
gtagttcgcc agttaatagt ttgcgcaacg ttgttgccat tgctacaggc atcgtggtgt      3660
cacgctcgtc gtttggtatg gcttcattca gctccggttc ccaacgatca aggcgagtta      3720
catgatcccc catgttgtgc aaaaaagcgg ttagctcctt cggtcctccg atcgttgtca      3780
gaagtaagtt ggccgcagtg ttatcactca tggttatggc agcactgcat aattctctta      3840
ctgtcatgcc atccgtaaga tgcttttctg tgactggtga gtactcaacc aagtcattct      3900
gagaatagtg tatgcggcga ccgagttgct cttgcccggc gtcaatacgg gataataccg      3960
cgccacatag cagaacttta aaagtgctca tcattggaaa acgttcttcg ggcgaaaac       4020
tctcaaggat cttaccgctg ttgagatcca gttcgatgta acccactcgt gcacccaact      4080
gatcttcagc atcttttact ttcaccagcg tttctgggtg agcaaaaaca ggaaggcaaa      4140
atgccgcaaa aaagggaata agggcgacac ggaaatgttg aatactcata ctcttccttt      4200
ttcaatatta ttgaagcatt tatcagggtt attgtctcat gagcggatac atatttgaat      4260
```

```
gtatttagaa aaataaacaa ataggggttc cgcgcacatt tccccgaaaa gtgccacctg    4320
acgtctaaga aaccattatt atcatgacat taacctataa aaataggcgt atcacgaggc    4380
cctttcgtc                                                            4389

<210> SEQ ID NO 37
<211> LENGTH: 7
<212> TYPE: DNA
<213> ORGANISM: Herpes simplex virus

<400> SEQUENCE: 37 tataagg                                                                 7

<210> SEQ ID NO 38
<211> LENGTH: 6
<212> TYPE: DNA
<213> ORGANISM: Herpes simplex virus

<400> SEQUENCE: 38 aataaa                                                                  6

<210> SEQ ID NO 39
<211> LENGTH: 3
<212> TYPE: DNA
<213> ORGANISM: Herpes simplex virus

<400> SEQUENCE: 39 taa                                                                     3

<210> SEQ ID NO 40
<211> LENGTH: 5336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgtg agaatcccga ggccgcccta cggaataaac ggaccccccg cacacaaagt     240
aggcgcggtt tctgtctgcc gtgacgtaaa acacaacgtc ccggtggtgc agggtggtgg     300
catagctgag ctccatggcc ggcgagccac ggggcggact tgggggggg gaatagtggg     360 gtggtgggag gagggtggtg ggagcaaggg ctggcggtgg cgcgaacggg acccgtgggt     420
tgctctcgcg cgtgccgccc gcgcgtaggg ttgtggccgg acgaggaaac tcccccact      480 gtggatcgcg gcgtcggtgc ttgggcaaac gacggcttcc gtcacgcacg gccggccttt     540
taaggacaac tccggcgca ttcccgacgt ggccctctgg gtgttttctt cgtttcctcc      600
cccaacccat cttccccct gccttccac tgactaaccg ccacgtcatc agcccgcggg     660
ggagggcgga cgcacggatg tgcggctcgc gaaccacatc cacccatgat ttgggcgtca     720
gggcgtgggt gtgaatttcg ggggttccgg gcccaacggc cgaggttat atcctgctgg     780 gacgtgactt cgccaggcac tcgcatccgc ggatactacc cgggtggggg ttgtgtgtag     840
aacccgcgcg gtgcttgttt gattttggcc tccgccccc atccctgaag cttgggtccg     900
gacccgggcc cgcgccgcca gcactacttt cggtttcgct gcctcgccgg ctccccgcac     960
```

-continued

```
cgaccatgac aatgcgggat gatgttcctt tgttggatcg cgagctggta gacgaggccg    1020
cgtgtggcgg ggaggacggc gaactgccgc tcgatgaaca gttttcgctg tcctcgtacg    1080
gcacgtctga ttttttttgtc agttcggcct actcgcgtct tccgccccac acccagccgg    1140
tcttttccaa gcgggtggtg atgtttgctt ggtcgttcct ggtcctcaag ccgctggagc    1200
tggtggccgc gggcatgtat tacgggtgga ccggacgggc ggtggcgccg gcatgtatta    1260
tagccgccgt cctcgcctac tatgtcacgt ggctggcacg ggcgctcctc ctgtacgtga    1320
acatcaaacg ggatcgcctg ccgttgtcgc cacccgtgtt ttgggggttg tgcgtgatca    1380
tgggcggcgc ggccctgtgc gccctggtgg cggccgccca tgagacgttc agtcccgacg    1440
ggcttttcca ttggatcacc gccagccagc tgctgccccg cacggatccc ctccgcgccc    1500
gttctctggg aatcgcctgc gcggccgcgc ccgccatgtg ggtggcggcg cggactgct    1560
ttgccgcctt taccaacttt tttctagcac gcttttggac cagggccatc ttgaaggcac    1620
ccgtcgcgtt ctaacggggg tgtggcgggg gggtatataa ggcaattggc cgtcccgtta    1680
ccaagaccaa cccagccagc gtatccaccc ccgcccgggt ccccgcggaa gcggaacggg    1740
gtatgtgata tgctaattaa atacatgcca cgtacttatg gtgtctgatt ggtccttgtc    1800
tgtgccggag gtggggcggg ggccccgccc gggggcggaa acgaggaggg gtttgggaga    1860
gccggccccg gcaccacggg tatataagca accggtgtcg acggcggggg tcgtcggggt    1920
ccgtgggtct cgcccctcc ccccatcgag agtccgtagg tgacctaccg ttgcgccacc    1980
accagaggcc atatccgaca ccccagcccc gacggcagcc gacagcccga agcttggtcg    2040
atatctatcg gagctgtgct agcgccactg gtacccgagc ggaattctgt ctagacccag    2100
cttttccctcc acccgcccgt cttttttttt tcctgtttgg ggcattgggt ttgatttttcc    2160
gacgttgctt ttacccacac acaccccctg tccccgcccc ccggggggg cttggactgg    2220
gagccgcgat tccgagggca ggtcccaata aaacccagac ccgagctccg ggggactgat    2280
tctcacctgg ggctcctgcg cacgacagac ctccccgtgc gtgctgctga gccctgcccc    2340
gcccctctc ccacacggtc ggtgccccc atctctgttt catcatcgtc ccggttgcgt    2400
tgcgcttttcc ggccctcccg cacccccgcg ttccggtgtc tcgcggcccg cgcgcatgat    2460
cacggattgt ttcgaagcag acatcgcgat ccctcgggt atctcgcgcc ccgatgccgc    2520
ggcgctgcag cggtgcgagg gtcgagtggt ctttctgccg accatccgcc gccagctggc    2580
gctcgcggac gtggcgcacg aatcgttcgt ctccggagga gttagtcccg acacgttggg    2640
gttgttgctg gcgtaccgca ggcgcttccc cgcggtaatc acgcgggtgc tgcccacgcg    2700
aatcgtcgcc tgccccgtgg acctgggcgct cacgcacgcc ggcaccgtca atctccgcaa    2760
cacctccccc gtcgacctct gcaacggggga tccgtcagc ctcgtcccgc ccgtcttcga    2820
gggccaggcg acgacgtgc gcctggagtc gctggacctc acgctgcggt ttccggtccc    2880
gctcccaacg cccctggccc gcgagatagt cgcgcggctg gtcgcccggg gcatccggga    2940
cctcaacccc gaccccgga cgcccgggga gctcccgac ctcaacgtgc tgtattacaa    3000
cggggcccgt ctctcgctcg tggccgacgt ccagcaactc gcctccgtaa acaccgagct    3060
gcggtcgctc gtcctcaaca tggtctactc cataaccgaa ggaccaccc tcatcctcac    3120
gctcatccc cggctgctcg cgctaagcgc ccaggacgga tacgtgaacg cgctcctgca    3180
gatgcagagc gtcacgcgag aagccgccca gctcatccac cccgaagccc ccatgctgat    3240
gcaggacggc gagcgcaggc tgccgcttta cgaggcgctg gtcgcctggc tggcacgc    3300
gggccaactc ggggacatcc tggccctggc cccggctcga gcttcctcgc tcactgactc    3360
```

```
gctgcgctcg tcgttcggc tgcggcgagc ggtatcagct cactcaaagg cggtaatacg    3420
gttatccaca gaatcagggg ataacgcagg aaagaacatg tgagcaaaag gccagcaaaa    3480
ggccaggaac cgtaaaaagg ccgcgttgct ggcgtttttc cataggctcc gcccccctga    3540
cgagcatcac aaaaatcgac gctcaagtca gaggtggcga acccgacag gactataaag    3600
ataccaggcg tttccccctg gaagctccct cgtgcgctct cctgttccga ccctgccgct    3660
taccggatac ctgtccgcct ttctcccttc gggaagcgtg gcgctttctc atagctcacg    3720
ctgtaggtat ctcagttcgg tgtaggtcgt tcgctccaag ctgggctgtg tgcacgaacc    3780
ccccgttcag cccgaccgct gcgccttatc cggtaactat cgtcttgagt ccaacccggt    3840
aagacacgac ttatcgccac tggcagcagc cactggtaac aggattagca gagcgaggta    3900
tgtaggcggt gctacagagt tcttgaagtg gtggcctaac tacggctaca ctagaaggac    3960
agtatttggt atctgcgctc tgctgaagcc agttaccttc ggaaaaagag ttggtagctc    4020
ttgatccggc aaacaaacca ccgctggtag cggtggtttt tttgtttgca agcagcagat    4080
tacgcgcaga aaaaaggat ctcaagaaga tcctttgatc ttttctacgg ggtctgacgc    4140
tcagtggaac gaaaactcac gttaagggat tttggtcatg agattatcaa aaaggatctt    4200
cacctagatc cttttaaatt aaaaatgaag ttttaaatca atctaaagta tatatgagta    4260
aacttggtct gacagttacc aatgcttaat cagtgaggca cctatctcag cgatctgtct    4320
atttcgttca tccatagttg cctgactccc cgtcgtgtag ataactacga tacgggaggg    4380
cttaccatct ggccccagtg ctgcaatgat accgcgagac ccacgctcac cggctccaga    4440
tttatcagca ataaaccagc cagccggaag ggccgagcgc agaagtggtc ctgcaacttt    4500
atccgcctcc atccagtcta ttaattgttg ccgggaagct agagtaagta gttcgccagt    4560
taatagtttg cgcaacgttg ttgccattgc tacaggcatc gtggtgtcac gctcgtcgtt    4620
tggtatggct tcattcagct ccggttccca acgatcaagg cgagttacat gatccccat     4680
gttgtgcaaa aaagcggtta gctccttcgg tcctccgatc gttgtcagaa gtaagttggc    4740
cgcagtgtta tcactcatgg ttatggcagc actgcataat tctcttactg tcatgccatc    4800
cgtaagatgc ttttctgtga ctggtgagta ctcaaccaag tcattctgag aatagtgtat    4860
gcggcgaccg agttgctctt gcccggcgtc aatacgggat aataccgcgc cacatagcag    4920
aactttaaaa gtgctcatca ttggaaaacg ttcttcgggg cgaaaactct caaggatctt    4980
accgctgttg agatccagtt cgatgtaacc cactcgtgca cccaactgat cttcagcatc    5040
ttttactttc accagcgttt ctgggtgagc aaaaacagga aggcaaaatg ccgcaaaaaa    5100
gggaataagg gcgacacgga aatgttgaat actcatactc ttccttttc aatattattg     5160
aagcatttat cagggttatt gtctcatgag cggatacata tttgaatgta tttagaaaaa    5220
taaacaaata ggggttccgc gcacatttcc ccgaaaagtg ccacctgacg tctaagaaac    5280
cattattatc atgacattaa cctataaaaa taggcgtatc acgaggccct ttcgtc        5336
```

<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Ala Phe Leu Thr Gly Ala Asp Arg Ser Val Arg Leu Ala

```
                         1               5                    10

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

His Gly Pro Ser Leu Tyr Arg Thr Phe
1               5

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gctcgagtgc gaaaaaacgt tc                                              22

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cggggcgctc ggctaac                                                    17
```